US009469616B2

(12) United States Patent
Li et al.

(10) Patent No.: US 9,469,616 B2
(45) Date of Patent: Oct. 18, 2016

(54) CYCLIC COMPOUNDS AND METHODS OF MAKING AND USING THE SAME

(71) Applicants: Cellceutix Corporation, Beverly, MA (US); University of Massachusetts, Boston, MA (US)

(72) Inventors: Yan Li, Boston, MA (US); Hitesh Thaker, Boston, MA (US); Gregory N. Tew, Boston, MA (US); Dahui Liu, Radnor, PA (US); Wenxi Pan, Radnor, PA (US); Richard W Scott, Radnor, PA (US); Xiaodong Fan, Radnor, PA (US)

(73) Assignees: Cellceutix Corporation, Beverly, MA (US); University of Massachusetts, Boston, MA (US)

( * ) Notice: Subject to any disclaimer, the term of this patent is extended or adjusted under 35 U.S.C. 154(b) by 0 days.

(21) Appl. No.: 14/365,148

(22) PCT Filed: Dec. 10, 2012

(86) PCT No.: PCT/US2012/068722
§ 371 (c)(1),
(2) Date: Jun. 13, 2014

(87) PCT Pub. No.: WO2013/090185
PCT Pub. Date: Jun. 20, 2013

(65) Prior Publication Data
US 2015/0031738 A1     Jan. 29, 2015

Related U.S. Application Data

(60) Provisional application No. 61/569,847, filed on Dec. 13, 2011, provisional application No. 61/604,623, filed on Feb. 29, 2012, provisional application No. 61/663,584, filed on Jun. 24, 2012.

(51) Int. Cl.
| | |
|---|---|
| *C07D 249/06* | (2006.01) |
| *C07C 279/08* | (2006.01) |
| *C07C 217/16* | (2006.01) |
| *C07D 209/12* | (2006.01) |
| *C07D 295/135* | (2006.01) |
| *A01N 39/00* | (2006.01) |
| *A01N 43/38* | (2006.01) |
| *A01N 43/647* | (2006.01) |
| *A01N 47/44* | (2006.01) |
| *C07C 217/04* | (2006.01) |
| *C07C 279/02* | (2006.01) |
| *C07D 209/08* | (2006.01) |

(52) U.S. Cl.
CPC ............. *C07D 249/06* (2013.01); *A01N 39/00* (2013.01); *A01N 43/38* (2013.01); *A01N 43/647* (2013.01); *A01N 47/44* (2013.01); *C07C 217/04* (2013.01); *C07C 217/16* (2013.01); *C07C 279/02* (2013.01); *C07C 279/08* (2013.01); *C07D 209/08* (2013.01); *C07D 209/12* (2013.01); *C07D 295/135* (2013.01)

(58) Field of Classification Search
CPC .......................... C07D 249/06; C07D 217/04
See application file for complete search history.

(56) References Cited

U.S. PATENT DOCUMENTS

| | | |
|---|---|---|
| 7,173,102 B2 | 2/2007 | DeGrado et al. |
| 2005/0287108 A1 | 12/2005 | DeGrado et al. |
| 2006/0041023 A1 | 2/2006 | DeGrado et al. |
| 2010/0081665 A1 | 4/2010 | Scott et al. |

FOREIGN PATENT DOCUMENTS

| | | |
|---|---|---|
| WO | 2004082643 A2 | 9/2004 |
| WO | 2005123660 A2 | 12/2005 |
| WO | 2006093813 A2 | 9/2006 |

OTHER PUBLICATIONS

Yang, Mar. 2011, Organometallics, vol. 30, p. 2236-2240.*
Tew et al., "Denovo design of biomimetic antimicrobial polymers", Proc. Natl. Acad. Sci. USA, 2002, 99, 5110-5114.
Barany et al., "Solid-phase peptide synthesis: a silver anniversary report", Int. J. Pept. Prot. Res., 1987, 30, 705-739.
CID 10338813—Compound Summary, Oct. 25, 2006 (1 page).
CID 667696—Compound Summary, Jul. 7, 2005 (1 page).

* cited by examiner

*Primary Examiner* — Rebecca Anderson
*Assistant Examiner* — Karen Cheng
(74) *Attorney, Agent, or Firm* — Pepper Hamilton LLP

(57) ABSTRACT

The present invention provides compounds, or pharmaceutically acceptable salts thereof, for inhibiting the growth of a microbe; treating a mammal having a microbial infection, mucositis, an ophthalmic infection, an otic infection, a cancer, or a *Mycobacterium* infection; inhibiting the growth of a *Mycobacterium* species; modulating an immune response in a mammal; or antagonizing unfractionated heparin, low molecular weight heparin, or a heparin/low molecular weight heparin derivative.

19 Claims, 2 Drawing Sheets

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: hBD-2 forward primer

<400> SEQUENCE: 1
gatgcctctt ccaggtgttt ttgg                                              24

<210> SEQ ID NO 2
<211> LENGTH: 20
<212> TYPE: DNA
<213> ORGANISM: Artificial Sequence
<220> FEATURE:
<223> OTHER INFORMATION: hBD-2 reverse primer

<400> SEQUENCE: 2
ttgttccagg accacaggtg                                                   20

<210> SEQ ID NO 3
<211> LENGTH: 28
<212> TYPE: DNA
<213> ORGANISM: Artificial Sequence
<220> FEATURE:
<223> OTHER INFORMATION: IL-8 forward primer

<400> SEQUENCE: 3
gcagctctgt gtgaaggtgc agttttgc                                          28

<210> SEQ ID NO 4
<211> LENGTH: 25
<212> TYPE: DNA
<213> ORGANISM: Artificial Sequence
<220> FEATURE:
<223> OTHER INFORMATION: IL-8 reverse primer

<400> SEQUENCE: 4
tttctgtgtt ggcgcagtgt ggtcc                                             25

<210> SEQ ID NO 5
<211> LENGTH: 19
<212> TYPE: DNA
<213> ORGANISM: Artificial Sequence
<220> FEATURE:
<223> OTHER INFORMATION: b-2-microgloublin forward primer

<400> SEQUENCE: 5
ctccgtggcc ttagctgtg                                                    19

<210> SEQ ID NO 6
<211> LENGTH: 21
<212> TYPE: DNA
<213> ORGANISM: Artificial Sequence
<220> FEATURE:
<223> OTHER INFORMATION: b-2-microgloublin reverse primer

<400> SEQUENCE: 6
ttggagtacg ctggatagcc t                                                 21
```

CYCLIC COMPOUNDS AND METHODS OF MAKING AND USING THE SAME

REFERENCE TO GOVERNMENT GRANTS

The present invention was supported by funds from the U.S. Government (NIH Grant Nos. AI-074866 and U01 AI-082192) and the U.S. Government may therefore have certain rights in the invention.

FIELD OF THE INVENTION

The present invention is directed, in part, to cyclic compounds, or pharmaceutically acceptable salts thereof, for inhibiting the growth of a microbe; treating a mammal having a microbial infection, mucositis, an ophthalmic infection, an otic infection, a cancer, or a *Mycobacterium* infection; inhibiting the growth of a *Mycobacterium* species; modulating an immune response in a mammal; or antagonizing unfractionated heparin, low molecular weight heparin, or a heparin/low molecular weight heparin derivative.

BACKGROUND OF THE INVENTION

Antimicrobial peptides (AMPs) represent a first line of defense against microbes for many species. AMPs are typically small (12-80 amino acids) cationic amphiphiles. There are two types of AMPs comprising ribosomally and nonribosomally synthesized peptides. Over 700 AMPs have been identified and are generally α-helical (magainin and cecropin) or disulfide-rich β-sheets (bactenecin and defensin). Although the peptides are composed of many different sequences, their physiochemical properties are remarkably similar. They adopt an amphiphilic architecture with positively charged groups segregated to one side of the secondary structure and hydrophobic groups on the opposite surface. In mammals, the peptides are produced and secreted in skin, mucosal surfaces and neutrophils, and act locally in response to infection. It is the overall physiochemical properties that are largely responsible for biological activity of these peptides. Some AMPs display very broad spectrum action against bacteria, yeast, fungus, protozoa, and even viruses. Anti-parasitic activities have also been reported for a number of host defense peptides. AMPs have remained an effective weapon against bacterial infection over evolutionary time indicating that their mechanism of action thwarts bacterial responses which lead to resistance against toxic substances. This premise is supported by direct experimental data showing that no appreciable resistance to the action of the AMPs occurs after multiple serial passages of bacteria in the presence of sub-lethal concentrations of the peptides.

Several synthetic peptides and peptoids have been synthesized to mimic the activity of the natural host defense proteins (DeGrado, Adv. Protein Chem., 1988, 51-124; Hamuro et al., J. Am. Chem. Soc., 1999, 121, 12200-12201; Porter et al., Nature (London), 2000, 404, 565; Porter et al., J. Am. Chem. Soc., 2002, 124, 7324-7330; Liu et al., J. Am. Chem. Soc., 2001, 123, 7553-7559; Patch et al., J. Am. Chem. Soc., 2003, 125, 12092-12093; and Seurynck et al., Biophysical Journal, 2003, 84, 298A-298A) and several of these have been shown to selectively kill tumorigenic cells (Papo et al., Biochemistry, 2003, 42, 9346-9354; Papo et al., Cancer Res., 2004, 64, 5779-5786; and Shin et al., Biochim Biophys. Acta, 2000, 1463, 209-218).

Tuberculosis (TB) is a highly contagious disease that affects one-third of the world's population today. There are 8 million newly reported cases each year and 3.1 million people die from the disease annually. TB is the leading cause of death of women, AIDS patients, and the young in the world. There are more deaths from TB than any other single infectious disease. Worldwide, 30 to 50% of AIDS deaths are caused by TB. Globally, the population weighted mean of multi-drug resistant (MDR) TB among all TB cases is estimated at about 5%. Extensively-drug resistant (XDR) TB is more expensive and difficult to treat than MDR-TB and outcomes for XDR-TB patients are much worse. *Mycobacterium tuberculosis* (*M. tuberculosis*) is the primary infectious agent for TB, and drug resistance has become a paramount issue, accounting for over 50 million infections world wide. Although several anti-infective agents have been identified that combat *M. tuberculosis* and other tuberculosis-causing organisms, the emergence of MDR and XDR organisms has severely limited their effectiveness. A current therapeutic strategy for active disease is to treat with multiple drugs for 6 to 9 months; a course of therapy that is difficult to manage for compliance, thereby exacerbating the development of resistance. Furthermore, many of the anti-TB agents interfere with HIV therapy creating a dangerous upward spiral in disease progression and severity in co-infected individuals.

Oral ulcerative mucositis is a common, painful, dose-limiting toxicity of chemotherapy and radiation therapy for cancer (Sonis, Nat. Rev. Cancer, 2004, 4, 277-284; Keefe et al., Cancer, 2007, 109, 820-831; Belim et al., Support Care Cancer, 2000, 8, 33-39; and Parulekar et al., Oral Oncol., 1998, 34, 63-71). The disorder is characterized by breakdown of the oral mucosa and results in the formation of ulcerative lesions. It can significantly affect nutritional intake, mouth care, and quality of life (Lalla et al., Dent. Clin. North Am., 2005, 49, 167-184; and Duncan et al., Head Neck, 2005, 27, 421-428). The ulcerations that accompany mucositis are frequent portals of entry for oral bacteria often leading to sepsis or bacteremia. For patients receiving high-dose chemotherapy prior to hematopoietic cell transplantation, oral mucositis has been reported to be the single most debilitating complication of transplantation (Belim et al., Support Care Cancer, 2000, 8, 33-39). Infections associated with the oral mucositis lesions can cause life-threatening systemic sepsis during periods of immunosuppression (Rapoport et al., J. Clin. Oncol., 1999, 17, 2446-2453). Mucositis results in increased hospital stays and re-admission rates, and can result in interruptions or early cessation of treatment regimens (Pico et al., The Oncologist, 1998, 3, 446-451; and Elting et al., Cancer, 2003, 98, 1531-1539). Moderate to severe mucositis occurs in virtually all patients who receive radiation therapy for tumors of the head and neck. Among patients who are treated with induction therapy for leukemia or with many of the conditioning regimens for bone marrow transplant, is not unusual for more than three-quarters of patients to develop moderate to severe mucositis (Belim et al., Support Care Cancer, 2000, 8, 33-39). Annually, nearly 60,000 patients receive a diagnosis of head and neck cancer (Jemal et al., CA Cancer J Clin., 2002, 52, 23-47) and severe mucositis occurs in up to 92% of these treated patients (Parulekar et al., Oral Oncol., 1998, 34, 63-71; Sonis et al., Cancer, 85, 2103-2113). In addition to quality of life issues, there is a substantial impact of oral mucositis on medical care resources and costs, estimated to be $17,000 per patient, which are related to increased hospitalization stays, medical treatments and medications (Nonzee et al., Cancer, 2008, 113, 1446-1452). Despite its frequency, severity and impact on patients' ability to tolerate cancer treatment, there is currently only one approved pharmaceutical for the prevention or treatment for oral mucositis. Palifermin (Kepivance®, recombinant human keratinocyte growth factor-1) was approved for a mucositis indication in patients with hematologic malignancies receiving stem cell transplants. Its efficacy may be related to mitogenic effects on mucosal epithelium and/or alteration of cytokine profiles, including down-regulation of TNF (Logan et al., Cancer Treatment Rev., 2007, 33, 448-460). Palifermin is not widely used due in part to concerns on the potential impact of a growth factor on antineoplastic treatment. Available agents include topical analgesics (lidocaine), barrier devices (GelClair), or rinses (Caphosol). Another agent proposed to be used for treatment of mucositis is NX002, which is a peptide derived from AMP-18 (see, U.S. Pat. Nos. 7,910,543 and 7,629,317).

Periodontitis is the most common cause of tooth loss in adults in the United States (Borrell et al., J. Dent. Res., 2005, 84, 924-930), occurring in 15-25% of the US population. Its etiology can be considered due to bacterial colonization by a variety of pathogenic microorganisms, including *Porphyromonas gingivalis*, which is associated with chronic periodontitis, and *Aggregatibacter actinomycetemcomitans*, which is associated with aggressive periodontitis. This colonization and subsequent invasion into the gingival epithelium leads to an innate immune response, including the production of such mediators as IL-1 and tumor necrosis factor (TNF)-α (Graves et al., J. Periodontol., 2003, 74, 391-401). This leads to inflammation, which ultimately results in the bone loss seen in this disease (reviewed in Cochran, J. Periodontol., 2008, 79, 1569-1576). While standard treatment involves mechanical removal of the biofilm, the use of systemic antibiotics has also been examined (reviewed in Herrera et al., J. Clin. Periodontol., 2008, 35, 45-66), as has the identification of therapeutic targets in the inflammatory response (reviewed in Kirkwood et al., Periodontol. 2000, 2007, 43, 294-315).

While periodontal disease is ultimately of bacterial etiology, from multispecies biofilms of Gram-negative anaerobic microorganisms, much of the deleterious effects are due to the resultant epithelial inflammatory response. Thus, development of a treatment that combines both anti-biofilm antibiotic activity with anti-inflammatory activity would be of great utility. Metabolic assays as well as culture and biomass measurement assays have demonstrated that mPE exhibits potent activity against biofilm cultures of both species. Furthermore, as little as 2 µg/ml mPE was sufficient to inhibit IL-1β-induced secretion of IL-8 in both gingival epithelial cells and THP-1 cells. This anti-inflammatory activity is associated with a reduction in activation of NF-κB, suggesting that mPE can act both as an anti-biofilm agent in an anaerobic environment as well as an anti-inflammatory agent in infected tissues.

Treatment and prevention of thrombosis are major clinical issues for medical and surgical patients. Heparin, a highly sulfated polysaccharide, is commonly used as prophylaxis against venous thromboembolism and to treat venous thrombosis, pulmonary embolism, unstable angina and myocardial infarction (see, for example, Walenga et al., "Factor Xa inhibition in mediating antithrombotic actions: application of a synthetic heparin pentasaccharide" In: Paris: Universite Pierre et Marie Curie, Paris VI; 1987; and Hirsh et. al., Chest, 2001, 119, 64-94). Heparin is also used as an anticoagulant during the extracorporeal blood circulation for kidney dialysis and coronary bypass surgery. Although heparin is an efficacious anticoagulant, there are many limitations associated with its clinical use. For example, heparin's heterogeneity and polydispersity lead to nonspecific protein binding and poorly predictive pharmacokinetic properties upon subcutaneous (s.c.), and even intravenous, injection (see, for example, Bendetowicz et. al., Thromb. Hemostasis., 1994, 71, 305-313). As a result, infusions of unfractionated heparin (UFH) are performed in the hospital where its anticoagulant effect can be measured to minimize the risk of bleeding. In addition to hemorrhage, administration of UFH is associated with 1-2% incidence of heparin-induced thrombocytopenia (HIT) (see, for example, Morabia, Lancet, 1986, 1, 1278-1279; Mureebe et. al., Vasc. Endovasc. Surg., 2002, 36, 163-170; and Lubenow et. al., Chest, 2002, 122, 37-42).

To address some of the shortcomings of UFH, low molecular weight heparins (LMWHs) have been developed. LMWHs are fragments of UFH produced by chemical or enzymatic depolymerization (see, for example, Hirsh et. al., Blood, 1992, 79, 1-17). Due to their smaller size and lower polydispersity, LMWHs are more reproducibly bioavailable after s.c. administration and have more predictable pharmacokinetics leading to greater safety (see, for example, Ofosu et. al., "Mechanisms of action of low molecular weight heparins and heparinoids." In: Hirsh J (ed). Antithrombotic Therapy, Bailliere's Clinical Haematology (Volume 3). London, UK: Bailliere Tindall, 1990, pp. 505-529). The smaller size of LMWHs is also associated with a lower ratio of anti-thrombin to anti-FXa activity (see, for example, Hirsh et. al., Chest, 2001, 119, 64-94). LMWHs are being used with greater frequency owing to their ease of administration, longer duration or action and reduced incidence of heparin-induced thrombocytopenia (see, for example, Hirsh et. al., Chest, 2004, 126 (Suppl 3), 188S-203S). LMWHs are commonly used to treat deep vein thrombosis, unstable angina, and acute pulmonary embolism, as well as thromboprophylactic agents in a wide range of clinical situations including orthopedic surgery, high risk pregnancy, and cancer therapy (see, for example, Hirsh et. al., Chest, 2004, 126 (Suppl 3), 188S-203S; Becker, J. Thrombosis and Thrombolysis, 1999, 7, 195; Antman et. al., Circulation, 1999, 100, 1593-601; Cohen et. al., New England J. Med., 1997, 337, 447; and Lee et. al., J Clin. Oncol., 2005, 23, 2123-9).

Fondaparinux is a heparin-derived pentasaccharide that represents the smallest fragment of heparin that is capable of accelerating antithrombin-mediated factor Xa inhibition (see, for example, Walenga et. al., Exp. Opin. Invest. Drugs, 2005, 14, 847-58). Fondaparinux is currently approved for the prophylaxis of deep vein thrombosis following hip repair and/or replacement, knee replacement and abdominal surgery and the treatment of DVT/PE when used in conjunction with warfarin. The most common complication of anticoagulation with LMWHs is hemorrhage. Many published clinical studies report 1% to 4% major (life-threatening) bleeding associated with LMWH therapy and there is a 5-fold increase in the overall death rate for acute coronary syndrome patients receiving anti-coagulant therapy that experience major bleeding (see, for example, Hirsh et. al., Chest, 2001, 119, 64-94; and Mehta et. al., J. Am. Coll. Cardiol., 2007, 50, 1742-1751).

Protamine, an arginine-rich heterogeneous peptide mixture isolated from fish sperm, is used routinely to neutralize the effects of heparin in patients who bleed while under treatment (see, for example, Ando et. al., in Kleinzeller, A. (ed): "Protamine: Molecular biology, biochemistry and biophysics" Vol 12. 1973. New York, Springer-Verlag, 1-109). Polycationic protamine binds to anionic heparin through electrostatic interactions, thereby neutralizing the anticoagulant effects of heparin. Although protamine is commonly used to neutralize UFH following coronary bypass surgery, it is unable to completely reverse the anticoagulant effects of LMWHs (see, for example, Hubbard et. al., Thromb. Haemost., 1985, 53, 86-89; Poon et. al., Thromb. Haemost., 1982, 47, 162-165; Massonnet-Castel et. al., Haemostasis, 1986, 16, 139-146; and Doutremepuich et. al., Semin Thromb. Hemost., 1985, 11, 318-322) or fondaparinux (see, for example, Walenga, "Factor Xa inhibition in mediating antithrombotic actions: application of a synthetic heparin pentasaccharide" In. Paris: Universite Pierre et Marie Curie, Paris VI; 1987), In addition, use of protamine for heparin reversal is associated with adverse reactions including systemic vasodilation and hypotension, bradycardia, pulmonary artery hypertension, pulmonary vasoconstriction, thrombocytopenia, and neutropenia (see, for example, Metz et. al., "Protamine and newer heparin antagonists" in Stoetling, R. K. (ed): Pharmacology and Physiology in Anesthetic Practice. Vol. 1. Philadelphia, Pa., J B Lippincott, 1-15, 1994; Weiler et. al., J. Allergy Clin. Immunol., 1985, 75, 297-303; Horrow, Anest. Analg., 1985, 64, 348-361; and Porsche et. al., Heart Lung J. Acute Crit. Care, 1999, 28, 418-428).

Therefore, there is a strong medical need for the development of a safe and effective antagonist for UFH and/or LMWH. The lack of an effective antagonist has limited the clinical use of the LMWHs and fondaparinux, especially in bypass procedures and instances where near term surgical procedures may be needed. There is also a strong medical need for an efficacious, nontoxic substitute for protamine. Further, efficacy against the anticoagulation properties of the LMWHs would substantially address an important and expanding medical market for which no effective antidote is available.

SUMMARY OF THE INVENTION

The present invention provides compounds of Formula I

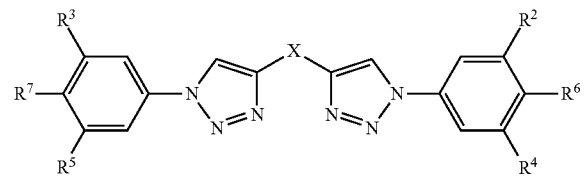

(I)

wherein: X is

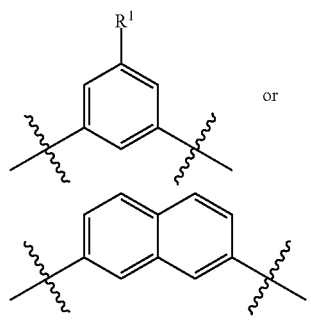

$R^1$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH=CH—CH$_2$NC(=N)NH$_2$, or —C≡C—(CH$_2$)$_2$—NC(=N)NH$_2$, where n is 2, 3, or 4; $R^2$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH=CH—CH$_2$NC(=N)NH$_2$, or —C≡C—(CH$_2$)$_2$—NC(=N)NH$_2$, where n is 2, 3, or 4; $R^3$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH=CH—CH$_2$NC(=N)NH$_2$, or —C≡C—(CH$_2$)$_2$—NC(=N)NH$_2$, where n is 2, 3, or 4; $R^4$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH=CH—CH$_2$NC(=N)NH$_2$, or —C≡C—(CH$_2$)$_2$—NC(=N)NH$_2$, where n is 2, 3, or 4; $R^5$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH=CH—CH$_2$NC(=N)NH$_2$, or —C≡C—(CH$_2$)$_2$—NC(=N)NH$_2$, where n is 2, 3, or 4; $R^6$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH=CH—CH$_2$NC(=N)NH$_2$, or —C≡C—(CH$_2$)$_2$—NC(=N)NH$_2$, where n is 2, 3, or 4; and $R^7$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH=CH—CH$_2$NC(=N)NH$_2$, or —C≡C—(CH$_2$)$_2$—NC(=N)NH$_2$, where n is 2, 3, or 4; or a pharmaceutically acceptable salt thereof.

The present invention also provides compounds of Formula II

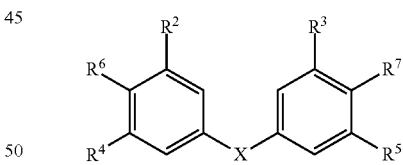

(II)

wherein: X is

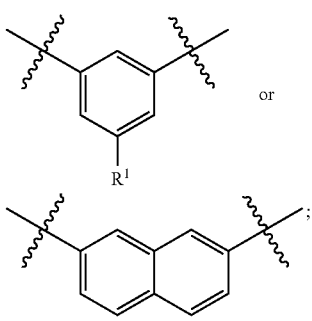

R[1] is H,

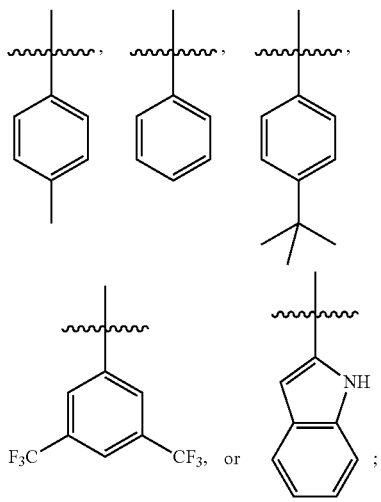

R[2] is H, —NH(CH$_2$)$_n$NH$_2$, —(CH$_2$)$_n$NH$_2$, —NH(CH$_2$)$_n$NC(=N)NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —C≡C—CH$_2$NH$_2$, —CH=CH—(CH$_2$)$_2$NC(=N)NH$_2$, —C≡C—(CH$_2$)$_2$NH$_2$, —CH=CH—CH$_2$NC(=N)NH$_2$, or —C≡C—(CH$_2$)$_2$—NC(=N)NH$_2$, where n is 2, 3, or 4; R[3] is H, —NH(CH$_2$)$_n$NH$_2$, —(CH$_2$)$_n$NH$_2$, —NH(CH$_2$)$_n$NC(=N)NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —C≡C—CH$_2$NH$_2$, —CH=CH—(CH$_2$)$_2$NC(=N)NH$_2$, —C≡C—(CH$_2$)$_2$NH$_2$, —CH=CH—CH$_2$NC(=N)NH$_2$, or —C≡C—(CH$_2$)$_2$—NC(=N)NH$_2$, where n is 2, 3, or 4; R[4] is H, —NH(CH$_2$)$_n$NH$_2$, —(CH$_2$)$_n$NH$_2$, —NH(CH$_2$)$_n$NC(=N)NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —C≡C—CH$_2$NH$_2$, —CH=CH—(CH$_2$)$_2$NC(=N)NH$_2$, —C≡C—(CH$_2$)$_2$NH$_2$, —CH=CH—CH$_2$NC(=N)NH$_2$, or —C≡C—(CH$_2$)$_2$—NC(=N)NH$_2$, where n is 2, 3, or 4; R[5] is H, —NH(CH$_2$)$_n$NH$_2$, —(CH$_2$)$_n$NH$_2$, —NH(CH$_2$)$_n$NC(=N)NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —C≡C—CH$_2$NH$_2$, —CH=CH—(CH$_2$)$_2$NC(=N)NH$_2$, —C≡C—(CH$_2$)$_2$NH$_2$, —CH=CH—CH$_2$NC(=N)NH$_2$, or —C≡C—(CH$_2$)$_2$—NC(=N)NH$_2$, where n is 2, 3, or 4; R[6] is H, —NH(CH$_2$)$_n$NH$_2$, —(CH$_2$)$_n$NH$_2$, —NH(CH$_2$)$_n$NC(=N)NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —C≡C—CH$_2$NH$_2$, —CH=CH—(CH$_2$)$_2$NC(=N)NH$_2$, —C≡C—(CH$_2$)$_2$NH$_2$, —CH=CH—CH$_2$NC(=N)NH$_2$, or —C≡C—(CH$_2$)$_2$—NC(=N)NH$_2$, where n is 2, 3, or 4; and R[7] is H, —NH(CH$_2$)$_n$NH$_2$, —(CH$_2$)$_n$NH$_2$, —NH(CH$_2$)$_n$NC(=N)NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —C≡C—CH$_2$NH$_2$, —CH=CH—(CH$_2$)$_2$NC(=N)NH$_2$, —C≡C—(CH$_2$)$_2$NH$_2$, —CH=CH—CH$_2$NC(=N)NH$_2$, or —C≡C—(CH$_2$)$_2$—NC(=N)NH$_2$, where n is 2, 3, or 4; or a pharmaceutically acceptable salt thereof.

The present invention also provides compounds of Formula III

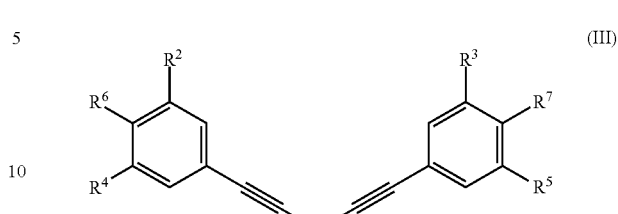

wherein: X is

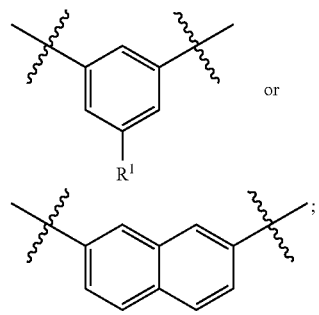

R[1] is H,

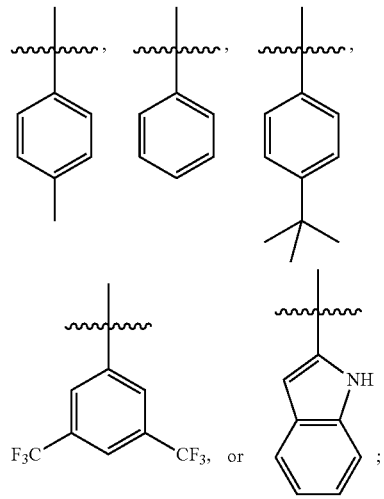

R[2] is H, —NH(CH$_2$)$_n$NH$_2$, —(CH$_2$)$_n$NH$_2$, —NH(CH$_2$)$_n$NC(=N)NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —C≡C—CH$_2$NH$_2$, —CH=CH—(CH$_2$)$_2$NC(=N)NH$_2$, —C≡C—(CH$_2$)$_2$NH$_2$, —CH=CH—CH$_2$NC(=N)NH$_2$, or —C≡C—(CH$_2$)$_2$—NC(=N)NH$_2$, where n is 2, 3, or 4; R[3] is H, —NH(CH$_2$)$_n$NH$_2$, —(CH$_2$)$_n$NH$_2$, —NH(CH$_2$)$_n$NC(=N)NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —C≡C—CH$_2$NH$_2$, —CH=CH—(CH$_2$)$_2$NC(=N)NH$_2$, —C≡C—(CH$_2$)$_2$NH$_2$, —CH=CH—CH$_2$NC(=N)NH$_2$, or —C≡C—(CH$_2$)$_2$—NC(=N)NH$_2$, where n is 2, 3, or 4; $R^4$ is H, —NH($CH_2$)$_n$$NH_2$, —($CH_2$)$_n$$NH_2$, —NH($CH_2$)$_n$NC(=N)$NH_2$, —O—($CH_2$)$_n$$NH_2$, —($CH_2$)$_n$NC(=N)$NH_2$, —O—($CH_2$)$_n$NC(=N)$NH_2$, —CH=CH—$CH_2$$NH_2$, —CH=CH—$CH_2$NC(=N)$NH_2$, —CH=CH—($CH_2$)$_2$$NH_2$, —C≡C—$CH_2$$NH_2$, —CH=CH—($CH_2$)$_2$NC(=N)$NH_2$, —C≡C—($CH_2$)$_2$$NH_2$, —CH=CH—$CH_2$NC(=N)$NH_2$, or —C≡C—($CH_2$)$_2$—NC(=N)$NH_2$, where n is 2, 3, or 4; $R^5$ is H, —NH($CH_2$)$_n$$NH_2$, —($CH_2$)$_n$$NH_2$, —NH($CH_2$)$_n$NC(=N)$NH_2$, —O—($CH_2$)$_n$$NH_2$, —($CH_2$)$_n$NC(=N)$NH_2$, —O—($CH_2$)$_n$NC(=N)$NH_2$, —CH=CH—$CH_2$$NH_2$, —CH=CH—$CH_2$NC(=N)$NH_2$, —CH=CH—($CH_2$)$_2$$NH_2$, —C≡C—$CH_2$$NH_2$, —CH=CH—($CH_2$)$_2$NC(=N)$NH_2$, —C≡C—($CH_2$)$_2$$NH_2$, —CH=CH—$CH_2$NC(=N)$NH_2$, or —C≡C—($CH_2$)$_2$—NC(=N)$NH_2$, where n is 2, 3, or 4; $R^6$ is H, —NH($CH_2$)$_n$$NH_2$, —($CH_2$)$_n$$NH_2$, —NH($CH_2$)$_n$NC(=N)$NH_2$, —O—($CH_2$)$_n$$NH_2$, —($CH_2$)$_n$NC(=N)$NH_2$, —O—($CH_2$)$_n$NC(=N)$NH_2$, —CH=CH—$CH_2$$NH_2$, —CH=CH—$CH_2$NC(=N)$NH_2$, —CH=CH—($CH_2$)$_2$$NH_2$, —C≡C—$CH_2$$NH_2$, —CH=CH—($CH_2$)$_2$NC(=N)$NH_2$, —C≡C—($CH_2$)$_2$$NH_2$, —CH=CH—$CH_2$NC(=N)$NH_2$, or —C≡C—($CH_2$)$_2$—NC(=N)$NH_2$, where n is 2, 3, or 4; and $R^7$ is H, —NH($CH_2$)$_n$$NH_2$, —($CH_2$)$_n$$NH_2$, —NH($CH_2$)$_n$NC(=N)$NH_2$, —O—($CH_2$)$_n$$NH_2$, —($CH_2$)$_n$NC(=N)$NH_2$, —O—($CH_2$)$_n$NC(=N)$NH_2$, —CH=CH—$CH_2$$NH_2$, —CH=CH—$CH_2$NC(=N)$NH_2$, —CH=CH—($CH_2$)$_2$$NH_2$, —C≡C—$CH_2$$NH_2$, —CH=CH—($CH_2$)$_2$NC(=N)$NH_2$, —C≡C—($CH_2$)$_2$$NH_2$, —CH=CH—$CH_2$NC(=N)$NH_2$, or —C≡C—($CH_2$)$_2$—NC(=N)$NH_2$, where n is 2, 3, or 4; or a pharmaceutically acceptable salt thereof.

The present invention also provides compounds of Formula IV

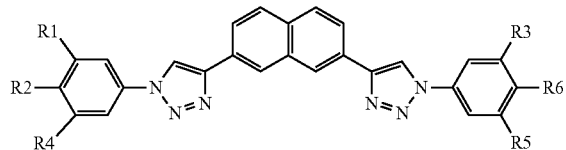

(IV)

wherein: $R^1$ is H, —NH($CH_2$)$_n$$NH_2$, —NH($CH_2$)$_n$NC(=N)$NH_2$, —($CH_2$)$_n$$NH_2$, —O—($CH_2$)$_n$$NH_2$, —($CH_2$)$_n$NC(=N)$NH_2$, —O—($CH_2$)$_n$NC(=N)$NH_2$, —CH=CH—$CH_2$$NH_2$, —CH=CH—$CH_2$NC(=N)$NH_2$, —CH=CH—($CH_2$)$_2$$NH_2$, —CH=CH—($CH_2$)$_2$NC(=N)$NH_2$, —C≡C—$CH_2$$NH_2$, —C≡C—($CH_2$)$_2$$NH_2$, —CH=CH—$CH_2$NC(=N)$NH_2$, or —C≡C—($CH_2$)$_2$—NC(=N)$NH_2$, where n is 2, 3, or 4; $R^2$ is H, —NH($CH_2$)$_n$$NH_2$, —NH($CH_2$)$_n$NC(=N)$NH_2$, —($CH_2$)$_n$$NH_2$, —O—($CH_2$)$_n$$NH_2$, —($CH_2$)$_n$NC(=N)$NH_2$, —O—($CH_2$)$_n$NC(=N)$NH_2$, —CH=CH—$CH_2$$NH_2$, —CH=CH—$CH_2$NC(=N)$NH_2$, —CH=CH—($CH_2$)$_2$$NH_2$, —CH=CH—($CH_2$)$_2$NC(=N)$NH_2$, —C≡C—$CH_2$$NH_2$, —C≡C—($CH_2$)$_2$$NH_2$, —CH=CH—$CH_2$NC(=N)$NH_2$, or —C≡C—($CH_2$)$_2$—NC(=N)$NH_2$, where n is 2, 3, or 4; $R^3$ is H, —NH($CH_2$)$_n$$NH_2$, —NH($CH_2$)$_n$NC(=N)$NH_2$, —($CH_2$)$_n$$NH_2$, —O—($CH_2$)$_n$$NH_2$, —($CH_2$)$_n$NC(=N)$NH_2$, —O—($CH_2$)$_n$NC(=N)$NH_2$, —CH=CH—$CH_2$$NH_2$, —CH=CH—$CH_2$NC(=N)$NH_2$, —CH=CH—($CH_2$)$_2$$NH_2$, —CH=CH—($CH_2$)$_2$NC(=N)$NH_2$, —C≡C—$CH_2$$NH_2$, —C≡C—($CH_2$)$_2$$NH_2$, —CH=CH—$CH_2$NC(=N)$NH_2$, or —C≡C—($CH_2$)$_2$—NC(=N)$NH_2$, where n is 2, 3, or 4; $R^4$ is H, —NH($CH_2$)$_n$$NH_2$, —NH($CH_2$)$_n$NC(=N)$NH_2$, —($CH_2$)$_n$$NH_2$, —O—($CH_2$)$_n$$NH_2$, —($CH_2$)$_n$NC(=N)$NH_2$, —O—($CH_2$)$_n$NC(=N)$NH_2$, —CH=CH—$CH_2$$NH_2$, —CH=CH—$CH_2$NC(=N)$NH_2$, —CH=CH—($CH_2$)$_2$$NH_2$, —CH=CH—($CH_2$)$_2$NC(=N)$NH_2$, —C≡C—$CH_2$$NH_2$, —C≡C—($CH_2$)$_2$$NH_2$, —CH=CH—$CH_2$NC(=N)$NH_2$, or —C≡C—($CH_2$)$_2$—NC(=N)$NH_2$, where n is 2, 3, or 4; $R^5$ is H, —NH($CH_2$)$_n$$NH_2$, —NH($CH_2$)$_n$NC(=N)$NH_2$, —($CH_2$)$_n$$NH_2$, —O—($CH_2$)$_n$$NH_2$, —($CH_2$)$_n$NC(=N)$NH_2$, —O—($CH_2$)$_n$NC(=N)$NH_2$, —CH=CH—$CH_2$$NH_2$, —CH=CH—$CH_2$NC(=N)$NH_2$, —CH=CH—($CH_2$)$_2$$NH_2$, —CH=CH—($CH_2$)$_2$NC(=N)$NH_2$, —C≡C—$CH_2$$NH_2$, —C≡C—($CH_2$)$_2$$NH_2$, —CH=CH—$CH_2$NC(=N)$NH_2$, or —C≡C—($CH_2$)$_2$—NC(=N)$NH_2$, where n is 2, 3, or 4; and $R^6$ is H, —NH($CH_2$)$_n$$NH_2$, —NH($CH_2$)$_n$NC(=N)$NH_2$, —($CH_2$)$_n$$NH_2$, —O—($CH_2$)$_n$$NH_2$, —($CH_2$)$_n$NC(=N)$NH_2$, —O—($CH_2$)$_n$NC(=N)$NH_2$, —CH=CH—$CH_2$$NH_2$, —CH=CH—$CH_2$NC(=N)$NH_2$, —CH=CH—($CH_2$)$_2$$NH_2$, —CH=CH—($CH_2$)$_2$NC(=N)$NH_2$, —C≡C—$CH_2$$NH_2$, —C≡C—($CH_2$)$_2$$NH_2$, —CH=CH—$CH_2$NC(=N)$NH_2$, or —C≡C—($CH_2$)$_2$—NC(=N)$NH_2$, where n is 2, 3, or 4; or a pharmaceutically acceptable salt thereof.

The present invention also provides compounds of Formula V

$R^1$-$A_1$-X—Z—X-$A_1$-$R^2$ (V)

or a pharmaceutically acceptable salt thereof, wherein: each X is, independently, —$NR^8$, —N($R^8$)N($R^8$)—, O, or S, wherein each $R^8$ is, independently, hydrogen or alkyl; each Z is, independently, C=O, C=S, or O=S=O; each $A_1$ is, independently, aryl optionally substituted with one or more W, or heteroaryl optionally substituted with one or more W; each W is, independently, —$CF_3$, halo, $C_{1-4}$alkyl, —O—($CH_2$)$_{1-5}$NHC(=NH)$NH_2$, —S—($CH_2$)$_{1-5}$N($CH_3$)$_2$, —N(($CH_2$)$_{1-5}$—$NH_2$)(($CH_2$)$_{1-5}$N($C_{1-4}$alkyl)$_2$), —N(($CH_2$)$_{1-5}$N($C_{1-4}$alkyl)$_2$)$_2$, heterocycle, —S—($CH_2$)$_{1-5}$NHC(=NH)$NH_2$, —S—($CH_2$)$_{1-5}$$NH_2$, —$C_{1-4}$alkyl, —S—($CH_2$)$_{1-5}$NHS(=O)$_2$—$C_{1-4}$alkyl, or O-heterocycle (wherein the heterocycle is optionally substituted with one or more cyano, amino, $C_{1-4}$alkyl, $C_{1-4}$alkoxy, guanidino, hydroxyl, amidino, or halo); and $R^1$ and $R^2$ are, independently, hydrogen, halo, —$NO_2$, —S—($CH_2$)$_{1-5}$NHC(=NH)$NH_2$, —$N^+$(=O)$O^-$, —$CF_3$, —O—($CH_2$)$_{1-5}$NHC(=NH)$NH_2$, —($CH_2$)$_{1-5}$NHC(=NH)$NH_2$, —S—($CH_2$)$_{1-5}$N($CH_3$)$_2$, amino, —NHC(=O)—($CH_2$)$_{1-5}$-aryl (wherein either or both the —($CH_2$)$_{1-5}$ or phenyl is optionally substituted), —O—($CH_2$)$_{1-5}$N($CH_3$)$_2$, —O-heterocycle (wherein the heterocycle is optionally substituted), —S-heterocycle (wherein the heterocycle is optionally substituted), —NHC(=O)—($CH_2$)$_{1-5}$NHC(=NH)$NH_2$, —NHC(=O)—($CH_2$)$_{1-5}$NHS(=O)$_2$—$C_{1-4}$alkyl, —NHC(=O)—$C_{1-4}$alkyl, —NHC(=O)—($CH_2$)$_{1-5}$NH-aryl (wherein either or both —NH and/or aryl is optionally substituted), or —NHC(=O)-aryl (wherein the aryl is optionally substituted), wherein the optional substituents are chosen from one or more cyano, amino, $C_{1-4}$alkyl, guanidino, hydroxyl, amidino, $C_{1-4}$alkoxy, $CF_3$, and halo.

The present invention also provides pharmaceutical compositions comprising any one or more of the foregoing compounds, or a pharmaceutically acceptable salt thereof, and a pharmaceutically acceptable carrier.

The present invention also provides methods of inhibiting the growth of a microbe comprising contacting the microbe with any one or more of the foregoing compounds, or pharmaceutically acceptable salt thereof.

The present invention also provides methods of treating a mammal having a microbial infection comprising administering to the mammal in need thereof an anti-microbial effective amount of any one or more of the foregoing compounds, or pharmaceutically acceptable salt thereof.

The present invention also provides methods of inhibiting the growth of a *Mycobacterium* species comprising contacting the *Mycobacterium* species with an effective amount of any one or more of the foregoing compounds, or a pharmaceutically acceptable salt thereof.

The present invention also provides methods of treating a mammal having a *Mycobacterium* infection comprising administering to the mammal in need thereof a therapeutically effective amount of any one or more of the foregoing compounds, or a pharmaceutically acceptable salt thereof.

The present invention also provides methods of treating oral mucositis in a mammal comprising administering to the mammal in need thereof a therapeutically effective amount of any one or more of the foregoing compounds, or a pharmaceutically acceptable salt thereof.

The present invention also provides methods for antagonizing unfractionated heparin, low molecular weight heparin, or a heparin/low molecular weight heparin derivative comprising administering to a mammal in need thereof any one or more of the foregoing compounds, or a pharmaceutically acceptable salt thereof.

The present invention also provides methods of inhibiting anti-Factor Xa in a mammal comprising administering to the mammal in need thereof a therapeutically effective amount of any one or more of the foregoing compounds, or a pharmaceutically acceptable salt thereof.

The present invention also provides methods of treating a microbial infection in an eye of a mammal comprising administering to one or more tissues of the eye of the mammal in need thereof an effective amount of any one or more of the foregoing compounds, or a pharmaceutically acceptable salt thereof.

The present invention also provides methods of treating a microbial infection in an ear of a mammal comprising administering to one or more tissues of the ear of the mammal in need thereof an effective amount of any one or more of the foregoing compounds, or a pharmaceutically acceptable salt thereof.

The present invention also provides methods for treating or reducing cancer, or inhibiting growth of a cancer cell, or inhibiting tumor growth, or reducing spread or metastasis of cancer in a mammal comprising administering to the mammal in need thereof an effective amount of any one or more of the foregoing compounds, or a pharmaceutically acceptable salt thereof.

The present invention also provides methods of modulating an immune response in a mammal comprising administering to the mammal in need thereof a therapeutically effective amount of any one or more of the foregoing compounds, or a pharmaceutically acceptable salt thereof.

The present invention also provides any one or more of the foregoing compounds for inhibiting anti-Factor Xa in a mammal; inhibiting the growth of a microbe; treating a mammal having a microbial infection; inhibiting the growth of a *Mycobacterium* species; treating a mammal having a *Mycobacterium* infection; treating oral mucositis in a mammal; treating a microbial infection in an ear of a mammal; treating a microbial infection in an eye of a mammal; treating or reducing cancer, or inhibiting growth of a cancer cell, or inhibiting tumor growth, or reducing spread or metastasis of cancer in a mammal; modulating an immune response in a mammal; or antagonizing unfractionated heparin, low molecular weight heparin, or a heparin/low molecular weight heparin derivative.

The present invention also provides any one or more of the foregoing compounds for use in the manufacture of a medicament for inhibiting anti-Factor Xa in a mammal; inhibiting the growth of a microbe; treating a mammal having a microbial infection; inhibiting the growth of a *Mycobacterium* species; treating a mammal having a *Mycobacterium* infection; treating oral mucositis in a mammal; treating a microbial infection in an ear of a mammal; treating a microbial infection in an eye of a mammal; treating or reducing cancer, or inhibiting growth of a cancer cell, or inhibiting tumor growth, or reducing spread or metastasis of cancer in a mammal; modulating an immune response in a mammal; or antagonizing unfractionated heparin, low molecular weight heparin, or a heparin/low molecular weight heparin derivative.

The present invention also provides uses of any one or more of the foregoing compounds for inhibiting anti-Factor Xa in a mammal; inhibiting the growth of a microbe; treating a mammal having a microbial infection; inhibiting the growth of a *Mycobacterium* species; treating a mammal having a *Mycobacterium* infection; treating oral mucositis in a mammal; treating a microbial infection in an ear of a mammal; treating a microbial infection in an eye of a mammal; treating or reducing cancer, or inhibiting growth of a cancer cell, or inhibiting tumor growth, or reducing spread or metastasis of cancer in a mammal; modulating an immune response in a mammal; or antagonizing unfractionated heparin, low molecular weight heparin, or a heparin/low molecular weight heparin derivative.

The present invention also provides uses of any one or more of the foregoing compounds in the manufacture of a medicament for inhibiting anti-Factor Xa in a mammal; inhibiting the growth of a microbe; treating a mammal having a microbial infection; inhibiting the growth of a *Mycobacterium* species; treating a mammal having a *Mycobacterium* infection; treating oral mucositis in a mammal; treating a microbial infection in an ear of a mammal; treating a microbial infection in an eye of a mammal; treating or reducing cancer, or inhibiting growth of a cancer cell, or inhibiting tumor growth, or reducing spread or metastasis of cancer in a mammal; modulating an immune response in a mammal; or antagonizing unfractionated heparin, low molecular weight heparin, or a heparin/low molecular weight heparin derivative.

DESCRIPTION OF EMBODIMENTS

Figure 1:
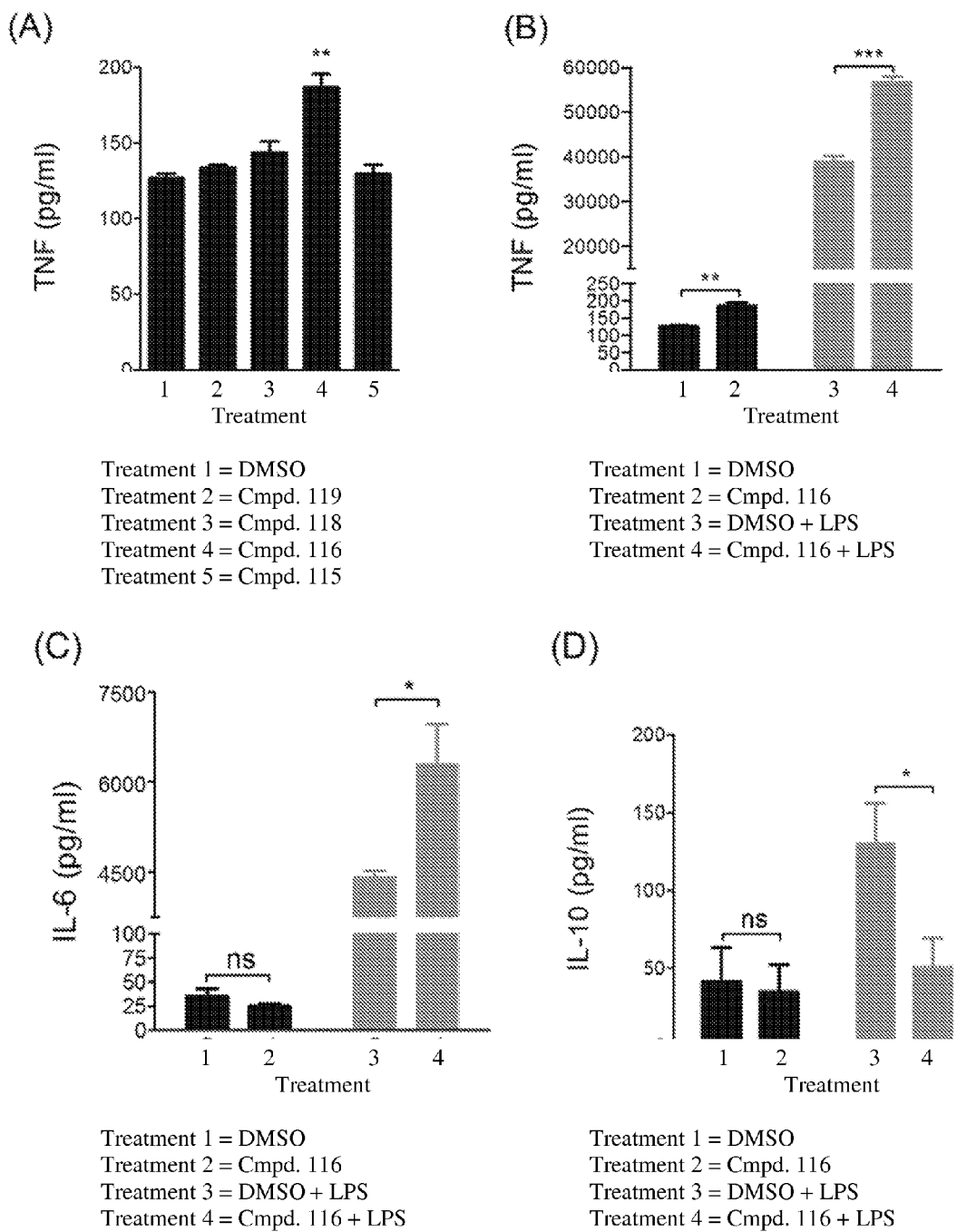
FIG. 1 shows RAW 264.7 cells preincubated with Compound (5.0 µg/mL) or 0.05% DMSO for 1 hour and stimulated with or without LPS (100 ng/mL) for 18 hours; supernatants were analyzed by ELISA for (A, B) TNF, (C) IL-6, and (D) IL-10 production; data are presented as mean±standard error of the mean (sem) for triplicate samples and are representative of three independent experiments (*, $P<0.05$; , $P<0.01$; *, $P<0.001$; ns, nonsignificant; the means were compared using Student's t test).

Unless defined otherwise, all technical and scientific terms have the same meaning as is commonly understood by one of ordinary skill in the art to which the embodiments disclosed belongs.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the term "acylamino" means an amino group substituted by an acyl group (e.g., —O—C(=O)—H or —O—C(=O)-alkyl). An example of an acylamino is —NHC(=O)H or —NHC(=O)CH$_3$. The term "lower acylamino" refers to an amino group substituted by a loweracyl group (e.g., —O—C(=O)—H or —O—C(=O)-C$_{1-6}$alkyl). An example of a lower acylamino is —NHC(=O)H or —NHC(=O)CH$_3$.

As used herein, the term "alkenyl" means a straight or branched alkyl group having one or more double carbon-carbon bonds and 2-20 carbon atoms, including, but not limited to, ethenyl, 1-propenyl, 2-propenyl, 2-methyl-1-propenyl, 1-butenyl, 2-butenyl, and the like. In some embodiments, the alkenyl chain is from 2 to 10 carbon atoms in length, from 2 to 8 carbon atoms in length, from 2 to 6 carbon atoms in length, or from 2 to 4 carbon atoms in length.

As used herein, the term "alkoxy" means a straight or branched —O-alkyl group of 1 to 20 carbon atoms, including, but not limited to, methoxy, ethoxy, n-propoxy, iso-propoxy, t-butoxy, and the like. In some embodiments, the alkoxy chain is from 1 to 10 carbon atoms in length, from 1 to 8 carbon atoms in length, from 1 to 6 carbon atoms in length, from 1 to 4 carbon atoms in length, from 2 to 10 carbon atoms in length, from 2 to 8 carbon atoms in length, from 2 to 6 carbon atoms in length, or from 2 to 4 carbon atoms in length.

As used herein, the term "alkyl" means a saturated hydrocarbon group which is straight-chained or branched. An alkyl group can contain from 1 to 20, from 2 to 20, from 1 to 10, from 2 to 10, from 1 to 8, from 2 to 8, from 1 to 6, from 2 to 6, from 1 to 4, from 2 to 4, from 1 to 3, or 2 or 3 carbon atoms. Examples of alkyl groups include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4-dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

As used herein, the term "alkylamino" means an amino group substituted by an alkyl group having from 1 to 6 carbon atoms. An example of an alkylamino is —NHCH$_2$CH$_3$.

As used herein, the term "alkylene" or "alkylenyl" means a divalent alkyl linking group. An example of an alkylene (or alkylenyl) is methylene or methylenyl (—CH$_2$—).

As used herein, the term "alkylthio" means an —S-alkyl group having from 1 to 6 carbon atoms. An example of an alkylthio group is —SCH$_2$CH$_3$.

As used herein, the term "alkynyl" means a straight or branched alkyl group having one or more triple carbon-carbon bonds and 2-20 carbon atoms, including, but not limited to, acetylene, 1-propylene, 2-propylene, and the like. In some embodiments, the alkynyl chain is 2 to 10 carbon atoms in length, from 2 to 8 carbon atoms in length, from 2 to 6 carbon atoms in length, or from 2 to 4 carbon atoms in length.

As used herein, the term "amidino" means —C(=NH)NH$_2$.

As used herein, the term "amino" means —NH$_2$.

As used herein, the term "aminoalkoxy" means an alkoxy group substituted by an amino group. An example of an aminoalkoxy is —OCH$_2$CH$_2$NH$_2$.

As used herein, the term "aminoalkyl" means an alkyl group substituted by an amino group. An example of an aminoalkyl is —CH$_2$CH$_2$NH$_2$.

As used herein, the term "aminosulfonyl" means —S(=O)$_2$NH$_2$.

As used herein, the term "aminoalkylthio" means an alkylthio group substituted by an amino group. An example of an aminoalkylthio is —SCH$_2$CH$_2$NH$_2$.

As used herein, the term "amphiphilic" means a three-dimensional structure having discrete hydrophobic and hydrophilic regions. An amphiphilic compound suitably has the presence of both hydrophobic and hydrophilic elements.

As used herein, the term "animal" includes, but is not limited to, humans and non-human vertebrates such as wild, domestic, and farm animals.

As used herein, the term "antagonize" or "antagonizing" means reducing or completely eliminating an effect, such as the anticoagulant effect of heparin.

As used herein, the phrase "anti-microbial effective amount" of a compound can be measured by the anti-microbial effectiveness of the compound. In some embodiments, an anti-microbial effective amount inhibits growth of a particular microbe by at least 10%, by at least 20%, by at least 30%, by at least 40%, by at least 50%, by at least 60%, by at least 70%, by at least 80%, by at least 90%, or by at least 95%. In some embodiments, an "anti-microbial effective amount" is also a "therapeutically effective amount" whereby the compound reduces or eliminates at least one harmful effect of a microbe on a mammal.

As used herein, the term "anti-TB" means that the compound inhibits, prevents, or destroys the growth or proliferation of a tuberculosis-causing organism, such as a *Mycobacterium* species.

As used herein, the term "aryl" means a monocyclic, bicyclic, or polycyclic (e.g., having 2, 3 or 4 fused rings) aromatic hydrocarbons. In some embodiments, aryl groups have from 6 to 20 carbon atoms or from 6 to 10 carbon atoms. Examples of aryl groups include, but are not limited to, phenyl, naphthyl, anthracenyl, phenanthrenyl, indanyl, indenyl, tetrahydronaphthyl, and the like.

As used herein, the term "arylalkyl" means a C$_{1-6}$alkyl substituted by aryl.

As used herein, the term "arylamino" means an amino group substituted by an aryl group. An example of an arylamino is —NH(phenyl).

As used herein, the term "arylene" means an aryl linking group, i.e., an aryl group that links one group to another group in a molecule.

As used herein, the term "cancer" means a spectrum of pathological symptoms associated with the initiation or progression, as well as metastasis, of malignant tumors.

As used herein, the term "carbamoyl" means —C(=O)—NH$_2$.

As used herein, the term "carbocycle" means a 5- or 6-membered, saturated or unsaturated cyclic ring, optionally containing O, S, or N atoms as part of the ring. Examples of carbocycles include, but are not limited to, cyclopentyl, cyclohexyl, cyclopenta-1,3-diene, phenyl, and any of the heterocycles recited above.

As used herein, the term "carrier" means a diluent, adjuvant, or excipient with which a compound is administered. Pharmaceutical carriers can be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used.

As used herein, the term "chemically nonequivalent termini" means a functional group such as an ester, amide, sufonamide, or N-hydroxyoxime that, when reversing the orientation of the functional group (e.g., —(C=O)O—) produces different chemical entities (e.g., —R$^1$C(=O)OR$^2$— vs. —R$^1$OC(=O)R$^2$—).

As used herein, the term, "compound" means all stereoisomers, tautomers, and isotopes of the compounds described herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "contacting" means bringing together of two elements in an in vitro system or an in vivo system. For example, "contacting" a heparin or LMWH with a compound includes the administration of a compound to an individual or patient, such as a human, having been administered a heparin, as well as, for example, introducing a compound into a sample containing a cellular or purified preparation containing the heparin, or before an individual has been administered a heparin.

As used herein, the term "cyano" means —CN.

As used herein, the term "cycloalkyl" means non-aromatic cyclic hydrocarbons including cyclized alkyl, alkenyl, and alkynyl groups that contain up to 20 ring-forming carbon atoms. Cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain from 3 to 15, from 3 to 10, from 3 to 8, from 3 to 6, from 4 to 6, from 3 to 5, or 5 or 6 ring-forming carbon atoms. Ring-forming carbon atoms of a cycloalkyl group can be optionally substituted by oxo or sulfido. Examples of cycloalkyl groups include, but are not limited to, cyclopropyl, cyclobutyl, cyclopentyl, cyclohexyl, cycloheptyl, cyclooctyl, cyclononyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (having a bond in common with) to the cycloalkyl ring, for example, benzo or thienyl derivatives of pentane, pentene, hexane, and the like (e.g., 2,3-dihydro-1H-indene-1-yl, or 1H-inden-2(3H)-one-1-yl).

As used herein, the term "cycloalkylalkyl" means a $C_{1-6}$alkyl substituted by cycloalkyl.

As used herein, the term "dialkylamino" means an amino group substituted by two alkyl groups, each having from 1 to 6 carbon atoms.

As used herein, the term "diazamino" means —N(NH$_2$)$_2$.

As used herein, the term "facially amphiphilic" or "facial amphiphilicity" means compounds with polar (hydrophilic) and nonpolar (hydrophobic) side chains that adopt conformation(s) leading to segregation of polar and nonpolar side chains to opposite faces or separate regions of the structure or molecule.

As used herein, the phrase "groups with chemically nonequivalent termini" means functional groups such as esters amides, sulfonamides and N-hydroxyoximes where reversing the orientation of the substituents, e.g. R$^1$C(=O)OR$^2$ vs. R$^1$O(O=)CR$^2$, produces unique chemical entities.

As used herein, the term "guanidino" means —NH(=NH)NH$_2$.

As used herein, the term "halo" means halogen groups including, but not limited to fluoro, chloro, bromo, and iodo.

As used herein, the term "haloalkoxy" means an —O-haloalkyl group. An example of an haloalkoxy group is OCF$_3$.

As used herein, the term "haloalkyl" means a $C_{1-6}$alkyl group having one or more halogen substituents. Examples of haloalkyl groups include, but are not limited to, CF$_3$, C$_2$F$_5$, CHF$_2$, CC$_3$, CHCl$_2$, C$_2$Cl$_5$, CH$_2$CF$_3$, and the like.

As used herein, the term "heparin" means naturally occurring unfractionated heparin and low molecular weight heparin, which can be used as an anticoagulant in diseases that feature thrombosis, as well as for prophylaxis in situations that lead to a high risk of thrombosis. The term "heparin" further includes anticoagulant agents that are derivatives of unfractionated heparin and/or LMWH, for example, by chemical modification or through enzymatic process. Examples of such heparin derivatives (for example, chemically modified unfractionated heparin and/or LMWH; or pentasaccharide) include fondaparinux. Examples of LMWH include, but are limited to, enoxaparin, reviparin, and tinzaparin.

As used herein, the term "heteroaryl" means an aromatic heterocycle having up to 20 ring-forming atoms (e.g., C) and having at least one heteroatom ring member (ring-forming atom) such as sulfur, oxygen, or nitrogen. In some embodiments, the heteroaryl group has at least one or more heteroatom ring-forming atoms, each of which are, independently, sulfur, oxygen, or nitrogen. In some embodiments, the heteroaryl group has from 3 to 20 ring-forming atoms, from 3 to 10 ring-forming atoms, from 3 to 6 ring-forming atoms, or from 3 to 5 ring-forming atoms. In some embodiments, the heteroaryl group contains 2 to 14 carbon atoms, from 2 to 7 carbon atoms, or 5 or 6 carbon atoms. In some embodiments, the heteroaryl group has 1 to 4 heteroatoms, 1 to 3 heteroatoms, or 1 or 2 heteroatoms. Heteroaryl groups include monocyclic and polycyclic (e.g., having 2, 3 or 4 fused rings) systems. Examples of heteroaryl groups include, but are not limited to, pyridyl, pyrimidinyl, pyrazinyl, pyridazinyl, triazinyl, furyl, quinolyl, isoquinolyl, thienyl, imidazolyl, thiazolyl, indolyl (such as indol-3-yl), pyrryl, oxazolyl, benzofuryl, benzothienyl, benzthiazolyl, isoxazolyl, pyrazolyl, triazolyl, tetrazolyl, indazolyl, 1,2,4- thiadiazolyl, isothiazolyl, benzothienyl, purinyl, carbazolyl, benzimidazolyl, indolinyl, pyranyl, oxadiazolyl, isoxazolyl, triazolyl, thianthrenyl, pyrazolyl, indolizinyl, isoindolyl, isobenzofuranyl, benzoxazolyl, xanthenyl, 2H-pyrrolyl, pyrrolyl, 3H-indolyl, 4H-quinolizinyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furazanyl, phenoxazinyl groups, and the like. Suitable heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

As used herein, the term "heteroarylalkyl" means a $C_{1-6}$alkyl group substituted by a heteroaryl group.

As used herein, the term "heteroarylamino" means an amino group substituted by a heteroaryl group. An example of a heteroarylamino is —NH-(2-pyridyl).

As used herein, the term "heteroarylene" means a heteroaryl linking group, i.e., a heteroaryl group that links one group to another group in a molecule.

As used herein, the term "heterocycle" or "heterocyclic ring" means a 5- to 7-membered mono- or bicyclic or 7- to 10-membered bicyclic heterocyclic ring system any ring of which may be saturated or unsaturated, and which consists of carbon atoms and from one to three heteroatoms chosen from N, O and S, and wherein the N and S heteroatoms may optionally be oxidized, and the N heteroatom may optionally be quaternized, and including any bicyclic group in which any of the above-defined heterocyclic rings is fused to a benzene ring. Particularly useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of heterocyclic groups include, but are not limited to, piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

As used herein, the term "heterocycloalkyl" means non-aromatic heterocycles having up to 20 ring-forming atoms including cyclized alkyl, alkenyl, and alkynyl groups, where one or more of the ring-forming carbon atoms is replaced by a heteroatom such as an O, N, or S atom. Hetercycloalkyl groups can be mono or polycyclic (e.g., fused, bridged, or spiro systems). In some embodiments, the heterocycloalkyl group has from 1 to 20 carbon atoms, or from 3 to 20 carbon atoms. In some embodiments, the heterocycloalkyl group contains 3 to 14 ring-forming atoms, 3 to 7 ring-forming atoms, or 5 or 6 ring-forming atoms. In some embodiments, the heterocycloalkyl group has 1 to 4 heteroatoms, 1 to 3 heteroatoms, or 1 or 2 heteroatoms. In some embodiments, the heterocycloalkyl group contains 0 to 3 double bonds. In some embodiments, the heterocycloalkyl group contains 0 to 2 triple bonds. Examples of heterocycloalkyl groups include, but are not limited to, morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, oxazolidinyl, isothiazolidinyl, pyrazolidinyl, thiazolidinyl, imidazolidinyl, pyrrolidin-2-one-3-yl, and the like. In addition, ring-forming carbon atoms and heteroatoms of a heterocycloalkyl group can be optionally substituted by oxo or sulfido. For example, a ring-forming S atom can be substituted by 1 or 2 oxo (form a S(O) or S(O)$_2$). For another example, a ring-forming C atom can be substituted by oxo (form carbonyl). Also included in the definition of heterocycloalkyl are moieties that have one or more aromatic rings fused (having a bond in common with) to the nonaromatic heterocyclic ring including, but not limited to, pyridinyl, thiophenyl, phthalimidyl, naphthalimidyl, and benzo derivatives of heterocycles such as indolene, isoindolene, 4,5,6,7-tetrahydrothieno[2,3-c]pyridine-5-yl, 5,6-dihydrothieno[2,3-c]pyridin-7(4H)-one-5-yl, isoindolin-1-one-3-yl, and 3,4-dihydroisoquinolin-1(2H)-one-3yl groups. Ring-forming carbon atoms and heteroatoms of the heterocycloalkyl group can be optionally substituted by oxo or sulfido.

As used herein, the term "heterocycloalkylalkyl" refers to a $C_{1-6}$alkyl substituted by heterocycloalkyl.

As used herein, the term "hydoxy" or "hydroxyl" means an —OH group.

As used herein, the term "hydroxyalkyl" or "hydroxylalkyl" means an alkyl group substituted by a hydroxyl group. Examples of a hydroxylalkyl include, but are not limited to, —CH$_2$OH and —CH$_2$CH$_2$OH.

As used herein, the term "individual" or "patient," used interchangeably, means any animal, including mammals, such as mice, rats, other rodents, rabbits, dogs, cats, swine, cattle, sheep, horses, or primates, such as humans.

As used herein, the phrase "inhibiting the growth" means reducing by any measurable amount the growth of one or more microbes, such as bacteria. In some embodiments, the inhibition of growth may result in cell death of the microbe.

As used herein, the phrase "in need thereof" means that the animal or mammal has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevelant.

As used herein, the phrase "in situ gettable" means embracing not only liquids of low viscosity that form gels upon contact with the eye or with lacrimal fluid in the exterior of the eye, but also more viscous liquids such as semi-fluid and thixotropic gels that exhibit substantially increased viscosity or gel stiffness upon administration to the eye.

As used herein, the phrase "integer from 1 to 5" means 1, 2, 3, 4, or 5.

As used herein, the term "isolated" means that the compounds described herein are separated from other components of either (a) a natural source, such as a plant or cell, such as a bacterial culture, or (b) a synthetic organic chemical reaction mixture, such as by conventional techniques.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the phrases "MDR-TB", "multi-drug resistant TB", and "multi-drug resistant Tuberculosis" mean TB with resistance to isoniazid and rifampicin, the two most powerful first line drugs.

As used herein, the term "microbe" means a bacteria, fungi, protozoa, or virus.

As used herein, the terms "modulate", "modulating", and "modulates" means either a decrease or increase.

As used herein, the term "nitro" means —NO$_2$.

As used herein, the term "n-membered", where n is an integer, typically describes the number of ring-forming atoms in a moiety, where the number of ring-forming atoms is n. For example, pyridine is an example of a 6-membered heteroaryl ring and thiophene is an example of a 5-membered heteroaryl ring.

As used herein, the phrase "ophthalmically acceptable" means having no persistent detrimental effect on the treated eye or the functioning thereof, or on the general health of the subject being treated. However, it will be recognized that transient effects such as minor irritation or a "stinging" sensation are common with topical ophthalmic administration of drugs and the existence of such transient effects is not inconsistent with the composition, formulation, or ingredient (e.g., excipient) in question being "ophthalmically acceptable" as herein defined.

As used used herein, the phrase "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent groups, provided that the normal valency of the designated atom or moiety is not exceeded, and that the substitution results in a stable compound. For example, if a methyl group is optionally substituted, then 3 hydrogen atoms on the carbon atom can be replaced with substituent groups.

As used herein, the phrase "otically acceptable" means having no persistent detrimental effect on the treated ear or the functioning thereof, or on the general health of the subject being treated.

As used herein, the phrase "pharmaceutically acceptable" means those compounds, materials, compositions, and/or dosage forms which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

As used herein, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfite, phosphate, acid phosphate, isonicotinate, borate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosylate, besylate, orthophoshate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. The present invention also includes quaternary ammonium salts of the compounds described herein, where the compounds have one or more tertiary amine moiety.

As used herein, the term "phenyl" means —C$_6$H$_5$. A phenyl group can be unsubstituted or substituted with one, two, or three suitable substituents.

As used herein, the terms "prevention" or "preventing" mean a reduction of the risk of acquiring a particular disease, condition, or disorder.

As used herein, the term "prodrug" means a derivative of a known direct acting drug, which derivative has enhanced delivery characteristics and therapeutic value as compared to the drug, and is transformed into the active drug by an enzymatic or chemical process.

As used herein, the term "purified" means that when isolated, the isolate contains at least 90%, at least 95%, at least 98%, or at least 99% of a compound described herein by weight of the isolate.

As used herein, the phrase "quaternary ammonium salts" means derivatives of the disclosed compounds with one or more tertiary amine moieties wherein at least one of the tertiary amine moieties in the parent compound is modified by converting the tertiary amine moiety to a quaternary ammonium cation via alkylation (and the cations are balanced by anions such as Cl$^-$, CH$_3$COO$^-$, and CF$_3$COO$^-$), for example methylation or ethylation.

As used herein, the term "semicarbazone" means =NNHC(=O)NH$_2$.

As used herein, the phrase "solubilizing agent" means agents that result in formation of a micellar solution or a true solution of the drug.

As used herein, the term "solution/suspension" means a liquid composition wherein a first portion of the active agent is present in solution and a second portion of the active agent is present in particulate form, in suspension in a liquid matrix.

As used herein, the phrase "substantially isolated" means a compound that is at least partially or substantially separated from the environment in which it is formed or detected.

As used herein, the phrase "suitable substituent" or "substituent" means a group that does not nullify the synthetic or pharmaceutical utility of the compounds described herein or the intermediates useful for preparing them. Examples of suitable substituents include, but are not limited to: C$_1$-C$_6$alkyl, C$_1$-C$_6$alkenyl, C$_1$-C$_6$alkynyl, C$_5$-C$_6$aryl, C$_1$-C$_6$alkoxy, C$_3$-C$_5$heteroaryl, C$_3$-C$_6$cycloalkyl, C$_5$-C$_6$aryloxy, —CN, —OH, oxo, halo, haloalkyl, —NO$_2$, —CO$_2$H, —NH$_2$, —NH(C$_1$-C$_8$alkyl), —N(C$_1$-C$_8$alkyl)$_2$, —NH(C$_6$aryl), —N(C$_5$-C$_6$aryl)$_2$, —CHO, —CO(C$_1$-C$_6$alkyl), —CO((C$_5$-C$_6$)aryl), —CO$_2$((C$_1$-C$_6$)alkyl), and —CO$_2$((C$_5$-C$_6$)aryl). One of skill in art can readily choose a suitable substituent based on the stability and pharmacological and synthetic activity of the compounds described herein.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

As used herein, the terms "treat," "treated," or "treating" mean both therapeutic treatment and prophylactic or preventative measures wherein the object is to prevent or slow down (lessen) an undesired physiological condition, disorder or disease, or obtain beneficial or desired clinical results. For purposes of this invention, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival as compared to expected survival if not receiving treatment. Thus, "treatment of cancer" or "treating cancer" means an activity that prevents, alleviates or ameliorates any of the primary phenomena (initiation, progression, metastasis) or secondary symptoms associated with the disease.

As used herein, the term "tumor" means a new growth of tissue in which the multiplication of cells is uncontrolled and progressive. The tumor that is particularly relevant to the invention is the malignant tumor, one in which the primary tumor has the properties of invasion or metastasis or which shows a greater degree of anaplasia than do benign tumors.

As used herein, the term "ureido" means —NHC(=O)—NH$_2$.

As used herein, the phrases "XDR-TB", "extensively drug resistant TB", and "extensively drug resistant Tuberculosis" mean MDR-TB with resistance to any one of the fluoroquinolone drugs and to at least one of the following three injectable second-line drugs: amikacin, capreomycin, or kanamycin.

At various places in the present specification, substituents of compounds may be disclosed in groups or in ranges. It is specifically intended that the invention include each and every individual subcombination of the members of such groups and ranges. For example, the term "$C_{1-6}$alkyl" is specifically intended to individually disclose methyl, ethyl, propyl, $C_4$alkyl, $C_5$alkyl, and $C_6$alkyl.

For compounds in which a variable appears more than once, each variable can be a different moiety selected from the Markush group defining the variable. For example, where a structure is described having two R groups that are simultaneously present on the same compound, the two R groups can represent different moieties selected from the Markush groups defined for R. In another example, when an optionally multiple substituent is designated in the form, for example,

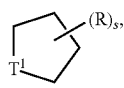

then it is understood that substituent R can occur s number of times on the ring, and R can be a different moiety at each occurrence. Further, in the above example, where the variable T$^1$ is defined to include hydrogens, such as when T$^1$ is CH$_2$, NH, etc., any H can be replaced with a substituent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

It is understood that the present invention encompasses the use, where applicable, of stereoisomers, diastereomers and optical stereoisomers of the compounds of the invention, as well as mixtures thereof. Additionally, it is understood that stereoisomers, diastereomers, and optical stereoisomers of the compounds of the invention, and mixtures thereof, are within the scope of the invention. By way of non-limiting example, the mixture may be a racemate or the mixture may comprise unequal proportions of one particular stereoisomer over the other. Additionally, the compounds can be provided as a substantially pure stereoisomers, diastereomers and optical stereoisomers (such as epimers).

The compounds described herein can be asymmetric (e.g., having one or more stereocenters). All stereoisomers, such as enantiomers and diastereomers, are intended to be included within the scope of the invention unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds are also included within the scope of the invention and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art, including, for example, fractional recrystallizaion using a chiral resolving acid which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as (3-camphorsulfonic acid. Other resolving agents suitable for fractional crystallization methods include, but are not limited to, stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds also include hydrates and solvates, as well as anhydrous and non-solvated forms.

Compounds can also include all isotopes of atoms occurring in the intermediates or final compounds. Isotopes include those atoms having the same atomic number but different mass numbers. For example, isotopes of hydrogen include tritium and deuterium.

Compounds can also include various charged states. For example, one or more moieties of any of the compounds described herein can be charged. In some instances, any moiety having an amino group can be $-NH_3^+$. Thus, each amino group existing in any compound described herein can, independently, be either $-NH_2$ or $-NH_3^+$.

In some embodiments, the compounds, or salts thereof, are substantially isolated. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

Although the disclosed compounds are suitable, other functional groups can be incorporated into the compound with an expectation of similar results. In particular, thioamides and thioesters are anticipated to have very similar properties. The distance between aromatic rings can impact the geometrical pattern of the compound and this distance can be altered by incorporating aliphatic chains of varying length, which can be optionally substituted or can comprise an amino acid, a dicarboxylic acid or a diamine. The distance between and the relative orientation of monomers within the compounds can also be altered by replacing the amide bond with a surrogate having additional atoms. Thus, replacing a carbonyl group with a dicarbonyl alters the distance between the monomers and the propensity of dicarbonyl unit to adopt an anti arrangement of the two carbonyl moiety and alter the periodicity of the compound. Pyromellitic anhydride represents still another alternative to simple amide linkages which can alter the conformation and physical properties of the compound. Modern methods of solid phase organic chemistry (E. Atherton and R. C. Sheppard, Solid Phase Peptide Synthesis A Practical Approach IRL Press Oxford 1989) now allow the synthesis of homodisperse compounds with molecular weights approaching 5,000 Daltons. Other substitution patterns are equally effective.

The compounds described herein also include derivatives referred to as prodrugs, which can be prepared by modifying functional groups present in the compounds in such a way that the modifications are cleaved, either in routine manipulation or in vivo, to the parent compounds. Examples of prodrugs include compounds as described herein that contain one or more molecular moieties appended to a hydroxyl, amino, sulfhydryl, or carboxyl group of the compound, and that when administered to a patient, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds. Preparation and use of prodrugs is discussed in T. Higuchi et al., "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference in their entireties.

Some of the compounds may be capable of adopting amphiphilic conformations that allow for the segregation of polar and nonpolar regions of the molecule into different spatial regions and provide the basis for a number of uses. For example, some compounds may adopt amphiphilic conformations that are capable of binding to heparin (including, for example, unfractionated heparin, low molecular weight heparin, and synthetically modified heparin or low molecular heparin derivatives). Although not wishing to be bound by any particular theory, it is believed that compounds can interact with heparin through electrostatic interactions.

Compounds containing an amine function can also form N-oxides. A reference herein to a compound that contains an amine function also includes the N-oxide. Where a compound contains several amine functions, one or more than one nitrogen atom can be oxidized to form an N-oxide. Examples of N-oxides include N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g., a peroxycarboxylic acid) (see, Advanced Organic Chemistry, by Jerry March, 4th Edition, Wiley Interscience).

The structures depicted herein may omit necessary hydrogen atoms to complete the appropriate valency. Thus, in some instances a carbon atom or nitrogen atom may appear to have an open valency (i.e., a carbon atom with only two bonds showing would implicitly also be bonded to two hydrogen atoms; in addition, a nitrogen atom with a single bond depicted would implicitly also be bonded to two hydrogen atoms). For example, "—N" would be considered by one skilled in the art to be "—$NH_2$." Thus, in any structure depicted herein wherein a valency is open, a hydrogen atom is implicit, and is only omitted for brevity.

The present invention provides compounds of Formula I

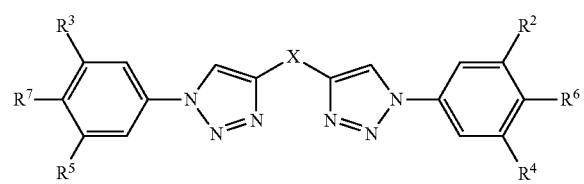

(I)

wherein:

X is

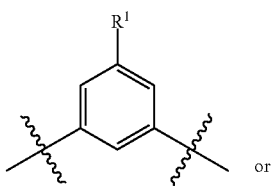

or

-continued

[naphthalene-2,7-diyl structure]

R¹ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —C≡C—CH₂NC(=N)NH₂, or —C≡C—(CH₂)₂—NC(=N)NH₂, where n is 2, 3, or 4;

R² is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —C≡C—CH₂NC(=N)NH₂, or —C≡C—(CH₂)₂—NC(=N)NH₂, where n is 2, 3, or 4;

R³ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —C≡C—CH₂NC(=N)NH₂, or —C≡C—(CH₂)₂—NC(=N)NH₂, where n is 2, 3, or 4;

R⁴ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —C≡C—CH₂NC(=N)NH₂, or —C≡C—(CH₂)₂—NC(=N)NH₂, where n is 2, 3, or 4;

R⁵ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —C≡C—CH₂NC(=N)NH₂, or —C≡C—(CH₂)₂—NC(=N)NH₂, where n is 2, 3, or 4;

R⁶ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —C≡C—CH₂NC(=N)NH₂, or —C≡C—(CH₂)₂—NC(=N)NH₂, where n is 2, 3, or 4; and R⁷ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —C≡C—CH₂NC(=N)NH₂, or —C≡C—(CH₂)₂—NC(=N)NH₂, where n is 2, 3, or 4;

or a pharmaceutically acceptable salt thereof.

In some embodiments, R¹ is H, —O—(CH₂)ₙNH₂, or —O—(CH₂)ₙNC(=N)NH₂, where n is 2, 3, or 4.

In some embodiments, R² is —O—(CH₂)ₙNH₂ or —O—(CH₂)ₙNC(=N)NH₂, where n is 2, 3, or 4.

In some embodiments, R³ is —O—(CH₂)ₙNH₂ or —O—(CH₂)ₙNC(=N)NH₂, where n is 2, 3, or 4.

In some embodiments, R⁴ is H, —O—(CH₂)ₙNH₂, or —O—(CH₂)ₙNC(=N)NH₂, where n is 2, 3, or 4.

In some embodiments, R⁵ is H, —O—(CH₂)ₙNH₂, or —O—(CH₂)ₙNC(=N)NH₂, where n is 2, 3, or 4.

In some embodiments, R⁶ is H, —O—(CH₂)ₙNH₂, or —O—(CH₂)ₙNC(=N)NH₂, where n is 2, 3, or 4.

In some embodiments, R⁷ is H, —O—(CH₂)ₙNH₂, or —O—(CH₂)ₙNC(=N)NH₂, where n is 2, 3, or 4.

In some embodiments, X is

[1,3,5-trisubstituted benzene with R¹ structure]

R¹ is H, —O—(CH₂)ₙNH₂, or —O—(CH₂)ₙNC(=N)NH₂, where n is 2, 3, or 4; R² is —O—(CH₂)ₙNH₂ or —O—(CH₂)ₙNC(=N)NH₂, where n is 2, 3, or 4; R³ is —O—(CH₂)ₙNH₂ or —O—(CH₂)ₙNC(=N)NH₂, where n is 2, 3, or 4; R⁴ is H, —O—(CH₂)ₙNH₂, or —O—(CH₂)ₙNC(=N)NH₂, where n is 2, 3, or 4; R⁵ is H, —O—(CH₂)ₙNH₂, or —O—(CH₂)ₙNC(=N)NH₂, where n is 2, 3, or 4; R⁶ is H, —O—(CH₂)ₙNH₂, or —O—(CH₂)ₙNC(=N)NH₂, where n is 2, 3, or 4; and R⁷ is H, —O—(CH₂)ₙNH₂, or —O—(CH₂)ₙNC(=N)NH₂, where n is 2, 3, or 4.

In some embodiments, R¹ is H, —O—(CH₂)₃NH₂, or —O—(CH₂)₃NC(=N)NH₂; R² is —O—(CH₂)₃NH₂ or —O—(CH₂)₃NC(=N)NH₂; R³ is —O—(CH₂)₃NH₂ or —O—(CH₂)₃NC(=N)NH₂; R⁴ is H, —O—(CH₂)₃NH₂, or —O—(CH₂)₃NC(=N)NH₂; R⁵ is H, —O—(CH₂)₃NH₂, or —O—(CH₂)₃NC(=N)NH₂; R⁶ is H, —O—(CH₂)₃NH₂, or —O—(CH₂)₃NC(=N)NH₂; and R⁷ is H, —O—(CH₂)₃NH₂, or —O—(CH₂)₃NC(=N)NH₂.

In some embodiments, X is

[naphthalene-2,7-diyl structure]

R² is —O—(CH₂)ₙNH₂ or —O—(CH₂)ₙNC(=N)NH₂, where n is 2, 3, or 4; R³ is —O—(CH₂)ₙNH₂ or —O—(CH₂)ₙNC(=N)NH₂, where n is 2, 3, or 4; R⁴ is H, —O—(CH₂)ₙNH₂, or —O—(CH₂)ₙNC(=N)NH₂, where n is 2, 3, or 4; R⁵ is H, —O—(CH₂)ₙNH₂, or —O—(CH₂)ₙNC(=N)NH₂, where n is 2, 3, or 4; R⁶ is H, —O—(CH₂)ₙNH₂, or —O—(CH₂)ₙNC(=N)NH₂, where n is 2, 3, or 4; and R⁷ is H, —O—(CH₂)ₙNH₂, or —O—(CH₂)ₙNC(=N)NH₂, where n is 2, 3, or 4.

In some embodiments, R² is —O—(CH₂)₃NH₂ or —O—(CH₂)₃NC(=N)NH₂; R³ is —O—(CH₂)₃NH₂ or —O—(CH₂)₃NC(=N)NH₂; R⁴ is H, —O—(CH₂)₃NH₂, or —O—(CH₂)₃NC(=N)NH₂; R⁵ is H, —O—(CH₂)₃NH₂, or —O—(CH₂)₃NC(=N)NH₂; R⁶ is H, —O—(CH₂)₃NH₂, or —O—(CH₂)₃NC(=N)NH₂; and R⁷ is H, —O—(CH₂)₃NH₂, or —O—(CH₂)₃NC(=N)NH₂.

In some embodiments, the compound of Formula I, or pharmaceutically acceptable salt thereof, is chosen from:

Compound 100
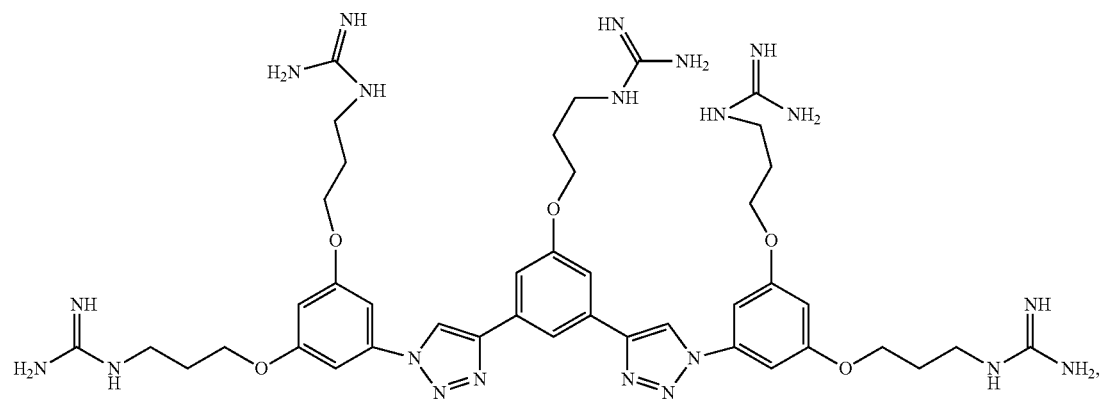
Compound 101
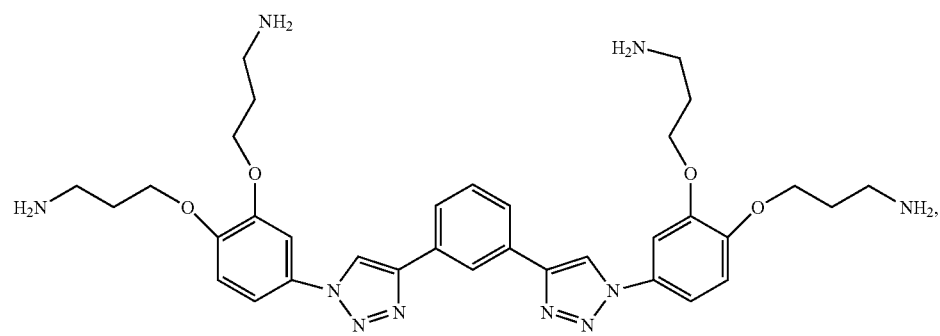
Compound 102
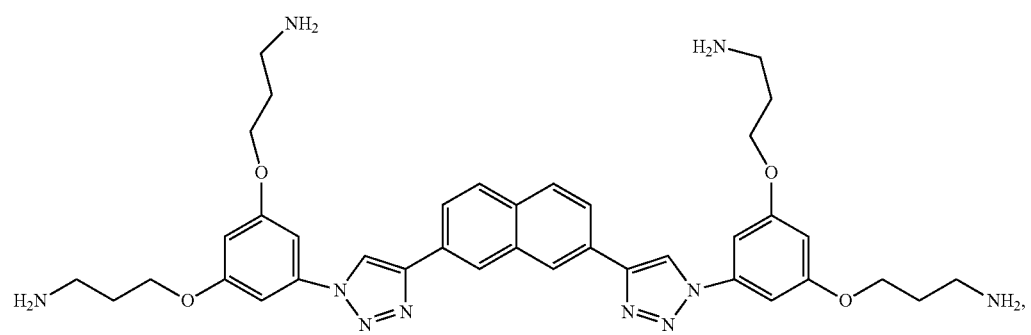
Compound 103
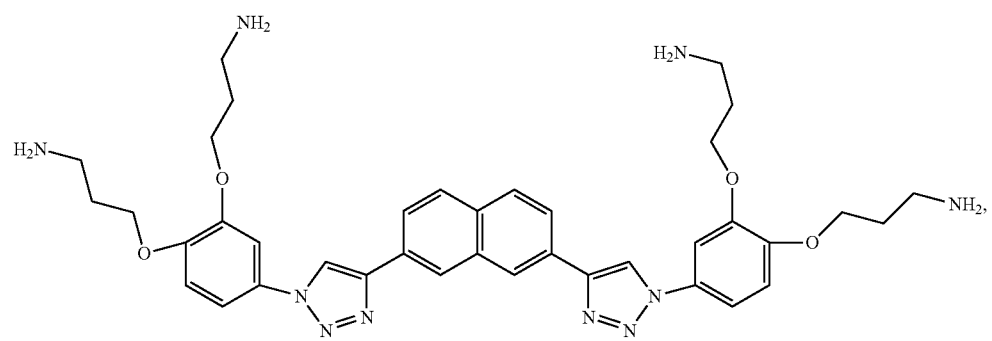

-continued
Compound 104
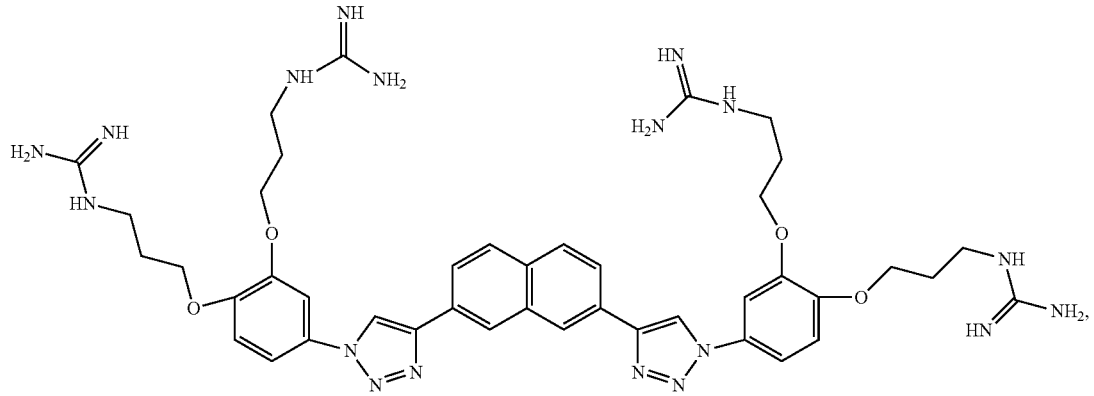
Compound 105
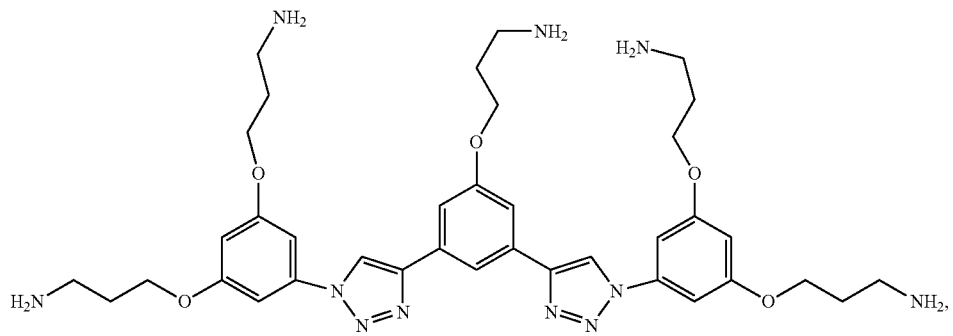
Compound 106 Compound 107
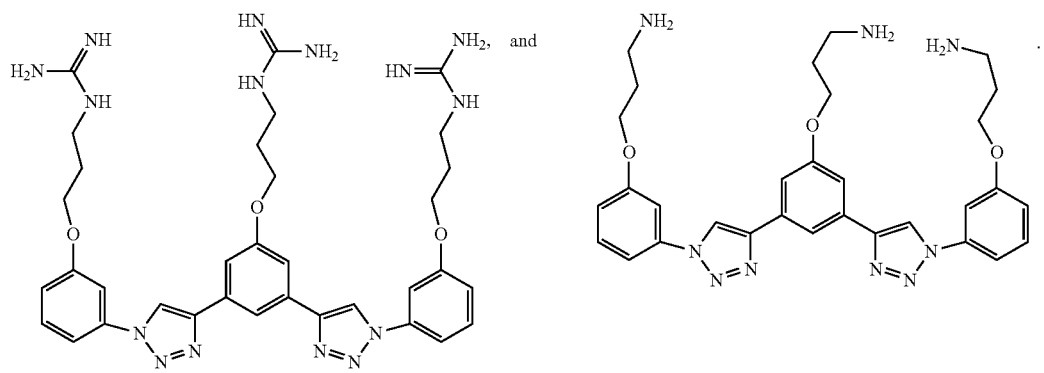
The present invention also provides compounds of Formula II
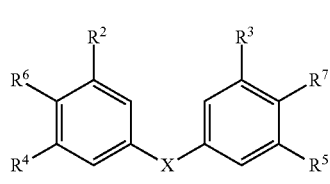
wherein:
X is
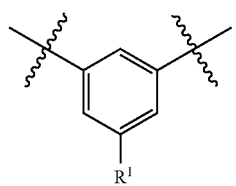
or -continued

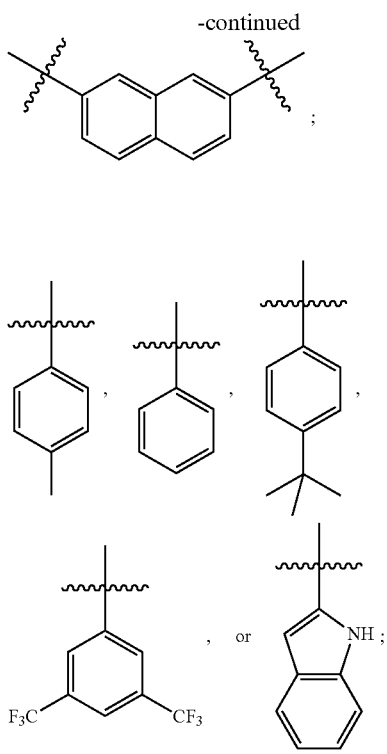

R¹ is H,
R² is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —CH≡CH—CH₂NC(=N)NH₂, or —C≡C—(CH₂)₂—NC(=N)NH₂, where n is 2, 3, or 4;

R³ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —CH≡CH—CH₂NC(=N)NH₂, or —C≡C—(CH₂)₂—NC(=N)NH₂, where n is 2, 3, or 4;

R⁴ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —CH≡CH—CH₂NC(=N)NH₂, or —C≡C—(CH₂)₂—NC(=N)NH₂, where n is 2, 3, or 4;

R⁵ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —CH≡CH—CH₂NC(=N)NH₂, or —C≡C—(CH₂)₂—NC(=N)NH₂, where n is 2, 3, or 4;

R⁶ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —CH≡CH—CH₂NC(=N)NH₂, or —C≡C—(CH₂)₂—NC(=N)NH₂, where n is 2, 3, or 4; and R⁷ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —CH≡CH—CH₂NC(=N)NH₂, or —C≡C—(CH₂)₂—NC(=N)NH₂, where n is 2, 3, or 4;

or a pharmaceutically acceptable salt thereof.

In some embodiments, R² is —O—(CH₂)ₙNH₂ or —O—(CH₂)ₙNC(=N)NH₂, where n is 2, 3, or 4.

In some embodiments, R³ is —O—(CH₂)ₙNH₂ or —O—(CH₂)ₙNC(=N)NH₂, where n is 2, 3, or 4.

In some embodiments, R⁴ is —O—(CH₂)ₙNH₂ or —O—(CH₂)ₙNC(=N)NH₂, where n is 2, 3, or 4.

In some embodiments, R⁵ is —O—(CH₂)ₙNH₂ or —O—(CH₂)ₙNC(=N)NH₂, where n is 2, 3, or 4.

In some embodiments, R⁶ is H, —O—(CH₂)ₙNH₂, or —O—(CH₂)ₙNC(=N)NH₂, where n is 2, 3, or 4.

In some embodiments, R⁷ is H, —O—(CH₂)ₙNH₂, or —O—(CH₂)ₙNC(=N)NH₂, where n is 2, 3, or 4.

In some embodiments, X is

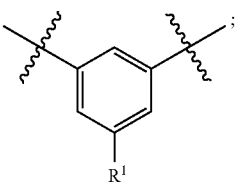

R¹ is H,

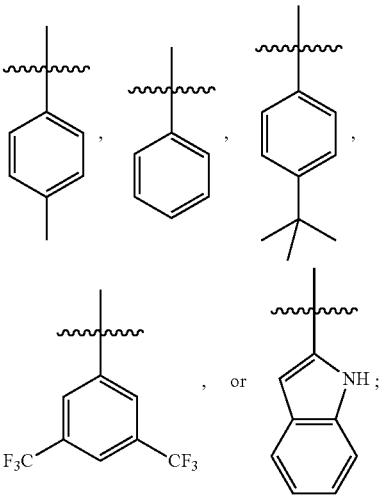

R² is H, —(CH₂)ₙNH₂, —O—(CH₂)ₙNH₂, —(CH₂)ₙNC(=N)NH₂, or —O—(CH₂)ₙNC(=N)NH₂, where n is 2, 3, or 4; R³ is H, —(CH₂)ₙNH₂, —O—(CH₂)ₙNH₂, —(CH₂)ₙNC(=N)NH₂, or —O—(CH₂)ₙNC(=N)NH₂, where n is 2, 3, or 4; R⁴ is H, —(CH₂)ₙNH₂, —O—(CH₂)ₙNH₂, —(CH₂)ₙNC(=N)NH₂, or —O—(CH₂)ₙNC(=N)NH₂, where n is 2, 3, or 4; R⁵ is H, —(CH₂)ₙNH₂, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; R$^6$ is H, —(CH$_2$)$_n$NH$_2$, —O—(CH$_2$)$_n$NH$_2$, or —O—(CH$_2$)$_n$NC(=N)NH$_2$, where n is 2, 3, or 4; and R$^7$ is H, —(CH$_2$)$_n$NH$_2$, —O—(CH$_2$)$_n$NH$_2$, or —O—(CH$_2$)$_n$NC(=N)NH$_2$, where n is 2, 3, or 4.

In some embodiments, R$^2$ is —O—(CH$_2$)$_n$NH$_2$ or —O—(CH$_2$)$_n$NC(=N)NH$_2$, where n is 2, 3, or 4; R$^3$ is —O—(CH$_2$)$_n$NH$_2$ or —O—(CH$_2$)$_n$NC(=N)NH$_2$, where n is 2, 3, or 4; R$^4$ is —O—(CH$_2$)$_n$NH$_2$ or —O—(CH$_2$)$_n$NC(=N)NH$_2$, where n is 2, 3, or 4; R$^5$ is —O—(CH$_2$)$_n$NH$_2$ or —O—(CH$_2$)$_n$NC(=N)NH$_2$, where n is 2, 3, or 4; R$^6$ is H or —O—(CH$_2$)$_n$NH$_2$, where n is 2, 3, or 4; and R$^7$ is H, or —O—(CH$_2$)$_n$NH$_2$, where n is 2, 3, or 4.

In some embodiments, X is

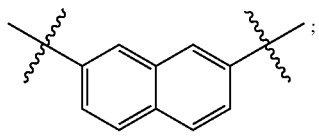 [SMILES: *c1ccc2ccc(*)cc2c1]

R$^2$ is H, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; R$^3$ is H, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; R$^4$ is H, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; R$^5$ is H, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; R$^6$ is H, —(CH$_2$)$_n$NH$_2$, —O—(CH$_2$)$_n$NH$_2$, or —O—(CH$_2$)$_n$NC(=N)NH$_2$, where n is 2, 3, or 4; and R$^7$ is H, —(CH$_2$)$_n$NH$_2$, —O—(CH$_2$)$_n$NH$_2$, or —O—(CH$_2$)$_n$NC(=N)NH$_2$, where n is 2, 3, or 4.

In some embodiments, R$^2$ is —O—(CH$_2$)$_n$NH$_2$ or —O—(CH$_2$)$_n$NC(=N)NH$_2$, where n is 2, 3, or 4; R$^3$ is —O—(CH$_2$)$_n$NH$_2$ or —O—(CH$_2$)$_n$NC(=N)NH$_2$, where n is 2, 3, or 4; R$^4$ is —O—(CH$_2$)$_n$NH$_2$ or —O—(CH$_2$)$_n$NC(=N)NH$_2$, where n is 2, 3, or 4; R$^5$ is —O—(CH$_2$)$_n$NH$_2$ or —O—(CH$_2$)$_n$NC(=N)NH$_2$, where n is 2, 3, or 4; R$^6$ is H or —O—(CH$_2$)$_n$NH$_2$, where n is 2, 3, or 4; and R$^7$ is H, or —O—(CH$_2$)$_n$NH$_2$, where n is 2, 3, or 4.

In some embodiments, the compound of Formula II, or pharmaceutically acceptable salt thereof, is chosen from:

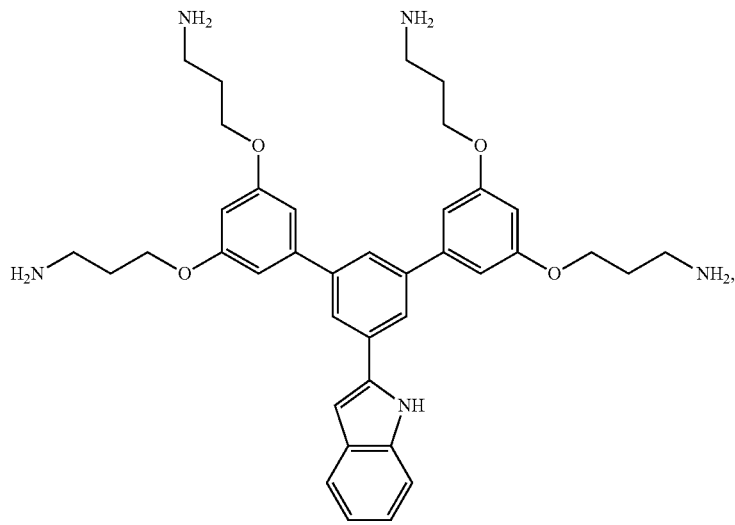

Compound 108

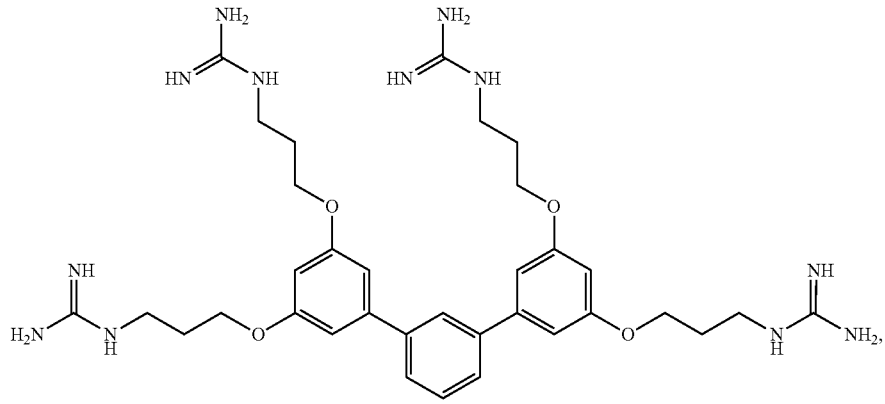

Compound 109

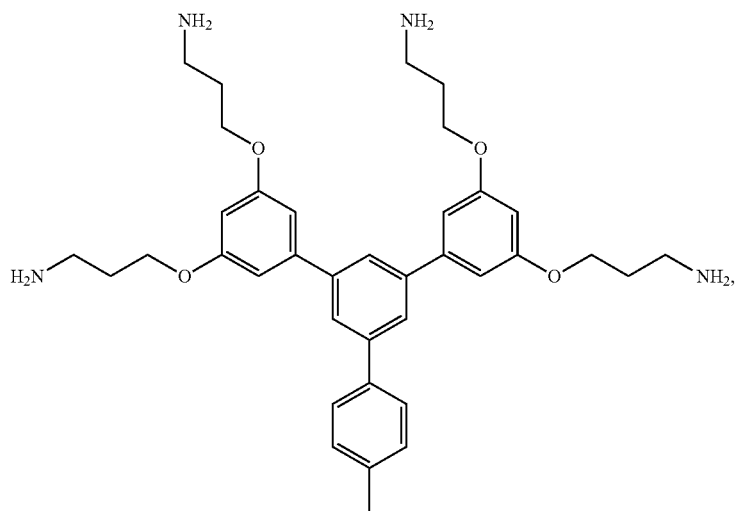
Compound 110
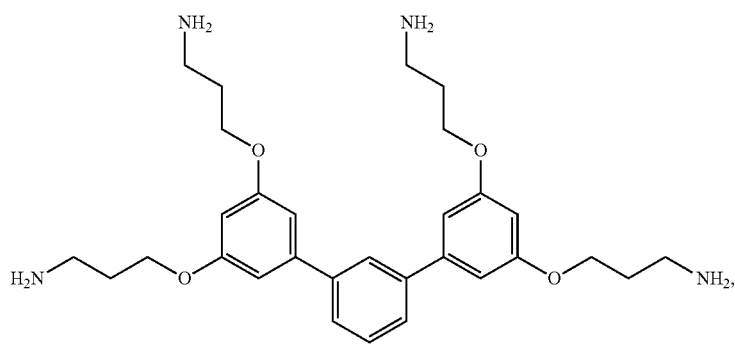
Compound 111
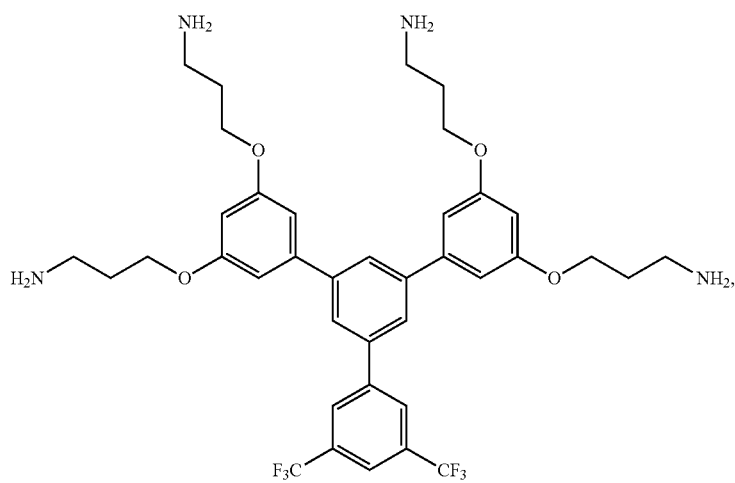
Compound 112

Compound 113
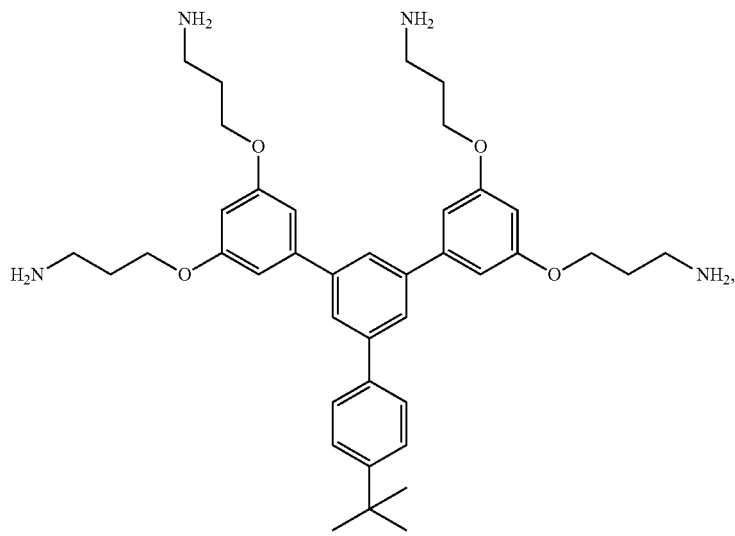
Compound 114
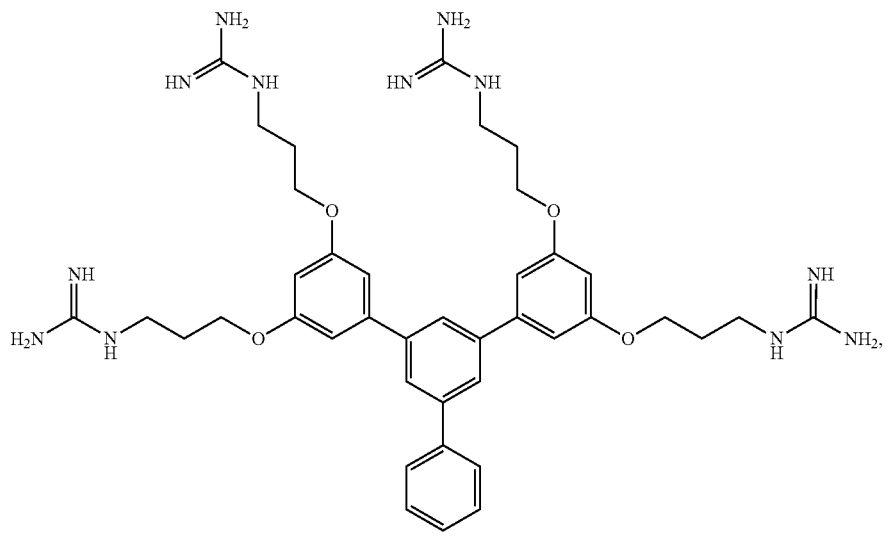
Compound 115
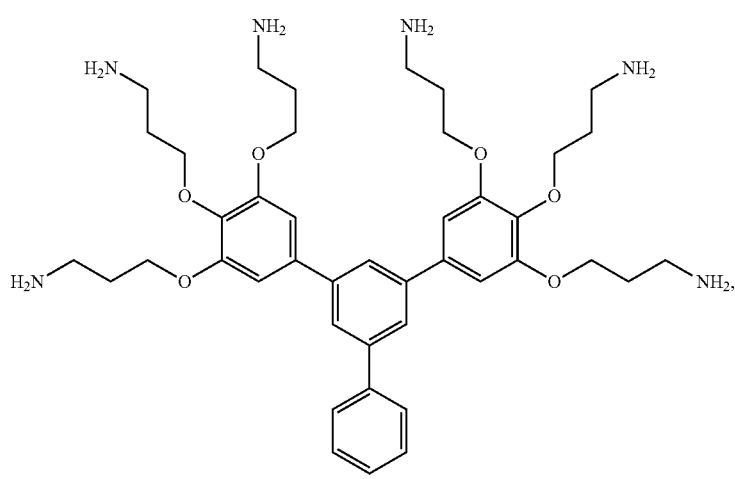

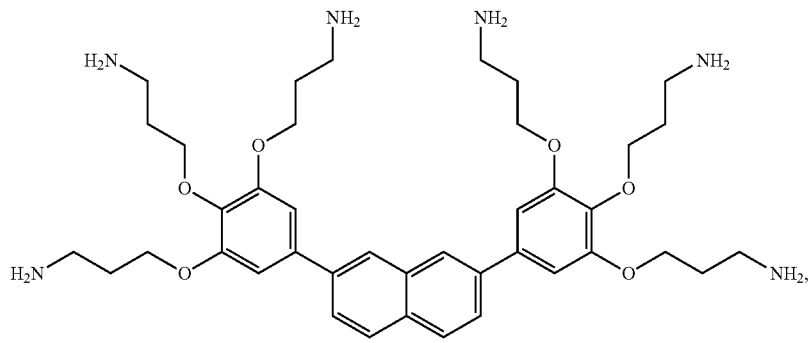
Compound 116
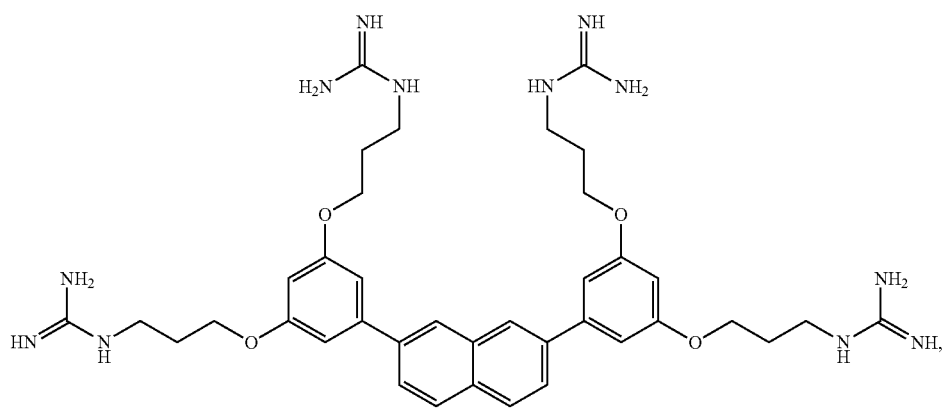
Compound 117
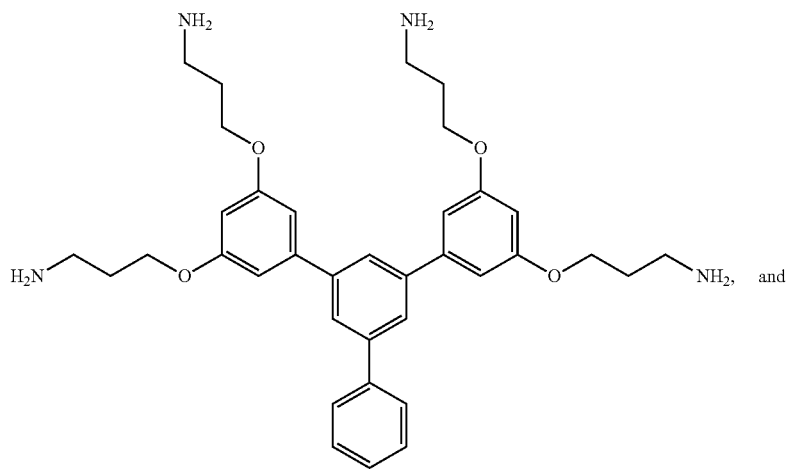
Compound 118
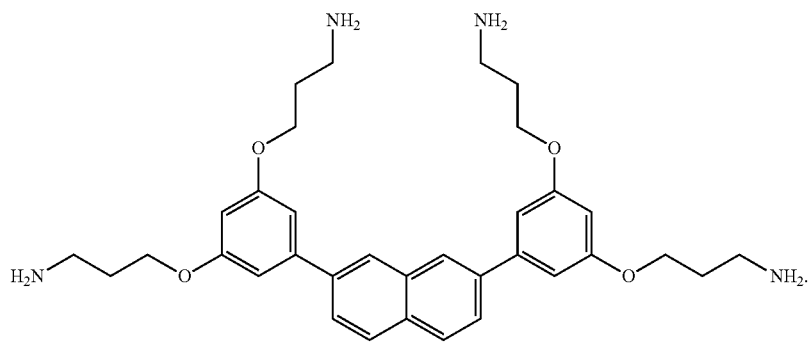
Compound 119

The present invention also provides compounds of Formula III

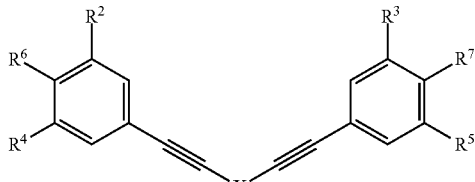

wherein:
X is

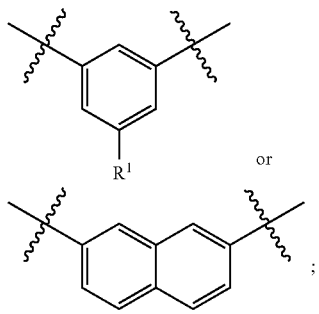

R¹ is H,

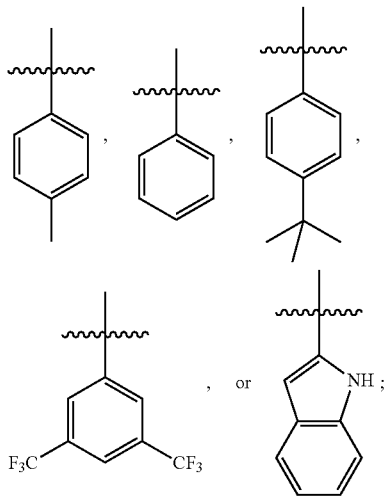

$R^2$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH≡CH—CH$_2$NC(=N)NH$_2$, or —C≡C—(CH$_2$)$_2$—NC(=N)NH$_2$, where n is 2, 3, or 4;

$R^3$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH≡CH—CH$_2$NC(=N)NH$_2$, or —C≡C—(CH$_2$)$_2$—NC(=N)NH$_2$, where n is 2, 3, or 4;

$R^4$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH≡CH—CH$_2$NC(=N)NH$_2$, or —C≡C—(CH$_2$)$_2$—NC(=N)NH$_2$, where n is 2, 3, or 4;

$R^5$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH≡CH—CH$_2$NC(=N)NH$_2$, or —C≡C—(CH$_2$)$_2$—NC(=N)NH$_2$, where n is 2, 3, or 4;

$R^6$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH≡CH—CH$_2$NC(=N)NH$_2$, or —C≡C—(CH$_2$)$_2$—NC(=N)NH$_2$, where n is 2, 3, or 4; and $R^7$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH≡CH—CH$_2$NC(=N)NH$_2$, or —C≡C—(CH$_2$)$_2$—NC(=N)NH$_2$, where n is 2, 3, or 4;

or a pharmaceutically acceptable salt thereof.

In some embodiments, X is

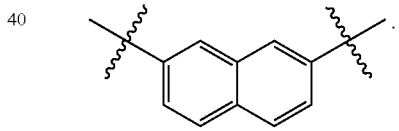

In some embodiments, $R^2$ is —O—(CH$_2$)$_n$NH$_2$ or —O—(CH$_2$)$_n$NC(=N)NH$_2$, where n is 2, 3, or 4.

In some embodiments, $R^3$ is —O—(CH$_2$)$_n$NH$_2$ or —O—(CH$_2$)$_n$NC(=N)NH$_2$, where n is 2, 3, or 4.

In some embodiments, $R^4$ is —O—(CH$_2$)$_n$NH$_2$ or —O—(CH$_2$)$_n$NC(=N)NH$_2$, where n is 2, 3, or 4.

In some embodiments, $R^5$ is —O—(CH$_2$)$_n$NH$_2$ or —O—(CH$_2$)$_n$NC(=N)NH$_2$, where n is 2, 3, or 4.

In some embodiments, $R^6$ is H, —O—(CH$_2$)$_n$NH$_2$, or —O—(CH$_2$)$_n$NC(=N)NH$_2$, where n is 2, 3, or 4.

In some embodiments, $R^7$ is H, —O—(CH$_2$)$_n$NH$_2$, or —O—(CH$_2$)$_n$NC(=N)NH$_2$, where n is 2, 3, or 4.

In some embodiments, X is

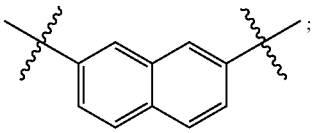 [SMILES: *c1ccc2ccc(*)cc2c1]

$R^2$ is —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4;
$R^3$ is —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4;
$R^4$ is —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4;
$R^5$ is —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4;
$R^6$ is H, —(CH$_2$)$_n$NH$_2$, —O—(CH$_2$)$_n$NH$_2$, or —O—(CH$_2$)$_n$NC(=N)NH$_2$, where n is 2, 3, or 4; and $R^7$ is H, —(CH$_2$)$_n$NH$_2$, —O—(CH$_2$)$_n$NH$_2$, or —O—(CH$_2$)$_n$NC(=N)NH$_2$, where n is 2, 3, or 4.

In some embodiments, $R^2$ is —O—(CH$_2$)$_n$NH$_2$ or —O—(CH$_2$)$_n$NC(=N)NH$_2$, where n is 2, 3, or 4; $R^3$ is —O—(CH$_2$)$_n$NH$_2$ or —O—(CH$_2$)$_n$NC(=N)NH$_2$, where n is 2, 3, or 4; $R^4$ is —O—(CH$_2$)$_n$NH$_2$ or —O—(CH$_2$)$_n$NC(=N)NH$_2$, where n is 2, 3, or 4; $R^5$ is —O—(CH$_2$)$_n$NH$_2$ or —O—(CH$_2$)$_n$NC(=N)NH$_2$, where n is 2, 3, or 4; $R^6$ is H or —O—(CH$_2$)$_n$NH$_2$, where n is 2, 3, or 4; and $R^7$ is H, or —O—(CH$_2$)$_n$NH$_2$, where n is 2, 3, or 4.

In some embodiments, the compound of Formula III, or pharmaceutically acceptable salt thereof, is:

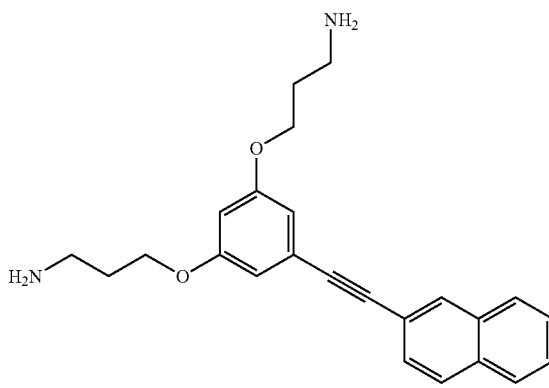

Compound 120

The present invention also provides compounds of Formula IV

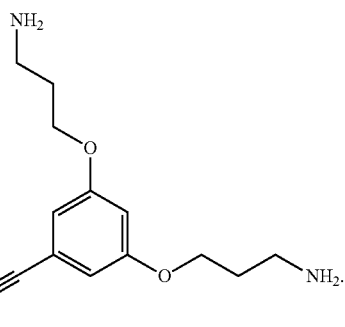

(IV)

wherein:
$R^1$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH≡CH—CH$_2$NC(=N)NH$_2$, or —C≡C—(CH$_2$)$_2$—NC(=N)NH$_2$, where n is 2, 3, or 4;

$R^2$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH≡CH—CH$_2$NC(=N)NH$_2$, or —C≡C—(CH$_2$)$_2$—NC(=N)NH$_2$, where n is 2, 3, or 4;

$R^3$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH≡CH—CH$_2$NC(=N)NH$_2$, or —C≡C—(CH$_2$)$_2$—NC(=N)NH$_2$, where n is 2, 3, or 4;

$R^4$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH≡CH—CH$_2$NC(=N)NH$_2$, or —C≡C—(CH$_2$)$_2$—NC(=N)NH$_2$, where n is 2, 3, or 4;

$R^5$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH≡CH—CH$_2$NC(=N)NH$_2$, or —C≡C—(CH$_2$)$_2$—NC(=N)NH$_2$, where n is 2, 3, or 4; and $R^6$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —CH≡CH—CH$_2$NC(=N)NH$_2$, or —C≡C—(CH$_2$)$_2$—NC(=N)NH$_2$, where n is 2, 3, or 4;

or a pharmaceutically acceptable salt thereof.

In some embodiments, $R^2$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; or $R^2$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; or $R^2$ is H, —(CH$_2$)$_n$NH$_2$, or —O—(CH$_2$)$_n$NH$_2$, where n is 2, 3, or 4; or $R^2$ is H or —(CH$_2$)$_n$NH$_2$, where n is 2, 3, or 4; or $R^2$ is H.

In any of the above embodiments, $R^4$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—

$(CH_2)_nNC(=N)NH_2$, where n is 2, 3, or 4; or $R^4$ is H, —NH$(CH_2)_nNH_2$, —$(CH_2)_nNH_2$, —O—$(CH_2)_nNH_2$, or —$(CH_2)_nNC(=N)NH_2$, where n is 2, 3, or 4; or $R^4$ is H, —$(CH_2)_nNH_2$, or —O—$(CH_2)_nNH_2$, where n is 2, 3, or 4; or $R^4$ is H or —$(CH_2)_nNH_2$, where n is 2, 3, or 4; or $R^4$ is H.

In any of the above embodiments, $R^5$ is H, —NH$(CH_2)_nNH_2$, —NH$(CH_2)_nNC(=N)NH_2$, —$(CH_2)_nNH_2$, —O—$(CH_2)_nNH_2$, —$(CH_2)_nNC(=N)NH_2$, or —O—$(CH_2)_nNC(=N)NH_2$, where n is 2, 3, or 4; or $R^5$ is H, —NH$(CH_2)_nNH_2$, —$(CH_2)_nNH_2$, —O—$(CH_2)_nNH_2$, or —$(CH_2)_nNC(=N)NH_2$, where n is 2, 3, or 4; or $R^5$ is H, —$(CH_2)_nNH_2$, or —O—$(CH_2)_nNH_2$, where n is 2, 3, or 4; or $R^5$ is H or —$(CH_2)_nNH_2$, where n is 2, 3, or 4; or $R^5$ is H.

In any of the above embodiments, $R^6$ is H, —NH$(CH_2)_nNH_2$, —NH$(CH_2)_nNC(=N)NH_2$, —$(CH_2)_nNH_2$, —O—$(CH_2)_nNH_2$, —$(CH_2)_nNC(=N)NH_2$, or —O—$(CH_2)_nNC(=N)NH_2$, where n is 2, 3, or 4; or $R^6$ is H, —NH$(CH_2)_nNH_2$, —$(CH_2)_nNH_2$, —O—$(CH_2)_nNH_2$, or —$(CH_2)_nNC(=N)NH_2$, where n is 2, 3, or 4; or $R^6$ is H, —$(CH_2)_nNH_2$, or —O—$(CH_2)_nNH_2$, where n is 2, 3, or 4; or $R^6$ is H or —$(CH_2)_nNH_2$, where n is 2, 3, or 4; or $R^6$ is H.

In any of the above embodiments, $R^1$ is H, —NH$(CH_2)_nNH_2$, —NH$(CH_2)_nNC(=N)NH_2$, —$(CH_2)_nNH_2$, —O—$(CH_2)_nNH_2$, —$(CH_2)_nNC(=N)NH_2$, or —O—$(CH_2)_nNC(=N)NH_2$, where n is 2, 3, or 4; or $R^1$ is H, —NH$(CH_2)_nNH_2$, —$(CH_2)_nNH_2$, —O—$(CH_2)_nNH_2$, or —$(CH_2)_nNC(=N)NH_2$, where n is 2, 3, or 4; or $R^1$ is —NH$(CH_2)_nNH_2$, —$(CH_2)_nNH_2$, or —O—$(CH_2)_nNH_2$, where n is 2, 3, or 4; or $R^1$ is —$(CH_2)_nNH_2$ or —O—$(CH_2)_nNH_2$, where n is 2, 3, or 4; or $R^1$ is —O—$(CH_2)_nNH_2$, where n is 2, 3, or 4.

In any of the above embodiments, $R^3$ is H, —NH$(CH_2)_nNH_2$, —NH$(CH_2)_nNC(=N)NH_2$, —$(CH_2)_nNH_2$, —O—$(CH_2)_nNH_2$, —$(CH_2)_nNC(=N)NH_2$, or —O—$(CH_2)_nNC(=N)NH_2$, where n is 2, 3, or 4; or $R^3$ is H, —NH$(CH_2)_nNH_2$, —$(CH_2)_nNH_2$, —O—$(CH_2)_nNH_2$, or —$(CH_2)_nNC(=N)NH_2$, where n is 2, 3, or 4; or $R^3$ is —NH$(CH_2)_nNH_2$, —$(CH_2)_nNH_2$, or —O—$(CH_2)_nNH_2$, where n is 2, 3, or 4; or $R^3$ is —$(CH_2)_nNH_2$ or —O—$(CH_2)_nNH_2$, where n is 2, 3, or 4; or $R^3$ is —O—$(CH_2)_nNH_2$, where n is 2, 3, or 4.

In some embodiments:
$R^2$ is H, —NH$(CH_2)_nNH_2$, —NH$(CH_2)_nNC(=N)NH_2$, —$(CH_2)_nNH_2$, —O—$(CH_2)_nNH_2$, —$(CH_2)_nNC(=N)NH_2$, or —O—$(CH_2)_nNC(=N)NH_2$, where n is 2, 3, or 4;
$R^4$ is H, —NH$(CH_2)_nNH_2$, —NH$(CH_2)_nNC(=N)NH_2$, —$(CH_2)_nNH_2$, —O—$(CH_2)_nNH_2$, —$(CH_2)_nNC(=N)NH_2$, or —O—$(CH_2)_nNC(=N)NH_2$, where n is 2, 3, or 4;
$R^5$ is H, —NH$(CH_2)_nNH_2$, —NH$(CH_2)_nNC(=N)NH_2$, —$(CH_2)_nNH_2$, —O—$(CH_2)_nNH_2$, —$(CH_2)_nNC(=N)NH_2$, or —O—$(CH_2)_nNC(=N)NH_2$, where n is 2, 3, or 4;
$R^6$ is H, —NH$(CH_2)_nNH_2$, —NH$(CH_2)_nNC(=N)NH_2$, —$(CH_2)_nNH_2$, —O—$(CH_2)_nNH_2$, —$(CH_2)_nNC(=N)NH_2$, or —O—$(CH_2)_nNC(=N)NH_2$, where n is 2, 3, or 4;
$R^1$ is H, —NH$(CH_2)_nNH_2$, —NH$(CH_2)_nNC(=N)NH_2$, —$(CH_2)_nNH_2$, —O—$(CH_2)_nNH_2$, —$(CH_2)_nNC(=N)NH_2$, or —O—$(CH_2)_nNC(=N)NH_2$, where n is 2, 3, or 4; and
$R^3$ is H, —NH$(CH_2)_nNH_2$, —NH$(CH_2)_nNC(=N)NH_2$, —$(CH_2)_nNH_2$, —O—$(CH_2)_nNH_2$, —$(CH_2)_nNC(=N)NH_2$, or —O—$(CH_2)_nNC(=N)NH_2$, where n is 2, 3, or 4.

In some embodiments:
$R^2$ is H, —NH$(CH_2)_nNH_2$, —$(CH_2)_nNH_2$, —O—$(CH_2)_nNH_2$, or —$(CH_2)_nNC(=N)NH_2$, where n is 2, 3, or 4;
$R^4$ is H, —NH$(CH_2)_nNH_2$, —$(CH_2)_nNH_2$, —O—$(CH_2)_nNH_2$, or —$(CH_2)_nNC(=N)NH_2$, where n is 2, 3, or 4;
$R^5$ is H, —NH$(CH_2)_nNH_2$, —$(CH_2)_nNH_2$, —O—$(CH_2)_nNH_2$, or —$(CH_2)_nNC(=N)NH_2$, where n is 2, 3, or 4;
$R^6$ is H, —NH$(CH_2)_nNH_2$, —$(CH_2)_nNH_2$, —O—$(CH_2)_nNH_2$, or —$(CH_2)_nNC(=N)NH_2$, where n is 2, 3, or 4;
$R^1$ is H, —NH$(CH_2)_nNH_2$, —$(CH_2)_nNH_2$, —O—$(CH_2)_nNH_2$, or —$(CH_2)_nNC(=N)NH_2$, where n is 2, 3, or 4; and
$R^3$ is H, —NH$(CH_2)_nNH_2$, —$(CH_2)_nNH_2$, —O—$(CH_2)_nNH_2$, or —$(CH_2)_nNC(=N)NH_2$, where n is 2, 3, or 4;

In some embodiments:
$R^2$ is H, —$(CH_2)_nNH_2$, or —O—$(CH_2)_nNH_2$, where n is 2, 3, or 4;
$R^4$ is H, —$(CH_2)_nNH_2$, or —O—$(CH_2)_nNH_2$, where n is 2, 3, or 4;
$R^5$ is H, —$(CH_2)_nNH_2$, or —O—$(CH_2)_nNH_2$, where n is 2, 3, or 4;
$R^6$ is H, —$(CH_2)_nNH_2$, or —O—$(CH_2)_nNH_2$, where n is 2, 3, or 4;
$R^1$ is —NH$(CH_2)_nNH_2$, —$(CH_2)_nNH_2$, or —O—$(CH_2)_nNH_2$, where n is 2, 3, or 4; and
$R^3$ is —NH$(CH_2)_nNH_2$, —$(CH_2)_nNH_2$, or —O—$(CH_2)_nNH_2$, where n is 2, 3, or 4.

In some embodiments:
$R^2$ is H or —$(CH_2)_nNH_2$, where n is 2, 3, or 4;
$R^4$ is H or —$(CH_2)_nNH_2$, where n is 2, 3, or 4;
$R^5$ is H or —$(CH_2)_nNH_2$, where n is 2, 3, or 4;
$R^6$ is H or —$(CH_2)_nNH_2$, where n is 2, 3, or 4;
$R^1$ is —$(CH_2)_nNH_2$ or —O—$(CH_2)_nNH_2$, where n is 2, 3, or 4; and
$R^3$ is —$(CH_2)_nNH_2$ or —O—$(CH_2)_nNH_2$, where n is 2, 3, or 4.

In some embodiments:
$R^2$, $R^4$, $R^5$, and $R^6$ are H;
$R^1$ is —O—$(CH_2)_nNH_2$, where n is 2, 3, or 4; and
$R^3$ is —O—$(CH_2)_nNH_2$, where n is 2, 3, or 4.

In some embodiments, the compound of Formula IV, or pharmaceutically acceptable salt thereof, is:

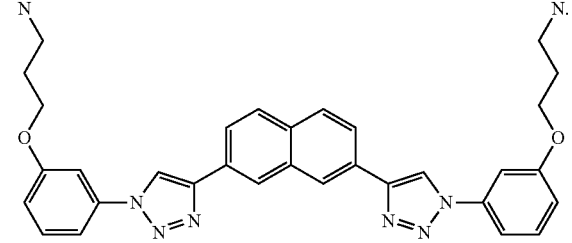

Compound 121

The present invention also provides compounds of Formula V:

$$R^1\text{-}A_1\text{-}X\text{—}Z\text{—}X\text{-}A_1\text{-}R^2 \qquad (V)$$

or a pharmaceutically acceptable salt thereof, wherein:
each X is, independently, —$NR^8$, —$N(R^8)N(R^8)$—, O, or S, wherein each $R^8$ is, independently, hydrogen or alkyl;
each Z is, independently, C=O, C=S, or O=S=O;

each $A_1$ is, independently, aryl optionally substituted with one or more W, or heteroaryl optionally substituted with one or more W;

each W is, independently, —$CF_3$, halo, $C_{1-4}$alkyl, —O—$(CH_2)_{1-5}$NHC(=NH)$NH_2$, —N$((CH_2)_{1-5}$—$NH_2)$ $((CH_2)_{1-5}$N$(C_{1-4}$alkyl$)_2)$, —N$((CH_2)_{1-5}$N$(C_{1-4}$alkyl$)_2)_2$, heterocycle, —S—$(CH_2)_{1-5}$NHC(=NH)$NH_2$, —S—$(CH_2)_{1-5}NH_2$, —S—$(CH_2)_{1-5}$N$(CH_3)_2$, —$C_{1-4}$alkyl, —S—$(CH_2)_{1-5}$NHS(=O)$_2$—$C_{1-4}$alkyl, O-heterocycle (wherein the heterocycle is optionally substituted with one or more cyano, amino, $C_{1-4}$alkyl, $C_{1-4}$alkoxy, guanidino, hydroxyl, amidino, or halo); and $R^1$ and $R^2$ are, independently, hydrogen, halo, —$NO_2$, —S—$(CH_2)_{1-5}$NHC(=NH)$NH_2$, —O—$(CH_2)_{1-5}$NHC(=NH)$NH_2$, —$CF_3$, —$N^+$(=O)$O^-$, —$(CH_2)_{1-5}$NHC(=NH)$NH_2$, amino, —S—$(CH_2)_{1-5}$N$(CH_3)_2$, —O—$(CH_2)_{1-5}$N$(CH_3)_2$, —O-heterocycle (wherein the heterocycle is optionally substituted), —S-heterocycle (wherein the heterocycle is optionally substituted), —NHC(=O)—$C_{1-4}$alkyl, —NHC(=O)—$(CH_2)_{1-5}$NHC(=NH)$NH_2$, —NHC(=O)—$(CH_2)_{1-5}$-aryl (wherein either or both the —$(CH_2)_{1-5}$ or phenyl is optionally substituted), —NHC(=O)—$(CH_2)_{1-5}$NH-aryl (wherein either or both —NH and/or aryl is optionally substituted), —NHC(=O)-aryl (wherein the aryl is optionally substituted), or —NHC(=O)—$(CH_2)_{1-5}$NHS(=O)$_2$—$C_{1-4}$alkyl, wherein the optional substituents are chosen from one or more cyano, amino, $C_{1-4}$alkyl, guanidino, hydroxyl, amidino, $C_{1-4}$alkoxy, $CF_3$, and halo.

In some embodiments, each X is, independently, —$NR^8$, O, or S, wherein each $R^8$ is, independently, hydrogen or alkyl. In some embodiments, each X is, independently, —$NR^8$, wherein each $R^8$ is, independently, hydrogen or $C_{1-4}$alkyl. In some embodiments, each X is NH.

In some embodiments, each Z is C=O.

In some embodiments, each $A_1$ is, independently, phenyl, pyridine, pyrimidine, pyrazine, or pyrazole, each optionally substituted. In some embodiments, each $A_1$ is, independently, phenyl, pyridine, pyrimidine, pyrazine, or pyrazole, each of which is substituted. In some embodiments, each $A_1$ is, independently, phenyl, pyridine, pyrimidine, or pyrazole, each of which is substituted. In some embodiments, both $A_1$ are substituted phenyl.

In some embodiments, each W is, independently, —$CF_3$, halo, $C_{1-4}$alkyl, —O—$(CH_2)_4$NHC(=NH)$NH_2$, —N$((CH_2)_2$—$NH_2)((CH_2)_2$N(Et)$_2)$, —N$((CH_2)_2$N(Et)$_2)_2$, or piperazine. In some embodiments, each W is, independently, —$CF_3$, Cl, BR, F, —C$(CH_3)_3$, —O—$(CH_2)_4$NHC(=NH)$NH_2$, —N$((CH_2)_2$—$NH_2)((CH_2)_2$N(Et)$_2)$, —N$((CH_2)_2$N(Et)$_2)_2$, or piperazine.

In some embodiments, $R^1$ and $R^2$ are, independently, hydrogen, Cl, F, —$NO_2$, —S—$(CH_2)_2$NHC(=NH)$NH_2$, —O—$(CH_2)_4$NHC(=NH)$NH_2$, —$CF_3$, or —$N^+$(=O)$O^-$.

In some embodiments: each X is NH; each Z is C=O; each $A_1$ is, independently, substituted phenyl; $R^1$ and $R^2$ are, independently, hydrogen, halo, —$NO_2$, —$N^+$(=O)$O^-$, —$CF_3$, —S—$(CH_2)_{1-5}$NHC(=NH)$NH_2$, or —O—$(CH_2)_{1-5}$NHC(=NH)$NH_2$; and each W is, independently, —$CF_3$, halo, $C_{1-4}$alkyl, —O—$(CH_2)_{1-5}$NHC(=NH)$NH_2$, —N$((CH_2)_{1-5}$—$NH_2)((CH_2)_{15}$N$(C_{1-4}$alkyl$)_2)$, —N$((CH_2)_{1-5}$N$(C_{1-4}$alkyl$)_2)_2$, or heterocycle.

In some embodiments: each X is NH; each Z is C=O; each $A_1$ is substituted phenyl; $R^1$ and $R^2$ are, independently, hydrogen, Cl, F, —$NO_2$, —S—$(CH_2)_2$NHC(=NH)$NH_2$, —$CF_3$, —$N^+$(=O)$O^-$, or —O—$(CH_2)_4$NHC(=NH)$NH_2$; and each W is, independently, —$CF_3$, Cl, —C$(CH_3)_3$, —O—$(CH_2)_4$NHC(=NH)$NH_2$, —N$((CH_2)_2$—$NH_2)$ $((CH_2)_2$N(Et)$_2)$, —N$((CH_2)_2$N(Et)$_2)_2$, or piperazine.

In some embodiments, the compound of Formula V, or pharmaceutically acceptable salt thereof, is chosen from:

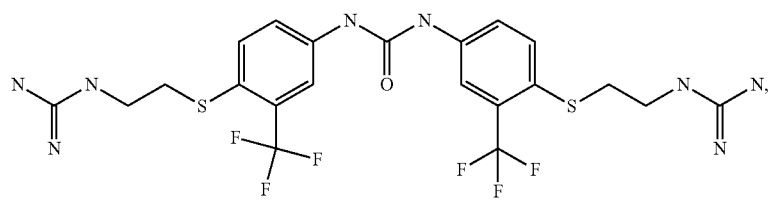

Compound 122

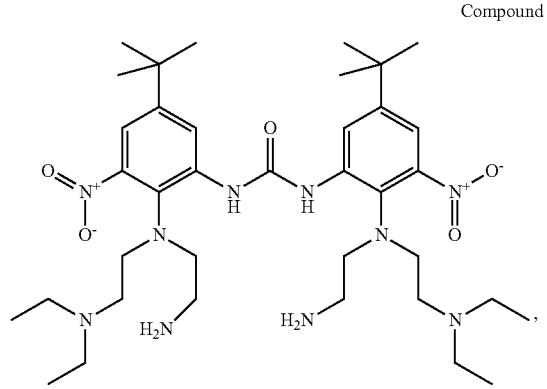

Compound 123

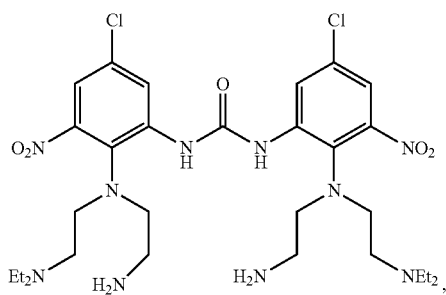

Compound 124

-continued
Compound 125
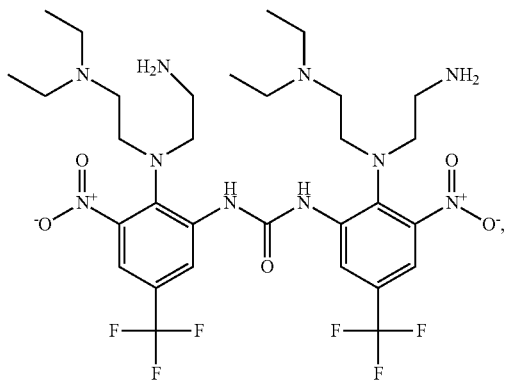
Compound 126
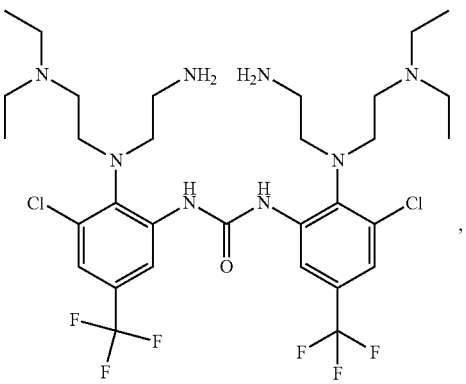
Compound 127
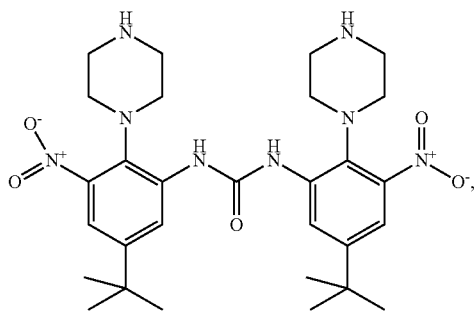
Compound 128
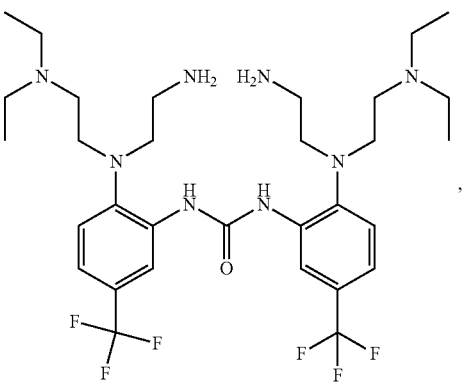
Compound 129
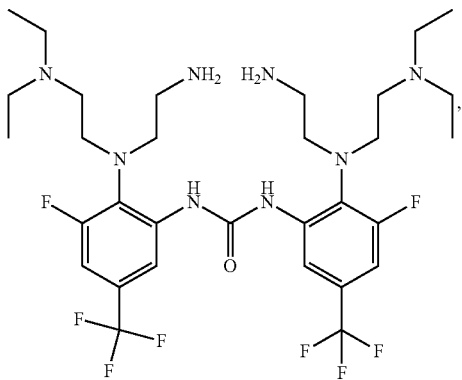
Compound 130
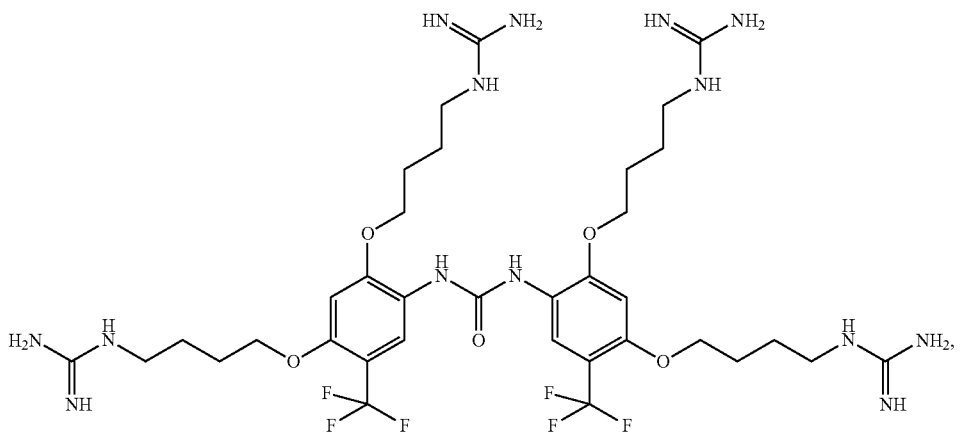

Compound 131

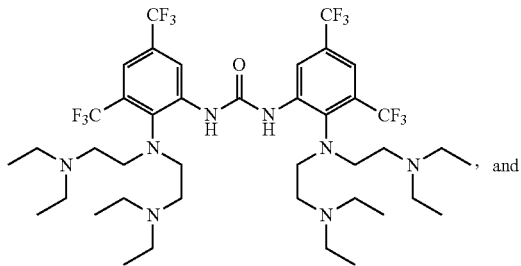

, and

Compound 132

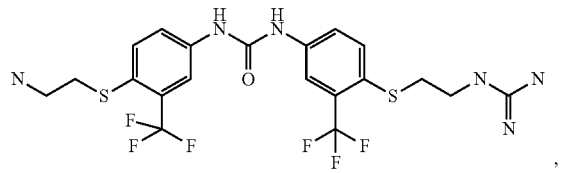

, or a pharmaceutically acceptable salt thereof.

Polyamides and polyesters that are useful for the present invention can be prepared by typical condensation polymerization and addition polymerization processes (see, for example, G. Odian, Principles of Polymerization, John Wiley & Sons, Third Edition (1991), and M. Steven, Polymer Chemistry, Oxford University Press (1999)). Most commonly, the polyamides are prepared by a) thermal dehydration of amine salts of carboxylic acids, b) reaction of acid chlorides with amines, and c) aminolysis of esters. Methods a) and c) are of limited use in polymerizations of aniline derivatives which are generally prepared utilizing acid chlorides. The skilled chemist, however, will recognize that there are many alternative active acylating agents, for example phosphoryl anhydrides, active esters or azides, which may replace an acid chloride and which, depending of the particular polymer being prepared, may be superior to an acid chloride. The acid chloride route is probably the most versatile and has been used extensively for the synthesis of aromatic polyamides.

Homopolymers derived from substituted aminobenzoic acid derivatives can also prepared in a stepwise fashion. A stepwise process comprises coupling an N-protected amino acid to an amine (or hydroxy group) and subsequently removing the amine-protecting group and repeating the process. These techniques have been highly refined for synthesis of specific peptides, allow for the synthesis of specific sequences, and both solid-phase and solution techniques for peptide synthesis are directly applicable to the present invention. An alternative embodiment of the present invention is the corresponding polysulfonamides that can be prepared in analogous fashion by substituting sulfonyl chlorides for carboxylic acid chlorides.

The most common method for the preparation of polyureas is the reaction of diamines with diisocyanates (see, Yamaguchi et al., Polym. Bull., 2000, 44, 247). This exothermic reaction can be carried out by solution techniques or by interfacial techniques. One skilled in organic and polymer chemistry will appreciate that the diisocyanate can be replaced with a variety of other bis-acylating agents, such as phosgene or N,N'-(diimidazolyl)carbonyl, with similar results. Polyurethanes are prepared by comparable techniques using a diisocyanate and a dialcohol or by reaction of a diamine with a bis-chloroformate.

The syntheses of compounds described herein can be carried out by routine and/or known methods such as those disclosed in, for example, U.S. Patent Application Publication Nos. 2005-0287108, 2006-0041023, U.S. Pat. No. 7,173,102, International Publication Nos. WO 2005/123660, WO 2004/082643, and WO 2006/093813, and U.S. Application Publication No. 2010-0081665, each of which is incorporated herein by reference in its entirety. Numerous pathways are available to incorporate polar and nonpolar side chains. Phenolic groups on the monomer can be alkylated. Alkylation of the commercially available phenol will be accomplished with standard Williamson ether synthesis for the non-polar side chain with ethyl bromide as the alkylating agent. Polar sidechains can be introduced with bifunctional alkylating agents such as BOC—NH(CH$_2$)$_2$Br. Alternately, the phenol group can be alkylated to install the desired polar side chain function by employing the Mitsonobu reaction with BOC—NH(CH$_2$)$_2$—OH, triphenyl phosphine, and diethyl acetylenedicarboxylate. Standard conditions for reduction of the nitro groups and hydrolysis of the ester afford the amino acid. With the aniline and benzoic acid in hand, coupling can be effected under a variety of conditions. Alternatively, the hydroxy group of the (di)nitrophenol can be converted to a leaving group and a functionality introduced under nucleophilic aromatic substitution conditions. Other potential scaffolds that can be prepared with similar sequences are methyl 2-nitro-4-hydroxybenzoate and methyl 2-hydroxy-4-nitrobenzoate.

Compounds described herein can also be synthesized by solid-phase synthetic procedures well know to those of skill in the art (see, Tew et al., Proc. Natl. Acad. Sci. USA, 2002, 99, 5110-5114; Barany et al., Int. J. Pept. Prot. Res., 1987, 30, 705-739; Solid-phase Synthesis: A Practical Guide, Kates, S. A., and Albericio, F., eds., Marcel Dekker, New York (2000); and Dorwald, F. Z., Organic Synthesis on Solid Phase: Supports, Linkers, Reactions, 2nd Ed., Wiley-VCH, Weinheim (2002)).

The compounds described herein can also be designed using computer-aided computational techniques, such as de novo design techniques, to embody the amphiphilic properties. In general, de novo design of compounds is performed by defining a three-dimensional framework of the backbone assembled from a repeating sequence of monomers using molecular dynamics and quantum force field calculations. Next, side groups are computationally grafted onto the backbone to maximize diversity and maintain drug-like properties. The best combinations of functional groups are then computationally selected to produce a cationic, amphiphilic structures. Representative compounds can be synthesized from this selected library to verify structures and test their biological activity. Novel molecular dynamic and coarse grain modeling programs have also been developed for this approach because existing force fields developed for biological molecules, such as peptides, were unreliable in these oligomer applications (see, Car et al., Phys. Rev. Lett., 1985, 55, 2471-2474; Siepmann et al., Mol. Phys., 1992, 75, 59-70; Martin et al., J. Phys. Chem., 1999, 103, 4508-4517; and Brooks et al., J. Comp. Chem., 1983, 4, 187-217). Several chemical structural series of compounds have been prepared. See, for example, International Publication No. WO 2002/100295, which is incorporated herein by reference in its entirety. The compounds described herein can be prepared in a similar manner. Molecular dynamic and coarse grain modeling programs can be used for a design approach. See, for example, U.S. Application Publication No. 2004-0107056, and U.S. Application Publication No. 2004-0102941, each of which is incorporated herein by reference in its entirety.

After verifying the suitability of the force field by comparing computed predictions of the structure and thermodynamic properties to molecules that have similar torsional patterns and for which experimental data are available, the fitted torsions can then be combined with bond stretching, bending, one-four, van der Waals, and electrostatic potentials borrowed from the CHARMM (see, Brooks et al., J. Comp. Chem., 1983, 4, 187-217) and TraPPE (Martin et al., J. Phys. Chem., 1999, 103, 4508-4517; and Wick et al., J. Phys. Chem., 2000, 104, 3093-3104) molecular dynamics force fields. To identify conformations that can adopt periodic folding patterns with polar groups and apolar groups lined up on the opposite sides, initial structures can be obtained with the Gaussian package (see, Frisch et al., Gaussian 98 (revision A.7) Gaussian Inc., Pittsburgh, Pa. 1998). Then, the parallelized plane-wave Car-Parrinello CP-MD (see, Car et al., Phys. Rev. Lett., 1985, 55, 2471-2474) program, (see, Rothlisberger et al., J. Chem. Phys., 1996, 3692-3700) can be used to obtain energies at the minimum and constrained geometries. The conformations of the compounds without side-chains can be investigated in the gas phase. Both MD and MC methods can be used to sample the conformations. The former is useful for global motions of the compound. With biasing techniques (see, Siepmann et al., Mol. Phys., 1992, 75, 59-70; Martin et al., J. Phys. Chem., 1999, 103, 4508-4517; and Vlugt et al., Mol. Phys., 1998, 94, 727-733), the latter allows efficient sampling for compounds with multiple local minimum configurations that are separated by relatively large barriers.

The potential conformations are examined for positions to attach pendant groups that will impart amphiphilic character to the secondary structure. Compounds selected from the gas phase studies with suitable backbone conformations and with side-chains at the optimal positions to introduce amphiphilicity can be further evaluated in a model interfacial system. n-hexane/water can be chosen because it is simple and cheap for calculations while it mimics well the lipid/water bilayer environment. Compound secondary structures that require inter-compound interactions can be identified by repeating the above-mentioned calculations using a periodically repeated series of unit cells of various symmetries (so called variable cell molecular dynamics or Monte Carlo technique) with or without solvent. The results of these calculations can guide the selection of candidates for synthesis.

The compounds described herein can be administered in any conventional manner by any route where they are active. Administration can be systemic, topical, or oral. For example, administration can be, but is not limited to, parenteral, subcutaneous, intravenous, intramuscular, intraperitoneal, transdermal, oral, buccal, sublingual, or ocular routes, or intravaginally, by inhalation, by depot injections, or by implants. The mode of administration can depend on the pathogen or microbe to be targeted. The selection of the specific route of administration can be selected or adjusted by the clinician according to methods known to the clinician to obtain the desired clinical response.

In some embodiments, it may be desirable to administer one or more compounds, or a pharmaceutically acceptable salt thereof, locally to an area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, wherein the implant is of a porous, non-porous, or gelatinous material, including membranes, such as sialastic membranes, or fibers.

The compounds described herein can be administered either alone or in combination (concurrently or serially) with other pharmaceuticals. For example, the compounds can be administered in combination with another anti-heparin agent, including, but not limited to, protamine molecules. The compounds can also be administered in combination with other anti-cancer or anti-neoplastic agents, or in combination with other cancer therapies other than chemotherapy, such as, for example, surgery or radiotherapy. In some embodiments, the compounds described herein can also be administered in combination with (i.e., as a combined formulation or as separate formulations) with antibiotics, such as, for example: 1) protein synthesis inhibitors including, but not limited to, amikacin, anisomycin, apramycin, azithromycin, blasticidine S, brefeldin A, butirosin, chloramphenicol, chlortetracycline, clindamycin, clotrimazole, cycloheximide, demeclocycline, dibekacin, dihydrostreptomycin, doxycycline, duramycin, emetine, erythromycin, fusidic acid, G 418, gentamicin, helvolic acid, hygromycin B, josamycin, kanamycin, kirromycin, lincomycin, meclocycline, mepartricin, midecamycin, minocycline, neomycin, netilmicin, nitrofurantoin, nourseothricin, oleandomycin, oxytetracycline, paromomycin, puromycin, rapamycin, ribostamycin, rifampicin, rifamycin, rosamicin, sisomicin, spectinomycin, spiramycin, streptomycin, tetracycline, thiamphenicol, thiostrepton, tobramycin, tunicamycin, tylosin, viomycin, and virginiamycin; 2) DNA synthesis interfering agents including, but not limited to, camptothecin, 10-deacetylbaccatin III, azacytidine, 7-aminoactinomycin D, 8-quinolinol, 9-dihydro-13-acetylbaccatin III, aclarubicin, actinomycin D, actinomycin I, actinomycin V, bafilomycin A1, bleomycin, capreomycin, chromomycin, cinoxacin, ciprofloxacin, cis-diammineplatinum(II) dichloride, coumermycin A1, L(+)-lactic acid, cytochalasin B, cytochalasin D, dacarbazine, daunorubicin, distamycin A, doxorubicin, echinomycin, enrofloxacin, etoposide, flumequine, formycin, fumagillin, ganciclovir, gliotoxin, lomefloxacin, metronidazole, mithramycin A, mitomycin C, nalidixic acid, netropsin, nitrofurantoin, nogalamycin, nonactin, novobiocin, ofloxacin, oxolinic acid, paclitaxel, phenazine, phleomycin, pipemidic acid, rebeccamycin, sinefungin, streptonigrin, streptozocin, succinylsulfathiazole, sulfadiazine, sulfadimethoxine, sulfaguanidine purum, sulfamethazine, sulfamonomethoxine, sulfanilamide, sulfaquinoxaline, sulfasalazine, sulfathiazole, trimethoprim, tubercidin, 5-azacytidine, cordycepin, and formycin A; 3) cell wall synthesis interfering agents including, but not limited to, (+)-6-aminopenicillanic acid, 7-Aminodesacetoxycephalosporanic acid, amoxicillin, ampicillin, azlocillin, bacitracin, carbenicillin, cefaclor, cefamandole, cefazolin, cefmetazole, cefoperazone, cefotaxime, cefsulodin, ceftriaxone, cephalexin, cephalosporin C, cephalothin, cephradine, cloxacillin, D-cycloserine, dicloxacillin, D-penicillamine, econazole, ethambutol, lysostaphin, moxalactam, nafcillin, nikkomycin Z, nitrofurantoin, oxacillin, penicillic, penicillin G, phenethicillin, phenoxymethylpenicillinic acid, phosphomycin, pipemidic acid, piperacillin, ristomycin, and vancomycin; 4) cell membrane permeability interfering agents (ionophores) including, but not limited to, 2-mercaptopyridine, 4-bromocalcimycin A23187, alamethicin, amphotericin B, calcimycin A23187, chlorhexidine, clotrimazole, colistin, econazole, hydrocortisone, filipin, gliotoxin, gramicidin A, gramicidin C, ionomycin, lasalocid A, lonomycin A, monensin, N-(6-aminohexyl)-5-chloro-1-naphthalenesulfonamide, narasin, nigericin, nisin, nonactin, nystatin, phenazine, pimaricin, polymyxin B, DL-penicillamine, polymyxin B, praziquantel, salinomycin, surfactin, and valinomycin; 5) enzyme inhibitors including, but not limited to, (+)-usnic acid, (±)-miconazole, (S)-(+)-camptothecin, 1-deoxymannojirimycin, 2-heptyl-4-hydroxyquinoline N-oxide, cordycepin, 1,10-phenanthroline, 6-diazo-5-oxo-L-norleucine, 8-quinolinol, antimycin, antipain, ascomycin, azaserine, bafilomycin, cerulenin, chloroquine, cinoxacin, ciprofloxacin, mevastatin, concanamycin A, concanamycin C, coumermycin A1, L(+)-lactic acid, cyclosporin A, econazole, enrofloxacin, etoposide, flumequine, formycin A, furazolidone, fusaric acid, geldanamycin, gliotoxin, gramicidin A, gramicidin C, herbimycin A, indomethacin, irgasan, lomefloxacin, mycophenolic acid, myxothiazol, N-(6-aminohexyl)-5-chloro-1-naphthalenesulfonamide, nalidixic acid, netropsin, niclosamide, nikkomycin, N-methyl-1-deoxynojirimycin, nogalamycin, nonactin, novobiocin, ofloxacin, oleandomycin, oligomycin, oxolinic acid, piericidin A, pipemidic acid, radicicol, rapamycin, rebeccamycin, sinefungin, staurosporine, stigmatellin, succinylsulfathiazole, succinylsulfathiazole, sulfadiazine, sulfadimethoxine, sulfaguanidine, sulfamethazine, sulfamonomethoxine, sulfanilamide, sulfaquinoxaline, sulfasalazine, sulfathiazole, triacsin C, trimethoprim, and vineomycin A1; and 6) membrane modifiers including, but not limited to, paracelsin.

The means and methods for administration are known in the art and an artisan can refer to various pharmacologic references for guidance (see, for example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980)).

The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). The standard dosing for protamine can be used and adjusted (i.e., increased or decreased) depending upon the factors described above. The selection of the specific dose regimen can be selected or adjusted or titrated by the clinician according to methods known to the clinician to obtain the desired clinical response.

The amount of a compound described herein that will be effective in the treatment and/or prevention of a particular disease, condition, or disorder will depend on the nature and extent of the disease, condition, or disorder, and can be determined by standard clinical techniques. In addition, in vitro or in vivo assays may optionally be employed to help identify optimal dosage ranges. The precise dose to be employed in the compositions will also depend on the route of administration, and the seriousness of the disorder, and should be decided according to the judgment of the practitioner and each patient's circumstances. However, a suitable dosage range for oral administration is, generally, from about 0.001 milligram to about 200 milligrams per kilogram body weight, from about 0.01 milligram to about 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In some embodiments, the oral dose is about 5 milligrams per kilogram body weight.

In some embodiments, suitable dosage ranges for intravenous (i.v.) administration are from about 0.01 mg to about 500 mg per kg body weight, from about 0.1 mg to about 100 mg per kg body weight, from about 1 mg to about 50 mg per kg body weight, or from about 10 mg to about 35 mg per kg body weight. Suitable dosage ranges for other modes of administration can be calculated based on the forgoing dosages as known by those skilled in the art. For example, recommended dosages for intradermal, intramuscular, intraperitoneal, subcutaneous, epidural, sublingual, intracerebral, intravaginal, transdermal administration or administration by inhalation are in the range of from about 0.001 mg to about 200 mg per kg of body weight, from about 0.01 mg to about 100 mg per kg of body weight, from about 0.1 mg to about 50 mg per kg of body weight, or from about 1 mg to about 20 mg per kg of body weight. Effective doses may be extrapolated from dose-response curves derived from in vitro or animal model test systems. Such animal models and systems are well known in the art.

The compounds described herein can be formulated for parenteral administration by injection, such as by bolus injection or continuous infusion. The compounds can be administered by continuous infusion subcutaneously over a period of about 15 minutes to about 24 hours. Formulations for injection can be presented in unit dosage form, such as in ampoules or in multi-dose containers, with an added preservative. The compositions can take such forms as suspensions, solutions or emulsions in oily or aqueous vehicles, and can contain formulatory agents such as suspending, stabilizing and/or dispersing agents. In some embodiments, the injectable is in the form of short-acting, depot, or implant and pellet forms injected subcutaneously or intramuscularly. In some embodiments, the parenteral dosage form is the form of a solution, suspension, emulsion, or dry powder.

For oral administration, the compounds described herein can be formulated by combining the compounds with pharmaceutically acceptable carriers well known in the art. Such carriers enable the compounds to be formulated as tablets, pills, dragees, capsules, emulsions, liquids, gels, syrups, caches, pellets, powders, granules, slurries, lozenges, aqueous or oily suspensions, and the like, for oral ingestion by a patient to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethylcellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds. Oral compositions can include standard vehicles such as mannitol, lactose, starch, magnesium stearate, sodium saccharine, cellulose, magnesium carbonate, etc. Such vehicles are suitably of pharmaceutical grade.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

For buccal administration, the compositions can take the form of, such as, tablets or lozenges formulated in a conventional manner.

For administration by inhalation, the compounds described herein can be delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, such as gelatin for use in an inhaler or insufflator can be formulated containing a powder mix of the compound and a suitable powder base such as lactose or starch.

The compounds described herein can also be formulated in rectal compositions such as suppositories or retention enemas, such as containing conventional suppository bases such as cocoa butter or other glycerides. The compounds described herein can also be formulated in vaginal compositions such as vaginal creams, suppositories, pessaries, vaginal rings, and intrauterine devices.

In transdermal administration, the compounds can be applied to a plaster, or can be applied by transdermal, therapeutic systems that are consequently supplied to the organism. In some embodiments, the compounds are present in creams, solutions, powders, fluid emulsions, fluid suspensions, semi-solids, ointments, pastes, gels, jellies, and foams, or in patches containing any of the same.

The compounds described herein can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In yet another embodiment, the compounds can be delivered in a controlled release system. In one embodiment, a pump may be used (see Langer, supra; Sefton, CRC Crit. Ref. Biomed. Eng., 1987, 14, 201; Buchwald et al., Surgery, 1980, 88, 507 Saudek et al., N. Engl. J. Med., 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., J. Macromol. Sci. Rev. Macromol. Chem., 1983, 23, 61; see, also Levy et al., Science, 1985, 228, 190; During et al., Ann. Neurol., 1989, 25, 351; Howard et al., J. Neurosurg., 1989, 71, 105). In yet another embodiment, a controlled-release system can be placed in proximity of the target of the compounds described herein, such as the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, Science, 1990, 249, 1527-1533) may be used.

It is also known in the art that the compounds can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In some embodiments, the compounds described herein can be used with agents including, but not limited to, topical analgesics (e.g., lidocaine), barrier devices (e.g., GelClair), or rinses (e.g., Caphosol).

In some embodiments, the compounds described herein can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

Suitable compositions include, but are not limited to, oral non-absorbed compositions. Suitable compositions also include, but are not limited to saline, water, cyclodextrin solutions, and buffered solutions of pH 3-9.

The compounds described herein, or pharmaceutically acceptable salts thereof, can be formulated with numerous excipients including, but not limited to, purified water, propylene glycol, PEG 400, glycerin, DMA, ethanol, benzyl alcohol, citric acid/sodium citrate (pH3), citric acid/sodium citrate (pH5), tris(hydroxymethyl)amino methane HCl (pH7.0), 0.9% saline, and 1.2% saline, and any combination thereof. In some embodiments, excipient is chosen from propylene glycol, purified water, and glycerin.

In some embodiments, the excipient is a multi-component system chosen from 20% w/v propylene glycol in saline, 30% w/v propylene glycol in saline, 40% w/v propylene glycol in saline, 50% w/v propylene glycol in saline, 15% w/v propylene glycol in purified water, 30% w/v propylene glycol in purified water, 50% w/v propylene glycol in purified water, 30% w/v propylene glycol and 5 w/v ethanol in purified water, 15% w/v glycerin in purified water, 30% w/v glycerin in purified water, 50% w/v glycerin in purified water, 20% w/v Kleptose in purified water, 40% w/v Kleptose in purified water, and 25% w/v Captisol in purified water. In some embodiments, the excipient is chosen from 50% w/v propylene glycol in purified water, 15% w/v glycerin in purified water, 20% w/v Kleptose in purified water, 40% w/v Kleptose in purified water, and 25% w/v Captisol in purified water. In some embodiments, the excipient is chosen from 20% w/v Kleptose in purified water, 20% w/v propylene glycol in purified water, and 15% w/v glycerin in purified water.

In some embodiments, the composition comprises 50 mg/mL of compound in 20% w/v Kleptose in purified water.

In some embodiments, the formulation can be lyophilized to a solid and reconstituted with, for example, water prior to use.

When administered to a mammal (e.g., to an animal for veterinary use or to a human for clinical use) the compounds can be administered in isolated form.

When administered to a human, the compounds can be sterile. Water is a suitable carrier when the compound of Formula I is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, capsule, capsule containing a liquid, powder, sustained-release formulation, suppository, aerosol, spray, or any other form suitable for use. Examples of suitable pharmaceutical carriers are described in Remington's Pharmaceutical Sciences, A. R. Gennaro (Editor) Mack Publishing Co.

In one embodiment, the compounds are formulated in accordance with routine procedures as a pharmaceutical composition adapted for administration to humans. Typically, compounds are solutions in sterile isotonic aqueous buffer. Where necessary, the compositions can also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound is to be administered by infusion, it can be dispensed, for example, with an infusion bottle containing sterile pharmaceutical grade water or saline. Where the compound is administered by injection, an ampoule of sterile water for injection or saline can be provided so that the ingredients may be mixed prior to administration.

The pharmaceutical compositions can be in unit dosage form. In such form, the composition can be divided into unit doses containing appropriate quantities of the active component. The unit dosage form can be a packaged preparation, the package containing discrete quantities of the preparations, for example, packeted tablets, capsules, and powders in vials or ampules. The unit dosage form can also be a capsule, cachet, or tablet itself, or it can be the appropriate number of any of these packaged forms.

The ophthalmic and otic compositions of the present invention can take the form of a liquid or solid, including, e.g., but not limited to, a solution, a suspension, an emulsion, a gel, an ointment, or a solid article that can be inserted in a suitable location in the eye or ear.

In some embodiments, a composition of the present invention is in the form of a liquid wherein the active agent (i.e., one of the facially amphiphilic polymers or oligomers disclosed herein) is present in solution, in suspension, as an emulsion, or as a solution/suspension. In some embodiments, the liquid composition is in the form of a gel. In other embodiments, the liquid composition is aqueous. In other embodiments, the composition is in the form of an ointment.

In yet other embodiments, the composition is in the form of a solid article. For example, in some embodiments, the ophthalmic composition is a solid article that can be inserted in a suitable location in the eye, such as between the eye and eyelid or in the conjunctival sac, where it releases the active agent as described, for example, U.S. Pat. No. 3,863,633; U.S. Pat. No. 3,867,519; U.S. Pat. No. 3,868,445; U.S. Pat. No. 3,960,150; U.S. Pat. No. 3,963,025; U.S. Pat. No. 4,186,184; U.S. Pat. No. 4,303,637; U.S. Pat. No. 5,443,505; and U.S. Pat. No. 5,869,079. Release from such an article is usually via the cornea, either via the lacrimal fluid that bathes the surface of the cornea, or directly to the cornea itself, with which the solid article is generally in intimate contact. Solid articles suitable for implantation in the eye in such fashion are generally composed primarily of polymers and can be bioerodible or non-bioerodible. Bioerodible polymers that can be used in the preparation of ocular implants carrying one or more of the anti-microbial, facially amphiphilic polymer or oligomer active agents in accordance with the present invention include, but are not limited to, aliphatic polyesters such as polymers and copolymers of poly(glycolide), poly(lactide), poly(epsilon-caprolactone), poly-(hydroxybutyrate) and poly(hydroxyvalerate), polyamino acids, polyorthoesters, polyanhydrides, aliphatic polycarbonates and polyether lactones. Suitable non-bioerodible polymers include silicone elastomers.

The ophthalmic and otic compositions are preferably sterile and have physical properties (e.g., osmolality and pH) that are specially suited for application to ophthalmic or otic tissues, including tissues that have been compromised as the result of preexisting disease, trauma, surgery or other physical conditions. For example, aqueous compositions of the invention typically have a pH in the range of from 4.5 to 8.0, from 6.0 to 8.0, from 6.5 to 8.0, or from 7.0 to 8.0.

Suitable ophthalmically acceptable compositions, formulations, and excipients are those that cause no substantial detrimental effect, even of a transient nature.

Suitable otically acceptable compositions, formulations, and excipients are those that cause no substantial detrimental effect, even of a transient nature.

Ophthalmically and otically acceptable excipients include, but are not limited to, viscosity-enhancing agents, preservatives, stabilizers, antioxidants, suspending agents, solubilizing agents, buffering agents, lubricating agents, ophthalmically or otically acceptable salts, and combinations thereof.

For example, aqueous ophthalmic compositions of the present invention, when in suspension or solution form, are suitably viscous or mucoadhesive, or both viscous or mucoadhesive, and thus comprise a viscosity-enhancing agent. Examples of suitable viscosity-enhancing agents include, but are not limited to, glycerin, polyvinyl alcohol, polyvinyl pyrrolidone, methylcellulose, hydroxypropylmethylcellulose, hydroxyethyl-cellulose, carboxymethylcellulose, hydroxypropylcellulose, and/or various gelling agents. For example, in some embodiments, the viscosity-enhancing agent is chosen from methylcellulose, hydroxypropyl-methylcellulose, polyvinyl alcohol, and glycerol. Such agents are generally employed in the compositions of the invention at a concentration of about 0.01% to about 3% by weight.

Thus, for ophthalmic compositions, in some embodiments, the ophthalmically acceptable excipient is a viscosity-enhancing agent or a promoter of mucoadhesion, such as carboxymethylcellulose. In such embodiments, the concentration of carboxymethylcellulose in the aqueous suspension or solution is 0.1% to 5% by weight or about 0.1% to about 2.5% by weight. The carboxymethylcellulose is preferably in the form of sodium carboxymethylcellulose substituted to a degree that the sodium content of the sodium carboxymethylcellulose is about 1% to about 20%.

In other embodiments, the ophthalmic composition is an in situ gellable aqueous composition such as an in situ gellable aqueous solution. Such a composition comprises a gelling agent in a concentration effective to promote gelling upon contact with the eye or with lacrimal fluid in the exterior of the eye, enabling the composition to remain in the eye for a prolonged period without loss by lacrimal drainage. Suitable gelling agents non-restrictively include thermosetting polymers such as tetra-substituted ethylene diamine block copolymers of ethylene oxide and propylene oxide (e.g., poloxamine 1307); polycarbophil; and polysaccharides such as gellan, carrageenan (e.g., kappa-carrageenan and iota-carrageenan), chitosan and alginate gums.

For example, in some embodiments of the present invention, the ophthalmic composition is an in situ gellable aqueous solution, suspension or solution/suspension, comprising from about 0.1% to about 6.5% or from about 0.5% to about 4.5% by weight, based on the total weight of the composition, of one or more compounds. A suitable gelling agent in this embodiment is polycarbophil. In other embodiments, the composition is an in situ gellable aqueous solution, suspension or solution/suspension, such as a solution, comprising about 0.1% to about 2% by weight of a polysaccharide that gels when it contacts an aqueous medium having the ionic strength of lacrimal fluid. A suitable polysaccharide is gellan gum, or a low acetyl clarified grade of gellan gum such as that sold under the trademark Gelrite®. Suitable partially deacylated gellan gums are disclosed in U.S. Pat. No. 5,190,927.

In yet other embodiments, the composition is an in situ gellable aqueous solution, suspension or solution/suspension, comprising about from 0.2% to about 3% or from about 0.5% to about 1% by weight of a gelling polysaccharide, chosen from gellan gum, alginate gum and chitosan, and about 1% to about 50% of a water-soluble film-forming polymer, preferably selected from alkylcelluloses (e.g., methylcellulose, ethylcellulose), hydroxyalkylcelluloses (e.g., hydroxyethylcellulose, hydroxypropyl methylcellulose), hyaluronic acid and salts thereof, chondroitin sulfate and salts thereof, polymers of acrylamide, acrylic acid and polycyanoacrylates, polymers of methyl methacrylate and 2-hydroxyethyl methacrylate, polydextrose, cyclodextrins, polydextrin, maltodextrin, dextran, polydextrose, gelatin, collagen, natural gums (e.g., xanthan, locust bean, acacia, tragacanth and carrageenan gums and agar), polygalacturonic acid derivatives (e.g., pectin), polyvinyl alcohol, polyvinylpyrrolidone and polyethylene glycol. The composition can optionally contain a gel-promoting counterion such as calcium in latent form, for example encapsulated in gelatin.

In yet other embodiments, the composition is an in situ gellable aqueous solution, suspension or solution/suspension comprising about 0.1% to about 5% of a carrageenan gum, e.g., a carrageenan gum having no more than 2 sulfate groups per repeating disaccharide unit, such as e.g., kappa-carrageenan, having 18-25% ester sulfate by weight, iota-carrageenan, having 25-34% ester sulfate by weight, and mixtures thereof.

In still other embodiments, the composition comprises a bioerodible polymer substantially as disclosed in U.S. Pat. No. 3,914,402.

In some embodiments, the composition comprises an ophthalmically acceptable mucoadhesive polymer, chosen from, for example, hydroxypropylmethylcellulose, carboxymethylcellulose, carbomer (acrylic acid polymer), poly(methylmethacrylate), polyacrylamide, polycarbophil, polyethylene oxide, acrylic acid/butyl acrylate copolymer, sodium alginate, and dextran.

Ophthalmic compositions of the invention can incorporate a means to inhibit microbial growth, for example through preparation and packaging under sterile conditions and/or through inclusion of an antimicrobially effective amount of an ophthalmically acceptable preservative.

Suitable preservatives include, but are not limited to, mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

Several preservatives may precipitate in the presence of other excipients in the composition and/or in the presence of the polymers and oligomers in the ophthalmic compositions. For example, benzalkonium chloride can precipitate in a composition using iota-carrageenan as a gelling agent. Thus, in those embodiments of the invention in which a preservative is present, the preservative is one that does not precipitate but remains in solution in the composition.

In some embodiments, the ophthalmic composition further comprises an additional ophthalmically acceptable excipient. The additional ophthalmically acceptable excipient is selected from a buffering agent, a solubilizing agent, a surfactant, a lubricating agent, and an ophthalmically acceptable salt, or any combination thereof.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight.

One or more antioxidants can also be included in the ophthalmic compositions. Suitable antioxidants include, but are not limited to, ascorbic acid, sodium metabisulfite, sodium bisulfite, acetylcysteine, polyquaternium-1, benzalkonium chloride, thimerosal, chlorobutanol, methyl paraben, propyl paraben, phenylethyl alcohol, edetate disodium, sorbic acid, or other agents know to those of skill in the art.

Such preservatives are typically employed at a level of from about 0.001% to about 1.0% by weight.

In some embodiments, the compounds are solubilized at least in part by an ophthalmically acceptable solubilizing agent. Certain ophthalmically acceptable nonionic surfactants, for example polysorbate 80, can be useful as solubilizing agents, as can ophthalmically acceptable glycols, polyglycols, e.g., polyethylene glycol 400 (PEG-400), and glycol ethers.

Suitable solubilizing agents for solution and solution/suspension compositions are cyclodextrins. Suitable cyclodextrins can be chosen from α-cyclodextrin, β-cyclodextrin, γ-cyclodextrin, alkylcyclodextrins (e.g., methyl-β-cyclodextrin, dimethyl-β-cyclodextrin, diethyl-β-cyclodextrin), hydroxyalkylcyclodextrins (e.g., hydroxyethyl-β-cyclodextrin, hydroxypropyl-β-cyclodextrin), carboxy-alkylcyclodextrins (e.g., carboxymethyl-β-cyclodextrin), sulfoalkylether cyclodextrins (e.g., sulfobutylether-β-cyclodextrin), and the like. Ophthalmic applications of cyclodextrins have been reviewed in Rajewski et al., Journal of Pharmaceutical Sciences, 1996, 85, 1155-1159.

An ophthalmically acceptable cyclodextrin can optionally be present in an ophthalmic composition at a concentration from about 1 to about 200 mg/ml, from about 5 to about 100 mg/ml, or from about 10 to about 50 mg/ml.

In some embodiments, the ophthalmic composition optionally contains a suspending agent. For example, in those embodiments in which the ophthalmic composition is an aqueous suspension or solution/suspension, the composition can contain one or more polymers as suspending agents. Useful polymers include, but are not limited to, water-soluble polymers such as cellulosic polymers, for example, hydroxypropyl methylcellulose, and water-insoluble polymers such as cross-linked carboxyl-containing polymers. However, in some embodiments, ophthalmic compositions do not contain substantial amounts of solid particulate matter, whether of the anti-microbial polymer or oligomer active agent, an excipient, or both, as solid particulate matter, if present, can cause discomfort and/or irritation of a treated eye.

One or more ophthalmically acceptable pH adjusting agents and/or buffering agents can be included in the ophthalmic compositions, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an ophthalmically acceptable range.

One or more ophthalmically acceptable salts can be included in the compositions of the invention in an amount required to bring osmolality of the composition into an ophthalmically acceptable range. Such salts include, but are not limited to, those having sodium, potassium or ammonium cations and chloride, citrate, ascorbate, borate, phosphate, bicarbonate, sulfate, thiosulfate or bisulfite anions. In some embodiments, salts include sodium chloride, potassium chloride, sodium thiosulfate, sodium bisulfite and ammonium sulfate. In some embodiments, the salt is sodium chloride.

Optionally an ophthalmically acceptable xanthine derivative such as caffeine, theobromine or theophylline can be included in the compositions, e.g., as disclosed in U.S. Pat. No. 4,559,343. Inclusion of the xanthine derivative can reduce ocular discomfort associated with administration of the composition.

Optionally one or more ophthalmically acceptable surfactants, preferably nonionic surfactants, or co-solvents can be included in the compositions to enhance solubility of the components of the compositions or to impart physical stability, or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40; polysorbate 20, 60 and 80; polyoxyethylene/polyoxypropylene surfactants (e.g., Pluronic® F-68, F84 and P-103); cyclodextrin; or other agents known to those of skill in the art. Typically, such co-solvents or surfactants are employed in the compositions at a level of from about 0.01% to about 2% by weight.

One or more ophthalmic lubricating agents can also be included optionally in the compositions to promote lacrimation or as a "dry eye" medication. Such agents include, but are not limited to, polyvinyl alcohol, methylcellulose, hydroxypropyl methylcellulose, polyvinylpyrrolidone, and the like. It will be understood that promotion of lacrimation is beneficial in the present invention only where lacrimation is naturally deficient, to restore a normal degree of secretion of lacrimal fluid. Where excessive lacrimation occurs, residence time of the composition in the eye can be reduced.

Ophthalmic compositions of the present invention typically include a combination of one or more of the optional excipients listed above. For example, in some embodiments, the ophthalmic composition can optionally further comprise glycerin in an amount from about 0.5% to about 5%, from about 1% to about 2.5%, or from about 1.5% to about 2% by weight. Glycerin can be useful to increase viscosity of the composition and for adjustment of osmolality. Independently of the presence of glycerin, the composition can also further comprise a cyclodextrin, such as hydroxypropyl-β-cyclodextrin, in an amount from about 0.5% to about 25% by weight, as a solubilizing agent, and an antimicrobially effective amount of a preservative, e.g., imidazolidinyl urea in an amount from about 0.03% to about 0.5%; methylparaben in an amount from about 0.015% to about 0.25%; propylparaben in an amount from about 0.005% to about 0.01%; phenoxyethanol in an amount from about 0.25% to about 1%; disodium EDTA in an amount from about 0.05% to about 0.2%; thimerosal in an amount from 0.001% to about 0.15%; chlorobutanol in an amount from about 0.1% to about 0.5%; and/or sorbic acid in an amount from about 0.05% to about 0.2%; all by weight.

The otic compositions also optionally comprise one or more otically acceptable excipients. Otically acceptable excipients include, but are not limited to, one or more of the preservatives, stabilizers, antioxidants, viscosity-enhancing agents, buffering agents, solubilizing agents, surfactants, lubricating agents, or acceptable salts described above, or combinations thereof, as described above for the ophthalmic compositions.

Thus, for example, in some embodiments, an otic composition optionally comprises one or more buffering agents, solubilizing agents, and antioxidants, typically in an aqueous solution. In some embodiments, the otic composition further comprises glycerin (e.g., anhydrous glycerin) or propylene glycol as a viscosity-enhancing agent. The otic composition may also comprise a surfactant in combination with the glycerin or propylene glycol to aid in the removal of cerum (ear wax). Sodium bicarbonate may also be used if wax is to be removed from the ear.

Thus, e.g., in some embodiments, the otic composition is a sterile aqueous solution comprising one or more of the disclosed polymers or oligomers, glycerin, sodium bicarbonate, and, optionally, a preservative, in purified water.

The ophthalmic and otic compositions can be prepared by methods known in the art and described in patents and publications cited herein and incorporated herein by reference.

The compounds described herein can also be incorporated into compositions such as, for example, polishes, paints, sprays, or detergents formulated for application to a surface to inhibit the growth of a *Mycobacterium* species thereon. These surfaces include, but are not limited to, countertops, desks, chairs, laboratory benches, tables, floors, bed stands, tools, equipment, doorknobs, windows, and the like. The compounds described herein can also be incorporated into soaps and hand lotions. The present compositions, including the cleansers, polishes, paints, sprays, soaps, and detergents, can contain one or more of the compounds described herein. In addition, the compositions can optionally contain one or more of each of the following: solvents, carriers, thickeners, pigments, fragrances, deodorizers, emulsifiers, surfactants, wetting agents, waxes, and/or oils. For example, in some embodiments, the compounds can be incorporated into a formulation for external use as a pharmaceutically acceptable skin cleanser, particularly for the surfaces of human hands. Cleansers, polishes, paints, sprays, soaps, hand lotions, and detergents and the like containing the compounds described herein can be useful in homes and institutions, particularly but not exclusively, in hospital settings for the prevention of nosocomial infections.

The present invention also provides pharmaceutical packs or kits comprising one or more containers filled with one or more compounds described herein. Optionally associated with such container(s) can be a notice in the form prescribed by a governmental agency regulating the manufacture, use or sale of pharmaceuticals or biological products, which notice reflects approval by the agency of manufacture, use or sale for human administration for treating a condition, disease, or disorder described herein. In some embodiments, the kit contains more than one compound described herein. In some embodiments, the kit comprises a compound described herein in a single injectable dosage form, such as a single dose within an injectable device such as a syringe with a needle.

The present invention also provides methods of inhibiting the growth of a microbe comprising contacting the microbe with one or more compounds described above, or a pharmaceutically acceptable salt thereof. In some embodiments, the compound can act as an antiseptic agent for cleansing surfaces, such as in, for example, kitchens and bathrooms. In these embodiments, the compound can be formulated for such uses by procedures well known to the skilled artisan.

The present invention also provides methods of treating a mammal having a microbial infection comprising administering to the mammal in need thereof an anti-microbial effective amount of one or more compounds described above, or a pharmaceutically acceptable salt thereof. In some embodiments, the mammal can be pre-diagnosed with a microbial infection prior to treatment. In some embodiments, no formal diagnosis may have been made; in such embodiments, the mammal may be suspected of having a microbial infection for which treatment is recognized as being desirable.

In some embodiments, the microbe is, or the microbial infection is due to, a gram-negative aerobe, a gram-positive aerobe, a gram-negative anaerobe, a gram-positive anaerobe, or a yeast. In some embodiments, the gram-negative aerobe is selected from, but not limited to, *Escherichia coli*, *Citrobacter freundii*, *Citrobacter diverus*, *Citrobacter koseri*, *Enterobacter cloacae*, *Enterobacter faecalis*, *Klebsiella pneumonia*, *Klebsiella oxytoca*, *Morganella morganii*, *Providencia stuartii*, *Proteus vulgaris*, *Proteus mirabilis*, *Serratia marcescens*, *Acinetobacter haemolyticus*, *Acinetobacter junii*, *Acinetobacter lwoffii*, *Haemophilus influenzae*, *Stenotrophomonas maltophilia*, and *Pseudomonas aeruginosa*. In some embodiments, the gram-positive aerobe is selected from, but not limited to, *Enterococcus faecalis*, *Enterococcus faecium*, *Mycobacterium tuberculosis*, *Staphylococcus aureus*, *Staphylococcus pneumoniae*, *Staphylococcus epidermidis*, *Staphylococcus saprophyticus*, *Staphylococcus colmii*, *Staphylococcus sciuri*, *Staphylococcus warneri*, *Streptococcus agalactiae*, *Streptococcus pyogenes*, *Streptococcus anginosus*, *Streptococcus mitis*, and *Streptococcus oralis*. In some embodiments, the gram-negative anaerobe is *Bacteroides fragilis*. In some embodiments, the gram-positive anaerobe is *Clostridium difficile* or *Clostridium perfringens*. In some embodiments, the mycobacterium is *Mycobacterium tuberculosis*, *Mycobacterium bovis*, *Mycobacterium africanum*, *Mycobacterium canetti*, or *Mycobacterium microti*. In some embodiments, the yeast is selected from, but not limited to, *Candida albicans* and *Candida krusei*. In some embodiments, the microbe is an antibiotic-resistant strain of bacteria, such as those recited in the Examples below.

The present invention also provides one or more compounds described above, or a pharmaceutically acceptable salt thereof, or a pharmaceutical composition comprising one or more compounds described above, for treating a microbial infection.

The present invention also provides one or more compounds described above, or a pharmaceutically acceptable salt thereof, or a pharmaceutical composition comprising one or more compounds described above, for use in the manufacture of a medicament for the treatment of a microbial infection.

The present invention also provides the use of one or more compounds described above, or a pharmaceutically acceptable salt thereof, or a pharmaceutical composition comprising one or more compounds described above, in the inhibition of growth of a microbe.

The present invention also provides the use of one or more compounds described above, or a pharmaceutically acceptable salt thereof, or a pharmaceutical composition comprising one or more compounds described above, in the treatment of a microbial infection in a mammal.

The ophthalmic or otic compositions possess anti-microbial activity and can be used in methods of treating or preventing ophthalmic infections in an eye of an animal, or otic infections in the ear of an animal.

Ophthalmic infections for which the compositions and methods are useful include, but are not limited to, infections of one or more tissues of the eye, including, for example, conjunctivitis, keratitis (including ulcerative keratitis with bacterial infection), keratoconjunctivitis (including, e.g., keratoconjunctivitis sicca (KCS) commonly found in dogs), blepharitis, blepharoconjunctivitis, dacryocystitis, hordeolum, corneal ulcers, orbital and preseptal cellulitis, and endophthalmitis. In some embodiments, the infected tissue is one that is directly bathed by the lacrimal fluid, as in conjunctivitis, keratitis, keratoconjunctivitis, blepharitis, and blepharoconjunctivitis. The ophthalmic compositions may also be used prophylactically in connection with various ophthalmic surgical procedures that create a risk of infection.

Otic infections for which the compositions and methods are useful include, but are not limited to, otitis externa and otitis media. With respect to the treatment of otitis media, the compositions are primarily useful in cases where the tympanic membrane has ruptured or tympanostomy tubes have been implanted. The otic compositions may also be used to treat infections associated with otic surgical procedures, such as tympanostomy, or to prevent such infections.

The ophthalmic and otic compositions are effective in killing or inhibiting the growth of a broad spectrum of pathogens or microbes often associated with ophthalmic and/or otic infections, including a range of bacteria (both gram-postive and gram-negative), fungi and viruses. For example, the ophthalmic and otic compositions are useful in killing or inhibiting the growth of any of the following clinically relevant ocular or otic pathogens, and can be administered topically to treat and/or prevent ophthalmic or otic infections caused by the following pathogens or mixtures of the following pathogens: *Staphylococcus* spp. (e.g., *Staphylococcus aureus*, *Staphylococcus epidermidis*), *Streptococcus* spp. (e.g., *Streptococcus viridans*, *Streptococcus pneumoniae*), *Enterococcus* spp., *Bacillus* spp., *Corynebacterium* spp., *Propionibacterium* spp., *Chlamydia* spp., *Moraxella* spp. (e.g., *Moraxella lacunata* and *Moraxella catarrhalis*), *Haemophilus* spp. (e.g., *Haemophilus influenza* and *Haemophilus aegyptius*), *Pseudomonas* spp. (e.g., *Pseudomonas aeruginosa*, and, for otic infections, *Pseudomonas otitidis*), *Serratia* spp. (e.g., *Serratia marcescens*), *Neisseria* spp., and *Mycoplasma* spp., as well as *Enterobacter* spp. (e.g., *Enterobacter aerogenes*), *Eschericia* spp. (e.g., *Eschericia coli*), *Klebsiella* spp. (e.g., *Klebsiella pneumoniae*), *Proteus* spp. (e.g., *Proteus mirabillis* and *Proteus vulgaris*), *Acinetobacter* spp. (e.g., *Acinetobacter calcoaceticus*), *Prevotella* spp., *Fusobacterium* spp., *Porphyromonas* spp., and *Bacteroides* spp. (e.g., *Bacteroides fragilis*). This list of microbes is purely illustrative and is in no way to be interpreted as restrictive.

Thus, for example, the ophthalmic compositions can be administered to treat or prevent a bacterial infection of the eye caused by one or more of the following species: *Staphylococcus aureus*, *Staphylococcus epidermidis*, *Streptococcus pneumoniae*, *Streptococcus pyogenes*, *Streptococcus viridans*, *Enterococcus faecalis*, *Corynebacterium* spp., *Propionibacterium* spp., *Moraxella catarrhalis* and *Haemophilus influenzae*.

Treatment of bacterial conjunctivitis by administering an ophthalmic composition of the present invention is appropriate where infection with one or more of the following species is present: *Staphylococcus aureus*, *Staphylococcus epidermidis*, *Streptococcus pneumoniae*, *Streptococcus pyogenes*, *Streptococcus viridans*, *Enterococcus faecalis*, *Corynebacterium* spp., *Propionibacterium* spp., *Moraxella catarrhalis* and *Haemophilus influenzae*.

Treatment of bacterial blepharitis by administering an ophthalmic composition of is appropriate where infection with one or more of the following species is present: *Staphylococcus aureus*, *Staphylococcus epidermidis* and *Streptococcus pneumoniae*.

Treatment of bacterial keratitis by administering an ophthalmic composition is also appropriate where infection with one or more of the following species is present: *Staphylococcus aureus*, *Staphylococcus epidermidis*, *Streptococcus pneumoniae* and *Streptococcus viridans*.

The otic compositions can also be administered to treat or prevent a bacterial infection of the ear caused by one or more of the following species: *Pseudomonas aeruginosa*, *Staphylococcus aureus*, *Staphylococcus epidermidis*, *Streptococcus pneumoniae*, *Moraxella catarrhalis*, *Pseudomonas otitidis*, and *Proteus* spp. (e.g., *Proteus mirabillis* and *Proteus vulgaris*), as well as one or more of the following anaerobes: *Prevotella* spp., *Fusobacterium* spp., *Porphyromonas* spp., and *Bacteroides* spp. (e.g., *Bacteroides fragilis*). Thus, for example, treatment of chronic suppurative otitis media by administering an otic composition is appropriate where infection with one or more of the following species is present: *Staphylococcus aureus*, *Pseudomonas aeruginosa*, *Eschericia coli*, *Klebsiella* spp. (e.g., *Klebsiella pneumoniae*), *Proteus* spp. (e.g., *Proteus mirabillis* and *Proteus vulgaris*), *Prevotella* spp., *Fusobacterium* spp., *Porphyromonas* spp., and *Bacteroides* spp. (e.g., *Bacteroides fragilis*).

The ophthalmic or otic compositions are also useful in killing or inhibiting the growth of clinically relevant ocular or otic fungi, and can be administered topically to treat and/or prevent ophthalmic or otic infections caused by one or more species of fungi, or a mixture of species of fungi, including, but not limited to, *Aspergillus* spp. (e.g., *Aspergillus fumigatus*, *Aspergillus favus*, *Aspergillus niger* and *Aspergillus terreus*), *Fusarium* spp. (e.g., *Fusarium solani*, *Fusarium moniliforme* and *Fusarium proliferartum*), *Malessezia* spp. (e.g., *Malessezia pachydermatis*), and/or *Candida* spp. (e.g., *Candida albicans*), as well as *Chrysosporium parvum*, *Metarhizium anisopliae*, *Phaeoisaria clematidis*, and *Sarcopodium oculorum*. This list of microbes is purely illustrative and is in no way to be interpreted as restrictive. The ophthalmic compositions can be administered to treat or prevent a fungal infection of the eye caused by one or more of the following species: *Aspegillus* spp., *Fusarium* spp., *Chrysosporium parvum*, *Metarhizium anisopliae*, *Phaeoisaria clematidis*, and *Sarcopodium oculorum*. For example, the ophthalmic composition can be administered to treat fungal keratitis caused by one or more *Aspergillus* spp. and/or *Fusarium* spp.

The otic compositions can also be administered to treat or prevent a fungal infection of the ear caused by one or more of the following species: *Candida* spp., *Aspegillus* spp., and/or *Malessezia* spp. (e.g., *Malessezia pachydermatis*).

The ophthalmic or otic compositions are also useful in killing or inhibiting the growth of clinically relevant ocular or otic viruses and can be administered topically to treat and/or prevent ophthalmic or otic infections caused by one or more viruses, including, but not limited to, adenoviruses and herpes viruses (including, e.g., Herpes simplex 1 virus and/or varicella-zoster virus), Eneroviruses and Cytomegaloviruses. Thus, for example, the ophthalmic compositions can be administered to treat or prevent a viral infection of the eye, e.g., Herpes keratitis, caused by Herpes simplex 1 virus.

In some embodiments, the ophthalmic or otic compositions are useful and effective in killing and/or preventing the growth of microbes that have developed significant levels of resistance to anti-microbial agents other than the disclosed compounds. For example, in some embodiments, the ophthalmic compositions and otic compositions are especially effective in methods of treating ophthalmic infections or otic infections cased by bacterial strains that have developed resistance to ciprofloxacin, e.g., Ciprofloxacin Resistant (CR) *S. aureus* and CR *S. epidermidis*, or to fluoroquinolone, or bacterial strains that have developed resistance to penicillin.

In some embodiments, the compositions are administered topically to one or more tissues of the eye or ear to treat an existing microbial infection, or as a prophylactic measure to prevent a microbial infection. Thus, for example, in some embodiments, an ophthalmic composition is administered topically to one or more tissues of the eye to treat an existing microbial infection, e.g., conjunctivitis, keratitis, blepharitis, or blepharoconjunctivitis.

In other embodiments, an ophthalmic composition is administered topically to one or more tissues of the eye as a prophylactic measure. That is, the compositions are administered for prophylactic uses, e.g., in connection with various ophthalmic surgical procedures that create a risk of infection. Thus, for example, a composition can be administered in a method of post-traumatic prophylaxis, especially post-surgical prophylaxis, to prevent infection after ocular surgery, or in a method of prophylaxis prior to ocular surgery, for example, administered prior to surgery to prevent infection as a consequence of surgery.

The ophthalmic and otic compositions possess broad-spectrum anti-microbial activity due to the facially amphiphilic and cationic properties of the facially amphiphilic polymers and oligomers in the compositions. As a consequence, an ophthalmic infection or an otic infection can be treated or prevented by administering only one of the compositions, rather than by administering two or more separate antimicrobial compositions or one antimicrobial composition containing a combination of antimicrobial agents.

For example, because the ophthalmic compositions can be used to treat or prevent both viral and bacterial ophthalmic infections in an eye, only one of the present compositions needs to be administered to the eye to treat a viral ophthalmic infection where there is a risk of a secondary bacterial infection. Similarly, for an eye infection caused by multiple strains of bacteria (e.g., by both gram-positive bacteria and gram-negative bacteria), only one composition containing one of the disclosed compounds needs to be administered, rather than a composition containing multiple anti-microbial agents, or a combination of separate treatments administered concurrently.

In some embodiments, the ophthalmic or otic compositions are administered with an additional anti-microbial agent, such as, e.g., an anti-bacterial, anti-fungal, or anti-viral agent. For example, the additional anti-microbial agent can be a second compound disclosed herein, or the additional anti-microbial agent can be another anti-microbial agent such as, for example, an antibiotic selected from the group consisting of aminoglycosides, cephalosporins, diaminopyridines, fluoroquinolones, sulfonamides and tetracyclines. Examples of useful antibiotics which can serve as additional anti-microbials include, but are not limited to, amikacin, azithromycin, cefixime, cefoperazone, cefotaxime, ceftazidime, ceftizoxime, ceftriaxone, chloramphenicol, ciprofloxacin, clindamycin, colistin, domeclocycline, doxycycline, erythromycin, gentamicin, mafenide, methacycline, minocycline, neomycin, norfloxacin, ofloxacin, oxytetracycline, polymyxin B, pyrimethamine, silver sulfadiazine, sulfacetamide, sulfisoxazole, tetracycline, tobramycin, and trimethoprim.

In those embodiments in which the ophthalmic or otic composition is administered with another anti-microbial agent, the present invention provides methods of treating or preventing multiple bacterial infections in an eye or an ear, the method comprising application to the eye or ear in co-therapy (including co-formulation) one or more compounds disclosed herein and one or more additional anti-microbial agents. "Co-therapy" herein means administration to the eye or ear, at the same time or sequentially, of an ophthalmically or otically acceptable composition comprising one or more of the compounds disclosed herein and a separate ophthalmically or otically acceptable composition of the additional anti-microbial agent, in a treatment regimen intended to provide a beneficial effect from co-action of the two types of antimicrobial agents. "Co-formulation" herein means that the compound and the additional anti-microbial agent are administered to the eye or ear as components of a single ophthalmically or otically acceptable composition.

The ophthalmic or otic compositions can also be used in co-therapy with one or more drugs, or medicaments, other than anti-microbial agents. Such medicaments other than anti-microbial agents can be co-administered to the eye or ear together with a composition. Thus, e.g., an ophthalmic composition invention can further comprise, in co-formulation with the facially amphiphilic polymer or oligomer active agent, a therapeutically and/or prophylactically effective amount of one or more medicaments that are other than anti-microbial agents.

These additional medicaments other than the compounds described herein can cooperate with the compounds described herein in treating and/or preventing an infective disease of the eye or ear, or can be used to treat a related or unrelated conditions simultaneously affecting the eye or ear.

Any medicament having utility in an ophthalmic or otic application can be used in co-therapy, co-administration or co-formulation with an ophthalmic or otic composition as described above. Such additional medicaments include, but are not limited to, anti-inflammatory agents (e.g., steroidal anti-inflammatory agents, non-steroidal anti-inflammatory agents (NSAIDs), and selective cyclooxygenase-2 inhibitors); topical and/or regional anesthetic agents; anti-allergic agents (e.g., anti-histamines); demulcents; acetylcholine blocking agents; adrenergic agonists, beta-adrenergic blocking agents and other anti-glaucoma agents; anti-hypertensives; anti-cataract agents; anti-microbial agents, and anti-allergic agents.

For example, ophthalmic and otic infections are frequently accompanied by inflammation of the infected ophthalmic and/or otic tissues and surrounding tissues. In addition, ophthalmic and otic surgical procedures that create a risk of microbial infections frequently also causes inflammation of the affected tissues. Thus, the ophthalmic and otic compositions can be co-formulated with an anti-inflammatory agent to combine the anti-infective activity of one or more antibiotics with the anti-inflammatory activity of one or more steroid or non-steroid agents in a single composition.

The anti-inflammatory agents can be steroidal or non-steroidal. Examples of suitable steroidal anti-inflammatory agents include, but are not limited to, dexamethasone; dexamethasone derivatives such as those disclosed in U.S. Pat. No. 5,223,492; rimexolone; prednisolone; fluorometholone; and hydrocortisone.

Examples of suitable non-steroidal anti-inflammatory agents include, but are not limited to, prostaglandin H synthetase inhibitors (Cos I or Cox II), also referred to as cyclooxygenase type I and type II inhibitors, such as diclofenac, flurbiprofen, ketorolac, suprofen, nepafenac, amfenac, indomethacin, naproxen, ibuprofen, bromfenac, ketoprofen, meclofenamate, piroxicam, sulindac, mefanamic acid, diflusinal, oxaprozin, tolmetin, fenoprofen, benoxaprofen, nabumetome, etodolac, phenylbutazone, aspirin, oxyphenbutazone, tenoxicam and carprofen;

cyclooxygenase type II selective inhibitors, such as vioxx, celecoxib, etodolac; PAF antagonists, such as apafant, bepafant, minopafant, nupafant and modipafant; PDE IV inhibitors, such as ariflo, torbafylline, rolipram, filaminast, piclamilast, cipamfylline, and roflumilast; inhibitors of cytokine production, such as inhibitors of the NFkB transcription factor; or other anti-inflammatory agents know to those skilled in the art.

Examples of suitable topical or regional anesthetic agents include, but are not limited to, benzocaine.

Examples of suitable anti-allergic agents include, but are not limited to, pemirolast, olopatadine, and the corticosteroids (prednisolone, fluorometholone, loteprenol and dexamthasone).

The additional medicament can be administered in co-therapy (including co-formulation) with the one or more facially amphiphilic polymers of the ophthalmic or otic composition. For example, in some embodiments, an ophthalmic composition of the present invention comprising one of the anti-microbial oligomer disclosed herein is administered in co-therapy with an anti-inflammatory agent, e.g., a glucocorticoid. The glucocorticoid can be co-formulated with the oligomer in a single ophthalmically acceptable composition, which is administered to one or more tissues of an eye, to not only treat or prevent an ophthalmic infection but also to treat and/or prevent inflammation.

The ophthalmic or otic compositions can be administered by any appropriate route of administration. In some aspects of the invention, the ophthalmic and otic compositions are administered topically, for example, the composition is topically administered in an antimicrobially effective amount to one or more tissues of the eye of the animal, or to one or more tissues of the ear of an animal.

In some embodiments, the response of the ophthalmic or otic infection to treatment is monitored and the treatment regimen is adjusted if necessary in light of such monitoring.

Frequency of administration is typically such that the dosing interval, for example, the period of time between one dose and the next, during waking hours is from about 2 to about 12 hours, from about 3 to about 8 hours, or from about 4 to about 6 hours. It will be understood by those of skill in the art that an appropriate dosing interval is dependent to some degree on the length of time for which the selected composition is capable of maintaining a concentration of the compound(s) in the lacrimal fluid and/or in the target tissue (e.g., the conjunctiva) above the $MIC_{90}$ (the minimum concentration of the oligomer or polymer which inhibits microbial growth by 90%). Ideally the concentration remains above the $MIC_{90}$ for at least 100% of the dosing interval. Where this is not achievable it is desired that the concentration should remain above the $MIC_{90}$ for at least about 60% of the dosing interval, or should remain above the $MIC_{90}$ for at least about 40% of the dosing interval.

In some embodiments, the ophthalmic composition is formulated as an in situ gettable aqueous liquid and is administered as eye drops. Typically each drop, generated by a conventional dispensing means, has a volume from about 10 to about 40 μL. From 1 to about 6 such drops typically provides a suitable dose of the compound in from about 25 to about 150 μL of the composition. For example, no more than 3 drops, no more than 2 drops, or no more than 1 drop, should contain the desired dose of the compound for administration to an eye. Where the composition is administered in a form other than eye drops, for example, as an ophthalmic ointment or as a solid implant, an equivalent dose is provided. Such a dose can be administered as needed, but typically administration to the eye 1 to about 6 times per day, in most cases from 2 to 4 times a day, provides adequate continuing relief or prevention of the infective disease indicated.

The ophthalmic compositions, such as aqueous suspension compositions, can be packaged in single-dose non-reclosable containers. Such containers can maintain the composition in a sterile condition and thereby eliminate need for preservatives such as mercury-containing preservatives, which can sometimes cause irritation and sensitization of the eye. Alternatively, multiple-dose reclosable containers can be used, in which case it is preferred to include a preservative in the composition.

In some embodiments, the ophthalmic composition is an aqueous solution, suspension or solution/suspension which is administered in the form of eye drops. In these embodiments, a desired dosage of the active agent can be administered by means of a suitable dispenser as a known number of drops into the eye. Examples of suitable dispensers are disclosed in International Patent Publication No. WO 96/06581.

The ophthalmic or otic compositions can be tested for anti-microbial activity by methods known to those of skill in the art. For example, anti-microbial assays suitable for testing the antimicrobial activity of the ophthalmic or otic compositions of the invention are described, for example, US Pat. Appl. Publ. No. US 2006-0041023 A1; Tew et al., Proc. Natl. Acad. Sci. USA, 2002, 99, 5110-5114; and Liu et al., J. Amer. Chem. Soc., 2001, 123, 7553-7559.

The activity of antimicrobials is generally expressed as the minimum concentration of a compound (active agent) required to inhibit the growth of a specified pathogen. This concentration is also referred to as the "minimum inhibitory concentration" or "MIC." The term "$MIC_{90}$" refers to the minimum concentration of an antimicrobial active agent required to inhibit the growth of ninety percent (90%) of the tested isolates for one particular organism. The concentration of a compound required to totally kill a specified bacterial species is referred to as the "minimum bactericidal concentration" or "MBC."

In some embodiments, an effective concentration of the compound in the composition will generally be from about 0.01% to about 20% by weight (wt %) of the composition, from about 0.05% to about 10% by weight, from about 0.1% to about 8.0% by weight, from about 0.5% to about 5.0% by weight, from about 1.0% to about 5.0% by weight, or from about 2.0% to about 4.0% of the composition. For example, in ophthalmic compositions in the form of solid suspensions, such as ointments, an effective concentration of the antimicrobial polymer or oligomer will generally be from about 1% to about 5% by weight (wt %) of the composition.

The present invention is also directed to a method for treating or preventing a microbial infection in an eye of an animal by administering to one or more tissues of the eye an antimicrobial ophthalmic composition, wherein the composition comprises a compound described herein in an amount effective to treat or prevent the infection.

In some embodiments of the methods of the present invention, the antimicrobial ophthalmic composition is administered topically to one or more tissues of the eye of the animal.

In some embodiments of the methods present invention, the ophthalmic composition is in a form selected from a solution, a suspension, an emulsion, a gel, an ointment, and a solid article suitable for ocular implant. In other embodiments, the ophthalmic composition is administered 2 to 4 times daily. In yet other embodiments, the oligomer in the ophthalmic composition is present in the composition at a concentration of about 0.01% to about 20% by weight.

In some embodiments of the methods of the present invention, the microbial ophthalmic infection is a bacterial infection. For example, in some embodiments, the bacterial infection is caused by *Staphylococcus, Streptococcus, Enterococcus, Bacillus, Corynebacterium, Moraxella, Haemophilus, Serratia, Pseudomonas,* or *Neisseria* spp. In other embodiments, the microbial infection is a fungal infection. For example, in some embodiments, the fungal infection is caused by *Aspergillus* or *Fusarium* spp. In yet other embodiments, the microbial infection is a viral infection. For example, in some embodiments, the viral infection is caused by a herpes virus. In some embodiments of the methods of the present invention, the ophthalmic infection is selected from bacterial keratitis, bacterial conjunctivitis, and corneal ulcers.

The present invention is also directed to an otic composition, comprising an effective amount of a compound described herein and an otically acceptable excipient.

The present invention is also directed to an antimicrobial otic composition, the composition comprising a) a compound described herein, or a pharmaceutically acceptable salt or solvate thereof, in an amount effective for treatment and/or prophylaxis of a microbial infection of an ear of an animal; and b) an otically acceptable excipient, wherein the composition is suitable for administration to one or more tissues of the ear.

The present invention is also directed to an otic composition for use in treatment or prevention of a microbial infection in an ear of an animal, wherein the composition comprises a compound described herein, or an acceptable salt or solvate thereof, in an amount effective to treat or prevent the infection when the composition is administered to one or more tissues of the ear.

The present invention is also directed to any of the otic compositions disclosed herein, wherein the composition is suitable for topical administration to one or more tissues of an ear of an animal.

The present invention is also directed to any of the otic compositions disclosed herein, wherein the composition is in a form selected from a solution, a suspension, an emulsion, a gel, an ointment, and a solid article suitable for otic implant.

The present invention is also directed to any of the otic compositions disclosed herein, wherein the polymer or oligomer is present in the otic composition at a concentration of about 0.01% to about 20% by weight.

The present invention is also directed to any of the otic compositions disclosed herein, wherein the otically acceptable excipient is selected from a preservative, a stabilizer, an antioxidant, and a viscosity-enhancing agent, or any combination thereof, such as any of those discussed above.

In some embodiments, the otic composition further comprises an additional medicament. The additional medicament is selected from an anti-inflammatory agent, an antimicrobial agent, an anesthetic agent, and an anti-allergic agent.

The present invention is further directed to a method of treating or preventing a microbial infection in an ear of an animal, the method comprising administering to an ear of an animal in need of the treating or preventing an effective amount of an otic composition.

The present invention is also directed to a method for treating or preventing a microbial infection in an ear of an animal by administering to one or more tissues of the ear an antimicrobial otic composition, wherein the composition comprises a compound described herein, in an amount effective to treat or prevent the infection.

In some embodiments, the antimicrobial otic composition is administered topically to one or more tissues of the ear of the animal.

In some embodiments, the otic composition is in a form selected from a solution, a suspension, an emulsion, a gel, an ointment, and a solid article suitable for otic implant. In other embodiments, the otic composition is administered 2 to 4 times daily. In yet other embodiments, the polymer or oligomer is present in the otic composition at a concentration of about 0.01% to about 20% by weight.

In some embodiments, the microbial otic infection is a bacterial infection. In other embodiments, the infection is a fungal infection. In yet other embodiments, the infection is a viral infection.

In some embodiments, the otic infection is selected from otitis externa and otitis media.

The present invention also provides methods of inhibiting the growth of a *Mycobacterium* species comprising contacting the *Mycobacterium* species with an effective amount of a compound described herein, or salt or pharmaceutically acceptable salt thereof.

In some embodiments, some of the compounds described herein rapidly kill *M. tuberculosis* (for example in vitro). In some embodiments, some of the compounds described herein possess low cytotoxicity against mammalian cells. In some embodiments, the $EC_{50}$ of the compounds used in the present invention (for mammalian cells) is greater than about 200 µM or greater than about 300 μM. In some embodiments, some of the compounds described herein have high selectivity against *M. tuberculosis* over mammalian cells. In some embodiments, the selective index (SI) values (the SI value is calculated by dividing the $EC_{50}$ by the $IC_{90}$) of some of the compounds described herein is greater than about 10, greater than about 20, greater than about 30, greater than about 40, greater than about 50, greater than about 60, greater than about 70, greater than about 80, greater than about 90, greater than about 100, greater than about 120, greater than about 150, or greater than about 200.

The present invention also provides methods of treating an animal having a *Mycobacterium* infection comprising administering to the animal a therapeutically effective amount of a compound or a pharmaceutically acceptable salt thereof. In some embodiments, the *Mycobacterium* infection is caused by a *Mycobacterium* species, such as *Mycobacterium tuberculosis*. In some embodiments, the *Mycobacterium* species is active, dormant, or semi-dormant. In some embodiments, the active, dormant, or semi-dormant *Mycobacterium* species is not killed or inhibited by known TB drugs. In some embodiments, the *Mycobacterium* species is multi-drug resistant TB, with resistance to isoniazid and rifampicin. In some embodiments, the *Mycobacterium* species is extensively drug resistant TB, with resistance to any one of the fluoroquinolone drugs and to at least one of the following three injectable second-line drugs: amikacin, capreomycin, or kanamycin. In some embodiments, the *Mycobacterium tuberculosis* is multi-drug resistant TB, with resistance to isoniazid and rifampicin. In some embodiments, the *Mycobacterium tuberculosis* is extensively drug resistant TB, with resistance to any one of the fluoroquinolone drugs and to at least one of the following three injectable second-line drugs: amikacin, capreomycin, or kanamycin. In some embodiments, the methods described herein create or cause no new drug resistance. In some embodiments, the compound is present within a pharmaceutical composition.

In some embodiments, the animal being treated, such as a human, is "in need thereof." That is, the animal is in need of treatment. Thus, in some embodiments, the animal is treated for the purpose of treating the *Mycobacterium* infection. In some embodiments, the animal has been diagnosed with a *Mycobacterium* infection or is suspected of having a *Mycobacterium* infection. In some embodiments, the animal, or human, is in a population at risk of having a *Mycobacterium* infection, such as in a prison or hospital.

Those skilled in the art will recognize that the compounds described herein can be tested for anti-TB activity by methods well known to those of skill in the art (see, e.g., Collins et al., Antimicrobial Agents and Chemotherapy, 1997, 41, 1004-1009). Any compound found to be active can be purified to homogeneity and re-tested to obtain an accurate $IC_{90}$ or $IC_{50}$. Because these compounds can work by directly lysing bacterial cell membranes (rather than working on any specific receptor or intracellular target), the same mechanism utilized by the host defense proteins, drug resistance to these compounds is unlikely to develop. This premise is supported by experimental data showing that a negligible incidence of resistance development was observed in vitro in serial passage challenge assays using *S. aureus*. Thus, targeting bacterial cell membranes rather than any specific receptor or intracellular target represents a highly innovative and novel approach for treating TB (including MDR-TB and/or XRD-TB) and serves as one manner to distinguish the present invention from others in this field.

In any of the methods described above and herein, the *Mycobacterium* species can be *Mycobacterium tuberculosis*. In some embodiments, the *Mycobacterium* species is active, dormant, or semi-dormant. In some embodiments, the active, dormant, or semi-dormant *Mycobacterium* species is not killed or inhibited by known TB drugs. In some embodiments, the *Mycobacterium* species is multi-drug resistant TB, with resistance to isoniazid and rifampicin. In some embodiments, the *Mycobacterium* species is extensively drug resistant TB, with resistance to any one of the fluoroquinolone drugs and to at least one of the following three injectable second-line drugs: amikacin, capreomycin, or kanamycin.

The present invention also provides compounds described herein, or compositions or pharmaceutical compositions comprising the same, for use in preparation of a medicament for treating a *Mycobacterium* infection (including *Mycobacterium tuberculosis*, including MDR-TB and XDR-TB) in an animal and/or for inhibiting the growth of a *Mycobacterium* species. The present invention also provides compounds described herein, or compositions comprising the same, for treating a *Mycobacterium* infection (including *Mycobacterium tuberculosis*, including MDR-TB and XDR-TB) in an animal and/or for inhibiting the growth of a *Mycobacterium* species.

The present invention also provides methods of treating and/or preventing mucositis in a mammal comprising administering to the mammal in need thereof a therapeutically effective amount of a compound described herein.

The compounds described herein may be useful for treating and/or preventing mucositis by administering to the patient an effective amount of a compound or a salt thereof, or a pharmaceutical composition comprising a compound or a salt thereof. The compound or salt, or composition thereof, can be administered systemically or topically and can be administered to any body site or tissue.

In some embodiments, the present methods for treating and/or preventing mucositis can be used in a patient who receives chemotherapy and/or radiation therapy for cancer. In some embodiments, the patient is receiving or will be receiving high-dose chemotherapy prior to hematopoietic cell transplantation. In some embodiments, the patient is receiving or will be receiving radiation therapy for tumors of the head and neck. In some embodiments, the patient is receiving or will be receiving induction therapy for leukemia. In some embodiments, the patient is receiving or will be receiving conditioning regimens for bone marrow transplant. In some embodiments, the patient is experiencing or will be experiencing basal epithelial cell death.

The present invention also provides compounds, or compositions comprising the same, for use in treating and/or preventing mucositis in a patient. The present invention also provides compounds, or compositions comprising the same, for use in treating and/or preventing mucositis. The present invention also provides compounds, or compositions comprising the same, for use in preparation of a medicament for treating and/or preventing mucositis in a patient.

The compounds described herein can also be administered in combination with other active ingredients such as, for example, palifermin and/or NX002, or other known compounds useful for treating and/or preventing mucositis.

The present invention also provides methods for treating and/or preventing mucositis in an animal comprising administering to the animal in need thereof an effective amount of a compound described herein. The present invention also provides methods for treating and/or preventing mucositis in an animal comprising administering to the animal in need thereof a composition of the invention. The present invention also provides methods for treating and/or preventing mucositis comprising administering to the animal an effective amount of a compound.

The present invention also provides methods of treating or reducing a cancer, inhibiting tumor growth, or treating or preventing spread or metastasis of cancer in a mammal comprising administering to the mammal in need thereof a therapeutically effective amount of a compound described herein or pharmaceutically acceptable salt thereof, or a pharmaceutical composition comprising the compound described herein or pharmaceutically acceptable salt thereof. In some embodiments, one or more compounds may be combined in the same composition for any of the methods disclosed herein.

The present invention also provides methods for killing or inhibiting growth of a cancer cell comprising contacting the cancer cell with an effective amount of a compound or pharmaceutically acceptable salt thereof, or a pharmaceutical composition comprising the compound or salt.

Thus, the compounds can be used as anti-cancer and anti-tumor agents, e.g., the compounds can kill or inhibit the growth of cancer cells. The compounds can also be used in methods of reducing cancer in an animal, or in methods of treating or preventing the spread or metastasis of cancer in an animal, or in methods of treating an animal afflicted with cancer. The compounds can also be used in methods of killing or inhibiting the growth of a cancer cell, or in methods of inhibiting tumor growth. In some embodiments, the compounds of the invention can act directly on the cancer cell rather than by acting indirectly such as by inhibition of angiogenesis.

The compounds can be tested for anti-cancer activity by methods known to those of skill in the art. Examples of anti-cancer assays include, but are not limited to, standard cell viability assays, such as the XTT assay, or by metabolic activity assays.

Generally, cancer refers to any malignant growth or tumor caused by abnormal and uncontrolled cell division; it may spread to other parts of the body through the lymphatic system or the blood stream. Cancers include both solid tumors and blood-borne tumors. Cancers that are treatable are broadly divided into the categories of carcinoma, lymphoma and sarcoma. Examples of carcinomas include, but are not limited to: adenocarcinoma, acinic cell adenocarcinoma, adrenal cortical carcinomas, alveoli cell carcinoma, anaplastic carcinoma, basaloid carcinoma, basal cell carcinoma, bronchiolar carcinoma, bronchogenic carcinoma, renaladinol carcinoma, embryonal carcinoma, anometroid carcinoma, fibrolamolar liver cell carcinoma, follicular carcinomas, giant cell carcinomas, hepatocellular carcinoma, intraepidermal carcinoma, intraepithelial carcinoma, leptomanigio carcinoma, medullary carcinoma, melanotic carcinoma, menigual carcinoma, mesometonephric carcinoma, oat cell carcinoma, squamal cell carcinoma, sweat gland carcinoma, transitional cell carcinoma, and tubular cell carcinoma. Sarcomas include, but are not limited to: amelioblastic sarcoma, angiolithic sarcoma, botryoid sarcoma, endometrial stroma sarcoma, ewing sarcoma, fascicular sarcoma, giant cell sarcoma, granulositic sarcoma, immunoblastic sarcoma, juxaccordial osteogenic sarcoma, coppices sarcoma, leukocytic sarcoma (leukemia), lymphatic sarcoma (lympho sarcoma), medullary sarcoma, myeloid sarcoma (granulocitic sarcoma), austiogenci sarcoma, periosteal sarcoma, reticulum cell sarcoma (histiocytic lymphoma), round cell sarcoma, spindle cell sarcoma, synovial sarcoma, and telangiectatic audiogenic sarcoma. Lymphomas include, but are not limited to: Hodgkin's disease and lymphocytic lymphomas, such as Burkitt's lymphoma, NPDL, NML, NH and diffuse lymphomas.

Thus, examples of cancers that can be treated using the compounds described herein include, but are not limited to, Hodgkin's disease, non-Hodgkin's lymphomas, acute lymphocytic leukemia, multiple myeloma, breast carcinomas, ovarian carcinomas, lung carcinomas, Wilms' tumor, testicular carcinomas, soft-tissue sarcomas, chronic lymphocytic leukemia, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis fungoides, head and neck carcinomas, osteogenic sarcoma, pancreatic carcinomas, acute granulocytic leukemia, hairy cell leukemia, rhabdomyosarcoma, Kaposi's sarcoma, genitourinary carcinomas, thyroid carcinomas, esophageal carcinomas, malignant hypercalcemia, renal cell carcinomas, endometrial carcinomas, polycythemia vera, essential thrombocytosis, adrenal cortex carcinomas, skin cancer, and prostatic carcinomas.

In some embodiments, the cancer is lung cancer (such as non-small cell lung cancer), breast cancer, prostate cancer, ovarian cancer, testicular cancer, colon cancer, renal cancer, bladder cancer, pancreatic cancer, glioblastoma, neuroblastoma, sarcomas such as Kaposi's sarcoma and Ewing's sarcoma, hemangiomas, solid tumors, blood-borne tumors, rhabdomyosarcoma, CNS cancer (such as brain cancer), retinoblastoma, neuroblastoma, leukemia, melanoma, kidney or renal cancer, and osteosarcoma.

The compounds can be used in methods of killing or inhibiting the growth of cancer cells, either in vivo or in vitro, or inhibiting the growth of a cancerous tumor.

Angiogenesis is also associated with blood-borne tumors, such as leukemias, any of various acute or chronic neoplastic diseases of the bone marrow in which unrestrained proliferation of white blood cells occurs, usually accompanied by anemia, impaired blood clotting, and enlargement of the lymph nodes, liver and spleen. It is believed to that angiogenesis plays a role in the abnormalities in the bone marrow that give rise to leukemia-like tumors.

Suitable angiogenesis-mediated disorders that may be treated or prevented with the compounds described herein include, but are not limited to, tumors and cancer associated disorders (e.g., retinal tumor growth), benign tumors (e.g., hemangiomas, acoustic neuromas, neurofibromas, trachomas, and pyogenic granulomas), solid tumors, blood borne tumors (e.g., leukemias, angiofibromas, and Kaposi sarcoma), tumor metastases, and other cancers which require neovascularization to support tumor growth, ocular neovascular-disorders (e.g., diabetic retinopathy, macular degeneration, retinopathy of prematurity, neovascular glaucoma, corneal graft rejection, and other ocular angiogenesis-mediated disorders), inflammatory disorders (e.g., immune and non-immune inflammation, rheumatoid arthritis, chronic articular rheumatism, inflammatory bowel diseases, psoriasis, and other chronic inflammatory disorders), endometriosis, other disorders associated with inappropriate or inopportune invasion of vessels (e.g., retrolental fibroplasia, rubeosis, and capillary proliferation in atherosclerotic plaques and osteoporosis), Osler-Webber Syndrome, myocardial angiogenesis, plaque neovascularization, telangiectasia, hemophiliac joints, and wound granulation. Other diseases in which angiogenesis plays a role in the maintenance or progression of the pathological state are known to those skilled in the art and are similarly intended to be included within the meaning of the term angiogenesis-mediated used herein.

Other diseases, conditions, or disorders include blindness, corneal transplant, myopic degeneration, complications related to AIDS, arthritis, scleroderma, stroke, heart disease, ulcers and infertility. For example, but not limited to, cancers, inflammatory arthritis (such as rheumatoid arthritis), diabetic retinopathy, as well as other neovascular diseases of the eye (or example, corneal neovascularization, neovascular glaucoma, retrolental fibroblasia and macular degeneration), arteriovenous malformations, conditions of excessive bleeding (menorrhagia), and angiofibroma.

The anti-angiogenic compositions provided herein are also useful in the treatment of diseases of excessive or abnormal stimulation of endothelial cells. These diseases include, but are not limited to, intestinal adhesions, Crohn's disease, atherosclerosis, scleroderma, and hypertrophic scars (i.e., keloids).

In some embodiments, the compounds are used in conjunction with other angiogenesis inhibitors. Angiogenic inhibitors are known in the art and can be prepared by known methods. For a description of angiogenic inhibitors and targets see, for example, Chen et al., Cancer Res. 55:4230-4233 (1995), Good et al., Proc. Natl. Acad. Sci. USA 87:6629-6628 (1990), O'Reilly et al., Cell 79:315-328 (1994), Parangi et al., Proc. Natl. Acad. Sci. USA 93:2002-2007 (1996), Rastinejad et al., Cell 56:345-355 (1989), Gupta et al., Proc. Natl. Acad. Sci. USA 92:7799-7803 (1995), Maione et al., Science 247:77-79 (1990), Angiolillo et al., J. Exp. Med. 182:155-162 (1995), Strieter et al., Biochem. Biophys. Res. Comm 210:51-57 (1995); Voest et al., J. Natl. Cancer Inst. 87:581-586 (1995), Cao et al., J. Exp. Med. 182:2069-2077 (1995), and Clapp et al., Endocrinology 133:1292-1299 (1993), which are hereby incorporated by reference in their entirety. For a description of additional angiogenic inhibitors see, for example, Blood et al., Bioch. Biophys Acta., 1032:89-118 (1990), Moses et al., Science, 248:1408-1410 (1990), Ingber et al., Lat Invest., 59:44-51 (1988), and U.S. Pat. Nos. 5,092,885 and 5,112, 946, which are hereby incorporated by reference in their entirety.

In another embodiment, the compounds are used in conjunction with other therapies, such as standard anti-inflammatory therapies, standard ocular therapies, standard dermal therapies, radiotherapy, tumor surgery, and conventional chemotherapy directed against solid tumors and for the control of establishment of metastases. The administration of the angiogenesis inhibitor is typically conducted during or after chemotherapy at time where the tumor tissue should respond to toxic assault by inducing angiogenesis to recover by the provision of a blood supply and nutrients to the tumor tissue. Additionally, the compounds are administered after surgery where solid tumors have been removed as a prophylaxis against metastasis. Cytotoxic or chemotherapeutic agents are those known in the art such as aziridine thiotepa, alkyl sulfonate, nitrosoureas, platinum complexes, NO classic alkylators, folate analogs, purine analogs, adenosine analogs, pyrimidine analogs, substituted urea, antitumor antibiotics, microtubulle agents, and asprignase.

The present invention also provides methods for inhibiting angiogenesis-mediated processes alone or in combination with other existing anti-inflammatory, anti-angiogenesis, anti-cancer, and ocular therapies.

The present invention also provides methods of modulating an immune response in a mammal comprising administering to the mammal in need thereof a therapeutically effective amount of a compound described herein or a pharmaceutically acceptable salt thereof, or a pharmaceutical composition comprising a compound described herein or a pharmaceutically acceptable salt thereof.

For the above-mentioned methods, the method of modulating an immune response comprises increasing or decreasing the production of a cytokine and/or chemokine, which may result in an increase or decrease of an immune response. In some embodiments, the cytokine is chosen from TNFalpha, IL-1Beta, IL-1alpha, IL-8, IL-6, IL-10, IL-11, IL-12, TGF-Beta, and IFNgamma. In some embodiments, the cytokine is chosen from TNFalpha, IL-6, and IL-10. In some embodiments, the chemokine is chosen from a CC chemokine, a CXC chemokine, a C chemokine, and a CX3C chemokine. CC chemokines include, but are not limited to, CCL1, CCL2, CCL3, CCL4, CCL5, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28. In some embodiments, the CC chemokine is chosen from CCL2 and CCL5. CXC chemokines include, but are not limited to, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17. In some embodiments, the CXC chemokine is chosen from CXCL1, CXCL8, and CXCL13. C chemokines include, but are not limited to, XCL1 and XCL2. CX3C chemokines include, but are not limited to, CX3CL1. In some embodiments, more than one cytokine and/or chemokine is increased or decreased. An increase or decrease in a cytokine and/or chemokine can be either at the nucleic acid level, the protein level, or the activity of the protein. In some embodiments, the compounds disclosed herein may serve as an adjuvant for the induction of an immune response in, for example, vaccines against, for example, hepatitis and influenza.

In some embodiments, the immune response is against an oral pathogen. In some embodiments, the oral pathogen is chosen from: *Aggregatibacter* spp. such as, for example, *Aggregatibacter actinomycetemcomitans*; *Porphyromonas* spp. such as, for example, *Porphyromonas gingivalis*; *Streptococcus* spp. such as, for example, *Streptococcus sanguis* and *Streptococcus mutans*, *Candida* spp. such as, for example, *Candida albicans*, *Candida glabrata*, *Candida krusei*, *Candida dubliniensis*, *Candida parapsilosis*, and *Candida tropicalis*; *Actinomyces* spp. such as, for example, *Actinomyces viscosus*; and *Lactobacillus* spp. such as, for example, *Lactobacillus casei*.

In some embodiments, the immune response is against a bacterial pathogen. In some embodiments, the bacterial pathogen is chosen from: *Staphylococcus* spp., such as, for example, *Staphylococcus aureus*, methicillin-resistant *Staphylococcus aureus*, and *Staphylococcus epidermidis*; *Streptococcus* spp. such as, for example, *Streptococcus pneumoniae*, *Streptococcus pyogenes*, and *Streptococcus viridans*; *Escherichia* spp. such as, for example, *E. coli*; *Enterococcus* spp. such as, for example, *Enterococcus faecalis* and *Enterococcus faecium*; *Psuedomonas* spp. such as, for example, *Pseudomonas aeruginosa*; *Acinetobacter* spp. such as, for example, *A. baumannii*; *Haemophilus* spp. such as, for example, *Haemophilus influenzae*; *Serratia* spp. such as, for example, *Serratia marcescens*; *Moraxella* spp. such as, for example, *Moraxella catarrhalis*; *Klebsiella* spp. such as, for example, *Klebsiella pneumoniae*; *Proteus* spp. such as, for example, *Proteus vulgaris* and *Proteus mirabilis*; *Bacteroides* spp. such as, for example, *Bacteroides fragalis*; *Clostridium* spp. such as, for example, *Clostridium difficile* and *Clostridium perfringens*; and *Propionibacterium* spp. such as, for example, *Propionibacterium acnes*.

In some embodiments, the modulation of an immune response increases or decreases or eliminates an immune response. In some embodiments, the methods of the present invention can increase or decrease an immune response by greater than about 50%, greater than about 60%, greater than about 70%, greater than about 80%, greater than about 85%, greater than about 88%, greater than about 90%, greater than about 92%, greater than about 95%, greater than about 98%, greater than about 99%, greater than about 99.2%, greater than about 99.5%, greater than about 99.8%, or greater than about 99.9%. The % increase or decrease in an immune response can be measured by routine immune assays such as, for example, measuring the amount of a particular cytokine produced (at the protein level, nucleic acid level, or protein activity level).

In some embodiments, the modulation, increase or decrease, of the immune response takes place in an epithelial cell and/or a myeloid-derived cell. In some embodiments, the cell is a T cell, B cell, or monocyte such as a macrophage. In some embodiments, the cell is a neutrophil.

The present invention also provides methods for antagonizing an anticoagulant agent (such as heparin including, for example, unfractionated heparin, low molecular weight heparin, synthetically modified heparin, and low molecular heparin derivatives) comprising administering to a mammal a compound described herein, or a pharmaceutically acceptable salt thereof, or a pharmaceutical composition comprising the same. The present invention provides methods for antagonizing an anticoagulant effect of heparin in an animal comprising administering to the animal in need thereof an effective amount of a compound, or a pharmaceutically acceptable salt thereof, or a pharmaceutical composition comprising the same. The present invention also provides methods for antagonizing the anticoagulant effect of heparin comprising contacting the heparin with an effective amount of a compound, or a pharmaceutically acceptable salt thereof, or a pharmaceutical composition comprising the same. The present invention also provides methods for inhibiting anti-Factor Xa comprising administering to a mammal a compound described herein, or a pharmaceutically acceptable salt thereof, or a pharmaceutical composition comprising the same.

The compounds may be useful as anti-heparin agents (i.e., antagonizing the anticoagulant effect of an anticoagulant such as unfractionated heparin, low molecular heparin, and a derivative of heparin or low molecular heparin) in a number of applications. For example, compounds may be used therapeutically to antagonize the anticoagulant effect of an anticoagulant agent (for example unfractionated heparin, low molecular heparin, or a derivative of heparin or low molecular heparin), present in a mammal. The anticoagulant effect of the anticoagulant agent (for example unfractionated heparin, low molecular heparin, or a derivative of heparin or low molecular heparin) present in a mammal may be antagonized by administering to the mammal an effective amount of a compound or a pharmaceutically acceptable salt thereof, or a pharmaceutical composition comprising the same.

Natural heparins have polysaccharide chains of varying lengths, or molecular weights (including salts). Natural heparin has polysaccharide chains of molecular weight from about 5000 to over 40,000 Daltons. Low-molecular-weight heparins (LMWHs), in contrast, are fragments of unfractionated heparins, and have short chains of polysaccharide (including salts). LMWHs have an average molecular weight of less than 8000 Da and at least 60% of all chains have a molecular weight less than 8000 Da.

In some embodiments, the methods of the present invention can effectively antagonize the anticoagulant effect of unfractionated heparin. In some embodiments, the methods of the present invention can effectively antagonize the anticoagulant effect of a low molecular weight heparin such as enoxaparin. In some embodiments, the methods of the present invention can effectively antagonize the anticoagulant effect of a synthetically modified heparin derivative such as fondaparinux.

In some embodiments, the method of the present invention can antagonize greater than about 50%, greater than about 60%, greater than about 70%, greater than about 80%, greater than about 85%, greater than about 88%, greater than about 90%, greater than about 92%, greater than about 95%, greater than about 98%, greater than about 99%, greater than about 99.2%, greater than about 99.5%, greater than about 99.8%, or greater than about 99.9% of the anticoagulant effect of heparin (including, for example, unfractionated heparin, low molecular weight heparin, and synthetically modified heparin or low molecular heparin derivatives). In some embodiments, the compound or salt thereof used in the present invention antagonizes the anticoagulant effect of an anticoagulant agent (including, for example, unfractionated heparin, low molecular weight heparin, and synthetically modified heparin or low molecular heparin derivatives) more effectively than protamine.

In some embodiments, the compound or salt thereof used in the present invention binds to heparin (including, for example, unfractionated heparin, low molecular weight heparin, and synthetically modified heparin or low molecular heparin derivatives) with an $EC_{50}$ of less than about 100, less than about 90, less than about 80, less than about 70, less than about 60, less than about 50, less than about 40, less than about 30, less than about 20, less than about 15, less than about 10, less than about 5, less than about 2, less than about 1, less than about 0.9, less than about 0.8, less than about 0.7, less than about 0.6, less than about 0.5, less than about 0.4, less than about 0.3, less than about 0.2, less than about 0.1, less than about 0.09, less than about 0.08, less than about 0.07, less than about 0.06, less than about 0.05, less than about 0.02, less than about 0.01, less than about 0.001, less than about 0.0001, or less than about 0.00001 µg/mL.

In some embodiments, the compound or salt thereof used in the present invention binds to heparin (including, for example, unfractionated heparin, low molecular weight heparin, and synthetically modified heparin or low molecular heparin derivatives) with an $EC_{50}$ less than about 100, less than about 90, less than about 80, less than about 70, less than about 60, less than about 50, less than about 40, less than about 30, less than about 20, less than about 15, less than about 10, less than about 5, less than about 2, less than about 1, less than about 0.9, less than about 0.8, less than about 0.7, less than about 0.6, less than about 0.5, less than about 0.4, less than about 0.3, less than about 0.2, less than about 0.1, less than about 0.09, less than about 0.08, less than about 0.07, less than about 0.06, less than about 0.05, less than about 0.02, less than about 0.01, less than about 0.001, less than about 0.0001, or less than about 0.00001 µM.

In some embodiments, the compound or salt thereof used in the present invention binds to heparin (including, for example, unfractionated heparin, low molecular weight heparin, and synthetically modified heparin or low molecular heparin derivatives) with an $EC_{50}$ of less than that of protamine (including protamine salt such as protamine sulfate).

In some embodiments, the compound or salt thereof used in the present invention can effectively antagonize the anticoagulant effect of an anticoagulant agent (including, for example, unfractionated heparin, low molecular weight heparin, and synthetically modified heparin or low molecular heparin derivatives) with a dosage of less than about 10, less than about 9, less than about 8, less than about 7, less than about 6, less than about 5, less than about 4, less than about 3, less than about 2, or 1 equivalent (by weight) to the heparin.

In some embodiments, the compound or salt thereof used in the present invention can effectively antagonize the anticoagulant effect of an anticoagulant agent (including, for example, unfractionated heparin, low molecular weight heparin, and synthetically modified heparin or low molecular heparin derivatives) through antagonizing the AT activity of the heparin, the anti-factor Xa activity of the heparin, the anti-factor IIa activity of the heparin, or any combination thereof.

In some embodiments, the method of the present invention can rapidly antagonize the anticoagulant effect of an anticoagulant agent (including, for example, unfractionated heparin, low molecular weight heparin, and synthetically modified heparin or low molecular heparin derivatives), for example, antagonize (or neutralize) greater than about 40%, greater than about 50%, greater than about 60%, greater than about 70%, greater than about 80, greater than about 90%, greater than about 95%, greater than about 98%, greater than about 99%, or greater than about 99.5% of the anticoagulant effect of the heparin in less than about 30, less than about 20, less than about 15, less than about 10, less than about 8, less than about 5, less than about 2, less than about 1, less than about 0.9, less than about 0.8, less than about 0.7, less than about 0.6, less than about 0.5, less than about 0.4, less than about 0.3, less than about 0.2, or less than about 0.1 minute.

In some embodiments, after the anticoagulant effect of heparin in a mammal during anticoagulant therapy is antagonized (for example, by 80% or more) by methods of the present invention, a new dose of heparin can effectively restore the anticoagulant therapy, for example, greater than about 80% or 90% of the anticoagulant effect of heparin of the new dose can be achieved in less than about 20, less than about 15, less than about 10, less than about 8, less than about 5, less than about 2, or less than about 1 minute.

In some embodiments, the present invention provides methods for antagonizing the anticoagulant effect of heparin with low or no toxicity, hemodynamic and/or hematological adverse side effects. In some embodiments, the methods have low or no side effects associated with use of protamine such as one or more selected from systemic vasodilation and hypotension, bradycardia, pulmonary artery hypertension, pulmonary vasoconstriction, thrombocytopenia, and neutropenia. In some embodiments, the methods have low or no side effects associated with use of protamine such as anaphylactic-type reactions involving both nonimmunogenic and immunogenic-mediated pathways. In some embodiments, the compounds and/or the salts have low or no antigenicity and/or immunogenicity comparing to those of protamine molecules. In some embodiments, the present methods for antagonizing the anticoagulant effect of heparin can preserve hemodynamic stability, such as during and/or following infusion.

In some embodiments, the present methods for antagonizing the anticoagulant effect of heparin can be used in a patient who receives anticoagulant therapy, for example, who uses fondaparinux for the prophylaxis of deep vein thrombosis following hip repair/replacement, knee replacement and abdominal surgery; uses UFH or LMWH for coronary bypass surgery; or or uses UFH or LMWH during and/or following blood infusion.

In some embodiments, the unfractionated heparin is antagonized. In some embodiments, the low molecular weight heparin is antagonized. In some embodiments, the low molecular weight heparin is enoxaparin, reviparin, or tinzaparin. In some embodiments, the heparin/low molecular weight heparin derivative is antagonized. In some embodiments, the heparin/low molecular weight heparin derivative is fondaparinux. In some embodiments, the mammal is a human.

In some embodiments, the weight ratio of the compound, or pharmaceutically acceptable salt thereof, to be administered, to the unfractionated heparin, low molecular weight heparin, or heparin/low molecular weight heparin derivative is less than about 10:1. In some embodiments, the weight ratio of the compound, or pharmaceutically acceptable salt thereof, to be administered, to the unfractionated heparin, low molecular weight heparin, or heparin/low molecular weight heparin derivative is less than about 5:1, less than about 10:1, less than about 25:1, or less than about 30:1. In some embodiments, the weight ratio of the compound, or pharmaceutically acceptable salt thereof, to be administered, to the unfractionated heparin, low molecular weight heparin, or heparin/low molecular weight heparin derivative is from about 1:1 to about 5:1, from about 1:1 to about 10:1, or from about 1:1 to about 25:1.

The present invention also provides compounds of any of the preceding embodiments, or a pharmaceutical composition comprising said compound, for antagonizing unfractionated heparin, low molecular weight heparin, or a heparin/low molecular weight heparin derivative in a mammal.

The present invention also provides for use of compounds of any of the preceding embodiments, or a pharmaceutical composition comprising said compound, for antagonizing unfractionated heparin, low molecular weight heparin, or a heparin/low molecular weight heparin derivative in a mammal.

The present invention also provides for use of compounds of any of the preceding embodiments, or a pharmaceutical composition comprising said compound, in the manufacture of a medicament for antagonizing unfractionated heparin, low molecular weight heparin, or a heparin/low molecular weight heparin derivative in a mammal.

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1

Synthesis of Compounds

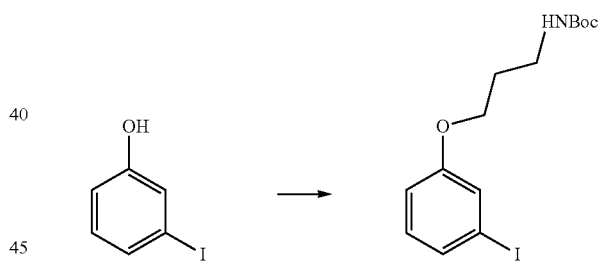

General Phenol Alkylation Method:
tert-Butyl(3-(3-iodophenoxyl)propyl)carbamate

To the solution of 3-iodophenol (500 mg, 2.27 mmol) in DMF (3 mL) was added $K_2CO_3$ (770 mg, 5.55 mmol), and the resultant mixture was allowed to stir for 20 minutes, followed by the addition of tert-butyl(3-bromopropyl)carbamate (648 mg, 2.70 mmol). The reaction mixture was heated to 45° C. with stilling overnight, and then cooled to room temperature. The solvent was removed under the reduced pressure and the residue was taken up to ethyl acetate (120 mL), washed with citric acid (aq., 10%, 50 mL), water (50 mL), and brine successively. The solution was dried over $Na_2SO_4$, concentrated under reduced pressure, and then purified with flash column chromatography (ethyl acetate:hexane=1:5) to yield the product (680 mg, 80%) as a white solid.

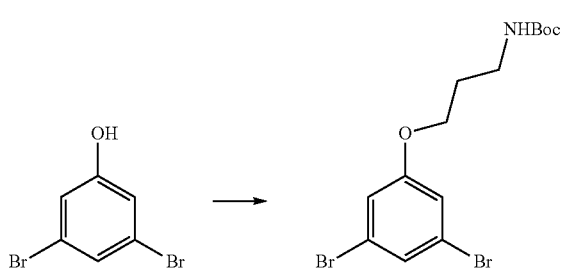 [SMILES: Oc1cc(Br)cc(Br)c1 ; CC(C)(C)OC(=O)NCCCOc1cc(Br)cc(Br)c1]

tert-butyl(3-(3,5-dibromophenoxyl)propyl)carbamate

Following to the general phenol alkylation method, tert-butyl(3-(3,5-dibromophenoxyl)propyl)-carbamate was synthesized from 3,5-dibromophenol and the yield is 94%.

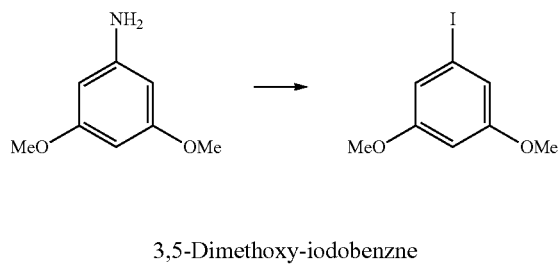

3,5-Dimethoxy-iodobenzne 3,5-Dimethoxyaniline (1.0 g, 6.5 mmol) was dissolved in 10 mL of water and cooled to −5~−10° C. To the resultant solution was added the concentrated $H_2SO_4$ (1.0 mL) to added dropwise, followed by the addition of $NaNO_2$ solution (0.54 g in 2 mL water) at the same temperature. The reaction mixture was allowed to stir for 20 minutes and then 5 mL of ether and KI solution (3.25 g in 2 mL water) were added successively. The reaction solution was gradually warmed to room temperature and allowed to stir overnight. The reaction mixture was extracted with ether (30 mL×2) and the combined ethereal layers was washed with $Na_2S_2O_3$ solution (20% w/v), HCl (aq., 1M), NaOH (aq., 2M) and brine successively. The separated red solution was dired over $MgSO_4$, concentrated under reduced pressure and purified by flash column chromatography (ethyl acetate:hexane=1:19) to yield the product (1.1 g, 64%) as as off-white solid.

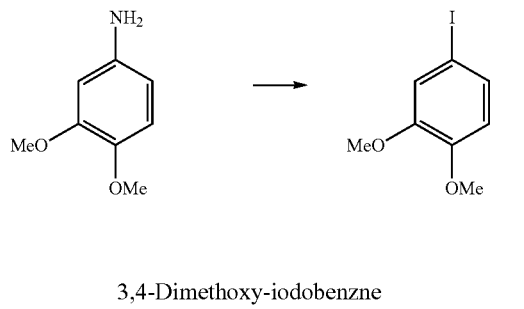

3,4-Dimethoxy-iodobenzne

Following the preparation of 3,5-dimethoxy-iodobenzne, 3,4-dimethoxy-iodobenzne was synthesized from 3,4-dimethoxyaniline in 85% yield.

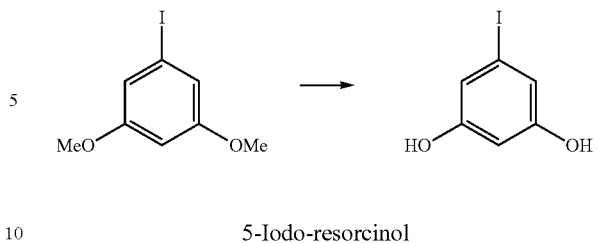

5-Iodo-resorcinol

To a 25 mL round-bottom flask, were added 3,5-dimethoxy-iodobenzne (0.50 g) and HI (aq., 47%). The resultant mixture was reflux for 48 hours, then cooled to room temperature and partitioned in water/ether (50 mL/50 mL). The aqueous layer was separated and extracted with fresh ether until it became colorless and clear. The ethereal layers were combined and washed with $NaHCO_3$ (saturated, aq.), water and brine. The solution was dried over $Na_2SO_4$, concentrated under reduced pressure and purified by column chromatography (ethyl acetate:hexane=1:3) to yield the product (0.25 g, 57%) as a sticky solid.

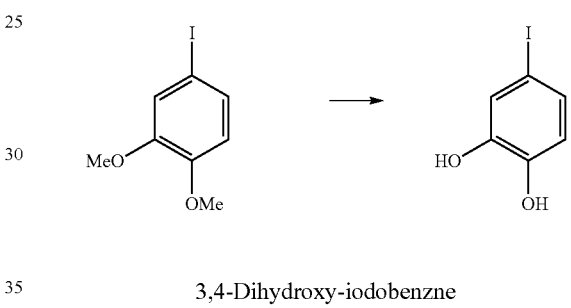

3,4-Dihydroxy-iodobenzne

Following the demethylation procedure of making 5-Iodo-resorcinol, 3,4-dihydroxy-iodobenzene was synthesized from 3,4-dimethoxy-iodobenzene in 81% yield.

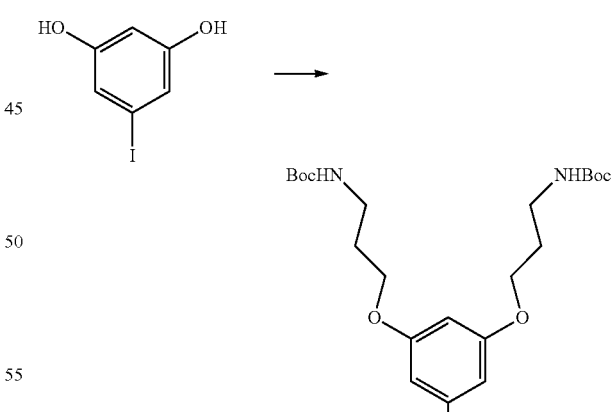

Di-tert-butyl(((5-bromo-1,3-phenylene)bis(oxy))bis(propane-3,1-diyl))dicarbamate Following the general phenol alkylation method, di-tert-butyl(((5-bromo-1,3-phenylene)bis(oxy))bis(propane-3,1-diyl)dicarbamate was synthesized from 5-iodo-resorcinol in 97% yield.

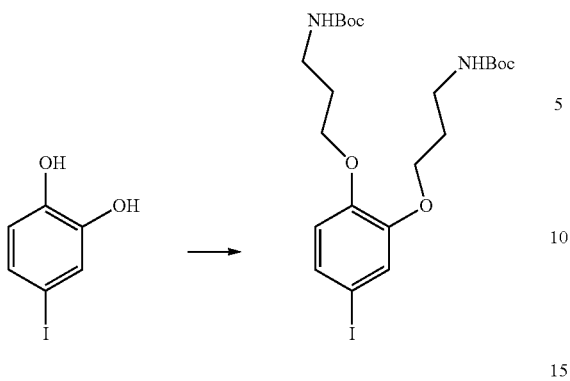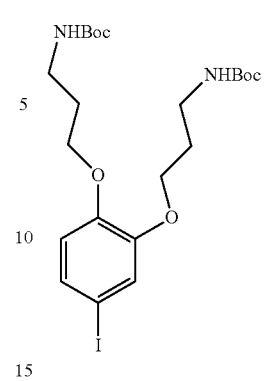

Di-tert-butyl(((4-iodo-1,2-phenylene)bis(oxy))bis(propane-3,1-diyl))dicarbamate

Following the general phenol alkylation method, di-tert-butyl(((4-iodo-1,2-phenylene)bis(oxy))bis(propane-3,1-diyl)dicarbamate was synthesized from 3,4-dihydroxy-iodobenzene in 99% yield.

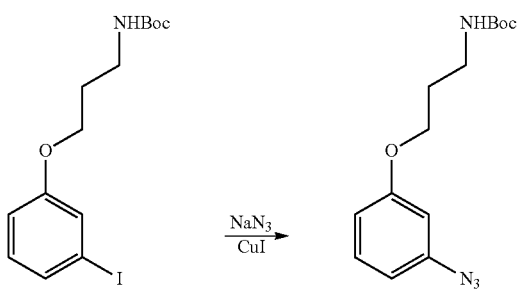 [SMILES: CC(C)(C)OC(=O)NCCCOc1cccc(I)c1 ; "CuI" ; CC(C)(C)OC(=O)NCCCOc1cccc(N=[N+]=[N-])c1 ; "NaN3"]

General Method of Making Azido Compounds:
tert-Butyl(3-(3-azidophenoxyl)propyl) carbamate Tert-butyl(3-(3-iodophenoxyl)propyl)carbamate (1.00 g, 2.96 mmol), CuI (58 mg, 0.30 mmol), L-proline (69 mg, 0.60 mmol), NaN₃ (384 mg, 5.90 mmol) and NaOH (24 mg 0.60 mmol) were added into degassed DMSO (6 mL) under N₂ and the resultant mixture was sealed and heated to 90° C. and allowed to keep at this temperature with stilling for 24 hours. Then mixture solution was cooled to room temperature, poured into 400 mL water, and extracted with ethyl acetate (150 mL×3). The combined organic layer was washed with water and brine, then dried over Na₂SO₄, concentrated under reduced pressure to yield oily crude product. The crude compound was purified by flash column chromatography (ethyl acetate:hexane=1:5) to yield the product (0.45 g, 60%) as a yellowish sticky solid.

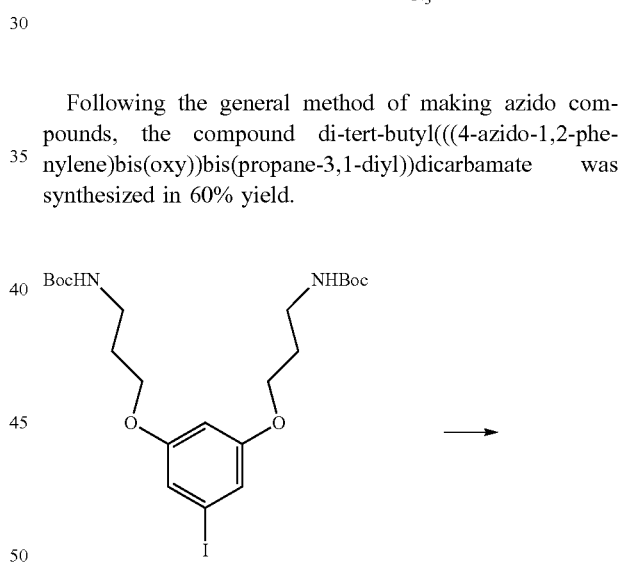

Following the general method of making azido compounds, the compound di-tert-butyl(((4-azido-1,2-phenylene)bis(oxy))bis(propane-3,1-diyl))dicarbamate was synthesized in 60% yield.

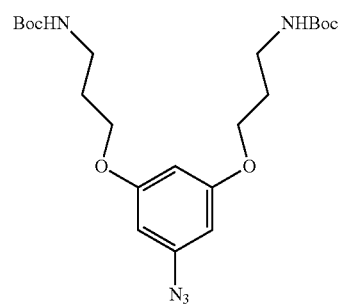

Following the general method of making azido compounds, the compound di-tert-butyl(((5-azido-1,3-phenylene)bis(oxy))bis(propane-3,1-diyl))dicarbamate was synthesized in 59% yield.

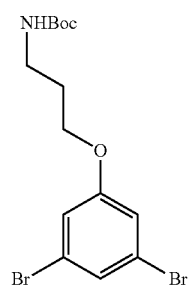

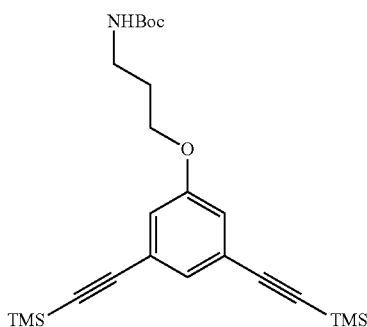

General Sonogashira Reaction to Introduce Two (trimethylsilyl)ethynyl Groups on Aromatic Cores tert-butyl(3-(3,5-bis((trimethylsilyl)ethynyl)phenoxy)propyl)carbamate To the solution of tert-butyl(3-(3,5-dibromophenoxyl)propyl)carbamate (2.20 g, 5.40 mmol) in dried THF (80 mL), were added trimethylsilylacetylene (6.1 mL, 43 mmol), CuI (103 mg, 0.54 mmol), Pd(PPh$_3$)$_4$ (624 mg, 0.54 mmol) and triethylamine (18.8 mL, 135 mmol) successively under N$_2$. The resultant mixture was shielded from light by aluminum foil wrap and heated to 55° C. with stirring for 18 hours. The reaction mixture was concentrated by removing the solvent under reduced pressure; the residue was taken up to diethyl ether, washed with water and dried over Na$_2$SO$_4$. After removal of solvent under reduced pressure, the residue was purified by flash column chromatography (ethyl acetate:hexane=1:6) to yield the product (2.2 g, 93%) as an off-white solid.

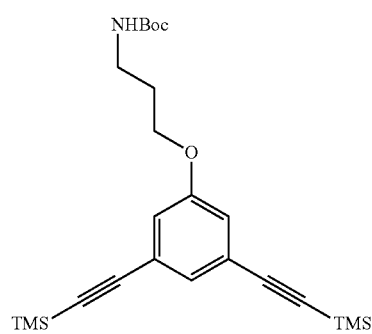

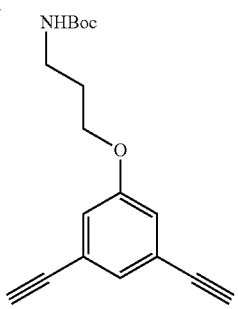

Tert-butyl(3-(3,5-diethynylphenoxy)propyl)carbamate

To the solution of tert-butyl(3-(3,5-bis((trimethylsilyl)ethynyl)phenoxy)propyl) carbamate (2.05 g, 4.60 mmol) in methanol/acetone (40 mL/80 mL), was added NaOH (75 mg, 1.84 mmol), and the resultant solution was allowed to stir at room temperature for 2 hours, followed by the removal of the solvent under reduced pressure. The residue was taken up to ethyl acetate, washed with water until the of aqueous layer pH<7, washed with brine and dried over MgSO$_4$. The solvent was then removed and the crude was purified through a silica plug (ethyl acetate:hexane=1:5.5) to yield the pure product (1.03 g, 75%) as a white solid.

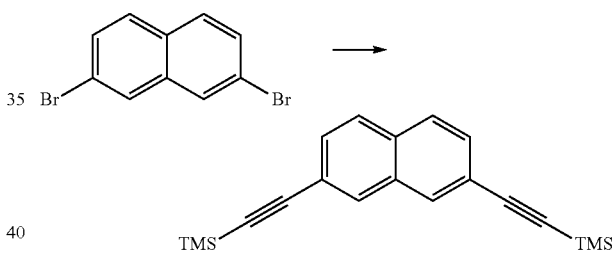

2,7-Bis((trimethylsilyl)ethynyl)naphthalene

Following the General Sonogashira reaction procedure, the product 2,7-bis((trimethylsilyl)ethynyl)naphthalene were synthesized from 2,7-dibromonaphthalene in 97% yield.

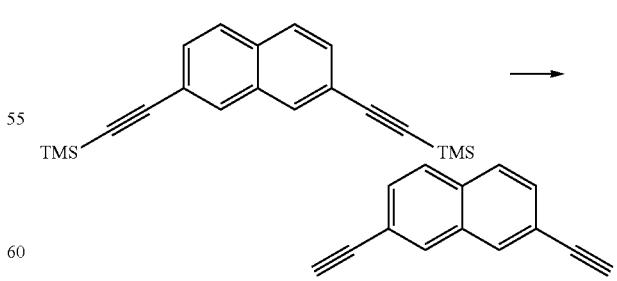

2,7-Diethynylnaphthalene

To the solution of 2,7-bis((trimethylsilyl)ethynyl)naphthalene (515 mg, 1.02 mmol) in THF/methanol (5 mL/5 mL), was added KF.2H$_2$O (752 mg, 8.00 mmol). The resultant reaction mixture was allowed to stir for 2 hours at room temperature. After removal of the solvent, the residue of reaction mixture was taken up to ethyl acetate, washed with water, and dried over MgSO$_4$. The solvent was evaporated under reduced pressure to yield the product (310 mg, 91%) as a slightly reddish solid.

Example 1A

Synthesis of Compound 107

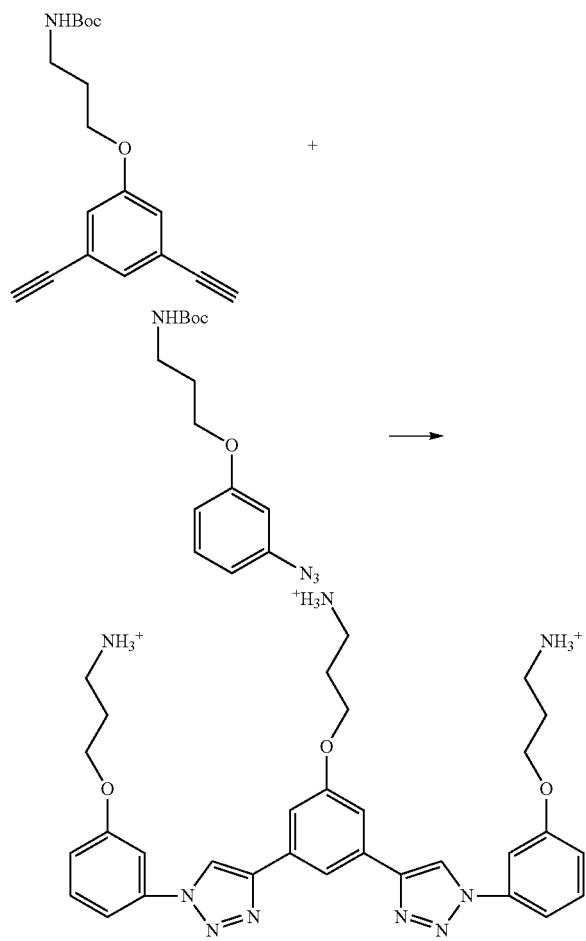

General Click Chemistry and Deprotection Procedure

To the solution of 2,7-diethynylnaphthalene (133 mg, 0445 mmol) and tert-butyl(3-(3-azidophenoxyl)propyl)carbamate (247 mg, 0.980 mmol) in t-BuOH (13 mL), were added sodium ascorbate (22.0 mg, 0.111 mmol) and a solution of CuSO$_4$.5H$_2$O (30.0 mg, 0.111 mmol) in water (13 mL). The reaction mixture was allowed to stir for 16 hours at room temperature and poured into water (300 mL). The resultant cloudy aqueous solution was extracted with ethyl acetate (60 mL×3), the organic layer were combined, washed with water, brine, and then dried over Na$_2$SO$_4$. After removal of the solvent under reduced pressure, the residue was purified by flash column chromatography (ethyl acetate:hexane=3:2) to yield the intermediate (320 mg) as an off-white solid. The intermediate was then added into TFA/dicloromethane (2 mL/4 mL) and the resultant solution was stirred for 2 hours at room temperature. The solvent was removed under reduced pressure, and the residue was washed with small amount of methanol (2 mL) for several times. The methanol was evaporated to yield Compound 107 (343 mg, 83%) as an off-white solid.

Example 1B

Synthesis of Compound 106

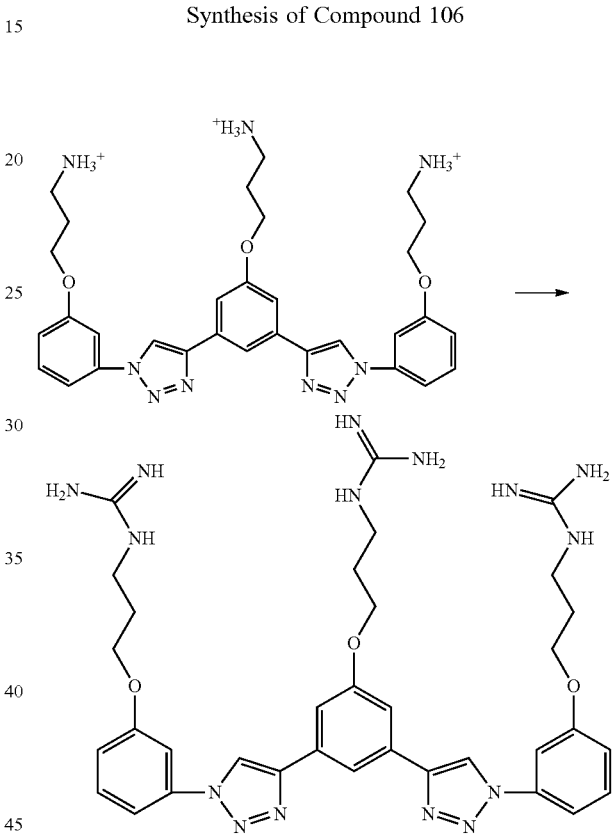

General Method of Converting Amino Groups to Guanidine Groups

To the solution of Compound 107 (130 mg, 0.140 mmol) and N,N-diisopropyl-ethylamine (0.29 mL, 1.68 mmol) in CH$_3$CN/THF (2 mL/4 mL), was added N,N'-di-Boc-1H-pyrazole-1-carboxamindine (200 mg, 0.630 mmol) at 0° C. The reaction mixture was allowed to gradually warm to room temperature and stirred overnight. The solvent was removed under reduced pressure and residue was taken up to ethyl acetate (50 mL), washed with citric acid solution (aq., 10%), NaHCO$_3$ solution (aq., saturated), and brine successively. The organic layer was separated and dried with Na$_2$SO$_4$, and the solvent was evaporated, followed by the purification with column chromatography to yield the intermediate (140 mg) as colorless oil. The intermediate was dissolved in TFA/DCM (1 mL/2 mL) and the solution was allowed to stir for 2 hours before removal of the solvent. The residue was washed with methanol for several times and dried in vacuum to yield Compound 106 (126 mg, 85%).

Example 1C
Synthesis of Compound 105
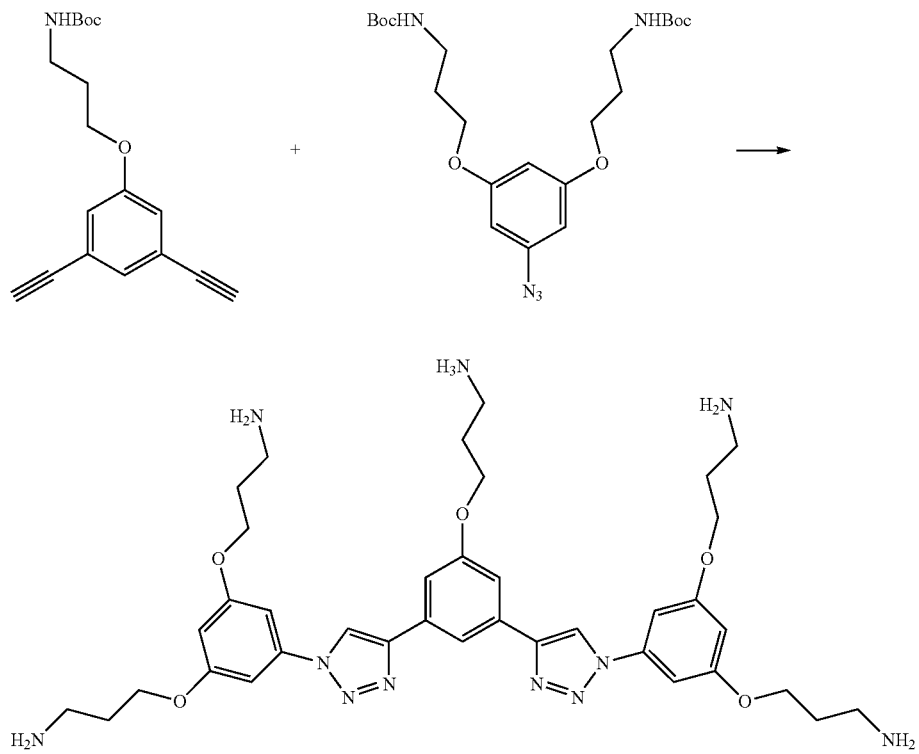 [SMILES: C#Cc1cc(C#C)cc(OCCCNC(=O)OC(C)(C)C)c1 ; CC(C)(C)OC(=O)NCCCOc1cc(N=[N+]=[N-])cc(OCCCNC(=O)OC(C)(C)C)c1 ; NCCCOc1cc(-c2cn(-c3cc(OCCCN)cc(OCCCN)c3)nn2)cc(-c2cn(-c3cc(OCCCN)cc(OCCCN)c3)nn2)c1]
Following the general click chemistry and deprotection procedure, Compound 105 was synthesized in 84% yield.
Example 1D
Synthesis of Compound 100
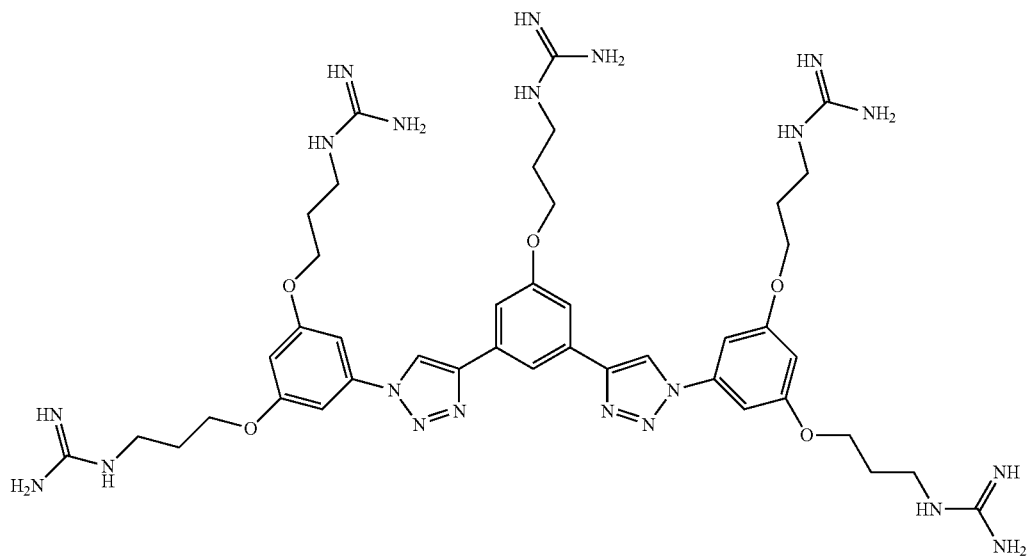 [SMILES: N=C(N)NCCCOc1cc(-c2cn(-c3cc(OCCCNC(=N)N)cc(OCCCNC(=N)N)c3)nn2)cc(-c2cn(-c3cc(OCCCNC(=N)N)cc(OCCCNC(=N)N)c3)nn2)c1]

Following the general method of converting amino groups to guanidine groups, Compound 100 was synthesized from Compound 105 in 50% yield.
Example 1E
Synthesis of Compound 103
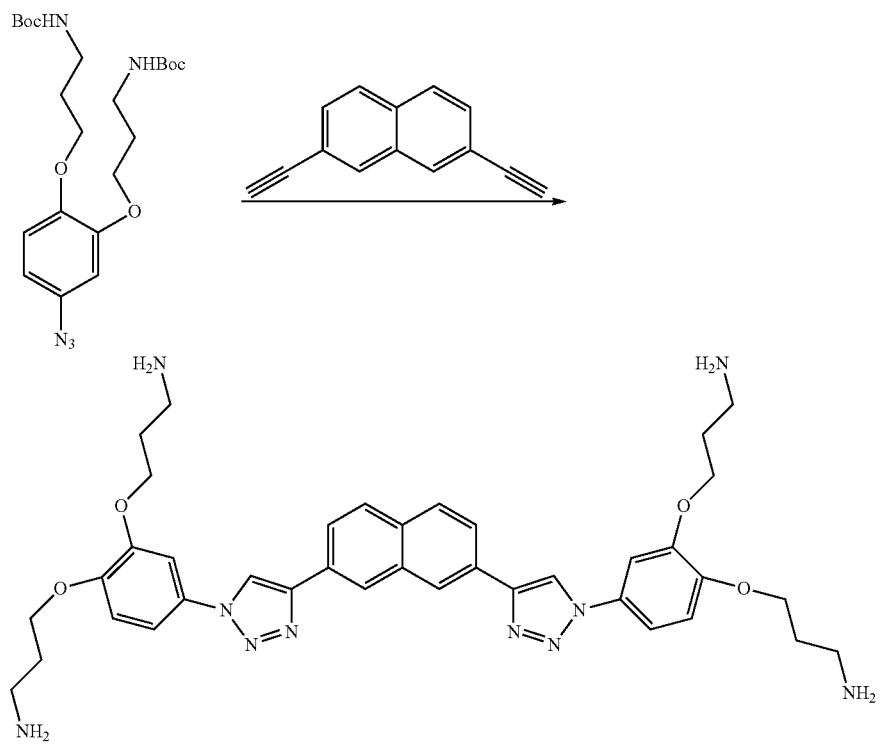
Following the general click chemistry and deprotection procedure, Compound 103 was synthesized in 42% yield.
Example 1F
Synthesis of Compound 104
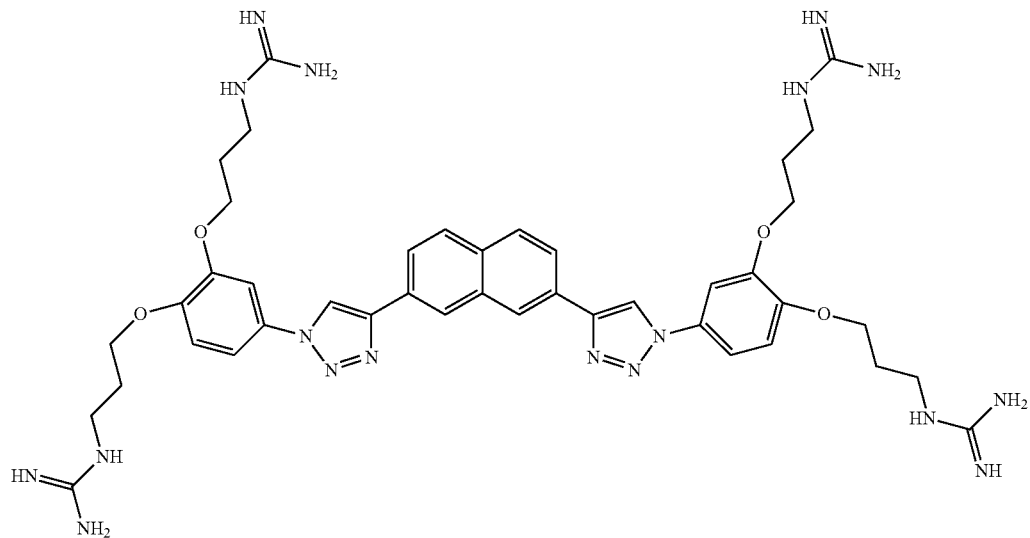 [SMILES: N=C(N)NCCCOc1ccc(-n2cc(-c3ccc4ccc(-c5cn(-c6ccc(OCCCNC(=N)N)c(OCCCNC(=N)N)c6)nn5)cc4c3)nn2)cc1OCCCNC(=N)N]

Following general method of converting amino groups to guanidine groups, Compound 104 was synthesized from Compound 103 in 55% yield.
Example 1G
Synthesis of Compound 102
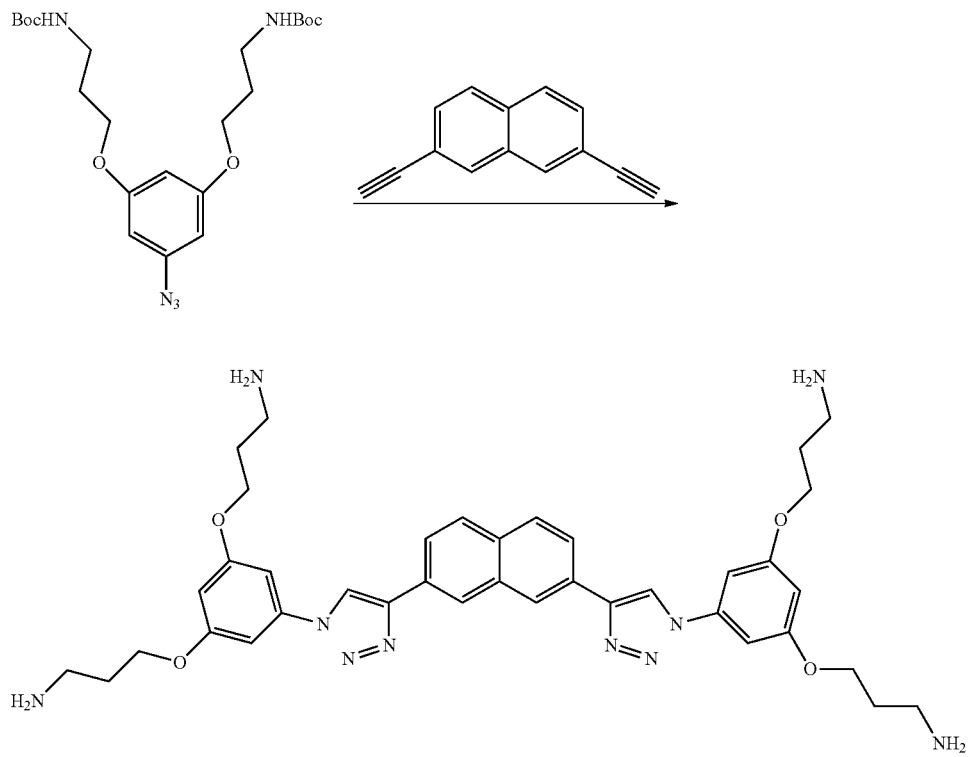
Following the general click chemistry and deprotection procedure, Compound 102 was synthesized in 41% yield.
Example 1H
Synthesis of Compound 101
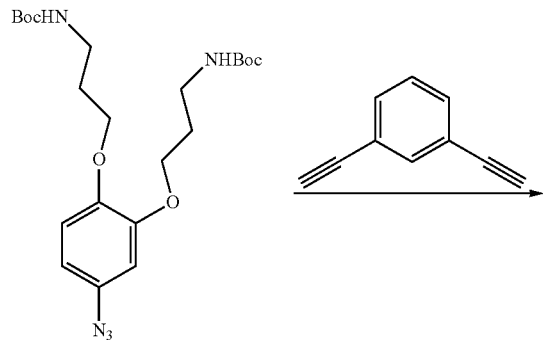

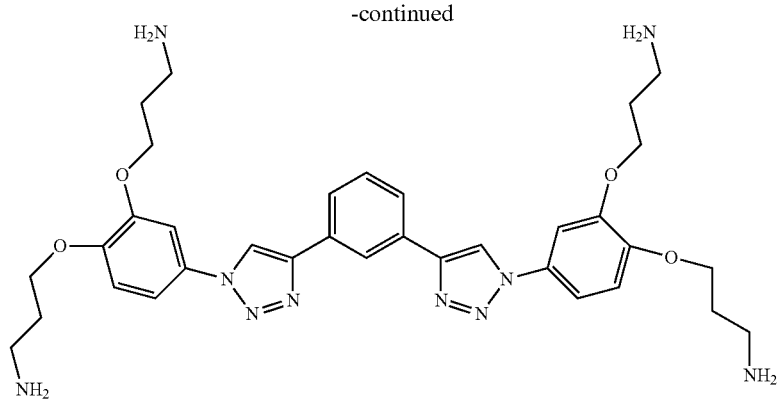
8
Following the general click chemistry and deprotection procedure, Compound 101 was synthesized in 41% yield
Example 1I
Synthesis of Compound 119
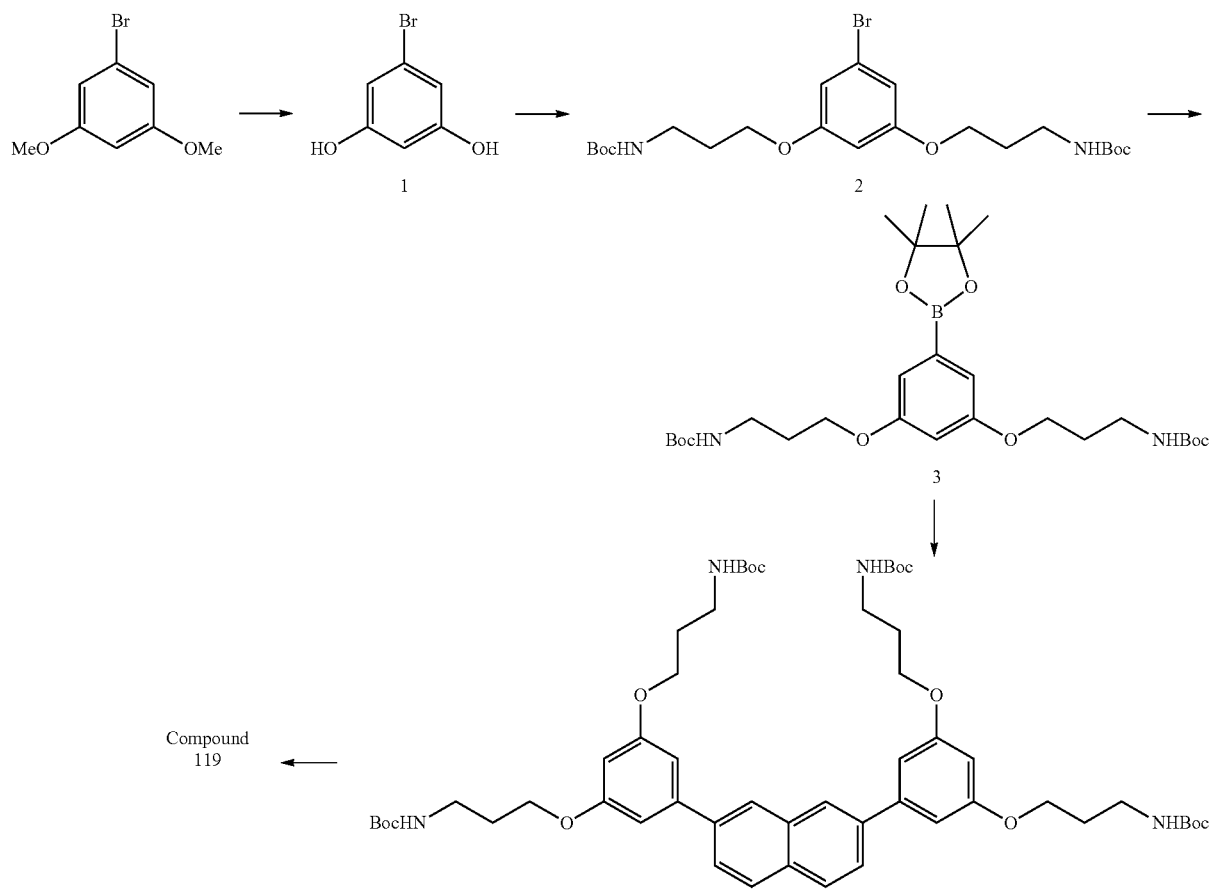

Synthesis of Compound 1:

In a clean dry round bottom flask, 1-bromo-3,5-dimethoxybenzene (8.00 g, 36.9 mmol) was added to 300 ml of dry dichloromethane. The solution was cooled down to 0° C. and BBr$_3$ (25.00 g, 100 mmol) was added dropwise. After 2 hours, the mixture was allowed to warm to room temperature and stirred over night. Methanol (10 ml) was added dropwise to terminate the reaction. The mixture was poured into water and stirred for 2 hours. Then saturated sodium bicarbonate (100 ml) was added and extracted with ethyl acetate. The organic layer was washed with saturated sodium bicarbonate, brine and then dried over Na$_2$SO$_4$. The residue, after concentration, was purified using chromatography using ethyl acetate/hexane (1:4 v/v) eluent. Yield=4.39 g (63%).

Synthesis of Compound 2:

Compound 1 (2.7 g, 14.3 mmol) and potassium carbonate (9.8 g, 71.4 mmol) were stirred in DMF (25 ml) and water (2.5 ml) at room temperature for 20 minutes and then heated to 44° C. 3-(Boc-amino) propyl bromide (10.89 g, 45.7 mmol) was added. The resulting mixture was stirred at 44° C. over night. The mixture was cooled down to room temperature and poured into a mixture of ethyl acetate and water. The organic layer was washed with brine and dried over Na$_2$SO$_4$. The residue after concentration was purified with chromatography ethyl acetate/hexane (1:4 v/v) eluent. Yield=6.13 g (83%).

Synthesis of Compound 3:

In a clean dry round bottom flask, compound 2 (3 g, 5.96 mmol), 4,4,5,5-tetramethyl-2-(4,4,5,5-tetramethyl-1,3,2-dioxaborolan-2-yl)-1,3,2-dioxaborolane (1.68 g, 6.56 mmol) and potassium acetate (2.92 g, 29.8 mmol) were stirred in DMSO (30 ml) at room temperature under N$_2$ protection. Then PdCl$_2$(dppf) (0.289 g, 0.357 mmol) was added. The resulting mixture was stirred at 80° C. overnight. Then the reaction was cooled down to room temperature. The mixture was filtered through celite and washed with ethyl acetate. The organic layer was washed with water, brine then dried over Na$_2$SO$_4$. Then residue after concentration is purified by chromatography (eluent: ethyl acetate/hexanes=3/7). Yield=2.27 g (70%).

Suzuki Coupling:

In a clean Schlenk tube, dibromonapthalene (0.3 g, 1.05 mmol) was added to compound 3 (1.32 g, 2.41 mmol), K$_3$PO$_4$ (0.890 g, 4.19 mmol) and PdCl$_2$(dppf) (42.5 mg, 0.052 mmol) along with 9 ml toluene and 0.9 ml water. The Schlenk tube was degassed by three freeze-pump-thaw cycles and then purged with nitrogen and the mixture was stirred at 95° C. for 20 hours. The reaction mixture, cooled to room temperature, was then quenched with water (25 mL) and extracted with ethyl acetate (30 mL×3). The combined organic layers were washed with a saturated aqueous solution of NaHCO$_3$ (50 mL) and brine (50 mL), dried over anhydrous Na$_2$SO$_4$ and evaporated under reduced pressure. The residue was purified using column chromatography using ethyl acetate/hexane mixture (2:3 v/v). Yield=0.65 g.

Deprotection:

The solid obtained from Suzuki Coupling step (150 mg) is stirred in a mixture of TFA and DCM (1:2 v/v) for 3 hours. The solution is concentrated and dried under overnight vacuum. The solid is then dissolved in minimal amount of methanol and precipitated using hexane/ether mixture (1:1 v/v). The mixture is centrifuged for 1 minute and the supernatant liquid is removed. The residue is dried to remove any residual solvent to yield Compound 119. The purity of compound is >95%.

Example 1J

Synthesis of Compound 117

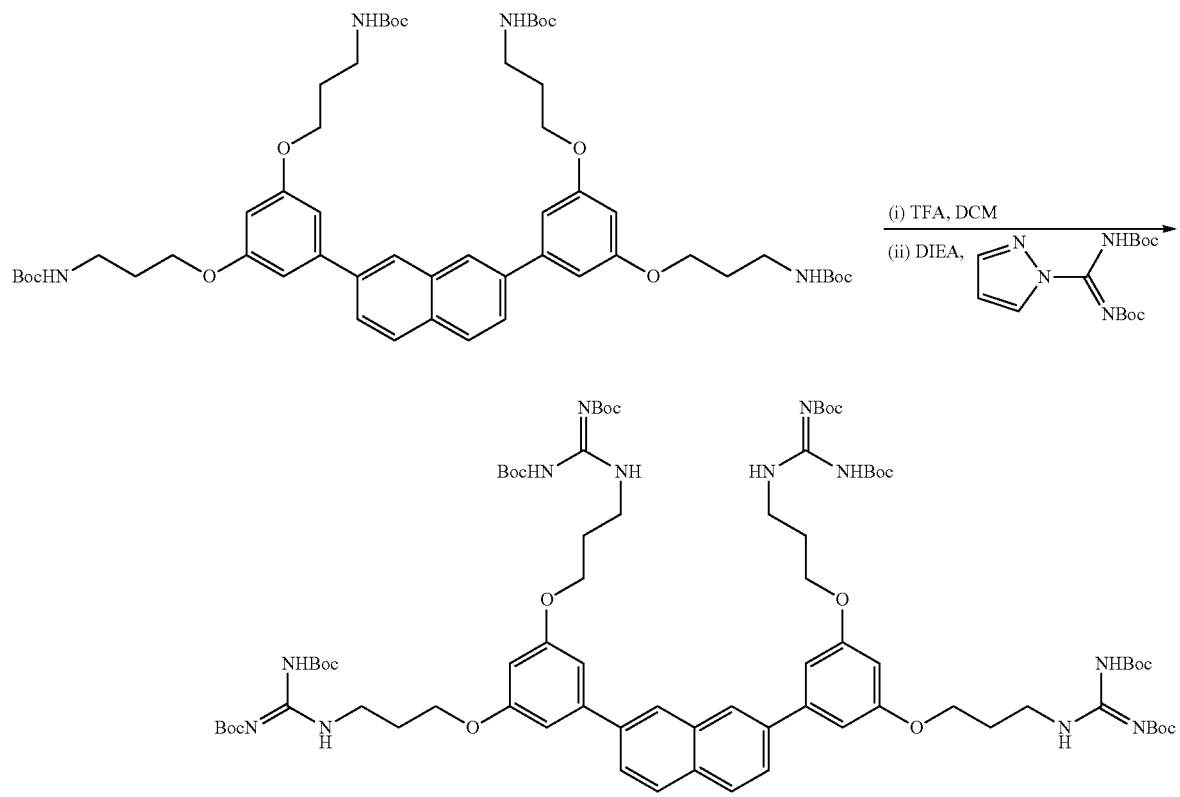

0.2 g of Compound 4 is deprotected using the above procedure. The residue was then redissolved in CH₃CN/THF (6 mL:3 mL). DIEA (0.36 mL, 2.05 mmol) was added to the solution at 0° C. After the addition of N,N'-bis(tertbutoxycarbonyl)-1H-pyrazole-1 carboxamidine (0.28 g, 0.904 mmol), the resulting mixture was stirred overnight. The solvent was removed and then the residue was dissolved in EtOAc and washed with 10% citric acid, saturated NaHCO₃ (aq.), and saturated NaCl (aq.). After drying on Na₂SO₄, the organic layer was filtered and concentrated under reduced pressure. The residue was purified by column chromatography (Hexane/ethyl acetate 3:2) to give compound 5. Yield=0.15 g (47%). Compound 5 is then deprotected using same procedure to yield Compound 117.

Example 1K

Synthesis of Compound 118 and BBr₃ (25.00 g, 100 mmol) was added dropwise. After 2 hours, the mixture was allowed to warm to room temperature and stirred over night. Methanol (10 ml) was added dropwise to terminate the reaction. The mixture was poured into water and stirred for 2 hours. Then saturated sodium bicarbonate (100 ml) was added and extracted with ethyl acetate. The organic layer was washed with saturated sodium bicarbonate, brine and then dried over Na₂SO₄. The residue, after concentration, was purified using chromatography using ethyl acetate/hexane (1:4 v/v) eluent. Yield=4.39 g (63%).

Synthesis of Compound 2:

Compound 1 (2.7 g, 14.3 mmol) and potassium carbonate (9.8 g, 71.4 mmol) were stirred in DMF (25 ml) and water (2.5 ml) at room temperature for 20 minutes and then heated to 44° C. 3-(Boc-amino) propyl bromide (10.89 g, 45.7 mmol) was added. The resulting mixture was stirred at 44° C. over night. The mixture was cooled down to room temperature and poured into a mixture of ethyl acetate and

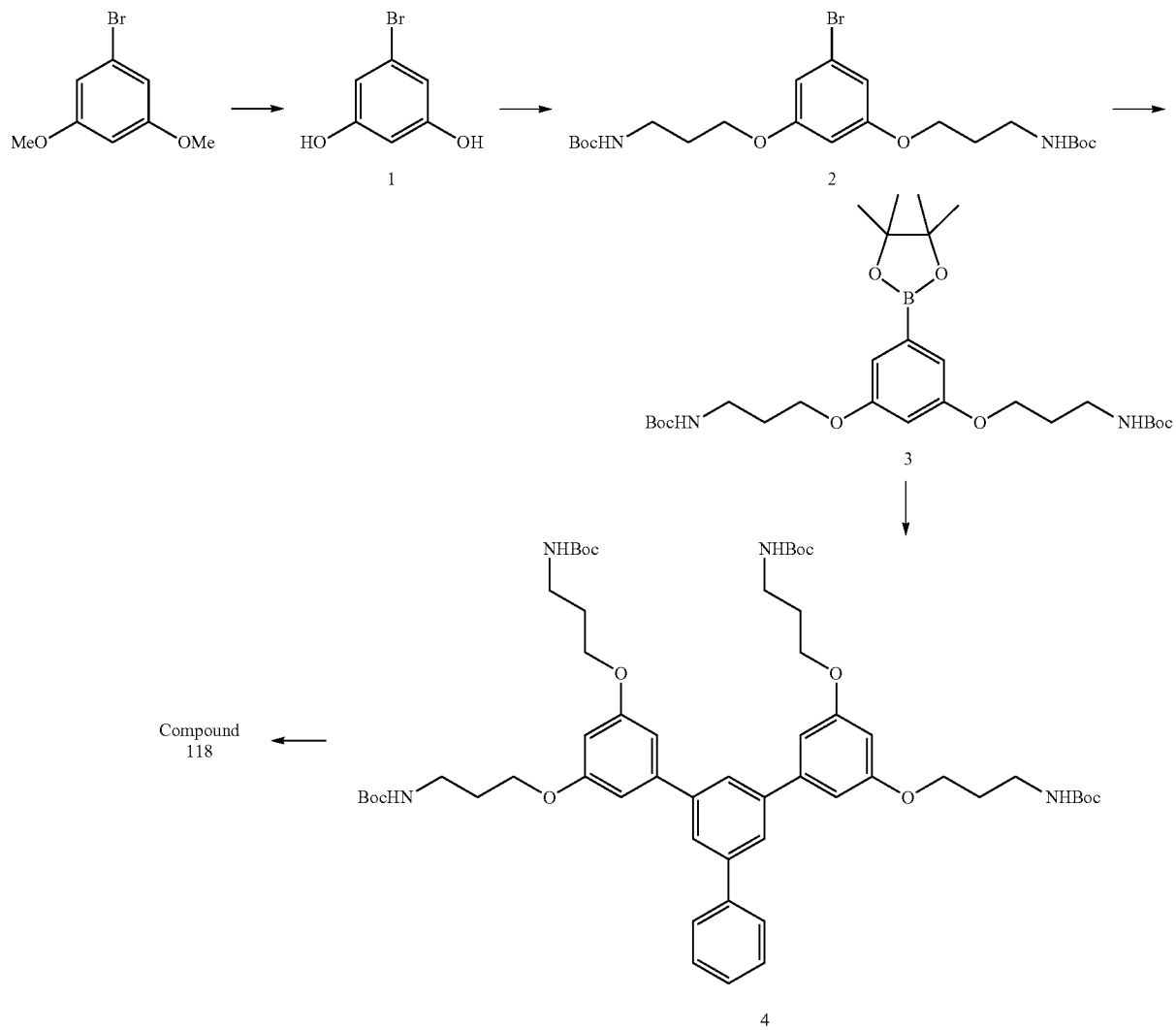

Synthesis of Compound 1:

In a clean dry round bottom flask, 1-bromo-3,5-dimethoxybenzene (8.00 g, 36.9 mmol) was added to 300 ml of dry dichloromethane. The solution was cooled down to 0° C.

water. The organic layer was washed with brine and dried over Na₂SO₄. The residue after concentration was purified with chromatography ethyl acetate/hexane (1:4 v/v) eluent. Yield=6.13 g (83%).

Synthesis of Compound 3:

In a clean dry round bottom flask, compound 2 (3 g, 5.96 mmol), 4,4,5,5-tetramethyl-2-(4,4,5,5-tetramethyl-1,3,2-dioxaborolan-2-yl)-1,3,2-dioxaborolane (1.68 g, 6.56 mmol) and potassium acetate (2.92 g, 29.8 mmol) were stirred in DMSO (30 ml) at room temperature under $N_2$ protection. Then $PdCl_2(dppf)$ (0.289 g, 0.357 mmol) was added. The resulting mixture was stirred at 80° C. overnight. Then the reaction was cooled down to room temperature. The mixture was filtered through celite and washed with ethyl acetate. The organic layer was washed with water, brine then dried over $Na_2SO_4$. Then residue after concentration is purified by chromatography (eluent: ethyl acetate/hexanes=3/7). Yield=2.27 g (70%).

Suzuki Coupling:

In a clean Schlenk tube, 1,3-dibromo-5-phenylbenzene (0.2 g, 0.64 mmol) was added to compound 3 (0.811 g, 1.474 mmol), $K_3PO_4$ (0.544 g, 2.564 mmol) and $PdCl_2(dppf)$ (26 mg, 0.032 mmol) along with 6 ml toluene and 0.6 ml water. The Schlenk tube was degassed by three freeze-pump-thaw cycles and then purged with nitrogen and the mixture was stirred at 95° C. for 20 hours. The reaction mixture, cooled to room temperature, was then quenched with water (25 mL) and extracted with ethyl acetate (30 mL×3). The combined organic layers were washed with a saturated aqueous solution of $NaHCO_3$ (50 mL) and brine (50 mL), dried over anhydrous $Na_2SO_4$ and evaporated under reduced pressure. The residue was purified using column chromatography using ethyl acetate/hexane mixture (2:3 v/v). Yield=0.26 g.

Deprotection:

The solid obtained from Suzuki Coupling step (150 mg) is stirred in a mixture of TFA and DCM (1:2 v/v) for 3 hours. The solution is concentrated and dried under overnight vacuum. The solid is then dissolved in minimal amount of methanol and precipitated using hexane/ether mixture (1:1 v/v). The mixture is centrifuged for 1 minute and the supernatant liquid is removed. The residue is dried to remove any residual solvent to yield Compound 118. The purity of compound is >95%.

Example 1L

Synthesis of Compound 114

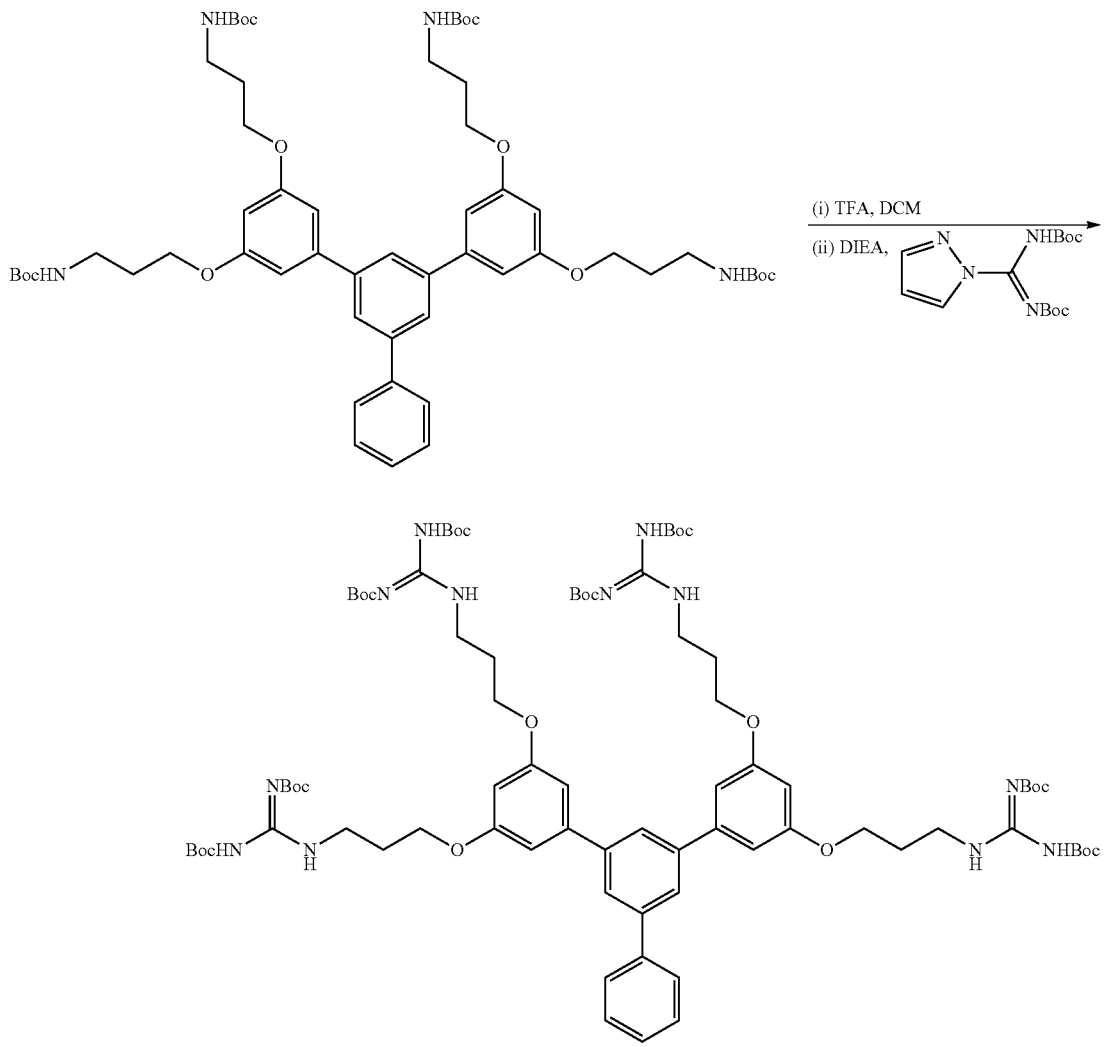

0.28 g of Compound 4 is deprotected using the above procedure. The residue was then redissolved in $CH_3CN$/THF (8 mL:4 mL). DIEA (0.74 mL, 4.2 mmol) was added to the solution at 0° C. After the addition of N,N'-bis(tert-butoxycarbonyl)-1H-pyrazole-1 carboxamidine (0.52 g, 1.68 mmol), the resulting mixture was stirred overnight. The solvent was removed and then the residue was dissolved in EtOAc and washed with 10% citric acid, saturated $NaHCO_3$ (aq.), and saturated NaCl (aq.). After drying on $Na_2SO_4$, the organic layer was filtered and concentrated under reduced pressure. The residue was purified by column chromatography (Hexane/ethyl acetate 3:2) to give compound 5. Yield=0.33 g (75%). Compound 5 is then deprotected using the same procedure to yeield Compound 114.

Example 1M

Synthesis of Compound 116

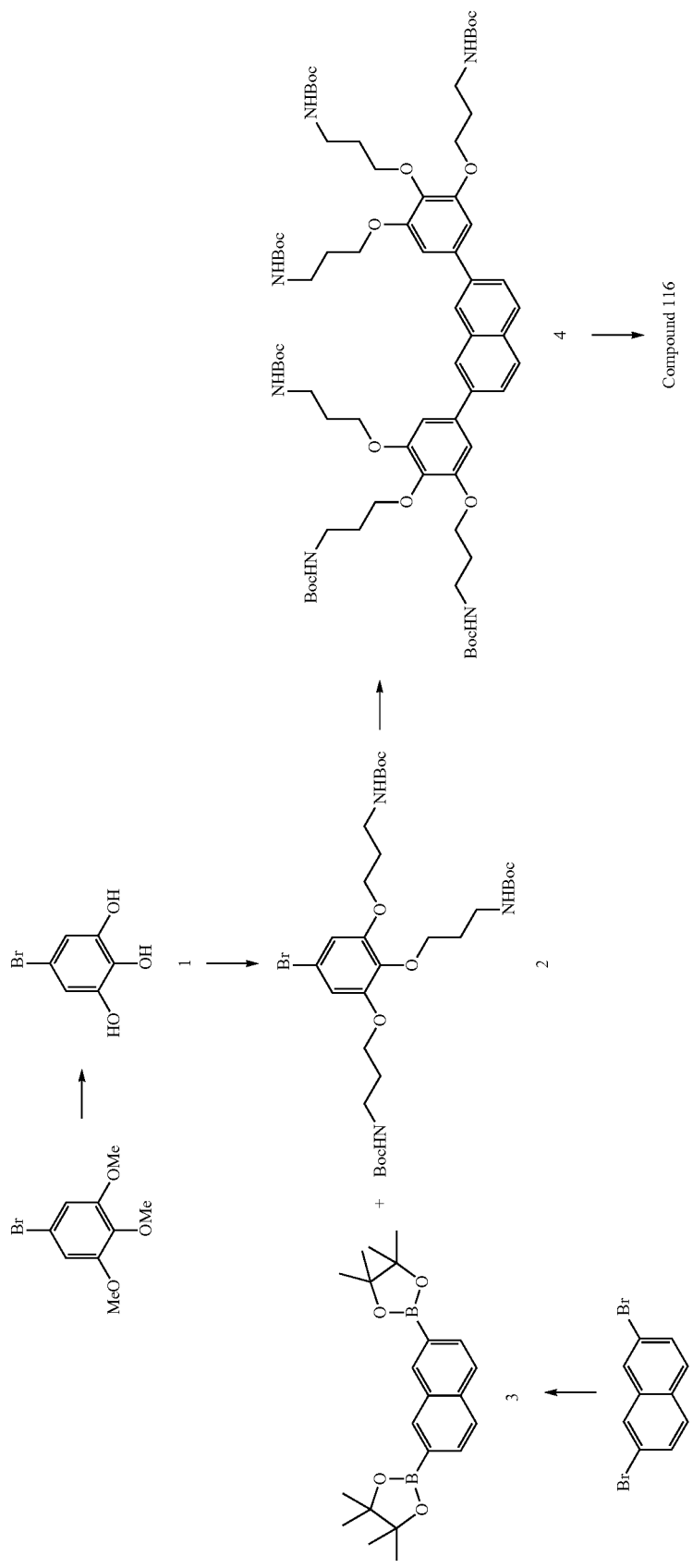

Synthesis of Compound 1:

To a $CH_2Cl_2$ solution (40 mL) of 5-bromo-1,2,3-trimethoxybenzene (4.94 g, 20 mmol) was slowly added, at −75° C. under nitrogen, a $CH_2Cl_2$ solution of $BBr_3$ (1 M, 60 mL), and the mixture was allowed to warm to 25° C. After overnight stirring, the reaction mixture was poured into ice/water (200 mL) and extracted with ethyl acetate. The combined organic extract was washed with water, dried over anhydrous $Na_2SO_4$, and filtered off from an insoluble fraction. The filtrate was evaporated to dryness under a reduced pressure and purified using column chromatography (ethyl acetate/$CH_2Cl_2$ mixture 1:9 v/v). Yield=2.21 g (54%).

Synthesis of Compound 2:

Compound 1 (1.6 g, 7.8 mmol) and potassium carbonate (8.83 g, 64 mmol) were stirred in DMF (30 ml) and water (3 ml) at room temperature for 30 minutes and then heated to 60° C. 3-(Boc-amino) propyl bromide (8.34 g, 35.1 mmol) was added. The resulting mixture was stirred at 60° C. overnight. The mixture was cooled down to room temperature and poured into a mixture of ethyl acetate and water. The organic layer was washed with brine and dried over $Na_2SO_4$. The residue after concentration was purified with chromatography ethyl acetate/hexane (3:7 v/v) eluent. Yield=3.5 g (66%).

Synthesis of Compound 3:

In a clean dry round bottom flask, dibromonapthalene (3 g, 10.49 mmol), 4,4,5,5-tetramethyl-2-(4,4,5,5-tetramethyl-1,3,2-dioxaborolan-2-yl)-1,3,2-dioxaborolane (5.90 g, 23.08 mmol) and potassium acetate (5.14 g, 52.45 mmol) were stirred in DMSO (30 ml) at room temperature under $N_2$ protection. Then $PdCl_2$(dppf) (0.424 g, 0.525 mmol) was added. The resulting mixture was stirred at 80° C. overnight. Then the reaction was cooled down to room temperature. The mixture was filtered through celite and washed with ethyl acetate. The organic layer was washed with water, brine then dried over $Na_2SO_4$. Then residue after concentration is purified by chromatography (eluent: $CH_2Cl_2$/hexanes=1/9). Yield=2.65 g (67%).

Suzuki Coupling (Synthesis of Compound 4):

In a clean Schlenk tube, compound 3 (0.3 g, 0.79 mmol) was added to compound 2 (1.23 g, 1.815 mmol), $K_3PO_4$ (0.67 g, 3.16 mmol) and $PdCl_2$(dppf) (31.9 mg, 0.04 mmol) along with 9 ml toluene and 0.9 ml water. The Schlenk tube was degassed by three freeze-pump-thaw cycles and then purged with nitrogen and the mixture was stirred at 95° C. for 20 hours. The reaction mixture, cooled to room temperature, was then quenched with water (25 mL) and extracted with ethyl acetate (30 mL×3). The combined organic layers were washed with a saturated aqueous solution of $NaHCO_3$ (50 mL) and brine (50 mL), dried over anhydrous $Na_2SO_4$ and evaporated under reduced pressure. The residue was purified using column chromatography using ethyl acetate/hexane/$CH_2Cl_2$ mixture (1:4:4 v/v/v). Yield=0.79 g.

Deprotection:

The solid obtained from Suzuki Coupling step (150 mg) is stirred in a mixture of TFA and DCM (1:2 v/v) for 3 hours. The solution is concentrated and dried under overnight vacuum. The solid is then dissolved in minimal amount of methanol and precipitated using hexane/ether mixture (1:1 v/v). The mixture is centrifuged for 1 minute and the supernatant liquid is removed. The residue is dried to remove any residual solvent to yield Compound 116. The purity of compound is >95%.

Example 1N

Synthesis of Compound 115

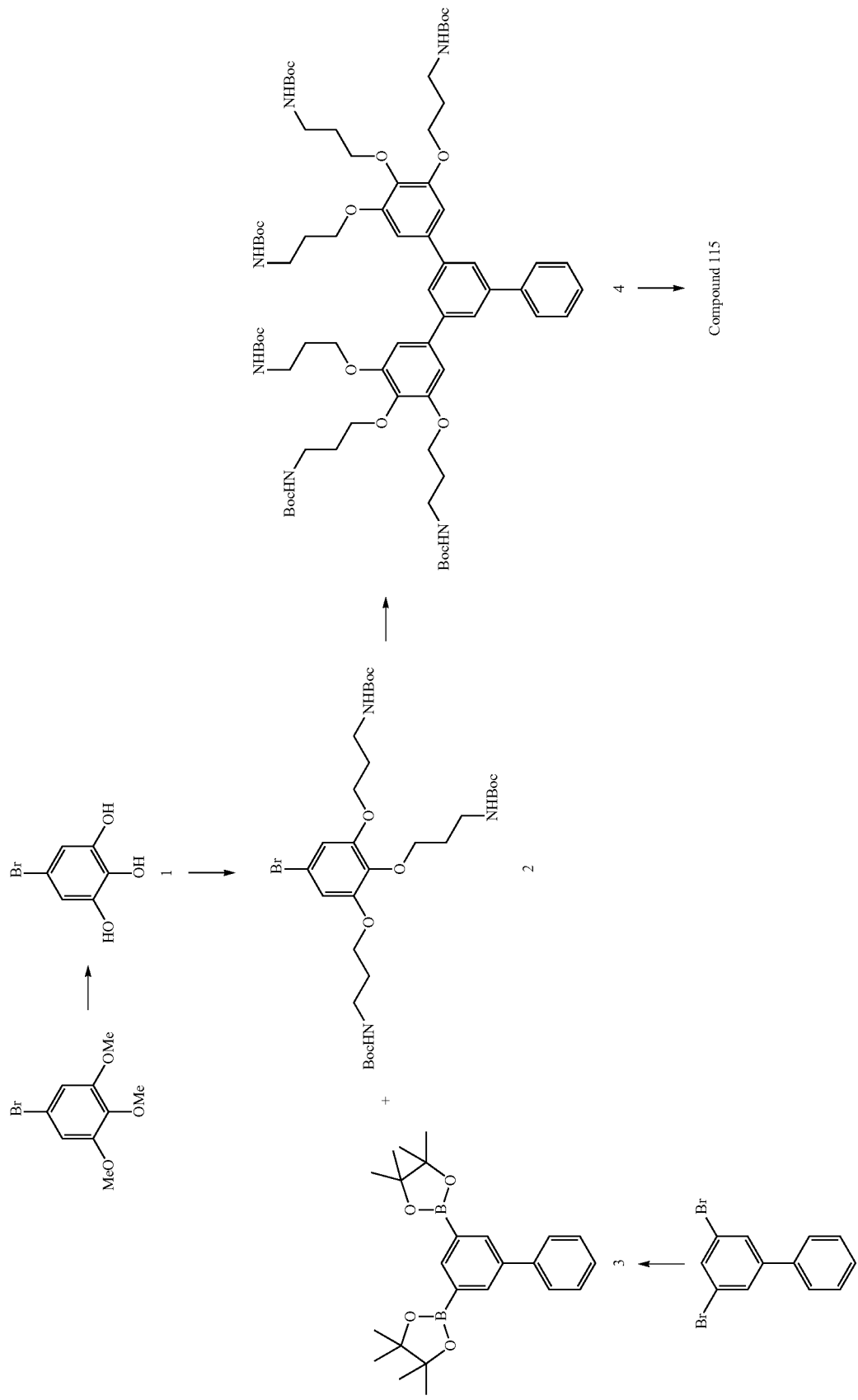

Synthesis of Compound 1:

To a $CH_2Cl_2$ solution (40 mL) of 5-bromo-1,2,3-trimethoxybenzene (4.94 g, 20 mmol) was slowly added, at −75° C. under nitrogen, a $CH_2Cl_2$ solution of $BBr_3$ (1 M, 60 mL), and the mixture was allowed to warm to 25° C. After overnight stirring, the reaction mixture was poured into ice/water (200 mL) and extracted with ethyl acetate. The combined organic extract was washed with water, dried over anhydrous $Na_2SO_4$, and filtered off from an insoluble fraction. The filtrate was evaporated to dryness under a reduced pressure and purified using column chromatography (ethyl acetate/$CH_2Cl_2$ mixture 1:9 v/v). Yield=2.21 g., (54%).

Synthesis of Compound 2:

Compound 1 (1.6 g, 7.8 mmol) and potassium carbonate (8.83 g, 64 mmol) were stirred in DMF (30 ml) and water (3 ml) at room temperature for 30 minutes and then heated to 60° C. 3-(Boc-amino) propyl bromide (8.34 g, 35.1 mmol) was added. The resulting mixture was stirred at 60° C. overnight. The mixture was cooled down to room temperature and poured into a mixture of ethyl acetate and water. The organic layer was washed with brine and dried over $Na_2SO_4$. The residue after concentration was purified with chromatography ethyl acetate/hexane (3:7 v/v) eluent. Yield=3.5 g (66%).

Synthesis of Compound 3:

In a clean dry round bottom flask, 1,3-dibromo-5-phenylbenzene (1 g, 3.2 mmol), 4,4,5,5-tetramethyl-2-(4,4,5,5-tetramethyl-1,3,2-dioxaborolan-2-yl)-1,3,2-dioxaborolane (1.80 g, 7.05 mmol) and potassium acetate (1.57 g, 16 mmol) were stirred in DMSO (30 ml) at room temperature under $N_2$ protection. Then $PdCl_2$(dppf) (0.13 g, 0.16 mmol) was added. The resulting mixture was stirred at 80° C. overnight. Then the reaction was cooled down to room temperature. The mixture was filtered through celite and washed with ethyl acetate. The organic layer was washed with water, brine then dried over $Na_2SO_4$. Then residue after concentration is purified by chromatography (eluent: $CH_2Cl_2$/hexanes=1/4). Yield=0.72 g (59%).

Suzuki Coupling (Synthesis of Compound 4):

In a clean Schlenk tube, compound 3 (0.25 g, 0.62 mmol) was added to compound 2 (0.96 g, 1.42 mmol), $K_3PO_4$ (0.52 g, 2.46 mmol) and $PdCl_2$(dppf) (25 mg, 0.03 mmol) along with 8 ml toluene and 0.8 ml water. The Schlenk tube was degassed by three freeze-pump-thaw cycles and then purged with nitrogen and the mixture was stirred at 95° C. for 20 hours. The reaction mixture, cooled to room temperature, was then quenched with water (25 mL) and extracted with ethyl acetate (30 mL×3). The combined organic layers were washed with a saturated aqueous solution of $NaHCO_3$ (50 mL) and brine (50 mL), dried over anhydrous $Na_2SO_4$ and evaporated under reduced pressure. The residue was purified using column chromatography using ethyl acetate/hexane mixture (2:3 v/v). Yield=0.64 g.

Deprotection:

The solid obtained from Suzuki Coupling step (150 mg) is stirred in a mixture of TFA and DCM (1:2 v/v) for 3 hours. The solution is concentrated and dried under overnight vacuum. The solid is then dissolved in minimal amount of methanol and precipitated using hexane/ether mixture (1:1 v/v). The mixture is centrifuged for 1 minute and the supernatant liquid is removed. The residue is dried to remove any residual solvent to give yield Compound 115. The purity of compound is >95%.

Example 1O

Synthesis of Compound 113

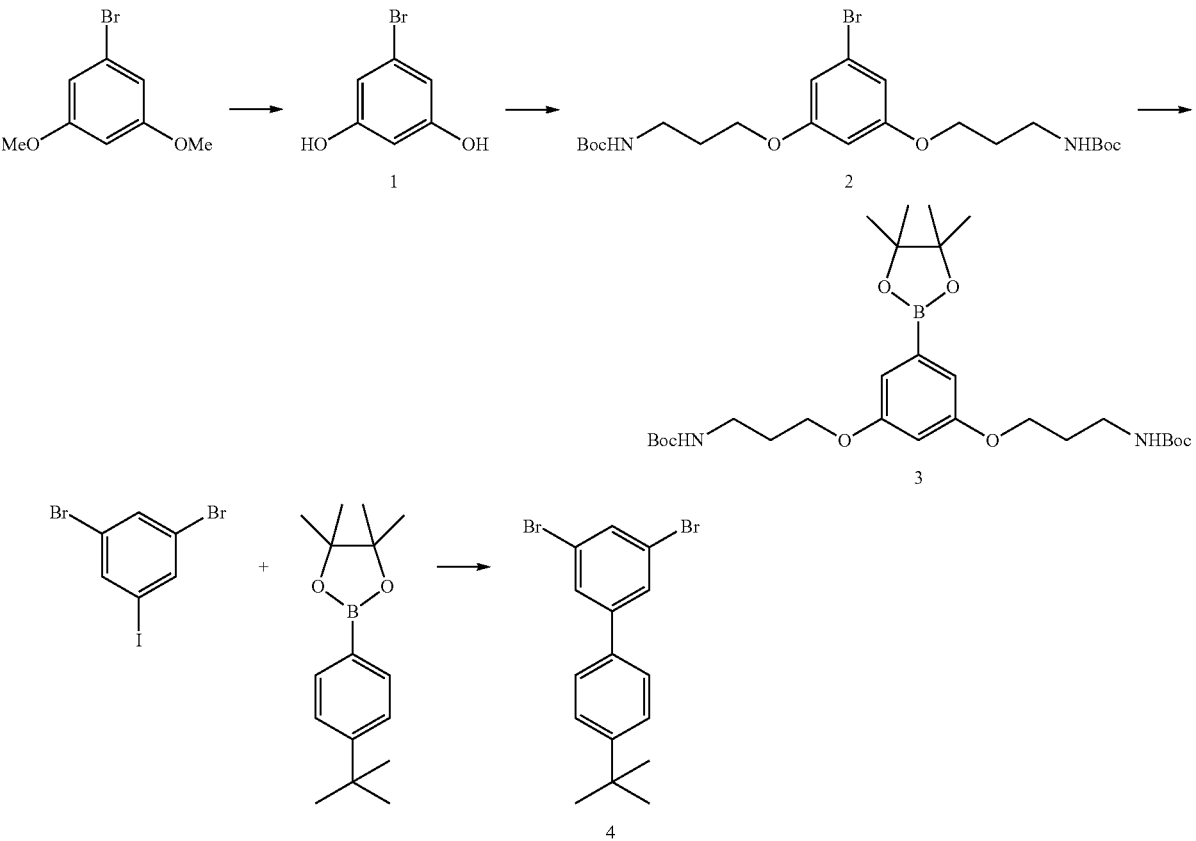

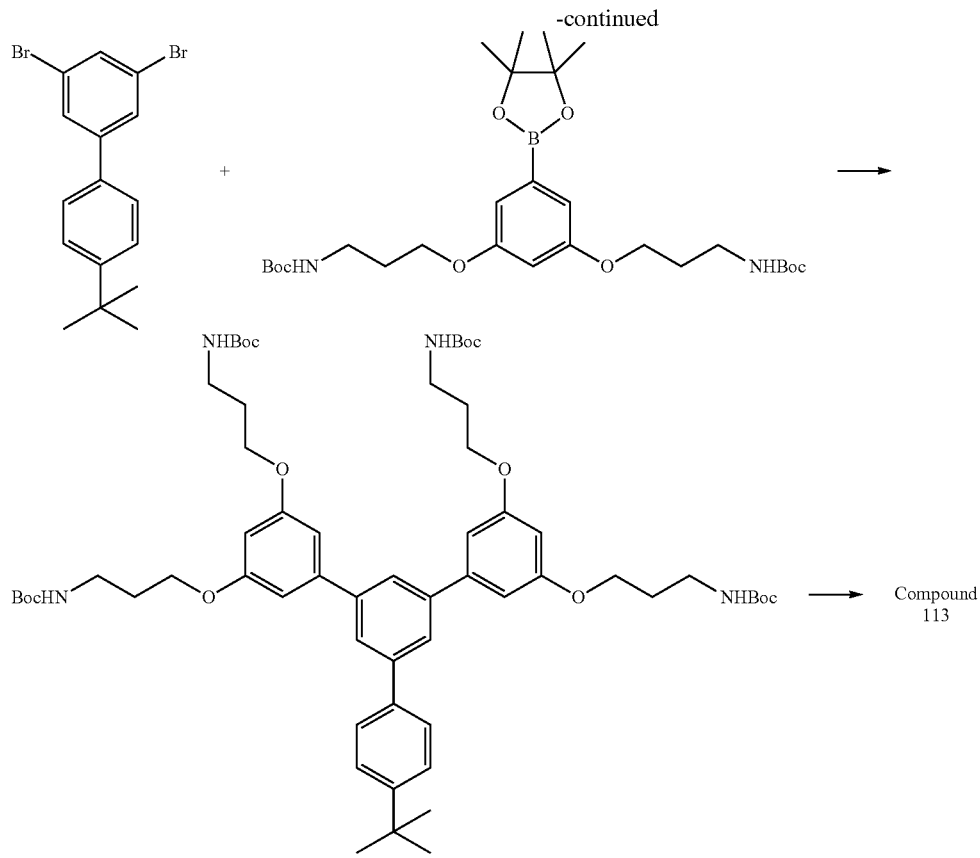

Synthesis of Compound 1:

In a clean dry round bottom flask, 1-bromo-3,5-dimethoxybenzene (8.00 g, 36.9 mmol) was added to 300 ml of dry dichloromethane. The solution was cooled down to 0° C. and BBr$_3$ (25.00 g, 100 mmol) was added dropwise. After 2 hours, the mixture was allowed to warm to room temperature and stirred over night. Methanol (10 ml) was added dropwise to terminate the reaction. The mixture was poured into water and stirred for 2 hours. Then saturated sodium bicarbonate (100 ml) was added and extracted with ethyl acetate. The organic layer was washed with saturated sodium bicarbonate, brine and then dried over Na$_2$SO$_4$. The residue, after concentration, was purified using chromatography using ethyl acetate/hexane (1:4 v/v) eluent. Yield=4.39 g, (63%).

Synthesis of Compound 2:

Compound 1 (2.7 g, 14.3 mmol) and potassium carbonate (9.8 g, 71.4 mmol) were stirred in DMF (25 ml) and water (2.5 ml) at room temperature for 20 minuets and then heated to 44° C. 3-(Boc-amino) propyl bromide (10.89 g, 45.7 mmol) was added. The resulting mixture was stirred at 44° C. overnight. The mixture was cooled down to room temperature and poured into a mixture of ethyl acetate and water. The organic layer was washed with brine and dried over Na$_2$SO$_4$. The residue after concentration was purified with chromatography ethyl acetate/hexane (1:4 v/v) eluent. Yield=6.13 g, (83%).

Synthesis of Compound 3:

In a clean dry round bottom flask, compound 2 (3 g, 5.96 mmol), 4,4,5,5-tetramethyl-2-(4,4,5,5-tetramethyl-1,3,2-dioxaborolan-2-yl)-1,3,2-dioxaborolane (1.68 g, 6.56 mmol) and potassium acetate (2.92 g, 29.8 mmol) were stirred in DMSO (30 ml) at room temperature under N$_2$ protection. Then PdCl$_2$(dppf) (0.289 g, 0.357 mmol) was added. The resulting mixture was stirred at 80° C. overnight. Then the reaction was cooled down to room temperature. The mixture was filtered through celite and washed with ethyl acetate. The organic layer was washed with water, brine then dried over Na$_2$SO$_4$. Then residue after concentration is purified by chromatography (eluent: ethyl acetate/hexanes=3/7). Yield=2.27 g, (70%).

Synthesis of Compound 4:

In a clean Schlenk tube, 1,3-dibromo-5-iodobenzene (1.81 g, 5 mmol) was added to 2-(4-tert-butylphenyl)-4,4,5,5-tetramethyl-1,3,2-dioxaborolane (1 g, 3.84 mmol), K$_3$PO$_4$ (1.63 g, 7.68 mmol) and PdCl$_2$(dppf) (0.155 g, 0.19 mmol) along with 10 ml toluene and 1 ml water. The Schlenk tube was degassed by three freeze-pump-thaw cycles and then purged with nitrogen and the mixture was stirred at 95° C. for 18 hours. The reaction mixture, cooled to room temperature, was then quenched with water (25 mL) and extracted with ethyl acetate (30 mL×3). The combined organic layers were washed with a saturated aqueous solution of NaHCO$_3$ (50 mL) and brine (50 mL), dried over anhydrous Na$_2$SO$_4$ and evaporated under reduced pressure. The residue was purified using column chromatography using pure hexane Yield=0.6 g, (43%).

Suzuki Coupling:

In a clean Schlenk tube, compound 4 (0.3 g, 0.82 mmol) was added to compound 3 (1.04 g, 1.89 mmol), K$_3$PO$_4$ (0.69 g, 3.28 mmol) and PdCl$_2$(dppf) (33.2 mg, 0.041 mmol) along with 6 ml toluene and 0.6 ml water. The Schlenk tube was degassed by three freeze-pump-thaw cycles and then purged with nitrogen and the mixture was stirred at 95° C. for 20 hours. The reaction mixture, cooled to room temperature, was then quenched with water (25 mL) and extracted with ethyl acetate (30 mL×3). The combined organic layers were washed with a saturated aqueous solution of NaHCO$_3$ (50 mL) and brine (50 mL), dried over anhydrous Na$_2$SO$_4$ and evaporated under reduced pressure. The residue was purified using column chromatography using ethyl acetate/hexane mixture (2:3 v/v). Yield=0.3 g.

Deprotection:

The solid obtained from Suzuki Coupling step (150 mg) is stirred in a mixture of TFA and DCM (1:2 v/v) for 3 hours. The solution is concentrated and dried under overnight vacuum. The solid is then dissolved in minimal amount of methanol and precipitated using hexane/ether mixture (1:1 v/v). The mixture is centrifuged for 1 minute and the supernatant liquid is removed. The residue is dried to remove any residual solvent to yield Compound 113. The purity of compound is >95%.

Example 1P

Synthesis of Compound 111

Synthesis of Compound 1:

In a clean dry round bottom flask, 1-bromo-3,5-dimethoxybenzene (8.00 g, 36.9 mmol) was added to 300 ml of dry dichloromethane. The solution was cooled down to 0° C. and BBr$_3$ (25.00 g, 100 mmol) was added dropwise. After 2 hours, the mixture was allowed to warm to room temperature and stirred over night. Methanol (10 ml) was added dropwise to terminate the reaction. The mixture was poured into water and stirred for 2 hours. Then saturated sodium bicarbonate (100 ml) was added and extracted with ethyl acetate. The organic layer was washed with saturated sodium bicarbonate, brine and then dried over Na$_2$SO$_4$. The residue, after concentration, was purified using chromatography using ethyl acetate/hexane (1:4 v/v) eluent. Yield=4.39 g, (63%).

Synthesis of Compound 2:

Compound 1 (2.7 g, 14.3 mmol) and potassium carbonate (9.86 g, 71.4 mmol) were stirred in DMF (25 ml) and water (2.5 ml) at room temperature for 20 minutes and then heated to 44° C. 3-(Boc-amino) propyl bromide (10.89 g, 45.7 mmol) was added. The resulting mixture was stirred at 44° C. overnight. The mixture was cooled down to room temperature and poured into a mixture of ethyl acetate and water. The organic layer was washed with brine and dried over Na$_2$SO$_4$. The residue after concentration was purified with chromatography ethyl acetate/hexane (1:4 v/v) eluent. Yield=6.13 g, (83%).

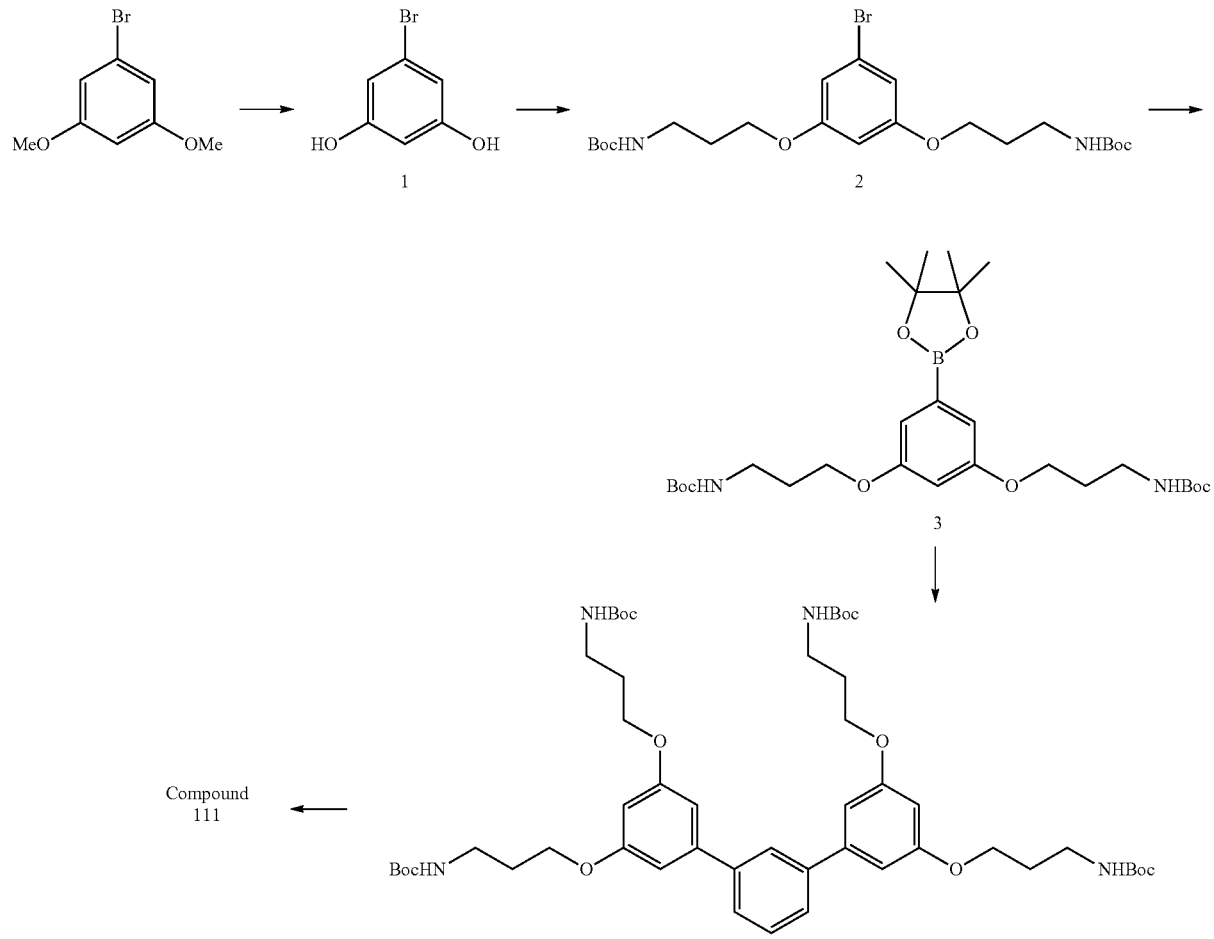

Synthesis of Compound 3:

In a clean dry round bottom flask, compound 2 (3 g, 5.96 mmol), 4,4,5,5-tetramethyl-2-(4,4,5,5-tetramethyl-1,3,2-dioxaborolan-2-yl)-1,3,2-dioxaborolane (1.68 g, 6.56 mmol) and potassium acetate (2.92 g, 29.8 mmol) were stirred in DMSO (30 ml) at room temperature under $N_2$ protection. Then $PdCl_2(dppf)$ (0.289 g, 0.357 mmol) was added. The resulting mixture was stirred at 80° C. overnight. Then the reaction was cooled down to room temperature. The mixture was filtered through celite and washed with ethyl acetate. The organic layer was washed with water, brine then dried over $Na_2SO_4$. Then residue after concentration is purified by chromatography (eluent: ethyl acetate/hexanes=3/7). Yield=2.27 g, (70%).

Suzuki Coupling:

In a clean Schlenk tube, dibromobenzene (0.2 g, 1 eq.) was added to compound 3 (1.073 g, 2.3 eq.), $K_3PO_4$ (0.719 g, 4 eq.) and $PdCl_2(dppf)$ (34.3 mg, 0.05 eq.) along with 5 ml toluene and 0.5 ml water. The Schlenk tube was degassed by three freeze-pump-thaw cycles and then purged with nitrogen and the mixture was stirred at 95° C. for 20 hours. The reaction mixture, cooled to room temperature, was then quenched with water (25 mL) and extracted with ethyl acetate (30 mL×3). The combined organic layers were washed with a saturated aqueous solution of $NaHCO_3$ (50 mL) and brine (50 mL), dried over anhydrous $Na_2SO_4$ and evaporated under reduced pressure. The residue was purified using column chromatography using ethyl acetate/hexane mixture (2:3 v/v).

Deprotection:

The solid obtained from Suzuki Coupling step (150 mg) is stirred in a mixture of TFA and DCM (1:2 v/v) for 3 hours. The solution is concentrated and dried under overnight vacuum. The solid is then dissolved in minimal amount of methanol and precipitated using hexane/ether mixture (1:1 v/v). The mixture is centrifuged for 1 minute and the supernatant liquid is removed. The residue is dried to remove any residual solvent to yield Compound 111. The purity of compound is >95%.

Example 1Q

Synthesis of Compound 109

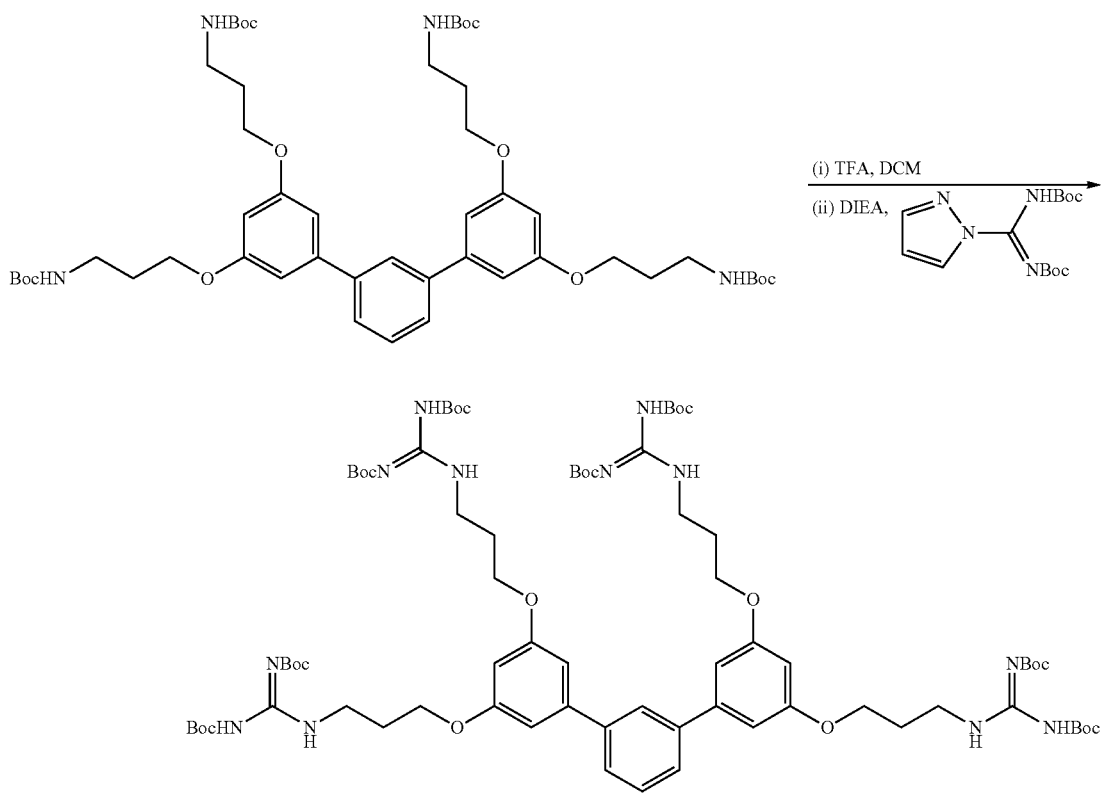

0.25 g of Compound 4 is deprotected using the above procedure. The residue was then redissolved in $CH_3CN$/THF (6 mL:3 mL). DIEA (0.48 mL, 2.708 mmol) was added to the solution at 0° C. After the addition of N,N'-bis(tertbutoxycarbonyl)-1H-pyrazole-1 carboxamidine (0.37 g, 1.19 mmol), the resulting mixture was stirred overnight. The solvent was removed and then the residue was dissolved in EtOAc and washed with 10% citric acid, saturated $NaHCO_3$ (aq.), and saturated NaCl (aq.). After drying on $Na_2SO_4$, the organic layer was filtered and concentrated under reduced pressure. The residue was purified by column chromatography (Hexane/ethyl acetate 3:2) to give compound 5. Yield=0.22 g, (54%). Compound 5 is then deprotected using same procedure to yield Compound 109.

Example 1R
Synthesis of Compound 112
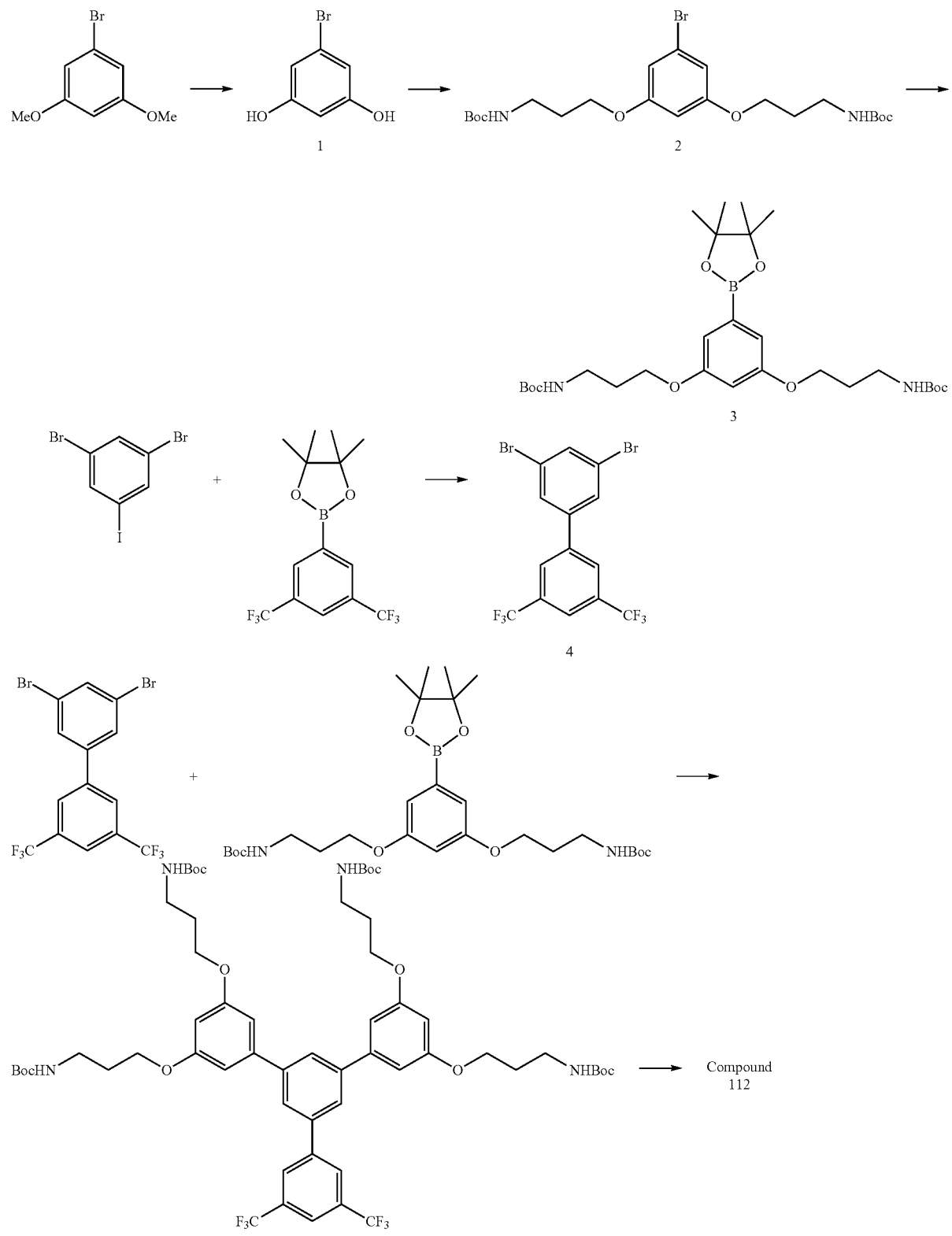

Synthesis of Compound 1:

In a clean dry round bottom flask, 1-bromo-3,5-dimethoxybenzene (8.00 g, 36.9 mmol) was added to 300 ml of dry dichloromethane. The solution was cooled down to 0° C. and $BBr_3$ (25.00 g, 100 mmol) was added dropwise. After 2 hours, the mixture was allowed to warm to room temperature and stirred over night. Methanol (10 ml) was added dropwise to terminate the reaction. The mixture was poured into water and stirred for 2 hours. Then saturated sodium bicarbonate (100 ml) was added and extracted with ethyl acetate. The organic layer was washed with saturated sodium bicarbonate, brine and then dried over $Na_2SO_4$. The residue, after concentration, was purified using chromatography using ethyl acetate/hexane (1:4 v/v) eluent. Yield=4.39 g, (63%).

Synthesis of Compound 2:

Compound 1 (2.7 g, 14.3 mmol) and potassium carbonate (9.8 g, 71.4 mmol) were stirred in DMF (25 ml) and water (2.5 ml) at room temperature for 20 minutes and then heated to 44° C. 3-(Boc-amino) propyl bromide (10.89 g, 45.7 mmol) was added. The resulting mixture was stirred at 44° C. overnight. The mixture was cooled down to room temperature and poured into a mixture of ethyl acetate and water. The organic layer was washed with brine and dried over $Na_2SO_4$. The residue after concentration was purified with chromatography ethyl acetate/hexane (1:4 v/v) eluent. Yield=6.13 g, (83%).

Synthesis of Compound 3:

In a clean dry round bottom flask, compound 2 (3 g, 5.96 mmol), 4,4,5,5-tetramethyl-2-(4,4,5,5-tetramethyl-1,3,2-dioxaborolan-2-yl)-1,3,2-dioxaborolane (1.68 g, 6.56 mmol) and potassium acetate (2.92 g, 29.8 mmol) were stirred in DMSO (30 ml) at room temperature under $N_2$ protection. Then $PdCl_2(dppf)$ (0.289 g, 0.357 mmol) was added. The resulting mixture was stirred at 80° C. overnight. Then the reaction was cooled down to room temperature. The mixture was filtered through celite and washed with ethyl acetate. The organic layer was washed with water, brine then dried over $Na_2SO_4$. Then residue after concentration is purified by chromatography (eluent: ethyl acetate/hexanes=3/7). Yield=2.27 g, (70%).

Synthesis of Compound 4:

In a clean Schlenk tube, 1,3-dibromo-5-iodobenzene (2.07 g, 5.73 mmol) was added to 2-[3,5-bis(trifluoromethyl)phenyl]-4,4,5,5-tetramethyl-1,3,2-dioxaborolane (1.5 g, 4.41 mmol), $K_3PO_4$ (1.87 g, 8.82 mmol) and $PdCl_2(dppf)$ (0.178 g, 0.22 mmol) along with 10 ml toluene and 1 ml water. The Schlenk tube was degassed by three freeze-pump-thaw cycles and then purged with nitrogen and the mixture was stirred at 95° C. for 18 hours. The reaction mixture, cooled to room temperature, was then quenched with water (25 mL) and extracted with ethyl acetate (30 mL×3). The combined organic layers were washed with a saturated aqueous solution of $NaHCO_3$ (50 mL) and brine (50 mL), dried over anhydrous $Na_2SO_4$ and evaporated under reduced pressure. The residue was purified using column chromatography using pure hexane Yield=0.95 g, (48%).

Suzuki Coupling:

In a clean Schlenk tube, compound 4 (0.35 g, 0.78 mmol) was added to compound 3 (0.99 g, 1.79 mmol), $K_3PO_4$ (0.66 g, 3.12 mmol) and $PdCl_2(dppf)$ (32 mg, 0.039 mmol) along with 6 ml toluene and 0.6 ml water. The Schlenk tube was degassed by three freeze-pump-thaw cycles and then purged with nitrogen and the mixture was stirred at 95° C. for 20 hours. The reaction mixture, cooled to room temperature, was then quenched with water (25 mL) and extracted with ethyl acetate (30 mL×3). The combined organic layers were washed with a saturated aqueous solution of $NaHCO_3$ (50 mL) and brine (50 mL), dried over anhydrous $Na_2SO_4$ and evaporated under reduced pressure. The residue was purified using column chromatography using ethyl acetate/hexane mixture (2:3 v/v). Yield=0.61 g.

Deprotection:

The solid obtained from Suzuki Coupling step (150 mg) is stirred in a mixture of TFA and DCM (1:2 v/v) for 3 hours. The solution is concentrated and dried under overnight vacuum. The solid is then dissolved in minimal amount of methanol and precipitated using hexane/ether mixture (1:1 v/v). The mixture is centrifuged for 1 minute and the supernatant liquid is removed. The residue is dried to remove any residual solvent to yield Compound 112. The purity of compound is >95%.

Example 1S

Synthesis of Compound 110

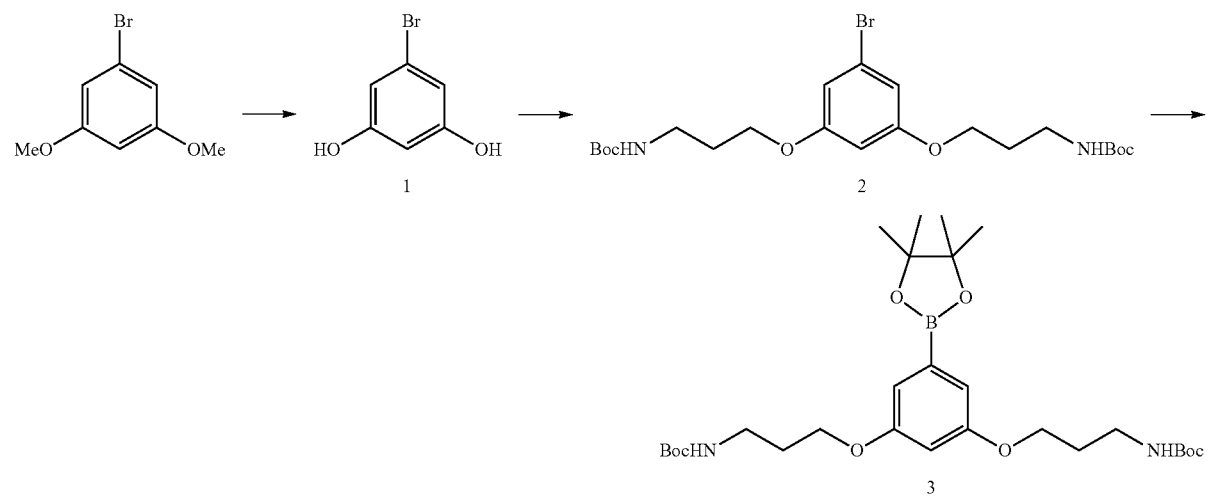

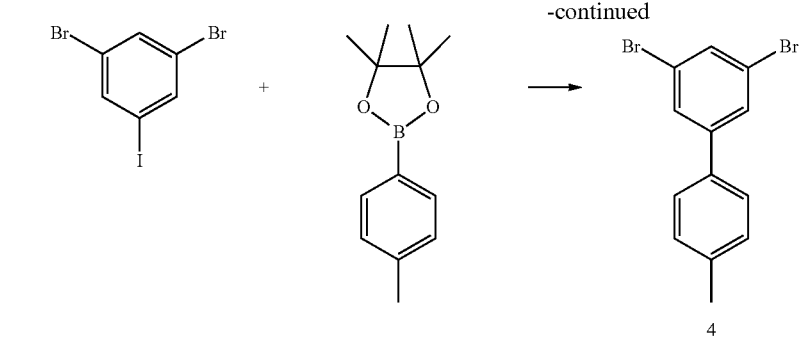

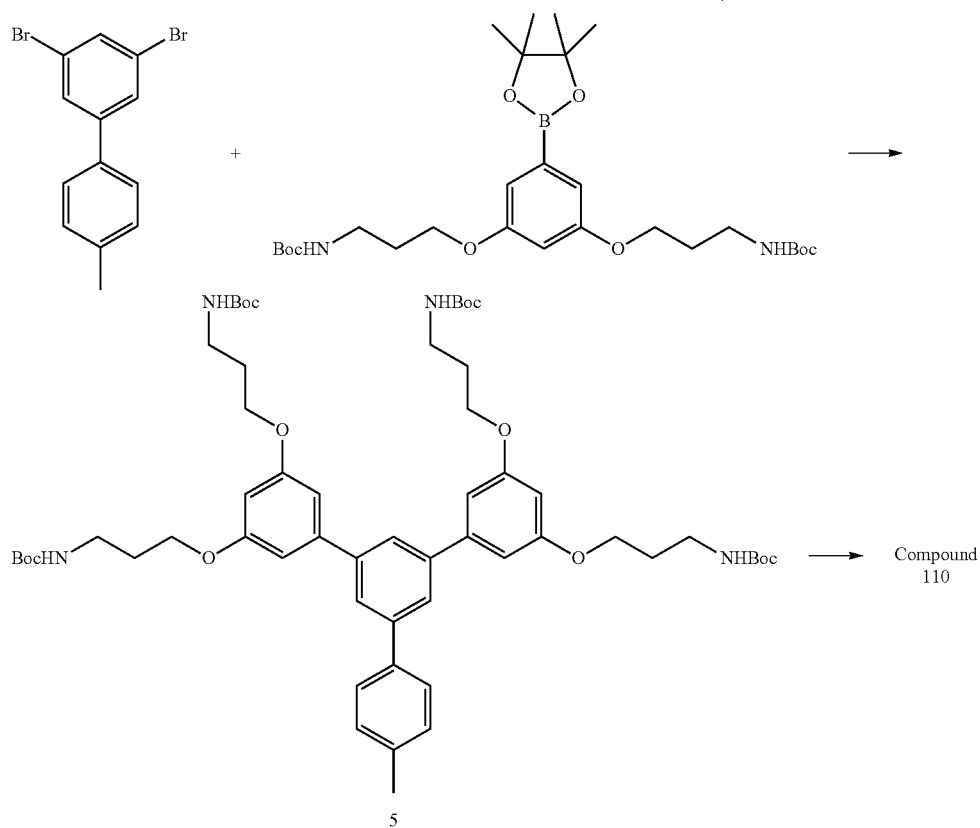

Synthesis of Compound 1:

In a clean dry round bottom flask, 1-bromo-3,5-dimethoxybenzene (8.00 g, 36.9 mmol) was added to 300 ml of dry dichloromethane. The solution was cooled down to 0° C. and $BBr_3$ (25.00 g, 100 mmol) was added dropwise. After 2 hours, the mixture was allowed to warm to room temperature and stirred over night. Methanol (10 ml) was added dropwise to terminate the reaction. The mixture was poured into water and stirred for 2 hours. Then saturated sodium bicarbonate (100 ml) was added and extracted with ethyl acetate. The organic layer was washed with saturated sodium bicarbonate, brine and then dried over $Na_2SO_4$. The residue, after concentration, was purified using chromatography using ethyl acetate/hexane (1:4 v/v) eluent. Yield=4.39 g, (63%).

Synthesis of Compound 2:

Compound 1 (2.7 g, 14.3 mmol) and potassium carbonate (9.8 g, 71.4 mmol) were stirred in DMF (25 ml) and water (2.5 ml) at room temperature for 20 minutes and then heated to 44° C. 3-(Boc-amino) propyl bromide (10.89 g, 45.7 mmol) was added. The resulting mixture was stirred at 44° C. overnight. The mixture was cooled down to room temperature and poured into a mixture of ethyl acetate and water. The organic layer was washed with brine and dried over $Na_2SO_4$. The residue after concentration was purified with chromatography ethyl acetate/hexane (1:4 v/v) eluent. Yield=6.13 g, (83%).

Synthesis of Compound 3:

In a clean dry round bottom flask, compound 2 (3 g, 5.96 mmol), 4,4,5,5-tetramethyl-2-(4,4,5,5-tetramethyl-1,3,2-dioxaborolan-2-yl)-1,3,2-dioxaborolane (1.68 g, 6.56 mmol) and potassium acetate (2.92 g, 29.8 mmol) were stirred in DMSO (30 ml) at room temperature under $N_2$ protection. Then $PdCl_2(dppf)$ (0.289 g, 0.357 mmol) was added. The resulting mixture was stirred at 80° C. overnight. Then the reaction was cooled down to room temperature. The mixture was filtered through celite and washed with ethyl acetate. The organic layer was washed with water, brine then dried over $Na_2SO_4$. Then residue after concentration is purified by chromatography (eluent: ethyl acetate/hexanes=3/7). Yield=2.27 g, (70%).

Synthesis of Compound 4:

In a clean Schlenk tube, 1,3-dibromo-5-iodobenzene (1.29 g, 3.57 mmol) was added to 4,4,5,5-tetramethyl-2-(4- methylphenyl)-1,3,2-dioxaborolane (0.6 g, 2.75 mmol), K$_3$PO$_4$ (1.17 g, 5.5 mmol) and PdCl$_2$(dppf) (67 mg, 0.083 mmol) along with 7 ml toluene and 0.7 ml water. The Schlenk tube was degassed by three freeze-pump-thaw cycles and then purged with nitrogen and the mixture was stirred at 95° C. for 18 hours. The reaction mixture, cooled to room temperature, was then quenched with water (25 mL) and extracted with ethyl acetate (30 mL×3). The combined organic layers were washed with a saturated aqueous solution of NaHCO$_3$ (50 mL) and brine (50 mL), dried over anhydrous Na$_2$SO$_4$ and evaporated under reduced pressure. The residue was purified using column chromatography using pure hexane Yield=0.41 g, (46%).

Suzuki Coupling:

In a clean Schlenk tube, compound 4 (0.2 g, 0.61 mmol) was added to compound 3 (0.78 g, 1.41 mmol), K$_3$PO$_4$ (0.52 g, 2.45 mmol) and PdCl$_2$(dppf) (25 mg, 0.03 mmol) along with 5 ml toluene and 0.5 ml water. The Schlenk tube was degassed by three freeze-pump-thaw cycles and then purged with nitrogen and the mixture was stirred at 95° C. for 20 hours. The reaction mixture, cooled to room temperature, was then quenched with water (25 mL) and extracted with ethyl acetate (30 mL×3). The combined organic layers were washed with a saturated aqueous solution of NaHCO$_3$ (50 mL) and brine (50 mL), dried over anhydrous Na$_2$SO$_4$ and evaporated under reduced pressure. The residue was purified using column chromatography using ethyl acetate/hexane mixture (2:3 v/v). Yield=0.53 g.

Deprotection:

The solid obtained from Suzuki Coupling step (150 mg) is stirred in a mixture of TFA and DCM (1:2 v/v) for 3 hours. The solution is concentrated and dried under overnight vacuum. The solid is then dissolved in minimal amount of methanol and precipitated using hexane/ether mixture (1:1 v/v). The mixture is centrifuged for 1 minute and the supernatant liquid is removed. The residue is dried to remove any residual solvent to yield Compound 110. The purity of compound is >95%.

Example 1T

Synthesis of Compound 120

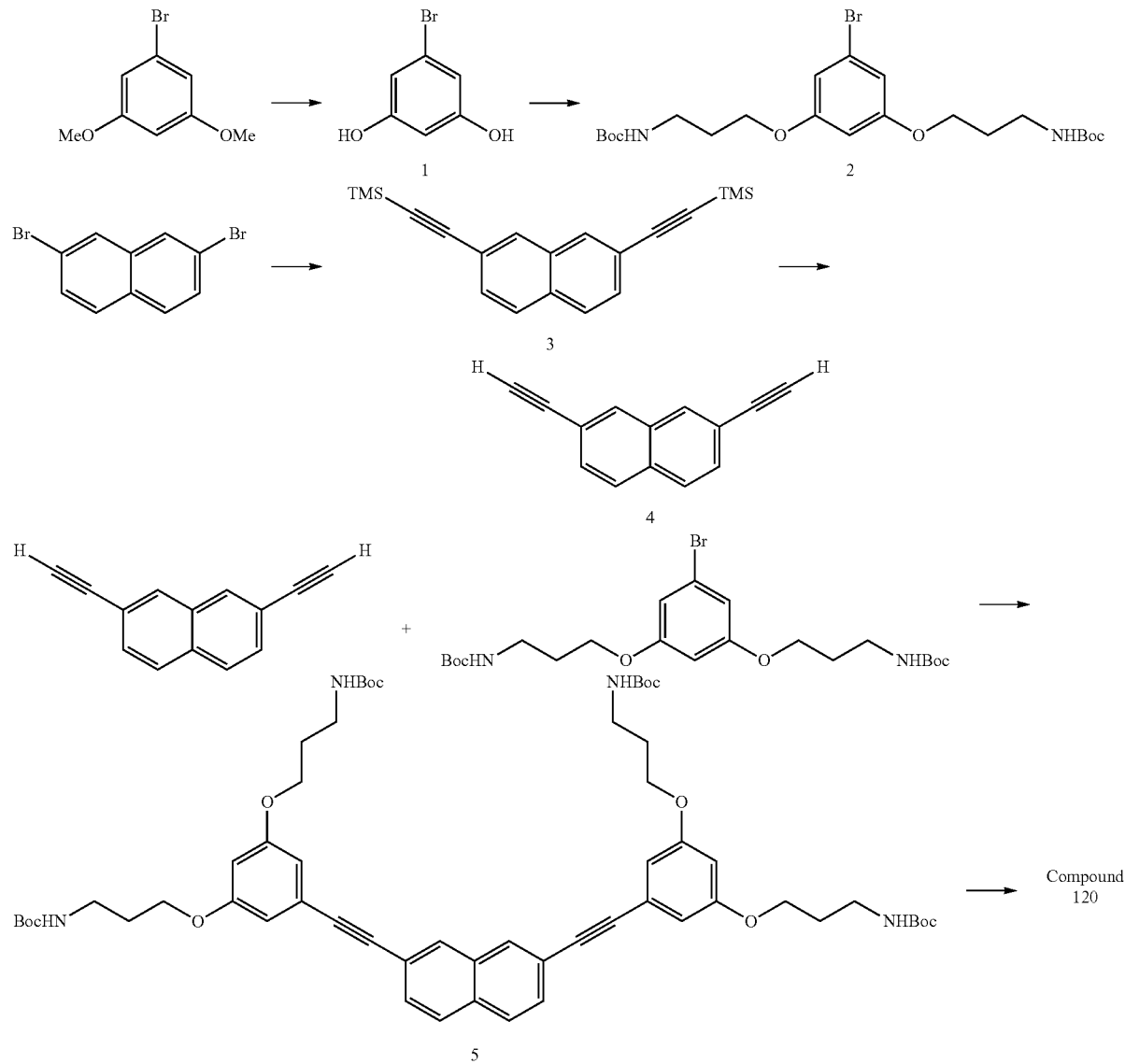

Synthesis of Compound 1:

In a clean dry round bottom flask, 1-bromo-3,5-dimethoxybenzene (8.00 g, 36.9 mmol) was added to 300 ml of dry dichloromethane. The solution was cooled down to 0° C. and BBr$_3$ (25.00 g, 100 mmol) was added dropwise. After 2 hours, the mixture was allowed to warm to room temperature and stirred over night. Methanol (10 ml) was added dropwise to terminate the reaction. The mixture was poured into water and stirred for 2 hours. Then saturated sodium bicarbonate (100 ml) was added and extracted with ethyl acetate. The organic layer was washed with saturated sodium bicarbonate, brine and then dried over Na$_2$SO$_4$. The residue, after concentration, was purified using chromatography using ethyl acetate/hexane (1:4 v/v) eluent. Yield=4.39 g, (63%).

Synthesis of Compound 2:

Compound 1 (2.7 g, 14.3 mmol) and potassium carbonate (9.8 g, 71.4 mmol) were stirred in DMF (25 ml) and water (2.5 ml) at room temperature for 20 minutes and then heated to 44° C. 3-(Boc-amino) propyl bromide (10.89 g, 45.7 mmol) was added. The resulting mixture was stirred at 44° C. overnight. The mixture was cooled down to room temperature and poured into a mixture of ethyl acetate and water. The organic layer was washed with brine and dried over Na$_2$SO$_4$. The residue after concentration was purified with chromatography ethyl acetate/hexane (1:4 v/v) eluent. Yield=6.13 g, (83%).

Synthesis of Compound 3:

To the solution of dibromonapthalene (1.54 g, 5.40 mmol) in dried THF (80 mL), were added trimethylsilylacetylene (6.1 mL, 43 mmol), CuI (103 mg, 0.54 mmol), Pd(PPh$_3$)$_4$ (624 mg, 0.54 mmol) and triethylamine (18.8 mL, 135 mmol) successively under N$_2$. The resultant mixture was shielded from light by aluminum foil wrap and heated to 55° C. with stirring for 18 hours. The reaction mixture was concentrated by removing the solvent under reduced pressure; the residue was taken up to diethyl ether, washed with water and dried over Na$_2$SO$_4$. After removal of solvent under reduced pressure, the residue was purified by flash column chromatography (pure hexane) to yield the product (97%) as an off-white solid.

Synthesis of Compound 4:

In a clean dry round bottom flask, potassium fluoride (KF.2H$_2$O 0.7 g, 7.49 mmol) was added to a solution of compound 3 (0.4 g, 1.24 mmol) in 5 ml of dry tetrahydrofuran (THF) and 5 ml of MeOH. The reaction was stirred overnight under nitrogen. The solvent was evaporated and the residue was extracted using ethyl acetate and water. The organic layer was washed with water 3 times and then washed with brine and dried over Na$_2$SO$_4$. The compound needed no further purification. Yield~quantitative.

Sonogashira Coupling:

To the solution of compound 4 (0.18 g, 1 mmol) in dried THF (20 mL), were added compound 2 (1.16 g, 2.3 mmol), CuI (19.45 mg, 0.1 mmol), Pd(PPh$_3$)$_4$ (0.115 g, 0.1 mmol) and triethylamine (3.5 mL, 25 mmol) successively under N$_2$. The resultant mixture was heated to 70° C. with stirring for 18 hours. The reaction mixture was concentrated by removing the solvent under reduced pressure; the residue was redissolved in ethyl acetate, washed with water and dried over Na$_2$SO$_4$. After removal of solvent under reduced pressure, the residue was purified by flash column chromatography using ethyl acetate/hexane mixture (2:3 v/v). Yield=0.36 g.

Deprotection:

The solid obtained from Sonogashira step (150 mg) is stirred in a mixture of TFA and DCM (1:2 v/v) for 3 hours. The solution is concentrated and dried under overnight vacuum. The solid is then dissolved in minimal amount of methanol and precipitated using hexane/ether mixture (1:1 v/v). The mixture is centrifuged for 1 minute and the supernatant liquid is removed. The residue is dried to remove any residual solvent to yield Compound 120. The purity of compound is >95%.

Example 1U

Synthesis of Compound 108

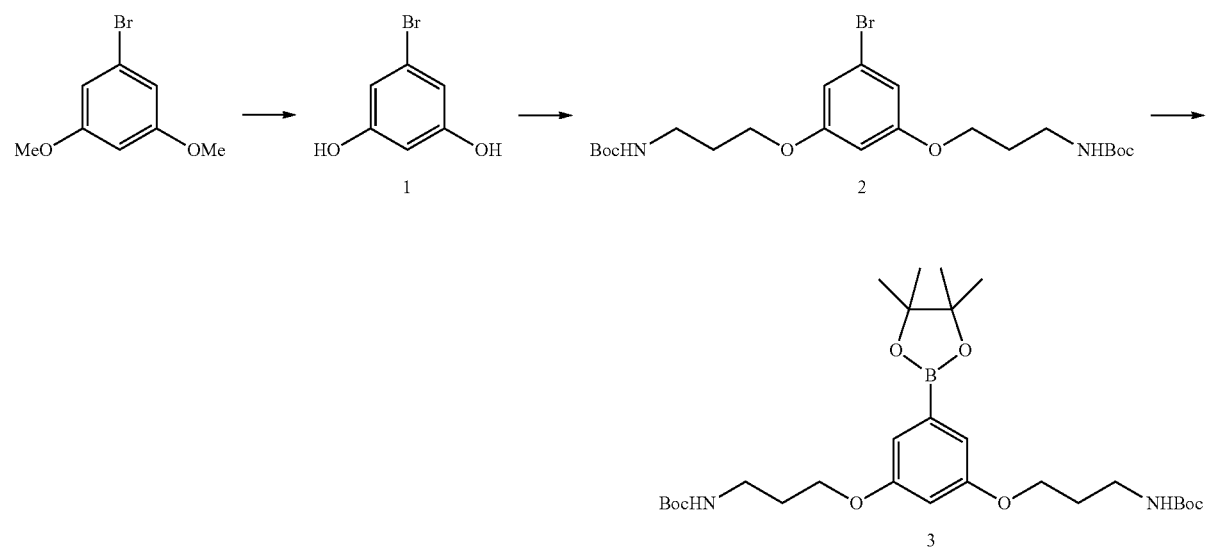

-continued

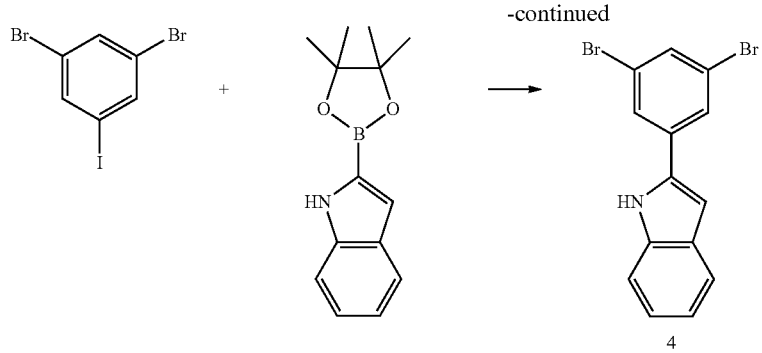

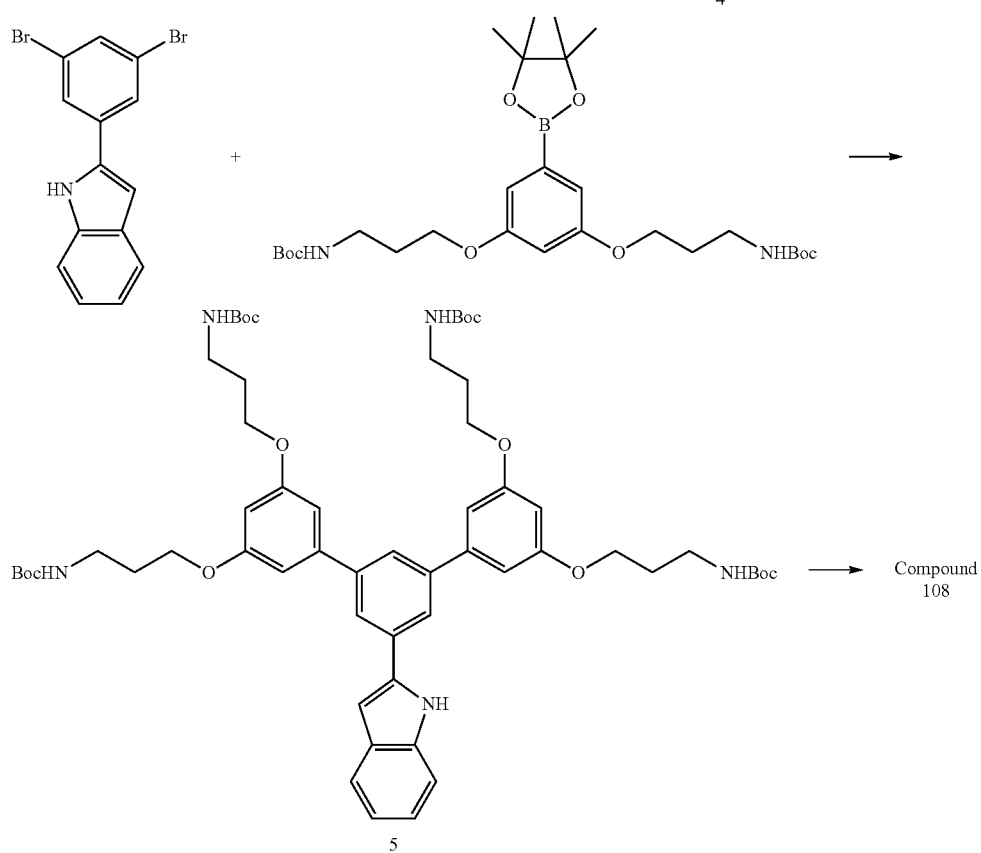

Synthesis of Compound 1:

In a clean dry round bottom flask, 1-bromo-3,5-dimethoxybenzene (8.00 g, 36.9 mmol) was added to 300 ml of dry dichloromethane. The solution was cooled down to 0° C. and BBr₃ (25.00 g, 100 mmol) was added dropwise. After 2 hours, the mixture was allowed to warm to room temperature and stirred over night. Methanol (10 ml) was added dropwise to terminate the reaction. The mixture was poured into water and stirred for 2 hours. Then saturated sodium bicarbonate (100 ml) was added and extracted with ethyl acetate. The organic layer was washed with saturated sodium bicarbonate, brine and then dried over Na₂SO₄. The residue, after concentration, was purified using chromatography using ethyl acetate/hexane (1:4 v/v) eluent. Yield=4.39 g, (63%).

Synthesis of Compound 2:

Compound 1 (2.7 g, 14.3 mmol) and potassium carbonate (9.8 g, 71.4 mmol) were stirred in DMF (25 ml) and water (2.5 ml) at room temperature for 20 minutes and then heated to 44° C. 3-(Boc-amino) propyl bromide (10.89 g, 45.7 mmol) was added. The resulting mixture was stirred at 44° C. overnight. The mixture was cooled down to room temperature and poured into a mixture of ethyl acetate and water. The organic layer was washed with brine and dried over Na₂SO₄. The residue after concentration was purified with chromatography ethyl acetate/hexane (1:4 v/v) eluent. Yield=6.13 g, (83%).

Synthesis of Compound 3:

In a clean dry round bottom flask, compound 2 (3 g, 5.96 mmol), 4,4,5,5-tetramethyl-2-(4,4,5,5-tetramethyl-1,3,2-dioxaborolan-2-yl)-1,3,2-dioxaborolane (1.68 g, 6.56 mmol) and potassium acetate (2.92 g, 29.8 mmol) were stirred in DMSO (30 ml) at room temperature under N₂ protection. Then PdCl₂(dppf) (0.289 g, 0.357 mmol) was added. The resulting mixture was stirred at 80° C. overnight. Then the reaction was cooled down to room temperature. The mixture was filtered through celite and washed with ethyl acetate. The organic layer was washed with water, brine then dried over Na$_2$SO$_4$. Then residue after concentration is purified by chromatography (eluent: ethyl acetate/hexanes=3/7). Yield=2.27 g, (70%).

Synthesis of Compound 4:

In a clean Schlenk tube, 1,3-dibromo-5-iodobenzene (1.93 g, 5.34 mmol) was added to 2-(4,4,5,5-tetramethyl-1,3,2-dioxaborolan-2-yl)-1H-indole (1 g, 4.11 mmol), K$_3$PO$_4$ (1.74 g, 8.22 mmol) and PdCl$_2$(dppf) (0.133 g, 0.164 mmol) along with 10 ml toluene and 1 ml water. The Schlenk tube was degassed by three freeze-pump-thaw cycles and then purged with nitrogen and the mixture was stirred at 95° C. for 18 hours. The reaction mixture, cooled to room temperature, was then quenched with water (25 mL) and extracted with ethyl acetate (30 mL×3). The combined organic layers were washed with a saturated aqueous solution of NaHCO$_3$ (50 mL) and brine (50 mL), dried over anhydrous Na$_2$SO$_4$ and evaporated under reduced pressure. The residue was purified using column chromatography using pure hexane. The product was recrystallized using hexanes. Yield=0.52 g, (36%).

Suzuki Coupling:

In a clean Schlenk tube, compound 4 (0.25 g, 0.71 mmol) was added to compound 3 (0.9 g, 1.64 mmol), K$_3$PO$_4$ (0.61 g, 2.85 mmol) and PdCl$_2$(dppf) (29 mg, 0.036 mmol) along with 6 ml toluene and 0.6 ml water. The Schlenk tube was degassed by three freeze-pump-thaw cycles and then purged with nitrogen and the mixture was stirred at 95° C. for 20 hours. The reaction mixture, cooled to room temperature, was then quenched with water (25 mL) and extracted with ethyl acetate (30 mL×3). The combined organic layers were washed with a saturated aqueous solution of NaHCO$_3$ (50 mL) and brine (50 mL), dried over anhydrous Na$_2$SO$_4$ and evaporated under reduced pressure. The residue was purified using column chromatography using ethyl acetate/hexane mixture (2:3 v/v). Yield=0.65 g.

Deprotection:

The solid obtained from Suzuki Coupling step (150 mg) is stirred in a mixture of TFA and DCM (1:2 v/v) for 3 hours. The solution is concentrated and dried under overnight vacuum. The solid is then dissolved in minimal amount of methanol and precipitated using hexane/ether mixture (1:1 v/v). The mixture is centrifuged for 1 minute and the supernatant liquid is removed. The residue is dried to remove any residual solvent to yield Compound 108. The purity of compound is >95%.

Example 2

Antimicrobial Activity—Minimum Inhibitory Concentrations (MIC)

The compounds are screened for antimicrobial activity against a number of clinically relevant pathogens. Minimum Inhibitory Concentrations (MIC) of each of the compounds are determined using standard procedures for clinical ocular isolates of Ciprofloxacin Susceptible (CS) *S. aureus* (CSSA), Ciprofloxacin Resistant (CR) *S. aureus* (CRSA), CS *S. epidermidis* (CSSE), CR *S. epidermidis* (CRSE), *St. pneumoniae* (SP), *St. viridans* group (SV), *Moraxella* Species (MS) (including *Moraxella catarrhalis*), *H. influenzae* (HI), *P. aeruginosa* (PA), *Serratia marcescens* (SM), *S. aureus* fluoroquinolone-susceptible, *S. aureus* fluoroquinolone-resistant, *S. epidermidis* (Coagulase-negative *Staphylococcus*) fluoroquinolone-susceptible, *S. epidermidis* (Coagulase-negative *Staphylococcus*) fluoroquinolone-resistant, and *Serratia marcescens*.

General Procedures:

Mueller-Hinton Broth in tubes is inoculated with isolates of *Staphylococcus aureus* fluoroquinolone-susceptible, *Staphylococcus aureus* fluoroquinolone-resistant, *Staphylococcus epidermidis* (Coagulase-negative *Staphylococcus*) fluoroquinolone-susceptible, *Staphylococcus epidermidis* (Coagulase-negative *Staphylococcus*) fluoroquinolone-resistant, *Pseudomonas aeruginosa* and *Serratia marcescens*, plus two controls (*Staphylococcus aureus* and *E. coli*) and incubated at 37° C. overnight on a shaker set at 250 rpm.

Mueller-Hinton Broth supplemented with 2% lysed horse blood in tubes is inoculated with isolates of *Streptococcus pneumoniae*, *Streptococcus viridans* group, and *Moraxella* species (including *Moraxella catarrhalis*) plus two controls (*Staphylococcus aureus* and *E. coli*) and incubated at 37° C. overnight. Additionally, Mueller-Hinton Broth in tubes is inoculated with two controls (*Staphylococcus aureus* and *E. coli*) and incubated at 37° C. overnight on a shaker set at 250 rpm.

HTM (*Haemophilus* Test Medium) in tubes is inoculated with isolates of *Haemophilus influenzae* plus two controls (*Staphylococcus aureus* and *E. coli*) and incubated at 37° C. overnight. Additionally, Mueller-Hinton Broth in tubes is inoculated with two controls (*Staphylococcus aureus* and *E. coli*) and incubated at 37° C. overnight on a shaker set at 250 rpm.

On the day of testing, a 640 µg/m (1280 µg/m for *Serratia marcescens* and *Pseudomonas aeruginosa*) concentration is prepared from a 1% stock solution in 0.01% acetic acid, 0.2% BSA in polypropylene tubes.

Serial doubling dilutions in 0.01% acetic acid, 0.2% BSA in 96 well polypropylene plates, which are used as reservoirs for the inoculation of the test plates, are carried out to obtain serial dilutions of test agents at 10 times the required test concentrations: 640, 320, 160, 80, 40, 20, 10, 5, 2.5, 1.25, and 0.625 µg/m (1280, 640, 320, 160, 80, 40, 20, 10, 5, 2.5, and 1.25 µg/m for *Serratia marcescens* and *Pseudomonas aeruginosa*).

Ten µl of diluted 10× test agents is added to each well of one row of the 96 well polypropylene plates from column 2 to column 12 (column 1 is a control for bacteria alone, with no peptide). Test agent concentrations in columns 2-12 are as follows: 64, 32, 16, 8, 4, 2, 1, 0.5, 0.25, 0.125, and 0.0625 µg/m (128, 64, 32, 16, 8, 4, 2, 1, 0.5, 0.25, and 0.125 µg/m for *Serratia marcescens* and *Pseudomonas aeruginosa*). The same peptide is in each of the 8 rows. One plate contains dilutions of one test agent and 8 bacterial isolates.

On the day of testing, the overnight bacterial broth cultures of *Staphylococcus aureus* fluoroquinolone-susceptible, *Staphylococcus aureus* fluoroquinolone-resistant, *Staphylococcus epidermidis* (Coagulase-negative *Staphylococcus*) fluoroquinolone-susceptible, *Staphylococcus epidermidis* (Coagulase-negative *Staphylococcus*) fluoroquinolone-resistant, *Serratia marcescens*, and *Pseudomonas aeruginosa*, plus two controls (*Staphylococcus aureus* and *E. coli*) are diluted in 5 ml of trypticase soy broth to yield turbidity equal to a 0.5 McFarland standard. The final inoculum for MIC testing for *Staphylococcus aureus* fluoroquinolone-susceptible, *Staphylococcus aureus* fluoroquinolone-resistant, *Staphylococcus epidermidis* (Coagulase-negative *Staphylococcus*) fluoroquinolone-susceptible, *Staphylococcus epidermidis* (Coagulase-negative *Staphylococcus*) fluoroquinolone-resistant, *Serratia marcescens*, and *Pseudomonas aeruginosa* is achieved by placing 0.05 ml of the turbidity adjusted sample to 5 ml of Mueller-Hinton broth.

Control Bacteria—The two control bacteria (*Staphylococcus aureus* and *E. coli*) are treated as above.

On the day of testing, the overnight bacterial broth cultures of *Streptococcus pneumoniae*, *Streptococcus viridans* and *Moraxella* species (including *Moraxella catarrhalis*) plus two controls (*Staphylococcus aureus* and *E. coli*) are diluted in 5 ml of trypticase soy broth to yield turbidity equal to a 0.5 McFarland standard. The final inoculum for MIC testing for *Streptococcus pneumoniae*, *Streptococcus viridans* and *Moraxella* species (including *Moraxella catarrhalis*) is achieved by placing 0.1 ml of the turbidity adjusted sample to 5 ml of Mueller-Hinton broth containing 2% lysed horse red blood cells.

Control Bacteria Set #1—this set of control bacteria are treated as the *Streptococcus pneumoniae*, *Streptococcus viridans* and *Moraxella* species (including *Moraxella catarrhalis*) test isolates above; the control bacteria is treated in the same manner and conditions as the test *Streptococcus pneumoniae*, *Streptococcus viridans* and *Moraxella* species (including *Moraxella catarrhalis*) isolates. This set of control bacteria is to determine whether there is a difference in the MICs by performing the MIC determinations in 2% lysed horse red blood cells with the standard method performed in Mueller-Hinton broth.

Control Bacteria Set #2—the control bacteria are added to 5 ml of Mueller-Hinton Broth without the 2% lysed horse red blood cells to achieve the standard inoculum concentration. This set of control bacteria is the normal control to determine whether the compounds are at the target MICs.

On the day of testing, the overnight bacterial broth cultures of *Haemophilus* species is diluted in 5 ml of trypticase soy broth to yield turbidity equal to a 0.5 McFarland standard. The final inoculum for MIC testing for *Haemophilus* species is achieved by placing 0.1 ml of the turbidity adjusted sample to 5 ml of HTM medium.

Control Bacteria Set #1—this set of control bacteria are treated as the *Haemophilus influenzae* test isolates above; the control bacteria are treated in the same manner and conditions as the test *Haemophilus influenzae* isolates. This set of control bacteria is to determine whether there is a difference in the MICs by performing the MIC determinations in HTM broth with the standard method performed in Mueller-Hinton broth.

Control Bacteria Set #2—the control bacteria are added to 5 ml of Mueller-Hinton Broth to achieve the standard inoculum concentration. This set of control bacteria is the normal control to determine whether the compounds are at the target MICs.

Ninety μl of the bacterial suspensions is dispensed in each well from column 1 to column 12. Each bacterial isolate is placed in one row of a 96 well polypropylene plate containing the test agents. The plates are placed on shaker at 15 minutes at room temperature, and then incubated at 37° C. overnight. MICs are determined visually as the lowest concentration of drug that inhibits visible bacterial growth.

The MICs of the compounds are compared statistically with the Kruskal-Wallis ANOVA with Duncan's Multiple Comparisons Test using True Epistat statistical software (True Epistat, Richardson, Tex.).

In some emebodiments, the bacteria have been isolated from cases of Keratitis, Endophthalmitis, Blepharitis and or Conjunctivitis. Most *Streptococcus pneumoniae* isolates are from cases of conjunctivitis. In some embodiments, the bacteria are fluoroquinolone-resistant, which indicates the bacteria are resistant to the second generation fluoroquinolones ciprofloxacin and ofloxacin but, not necessarily resistant to the fourth generation fluoroquinolones gatifloxacin and moxifloxacin by CLSI serum standards.

Actual results from a representative MIC assay are shown below in Table 1. Data is expressed as $MIC_{50}$ in μg/ml. The bacterial isolates were as follows: *E. coli* (25922); *S. aureus* (27660); *E. faecalis* (29212); *P. aeruginosa* (10145); and *K. pneumoniae* (13883).

TABLE 1

| Compound | E. coli | S. aureus | E. faecalis | P. Aeruginosa | K. Pnuemnoiae |
|---|---|---|---|---|---|
| 108 | 6.25 | 1.56 | 12.5 | 25 | >50 |
| 120 | 3.13 | 3.13 | 1.56 | 6.25 | 6.25 |
| 100 | 50 | 50 | 25 | >50 | >50 |
| 101 | >50 | 12.5 | 12.5 | 50 | >50 |
| 109 | 1.56 | 0.4 | 1.56 | 12.5 | 6.25 |
| 102 | >50 | 12.5 | 25 | >50 | 50 |
| 103 | >50 | 25 | 25 | 50 | >50 |
| 104 | >50 | 25 | 25 | 50 | >50 |
| 110 | 3.13 | 0.78 | 1.56 | 25 | 6.25 |
| 105 | 50 | 25 | >50 | 50 | >50 |
| 111 | 50 | 12.5 | 50 | >50 | >50 |
| 112 | 3.13 | 1.56 | 1.56 | 12.5 | 3.13 |
| 113 | 3.13 | 1.56 | 1.56 | 12.5 | 3.13 |
| 106 | 25 | 1.56 | 50 | 50 | >50 |
| 107 | >50 | 50 | 25 | 25 | >50 |
| 114 | 1.56 | 0.78 | 3.13 | 12.5 | 1.56 |
| 115 | 6.25 | 12.5 | >50 | 25 | 12.5 |
| 116 | 3.13 | 3.13 | 25 | 25 | 25 |
| 117 | 1.56 | 1.56 | 0.78 | 12.5 | 1.56 |
| 118 | 3.13 | 12.5-25 | 1.56-3.13 | 25 | 12.5-25 |
| 119 | 25 | 12.5 | 6.25 | 25 | 50 |

A new series of aryl compounds was designed to evaluate the effect of charge and aromatic group hydrophobicity on the biological activity while still maintaining an amphiphilic topology. Four and six cationic charges were investigated, and three different central rings were used to tune the overall hydrophobicity: benzene, naphthalene, and phenylbenzene. The hydrophobicities of the aryl compounds were quantified using reversed-phase HPLC retention times (Rt). The antimicrobial activities (expressed as minimum inhibitory concentration (MIC)) of these compounds were tested against four pathogens, including both Gram-negative and Gram-positive bacteria, and their hemolysis (evaluated in terms of $HC_{50}$, the lowest concentration that causes 50% hemolysis of red blood cells (RBCs)) was tested against human RBCs.

Table 2 summarizes the biological activities of the compounds in comparison with MSI-78. Relative to the previously studied triaryl benzene oligomers, Compound 111 containing a benzene central ring showed a significant decrease in hemolytic activity ($HC_{50}$>1000 μg/mL vs 36 μg/mL), although the antimicrobial activity was still low. The reduced toxicity was attributed to the increase in hydrophilicity due to the greater number of cationic charges (4 vs 2). Changing the central ring from benzene (Compound 111) to naphthalene (Compound 119) increased the hydrophobicity but did not alter the antimicrobial activity. Compound 119 was more hemolytic and thus had a lower selectivity than Compound 111. Compound 118 with a pendant phenyl group was the most hydrophobic among the three compounds in the series containing four charges (Rt=28.8 min). Relative to Compound 119, Compound 118 showed an 8-fold increase in antimicrobial activity against *Escherichia coli* (MIC=3.13 μg/mL) as well as a higher $HC_{50}$ and thus an improved selectivity of 172. The increased activity against *E. coli* for Compound 118 was attributed to the arrangement of the hydrophobic pendant aromatic ring, which is known to insert into the membrane interface.

To elucidate the role of charge, Compounds 116 and 115, each with six charges, were designed and synthesized for comparison to their analogues with four charges (Compounds 119 and 118, respectively). Compounds 116 and 115 containing naphthalene and phenylbenzene central rings, respectively, had higher $HC_{50}$ values (i.e., were less toxic against RBCS) than Compounds 119 and 118. Compound 116 showed improved antimicrobial activity against both *Staphylococcus aureus* and *E. coli* relative to Compound 119, resulting in a very high selectivity of 200. This was almost 20 times higher than the selectivity of MSI-78, and the potency was also increased (MIC≈3 μg/mL vs 16 μg/mL for MSI-78). Compound 115 did not show a significant improvement in the antimicrobial activity relative to Compound 118, which was already active, but it had better selectivity for *S. aureus*. These data confirm that increasing the charge improves the selectivity.

TABLE 2

| Compound[†] | MIC (μg/ml) | | $HC_{50}$ | Selectivity ($HC_{50}$/MIC) | |
|---|---|---|---|---|---|
| | S. aureus | E. coli | (μg/ml) | S. aureus | E. coli |
| 111 | 12.5 | 50 | >1000 | >80 | >20 |
| 119 | 12.5 | 25 | 195 | 15.6 | 7.8 |
| 118 | 12.5 | 3.13 | 537 | 43 | 171.5 |
| 116 | 3.13 | 3.13 | 656 | 209.6 | 209.6 |
| 115 | 6.25 | 6.25 | >1000 | >160 | >160 |
| MSI-78[††] | 8-16 | 16-32 | 120 | 8-15 | 4-8 |

[†]Each —O—$(CH_2)_3$—$NH_2$ group of the listed compounds is charged as follows: —O—$(CH_2)_3$—$NH_3^+$
[††]Data from Thaker, et al., J. Med. Chem., 2011, 54, 2241.

Example 3

Antimicrobial Activity Vs. Gram-Positive Clinical Isolates and Gram-Negative Clinical Isolates The compound are evaluated in vitro in accordance with defined CLSI documents specific to the organisms (aerobic, anaerobic or yeast) tested in this study. Ampicillin, ceftazidime, cefuroxime, ciprofloxacin, linezolid, and vancomycin are tested alongside as comparator agents for aerobic bacteria; clindamycin and metronidazole are tested as comparators for anaerobes; fluconazole is tested as a comparator for yeast isolates. Stock solutions of Compounds are prepared in dimethyl sulfoxide (DMSO). Ampicillin, ceftazidime, cefuroxime, ciprofloxacin, linezolid, vancomycin, metronidazole, clindamycin, and fluconazole are prepared each according to its manufacturer's guideline.

Aerobes (M7-A7)1

Minimum inhibitory concentrations (MICS) in μg/m are determined according to CLSI guideline M7-A7 by broth microdilution. All aerobes are tested using Mueller-Hinton broth medium with the exception of *Streptococcus* spp., which is tested using cation-adjusted Mueller-Hinton broth supplemented with 2-5% lysed horse blood.

Example 4

MICs with *Staphylococcus* Species with Defined Resistance Phenotypes

Evaluation of the susceptibility profiles of Compounds against selected isolates is carried out in vitro by broth microdilution methodology using Mueller-Hinton broth medium according to CLSI document M7-A7. CLSI interpretive breakpoints are applied where applicable as directed by CLSI document M100-S17.

Example 5

Cytotoxicity and Selectivity

Cytotoxicity of the compounds are evaluated in a colorimetric assay using a transformed human liver cell line (HepG2, HB-8065) and an embryonic mouse cell line (NIH/3T3 cells, CRL-1658). This assay measures the bioreduction of a novel tetrazolium compound to a soluble formazan product by viable cells. HepG2 cells are seeded in 96 well plates at $2\times10^4$ cells/well in MEM medium with 10% fetal bovine serum (FBS) 24 hours prior to use. NIH/3T3 cells are seeded in 96 well plates at $2\times10^4$ cells/well in DMEM medium with 10% bovine calf serum (BCS) 24 hours prior to use. Cell monolayers are rinsed in serum-free media and incubated for one hour with a Compound in serum-free media. After incubation, the media is replaced with serum supplemented media and live cells are measured using the Cell Titer 96 Aqueous Non-Proliferation Assay kit (Promega, Madison, Wis.). $EC_{50}$ values are determined using a four parameter logistic equation: $Y=Bottom+(Top-Bottom)/(1+10\char`^((Log\ EC_{50}-X)*HillSlope))$.

Actual results from a representative cytotoxicity assay are shown below in Table 3. Data is expressed as $EC_{50}$ in μg/ml.

TABLE 3

| Compound | NIH 3T3 | HepG2 |
|---|---|---|
| 108 | | |
| 120 | 15.2 | 36.4 |
| 100 | 23.2 | 48.6 |
| 101 | 52.4 | |
| 109 | 69.0 | |
| 102 | 36.1 | 48.4 |
| 103 | 32.7 | 55.5 |
| 104 | 34.7 | 54 |
| 110 | 129.3 | |
| 105 | 83.4 | |
| 111 | 814.3 | >1021 |
| 112 | 69.4 | |
| 113 | 99.5 | |
| 106 | 190.9 | |
| 107 | 131.0 | |
| 114 | 33.6 | 40.4 |
| 115 | 109.5 | |
| 116 | 165.4 | |
| 117 | 31.6 | |
| 118 | 240.6 | |

Cytotoxicity of the compounds is also evaluated in a hemolysis assay using human erythrocytes. Pooled whole human blood is centrifuged to separate the red blood cells (RBC). The isolated RBCs are rinsed and diluted in Tris-buffered saline (TBS buffer, pH 7.4) to obtain a 0.22% RBC stock suspension. 5 μL of a Compound stock solution is added to 45 μL of RBC suspension and incubated with shaking for 1 hour at 37° C. At the conclusion of the incubation time, samples are centrifuged and 30 μL of the supernatant is added to 100 μL of water. $OD_{414}$ measurements are read for hemoglobin concentration. The bee venom peptide melittin is used as a positive control. $EC_{50}$ values are determined as described above.

Example 6

Time-Kill Vs *S. Aureus* (ATCC 27660)

Time-kill studies of the compounds versus *E. coli* ATCC25922, *E. coli* (lab strain) D31, and *S. aureus*

ATCC27660 are determined in a standard protocol by measuring the time it takes to reduce the initial inoculums 3 log units. Three ml of cation-adjusted Mueller-Hinton medium is inoculated with 20 μL of frozen bacterial stock and incubated at 37° C. on a shaker platform (250 rpm) overnight. The suspension is diluted to approximately $5 \times 10^5$ cfu/mL and treated with 2×, 5×, 10×, and 20×MIC (MIC=1 μg/mL). The compound stock solutions are prepared at 10 mg/mL in DMSO. Time points are collected and viable bacteria are counted on MH Agar plates after an 18 hour incubation.

Example 7

Serial Passage Resistance in MSSA (ATCC 29213) and MRSA (ATCC 33591)

Frozen bacterial stocks (20 μL) of *S. aureus* ATCC29213 or methicillin-resistant *S. aureus* (MRSA ATCC 33591) are inoculated into 3 mL cation-adjusted Mueller-Hinton medium and incubated at 37° C. on a shaker platform (250 rpm) overnight. The suspension is diluted to approximately $5 \times 10^5$ cfu/mL and inoculated into a polypropylene (Costar) 96-well round bottom plate (90 μL volumes). Stock solutions of the compounds and norfloxacin (Sigma Aldrich, St. Louis, Mo.; Catalogue #N9890) are prepared in DMSO and serial two-fold dilutions of compound are made in 0.01% acetic acid, 0.2% bovine serum albumin directly in the wells of the polypropylene plate at 10 μL/well. Final concentrations of the compounds are 50, 25, 12.5, 6.25, 3.13, 1.56, 0.78, 0.39, 0.19, 0.098, 0.049, and 0.024 μg/mL. Final concentration ranges of norfloxacin are 100, 50, 25, 12.5, 6.25, 3.13, 1.56, 0.78, 0.39, 0.19, 0.098, and 0.049 μg/mL. DMSO concentrations do not exceed 1% in the assay. All samples are performed in triplicate. Following a 24 hour incubation at 37° C., cell growth is assessed by observing the presence of "acceptable growth", defined by CLSI as a ≥2 mm button or definite turbidity. The MIC wells are defined as the lowest concentration where acceptable growth is not observed. For serial passage, 50 μL aliquots are taken from 2 of 3 replicate wells at 0.5×MIC and combined into 900 μL of fresh cation-adjusted Mueller-Hinton medium. The $OD_{600}$ is measured and the cell suspensions are inoculated into polypropylene 96-well round bottom plates (90 μL volumes) at approximately $5 \times 10^5$ cfu/mL. Ten μL of compound stock solutions are added previously to the wells to achieve the concentration ranges for each compound described above. All samples are performed in triplicate. The plates are incubated for 24 hours at 37° C. This process is repeated for a total of 17 passages and MIC values are recorded at each passage.

Example 8

In Vitro Metabolic Stability of Compounds—Blood Plasma

Pooled plasma samples from human (mixed gender), rat (mixed breed and gender) and dog (mixed breed and gender) are incubated with the compounds (5 μM) at 37° C. for 0 and 60 minutes (duplicate samples). Incubations are terminated by addition of ice-cold precipitation solvent (acetonitrile: glacial acetic acid, 9:1 v/v). Supernatants are diluted with equal volume of 0.1% formic acid and analyzed by HPLC-MS/MS. Plasma stability is reported as % parent compound at 60 minutes relative to amount of parent at 0 minutes.

Example 9

Efficacy of Compounds in the Mouse Thigh Burden Model

Female 6-7-week old CD-1 mice are made neutropenic with cyclophosphamide (150 mg/kg, i.p.) on days 4 and 1 before i.m. inoculation with *S. aureus* (ATCC 13709). *S. aureus* inoculum is prepared by transferring colonies from 18-20-hour tryptic soy agar (TSA) cultures to sterile PBS. The density is adjusted to approximately $10^6$ cfu/mL with the aid of a spectrophotometer, and the inoculum concentration is determined by the dilution plate count method. Mice are inoculated by injecting each posterior thigh with 0.1 mL of inoculum. The compounds are given to separate groups of mice (4 females/group) by i.v. bolus doses of 1 or 2 mg/kg/dose at 1 and 5, 1 and 9, or 1 and 13 hours post inoculation. A separate control group of mice receive the inoculum without antibiotic treatment. The compounds are dissolved 50%/50% v/v sterile USP purified water/PBS. Thighs are harvested at 25 hours after inoculation. Thigh muscle and bone tissue are homogenized, aliquots of serial dilutions are plated on TSA and incubated at 37° C. for 20 hours, and colony counts are obtained to calculate cfu/thigh.

Example 10

Efficacy Vs. Vancomycin in the Rat Thigh Burden Model

For each experiment, female 8-9-week old femoral vein cannulated Crl:CD(SD) rats are made neutropenic with cyclophosphamide (150 mg/kg, i.p.) on days 4 and 1 before i.m. inoculation with *S. aureus* (ATCC 13507). A suspension of *S. aureus* is prepared from colonies obtained from an overnight culture, placed in PBS, and adjusted to approximately $10^7$ cfu/mL with the aid of a spectrophotometer. Each rat is injected with 0.2 mL of inoculum into the thigh muscle of the right hind leg. Thighs are harvested at 25 hours after inoculation and processed to determine cfu/thigh. The compounds are given by i.v. bolus injection into a tail vein or 1-hour i.v. infusion, or 4-hour i.v. infusion via the femoral vein cannulae at different time intervals following inoculation. Separate inoculation control groups are included in each experiment, and vancomycin groups are included as comparative agents in the first and second experiments. Each group, including the controls and comparative agent, consists of 4 or more rats.

Example 11

Efficacy of Compounds in Mouse Sepsis Model: *S. aureus* Infection

Sterile saline, vancomycin, or the compounds are administered to separate groups of 8-week old female CD-1 mice (8 mice/group) 1 and 7 hours after i.p. injections of *S. aureus* (ATCC 13709, $5 \times 10^7$ cfu/mL in 5% mucin, 0.5 mL/mouse). The compounds were dissolved in 50%/50% v/v sterile USP purified water/TBS. A suspension of *S. aureus* is prepared from colonies transferred from the TSA plate to sterile PBS. An aliquot of the stock suspension is added to 5% mucin for a final concentration of about $5 \times 10^7$ cfu/mL. The mice are observed for 6 days following inoculation for mortality.

Example 12

Acute Toxicity Studies—Maximum Tolerated Doses

Maximum tolerated dose (MTD) determinations are made in ascending/descending dose studies in mice and rats. The compounds are administered by either i.v. bolus injection in the tail vein of mice and rats or by i.v. infusion via catheter in the femoral vein of rats. At each dose, two to three animals are administered compound and clinical signs are recorded over a 4 to 7 day period. Gross necropsy is performed at the conclusion of the study.

Example 13

Pharmacokinetics of Compounds in Rats

Crl:CD (SD) rats are administered compounds by i.v. bolus injection at the indicated dosages. Plasma is prepared from blood samples taken at 9 time points (n=3) over 28 hours. Compound levels are determined by HPLC-MS/MS. All animals are fitted with two jugular vein cannula (JVC), one each for dose administration and blood collection. Each route of administration is dosed as N=3 Animals are supplied with a commercial rodent diet and water ad libitum. Each rat receives a bolus dosed via the appropriate route of administration at time zero on the day of dosing.

Each blood sample is collected from the rats via a JVC and placed into chilled polypropylene tubes containing sodium EDTA as an anticoagulant. Samples are centrifuged at a temperature of 4° C. and at a speed of 13,000 rpm for 5 minutes. Samples are maintained chilled throughout processing. Each plasma sample is then transferred into labeled polypropylene tubes, placed on dry ice, and stored in a freezer set to maintain −60° C. to −80° C.

Plasma study samples are extracted and analyzed using a previously developed method. A single standard curve and six replicates of quality control samples at three concentrations are extracted using DMSO containing 0.1% formic acid. Plasma samples (50 µL) are added to 150 µL solvent and centrifuged. Supernatants are analyzed by LC/MSMS using a Perkin Elmer series 200 micropump and PE Sciex API4000 Electrospray mass spectrometer. Standard curves are prepared at concentrations of 10000, 5000, 1000, 500, 250, 100, 50 and 25 ng/mL. Quality control samples are prepared at concentrations of 5000, 500, and 50 ng/mL. The standard curve and quality control samples are prepared from independently prepared stock solutions. At least ⅝ of standards must have accuracy within ±15%, except at the LLOQ where ±20% is acceptable. Two thirds of the batch QCs must have accuracy within ±15% of nominal, and at least one QC must pass at each level in order for the run to be accepted.

Individual plasma concentration versus time data for the compounds is subjected to non-compartmental analysis using the pharmacokinetic program WinNonlin v4.1. Plasma concentrations below the limit of quantitation (25 ng/ml) are assigned a value of zero for pharmacokinetic analysis. Nominal dosing concentrations are used in all calculations.

Example 14

Ker-1

One purpose of the following experiments is to compare the efficacy of one or more compounds and vancomycin in the treatment of a fluoroquinolone-resistant, methicillin-resistant *Staphylococcus aureus* infection in the NZW rabbit keratitis model with or without intact corneal epithelia.

Fifteen rabbits are used from Myrtles' Rabbitry, Thompson Station, Tenn. The clinical isolate of fluoroquinolone-resistant, methicillin-resistant (MRSA) *Staphylococcus aureus* (K950) is subcultured on 5% sheep blood agar and incubated at 37° C. in 6% $CO_2$ overnight. The next morning, the MRSA strain is suspended in sterile trypticase soy broth to a 0.5 McFarland Standard, containing approximately $5\times10^8$ cfu/ml of bacteria. The absorbance of the suspension is measured at 650 nm using a Beckman DU-70 spectrophotometer. OD readings of 0.07 corresponded to $5\times10^8$ cfu/ml of bacteria. This concentration is appropriately diluted in sterile trypticase soy broth to provide the inoculum of approximately 1,000 ($1.0\times10^3$) cfu/eye in 25 µl. Colony counts are performed on the inoculum to determine the actual cfu inoculated. Following general anesthesia with ketamine and xylazine and topical anesthesia with proparacaine and prior to bacterial inoculation in the left eyes, 6 mm areas of the corneal epithelia is removed centrally with an Amoils epithelial scrubber. Nothing is done to the right eyes. The 15 rabbits are then inoculated intrastromally in both eyes with 25 µl of the bacterial dilution of approximately $10^3$ cfu/eye of the bacteria. The bacterial inoculation of the left eyes is directly under the epithelial defect created by the Amoils epithelial scrubber. The epithelia are removed in the left corneas in order to determine whether this layer of the cornea is a barrier for compound penetration when compared to the right cornea with an intact epithelium. A colony count is performed on the inoculum to determine the actual cfu inoculated. The rabbits are immediately treated with analgesia in the form of and intramuscular injection of ketoprofen, 1.5 mg/kg. After 4 hours, the 15 rabbits are divided into 4 treatment groups and one untreated control group sacrificed at the onset of therapy. Both eyes of each rabbit of the treatment groups are treated with one 37 µl drop of the coded solutions or control Saline or 1 drop of vancomycin from its dropper bottle. The compound concentrations are masked and labeled appropriately. The masked concentrations are appropriately labeled but the specific concentrations of solutions are not known to the lab workers who carried out the experiment. The vancomycin and control (Tris-Buffered Saline) are not masked.

Groups:

| Group | Left Eye | Right Eye | Rx - Both Eyes | Treatment Regimen | Rabbit # |
|---|---|---|---|---|---|
| I | Abraded Epithelium | Intact Epithelium | Compound | Every 15 minutes for 5 hours (21 total doses) | 1-3 |
| II | Abraded Epithelium | Intact Epithelium | Compound | Every 15 minutes for 5 hours (21 total doses) | 4-6 |
| III | Abraded Epithelium | Intact Epithelium | Vancomycin (50 mg/ml) (Van) | Every 15 minutes for 5 hours (21 total doses) | 7-9 |

-continued

| Group | Left Eye | Right Eye | Rx - Both Eyes | Treatment Regimen | Rabbit # |
|---|---|---|---|---|---|
| IV | Abraded Epithelium | Intact Epithelium | Tris-Buffered Saline (Con) | Every 15 minutes for 5 hours (21 total doses) | 10-12 |
| V | Abraded Epithelium | Intact Epithelium | Sacrifice at Onset of Therapy (4 hours PI) (ONSET) | None | 13-15 |

Treatment is scheduled for every 15 minutes for 5 hours (21 total doses). The 3 rabbits in group V are sacrificed 4 hours PI and large 9.5 mm buttons are removed from the corneas. These are placed in 1 ml of PBS and kept on ice. The corneal buttons are homogenized for 25 seconds on ice using the motorized homogenizer. After homogenization, colony counts are done on the homogenates using 5% sheep blood agar plates to determine the amount of bacteria contained in the corneas at the onset of therapy. Following the completion of therapy, the eyes are examined for clinical signs of infection. One hour after the final treatment, the treated rabbits (Groups I-IV) are sacrificed and large 9.5 mm buttons are removed from the corneas. These are placed in 1 ml of PBS and kept on ice. The corneal buttons are homogenized for 25 seconds on ice using the motorized homogenizer. After homogenization, colony counts are performed on the homogenates using 5% sheep blood agar plates to determine the amount of bacteria contained in the corneas after treatment. The next morning, the plates are counted and the number of cfu/eye of Staphylococcus aureus was determined for each cornea.

Formulations: 1) the compounds, on the day of treatment, are dissolved in 5 ml of Tris-Buffered Saline (TBS) before use. The solution is stored at room temperature during the 5 hours of use. 37 µl drops are instilled using a Rainin EDP electronic pipet set in the multi-dispense mode. 2) 5% Vancomycin (50 mg/ml): Vancomycin (50 mg/ml) eye drops is purchased from the UPMC pharmacy as the fortified preparation used in patients. Vancomycin is administered using is supplied dropper bottle. 3) Control (Tris-Buffered Saline): 37 µl drops are instilled using a Rainin EDP electronic pipet set in the multi-dispense mode.

Example 15

Ker-2

One purpose of the following experiments is to compare the efficacy of 0.25% Compound, with and without 0.005% benzalkonium chloride, and 5% vancomycin in the treatment of a fluoroquinolone-resistant, methicillin-resistant Staphylococcus aureus infection in the NZW rabbit keratitis model with or without intact corneal epithelia. The 0.005% benzalkonium chloride is added to try to increase the penetration of 0.25% Compound through the corneal epithelium.

Fifteen rabbits are used from Myrtles' Rabbitry, Thompson Station, Tenn. The clinical isolate of fluoroquinolone-resistant, methicillin-resistant (MRSA) Staphylococcus aureus (K950) is subcultured on 5% sheep blood agar and incubated at 37° C. in 6% $CO_2$ overnight. The next morning, the MRSA strain is suspended in sterile trypticase soy broth to a 0.5 McFarland Standard, containing approximately $5\times10^8$ cfu/ml of bacteria. The absorbance of the suspension is measured at 650 nm using a Beckman DU-70 spectrophotometer. OD readings of 0.07 corresponded to $5\times10^8$ cfu/ml of bacteria. This concentration is appropriately diluted in sterile trypticase soy broth to provide the inoculum of approximately 1,000 ($1.0\times10^3$) cfu/eye in 25 µl. Colony counts are performed on the inoculum to determine the actual cfu inoculated. Following general anesthesia with ketamine and xylazine and topical anesthesia with proparacaine and prior to bacterial inoculation in the left eyes, 6 mm areas of the corneal epithelia is removed centrally with an Amoils epithelial scrubber. Nothing is done to the right eyes. The 15 rabbits are then inoculated intrastromally in both eyes with 25 µl of the bacterial dilution of approximately $10^3$ cfu/eye of the bacteria. The bacterial inoculation of the left eyes is directly under the epithelial defect created by the Amoils epithelial scrubber. The epithelia are removed in the left corneas in order to determine whether this layer of the cornea is a barrier for the Compound penetration when compared to the right cornea with an intact epithelium. A colony count is performed on the inoculum to determine the actual cfu inoculated. The rabbits are immediately treated with analgesia in the form of and intramuscular injection of ketoprofen, 1.5 mg/kg. After 4 hours, the 15 rabbits are divided into 4 treatment groups and one untreated control group sacrificed at the onset of therapy. Both eyes of each rabbit of the treatment groups are treated with one 37 µl drop of the solutions or control Saline or 1 drop of vancomycin from its dropper bottle.

Groups:

| Group | Left Eye | Right Eye | Rx - Both Eyes | Treatment Regimen | Rabbit # |
|---|---|---|---|---|---|
| I | Abraded Epithelium | Intact Epithelium | 0.25% Compound | Every 15 minutes for 5 hours (21 total doses) | 1-3 |
| II | Abraded Epithelium | Intact Epithelium | 0.25% Compound with 0.005% BAK | Every 15 minutes for 5 hours (21 total doses) | 4-6 |
| III | Abraded Epithelium | Intact Epithelium | Vancomycin (50 mg/ml) (Van) | Every 15 minutes for 5 hours (21 total doses) | 7-9 |

-continued

| Group | Left Eye | Right Eye | Rx - Both Eyes | Treatment Regimen | Rabbit # |
|---|---|---|---|---|---|
| IV | Abraded Epithelium | Intact Epithelium | Tris-Buffered Saline (Con) | Every 15 minutes for 5 hours (21 total doses) | 10-12 |
| V | Abraded Epithelium | Intact Epithelium | Sacrifice at Onset of Therapy (4 hours PI) (ONSET) | None | 13-15 |

Treatment is scheduled for every 15 minutes for 5 hours (21 total doses). The 3 rabbits in group V are sacrificed 4 hours PI and large 9.5 mm buttons are removed from the corneas. These are placed in 1 ml of PBS and kept on ice. The corneal buttons are homogenized for 25 seconds on ice using the motorized homogenizer. After homogenization, colony counts are done on the homogenates using 5% sheep blood agar plates to determine the amount of bacteria contained in the corneas at the onset of therapy. Following the completion of therapy, the eyes are examined for clinical signs of infection. One hour after the final treatment, the treated rabbits (Groups I-IV) are sacrificed and large 9.5 mm buttons are removed from the corneas. These are placed in 1 ml of PBS and kept on ice. The corneal buttons are homogenized for 25 seconds on ice using the motorized homogenizer. After homogenization, colony counts are performed on the homogenates using 5% sheep blood agar plates to determine the amount of bacteria contained in the corneas after treatment. The next morning, the plates are counted and the number of cfu/eye of *Staphylococcus aureus* was determined for each cornea.

Formulations: 1) 0.25% Compound, on the day of treatment, is dissolved in 6.04 ml of Tris-Buffered Saline (TBS) to yield 0.25% Compound. The solution is stored at room temperature during the 5 hours of use. 37 µl drops are instilled using a Rainin EDP electronic pipet set in the multi-dispense mode. 2) 0.25% Compound with 0.005% Benzalkonium Chloride (BAK), on the day of treatment, is dissolved in 6.288 ml of Tris-Buffered Saline (TB S) before use. Then, 0.032 ml (32 µl) of 1% Benzalkonium Chloride is added to the solution to yield a total volume of 6.32 ml of 0.25% Compound. The solution is stored at room temperature during the 5 hours of use. 37 µl drops are instilled using a Rainin EDP electronic pipet set in the multi-dispense mode. This solution is designated PMX-B. 3) 5% Vancomycin (50 mg/ml): Vancomycin (50 mg/ml) eye drops are purchased from the UPMC pharmacy as the fortified preparation used in patients. Vancomycin is administered using a supplied dropper bottle. 4) Control (Tris-Buffered Saline): 37 µl drops of Tris-Buffered Saline are instilled using a Rainin EDP electronic pipet set in the multi-dispense mode.

Example 16

Ker-3

One purpose of the following experiments is to determine the efficacy of 0.25% Compound, with and without 200 µM Farnesol, and 200 µM Farnesol in the treatment of a fluoroquinolone-resistant and methicillin-resistant *Staphylococcus aureus* infection in the NZW rabbit keratitis model with or without intact corneal epithelia. The 200 µM Farnesol is added to try to increase the efficacy and penetration of 0.25% compound through the corneal epithelium.

Fifteen rabbits are used from Myrtles' Rabbitry, Thompson Station, Tenn. The clinical isolate of fluoroquinolone-resistant and methicillin-resistant (MRSA) *Staphylococcus aureus* (K950) is subcultured on 5% sheep blood agar and incubated at 37° C. in 6% $CO_2$ overnight. The next morning, the MRSA strain is suspended in sterile trypticase soy broth to a 0.5 McFarland Standard, containing approximately $5 \times 10^8$ CFU/ml of bacteria. The absorbance of the suspension is measured at 650 nm using a Beckman DU-70 spectrophotometer. OD readings of 0.07 corresponded to $5 \times 10^8$ CFU/ml of bacteria. This concentration is appropriately diluted in sterile trypticase soy broth to provide the inoculum of approximately 1,000 ($1.0 \times 10^3$) CFU/eye in 25 µl. Colony counts are performed on the inoculum to determine the actual CFU inoculated. Following general anesthesia with ketamine and xylazine and topical anesthesia with proparacaine and prior to bacterial inoculation in the left eyes, 6 mm areas of the corneal epithelia are removed centrally from the left eyes with an Amoils epithelial scrubber. Nothing is done to the right eyes. The 15 rabbits are then inoculated intrastromally in both eyes with 25 µl of the bacterial dilution of approximately $10^3$ cfu/eye of the bacteria. The bacterial inoculation of the left eyes is directly under the epithelial defect created by the Amoils epithelial scrubber. The epithelia are removed in the left corneas in order to determine whether this layer of the cornea is a bather for drug penetration when compared to the right cornea with an intact epithelium. A colony count is performed on the inoculum to determine the actual CFU inoculated. The rabbits are immediately treated with analgesia in the form of an intramuscular injection of ketoprofen, 1.5 mg/kg. After 4 hours, the 15 rabbits are divided into 4 treatment groups and one untreated control group sacrificed at the onset of therapy. Both eyes of each rabbit of the treatment groups are treated with one 37 µl drop of the solutions or control Saline.

Groups:

| Group | Left Eye | Right Eye | Rx - Both Eyes | Treatment Regimen | Rabbit # |
|---|---|---|---|---|---|
| I | Abraded Epithelium | Intact Epithelium | 0.25% Compound | Every 15 minutes for 5 hours (21 total doses) | 1-3 |
| II | Abraded Epithelium | Intact Epithelium | 0.25% Compound + | Every 15 minutes for 5 hours (21 total | 4-6 |

-continued

| Group | Left Eye | Right Eye | Rx - Both Eyes | Treatment Regimen | Rabbit # |
|---|---|---|---|---|---|
| | | | 200 µM Farnesol (P + F) | doses) | |
| III | Abraded Epithelium | Intact Epithelium | 200 µM Farnesol (FARN) | Every 15 minutes for 5 hours (21 total doses) | 7-9 |
| IV | Abraded Epithelium | Intact Epithelium | Tris-Buffered Saline (CON) | Every 15 minutes for 5 hours (21 total doses) | 10-12 |
| V | Abraded Epithelium | Intact Epithelium | Sacrifice at Onset of Therapy (4 hours PI) (ONSET) | None | 13-15 |

Treatment is scheduled for every 15 minutes for 5 hours (21 total doses). The 3 rabbits in group V are sacrificed 4 hours PI and large 9.5 mm buttons are removed from the corneas. These are placed in 1 ml of PBS and kept on ice. The corneal buttons are homogenized for 25 seconds on ice using the motorized homogenizer. After homogenization, colony counts are done on the homogenates using 5% sheep blood agar plates to determine the amount of bacteria contained in the corneas at the onset of therapy. Following the completion of therapy, the eyes are examined for clinical signs of infection. One hour after the final treatment, the treated rabbits (Groups I-IV) are sacrificed and large 9.5 mm buttons are removed from the corneas. These are placed in 1 ml of PBS and kept on ice. The corneal buttons are homogenized for 25 seconds on ice using the motorized homogenizer. After homogenization, colony counts are done on the homogenates using 5% sheep blood agar plates to determine the amount of bacteria contained in the corneas after treatment. The next morning, the plates are counted and the number of CFU/eye of *Staphylococcus aureus* is determined for each cornea.

Formulations: 1) 0.25% Compound powder is stored at 4° C. until use. Upon use, the tube is removed from the refrigerator and 3.28 ml of S1 (sterile water for injection) is added and vortexed until the solid is completely dissolved. Then 3.28 ml of S2 (2×TBS) is added and vortexed for 10 seconds. 37 µl drops are instilled using a Rainin EDP electronic pipet set in the multi-dispense mode; 2) 0.25% Compound with 200 µM Farnesol (P+F): Tube G2 of Compound powder is stored at 4° C. until use. Upon use, the tube is removed from the refrigerator and 3.33 ml of S1 (sterile water for injection) is added and vortexed until the solid is completely dissolved. Then 3.33 ml of S3 (400 µM Farnesol+2% Propylene Glycol in 2×TBS) is added and vortexed for 10 seconds. 37 µl drops are instilled using a Rainin EDP electronic pipet set in the multi-dispense mode; 3) 200 µM Farnesol (FARN): Tube G3 containing about 8 ml of 200 µM Farnesol in 1% Propylene Glycol (PG) and TBS is stored at 4° C. until use. 37 µl drops are instilled using a Rainin EDP electronic pipet set in the multi-dispense mode; 4) Control (Tris-Buffered Saline, CON): Tube G4 containing about 8 ml of Tris-Buffered Saline (10 mM TRIS, 150 mM NaCl, pH=7.4) is stored at 4° C. until use. 37 µl drops are instilled using a Rainin EDP electronic pipet set in the multi-dispense mode.

Example 17

Bacterial Strains and Culture

*Aggregatibacter actinomycetemcomitans* 1005 (Aa) (obtained from Dr. Helen Schreiner, New Jersey Dental School) are cultured on TSB agar (4% trypticase soy broth, 0.6% yeast extract, 0.8% dextrose, 0.4% $NaHCO_3$, 75 µg/mL bactracin, 5 µg/mL vancomycin) at 37° C., 10% $CO_2$. Single colonies are inoculated to TSB broth in 75-$cm^2$ tissue culture flasks. Biofilm is harvest upon the 90% confluence and resuspended into 1 mL PBS. Resuspension is vortexed vigorously for 1 minute and allowed to settle for 10 minutes. The supernatant is then diluted to $2.5 \times 10^7$ before seeded to 96-well plates to obtain even biofilms. *Porphyromonas gingivalis* W381 (obtained from Dr. Christopher Cutler, Stony Brook University Dental School) are cultured on TSB-blood agar (3% trypticase soy broth, 5% defibrinated sheep blood, 5 µg/mL hemin, 0.5 µg/mL menadione, and 0.2 mg/mL $KNO_3$) in an anaerobic chamber (80% $N_2$, 10% $H_2$, and 10% $CO_2$) at 37° C. For biofilm formation, the same protocol as Aa under anaerobic condition was used.

Example 18

Antimicrobial Assays

Aa biofilms are cultured into 96-well plates (tissue culture treated, Falcon) for 18 hours. Serial dilutions of the mimetic compounds are made in 100 µL RPMI-1640 without Phenol red and added directly to the wells. Plates are cultured at 37° C., 10% $CO_2$ for 24 hours. Medium is removed, and cell viability is evaluated by XTT assay using the In Vitro Toxicology Assay Kit (Sigma) according to the manufacturer's protocol. Metabolic activity is measured by reading in a plate-reader at 450 nm To determine cell viability by plating, the wells are scraped and resuspended in growth medium, and plated onto TSB agar. Colonies are counted after 72 hours. All assays are performed in duplicate.

Example 19

Cell Culture and Stimulation

The oral keratinocyte cell line OKF6/TERT (obtained from Dr. James Rhinewald, Harvard University) is cultured in Keratinocyte growth medium (Lonza) with hEGF, BPE (Bovine Pituitary Extract). Cells are subcultured in 6-well dishes 18 hours before stimulation. Cells are treated with 2 µg/mL, 5 µg/mL mPE with and without IL-113 stimulation (100 ng/mL, 24 hours) for 2 hours, 4 hours and 18 hours. THP-1 cells are grown in suspension at RPMI 1640 with 10% FBS, and stimulated similarly.

Example 20

Ophthalmic Ointment Formulation

The following represents an example of a typical ophthalmic ointment formulation comprising an antimicrobial compound.

| Ophthalmic Ointment | |
|---|---|
| Ingredient | Amount (weight %) |
| Compound | 0.35 |
| Mineral Oil, USP | 2.0 |
| White petrolatum, USP | q.s. 100 |

Example 21

Ophthalmic Ointment Formulation

The following represents an example of a typical ophthalmic ointment formulation comprising an antimicrobial compound and an anti-inflammatory agent.

| Ophthalmic Ointment | |
|---|---|
| Ingredient | Amount (weight %) |
| Compound | 0.3 |
| Dexamethasone | 0.1 |
| Chlorobutanol, Anhydrous, NF | 0.5 |
| Mineral Oil, USP | 5.0 |
| White petrolatum, USP | q.s. 100 |

Example 22

Ophthalmic/Otic Solution Formulation

The following represents an example of a typical ophthalmic/otic solution formulation comprising an antimicrobial compound.

| Ophthalmic/Otic Solution | |
|---|---|
| Ingredient | Amount (weight %) |
| Compound | 0.35 |
| Sodium Acetate | 0.3 |
| Acetic Acid | 0.04 |
| Mannitol | 4.60 |
| EDTA | 0.05 |
| Benzalkonium chloride | 0.006 |
| Water | q.s. 100 |

Example 23

Ophthalmic/Otic Suspension Formulation

The following represents an example of a typical ophthalmic/otic suspension formulation comprising an antimicrobial compound and an anti-inflammatory agent (dexamethasone).

| Ophthalmic/Otic Suspension | |
|---|---|
| Ingredient | Amount (weight %) |
| Compound | 0.3 |
| Dexamethasone, micronized USP | 0.10 |
| Benzalkonium chloride | 0.01 |
| Edetate Disodium USP | 0.01 |
| Sodium chloride USP | 0.3 |
| Sodium sulfate USP | 1.2 |
| Tyloxapol USP | 0.05 |
| Hydroxyethylcellulose | 0.25 |
| Sulfuric Acid and/or Sodium hydroxide, NF | q.s. for pH adjustment to 7.0-8.0 |
| Purified sterilized water | q.s. to 100 |

Example 24

Toxicity

The ocular toxicity of several concentrations of Compound, using the Draize ocular toxicity scoring system, in the NZW rabbit ocular toxicity model is carried out.

Nine rabbits are used from Myrtles' Rabbitry, Thompson Station, Tenn. and are subsequently divided into 5 groups:

| Group | Oligomer 2 Concentration | N Rabbits | N Eyes | Rabbit Numbers |
|---|---|---|---|---|
| I | 1% Compound | 2 | 4 | 1-2 |
| II | 0.25% Compound | 2 | 4 | 3-4 |
| III | 0.1% Compound | 2 | 4 | 5-6 |
| IV | 0.01% Compound | 2 | 4 | 7-8 |
| V | Tris-Buffered Saline | 1 | 2 | 9 |

Rabbits are treated in both eyes with (37 µl) topical drops every 30 minutes for 3 hours (7 total doses). One rabbit is treated with Tris-Buffered Saline and serves as a negative control. Rabbits are evaluated in a masked fashion for ocular toxicity by an ophthalmologist with specialty training in corneal and external disease. Ocular toxicity is evaluated using the Draize scoring system after treatment on Day 0 and on Day 3 post treatment for any delayed toxicity (Draize et al., J. Pharmacol. Exp. Ther., 1944, 82, 377-390).

Formulations: 1) 1% Compound: 31.36 mg of Compound in powder form is stored at −20° C. until use. The vial containing Compound is removed from the freezer and 3.126 ml of Tris-Buffered Saline (TBS) is added to the vial to yield 3.126 ml of 1% (10 mg/ml) Compound; 2) 0.25% Compound: 0.5 ml of 1% Compound is added to 1.5 ml of TBS to yield 2 ml of 0.25% Compound; 3) 0.1% Compound: 0.2 ml of 1% Compound is added to 1.8 ml of TBS to yield 2 ml of 0.1% Compound; 4) 0.01% Compound: 0.2 ml of 0.1% Compound is added to 1.8 ml of TBS to yield 2 ml of 0.01% Compound; and 5) Tris-Buffered Saline: 25 ml of Tris-Buffered Saline (10 mM TRIS, 150 mM NaCl, pH=7.4) is filter sterilized prior to use in preparation of the above samples and use in rabbits.

A brief summary of the Draize scoring system for ocular lesions is provided below 1. Cornea
   A. Opacity-degree of density (area most dense taken for reading)
      No Opacity . . . 0
      Scattered or diffuse area, details of iris clearly visible . . . 1

Easily discernible translucent areas, details of iris slightly obscured . . . 2
Opalescent areas, no details of iris visible, size of pupil barely discernible . . . 3
Opaque, iris invisible . . . 4
B. Area of cornea involved
One quarter (or less) but not zero . . . 1
Greater than one quarter, but less than half . . . 2
Greater than half. but less than three quarters . . . 3
Greater than three quarters, up to whole area . . . 4
A×B×5 Total Maximum=80
2. Iris
A Values
Normal . . . 0
Folds above normal, congestion, swelling, circumcorneal injection (any or all of these or combination of any thereof) iris still reacting to light (sluggish reaction is positive) . . . 1
No reaction to light, hemorrhage, gross destruction (any or all of these) 2

*A*×5 Total Maximum=10

3. Conjunctivae
A. Redness (refers to palpebral and bulbar conjunctivas excluding cornea and iris)
Vessels normal . . . 0
Vessels definitely injected above normal . . . 1
More diffuse, deeper crimson red, individual vessels not easily discernible . . . 2
Diffuse beefy red . . . 3
B. Chemosis
No swelling . . . 0
Any swelling above normal (includes nictitating membrane) . . . 1
Obvious swelling with partial eversion of lids . . . 2
Swelling with lids about half-closed . . . 3
Swelling with lids about half-closed to completely closed . . . 4
C. Discharge
No discharge . . . 0
Any amount different from normal (does not include small amounts observed in
inner canthus of normal animals) . . . 1
Discharge with moistening of the lids and hairs just adjacent to lids . . . 2
Discharge with moistening of the lids and hairs, and considerable area around the eye . . . 3

Score (*A*+*B*+*C*)×2 Total Maximum=20

Total Maximum Score: 110 represents the sum of all scores obtained for the cornea, iris and conjunctivae.
Classification of Eye Irritation Scores:

| MMTS | Classification | Symbol |
| --- | --- | --- |
| 0.0-0.5 | Non-Irritating | N |
| 0.6-2.5 | Practically Non-Irritating | PN |
| 2.6-15.0 | Minimally Irritating | M1 |
| 15.1-25.0 | Mildly Irritating | M2 |
| 25.1-50.0 | Moderately Irritating | M3 |
| 50.1-80.0 | Severely Irritating | S |
| 80.1-100.0 | Extremely Irritating | E |
| 100.1-110.0 | Maximally Irritating | Mx |

MMTS = Maximum Mean Total Score (The mean total score per group) Kay et al., J. Soc. Cos. Chem., 1962, 13, 281-289.

Example 25

Susceptibility Assays Versus *M. tuberculosis* (H37Rv Strain) and Cytotoxicity Assays Versus Monkey VERO Cells To evaluate the effects of compounds on inhibiting the growth of a *M. tuberculosis* species, susceptibility assays of some compounds on *M. tuberculosis* (H37Rv strain) and cytotoxicity assays of some compounds on monkey VERO cells are performed.

The antimicrobial screen is conducted against the H37Rv strain of *M. tuberculosis* in BACTEC 12B medium using the Microplate Alamar Blue Assay (MABA) (see, e.g., Collins et al., Antimicrobial Agents and Chemotherapy, 1997, 41(5), 1004-1009). Compounds are tested in ten 2-fold dilutions to determine $IC_{90}$ values (an $IC_{90}$ value is defined as the concentration effecting a reduction in fluorescence of 90% relative to controls). Viability in the VERO cell cytotoxicity assay is measured after a 72 hour exposure using a luminescent cell viability assay that determines the number of viable cells based on quantitation of ATP. Cytotoxicity is determined using a curve fitting program to calculate $EC_{50}$ values. An SI (Selectivity Index) value is calculated by dividing the $EC_{50}$ by the $IC_{90}$.

Example 26

Cytotoxicity

Colorimetric Assay:

Cytotoxicity is evaluated in a colorimetric assay using a transformed human liver cell line (HepG2, HB-8065) and an embryonic mouse cell line (NIH/3T3 cells, CRL-1658). This assay measures the bioreduction of a novel tetrazolium compound to a soluble formazan product by viable cells. HepG2 cells are seeded in 96 well plates at $3\times10^4$ cells/well in MEM medium with 10% fetal bovine serum (FBS) 24 hours prior to use. NIH/3T3 cells are seeded in 96 well plates at $2\times10^4$ cells/well in DMEM medium with 10% bovine calf serum (BCS) 24 hours prior to use. Cell monolayers are rinsed in serum-free media and incubated for one hour with test agent in serum-free media. After incubation, the media is replaced with serum supplemented media and live cells are measured using the Cell Titer 96 Aqueous Non-Proliferation Assay kit (Promega, Madison, Wis.). $EC_{50}$ values are determined using a four parameter logistic equation: Y=Bottom+(Top−Bottom)/(1+10^((Log EC50−X)*HillSlope)).

Hemolysis Assay:

Cytotoxicity is also evaluated in a hemolysis assay using isolated human erythrocytes. Pooled whole human blood is centrifuged to separate the red blood cells (RBC). The isolated RBCs are rinsed and diluted in Tris-buffered saline (TBS buffer, pH 7.4) to obtain a 0.22% RBC stock suspension. Serial two-fold dilutions of test agent are assayed over a concentration range of 1000 to 0.48 μg/m with shaking for 1 hour at 37° C. At the conclusion of the incubation time, samples are centrifuged and 30 μl of the supernatant was added to 100 μl $H_2O$. $OD_{405}$ measurements are read for hemoglobin concentration. The bee venom peptide melittin is used as a positive control. $EC_{50}$ values are determined using a four parameter logistic equation: Y=Bottom+(Top−Bottom)/(1+10^((Log EC50−X)*HillSlope)).

Example 27

Clotting and Amidolytic Assays aPTT Clotting Assay:

Unfractionated heparin is mixed with plasma at a final concentration of 0.4 U/mL (or concentration which increases aPTT time to between 120 and 300 seconds). Different concentrations of test compound are added (typically 0.15 to 20 µg/mL range). The ACL Elite Hemostasis analyzer (Beckman Coulter™) is used to add aPTT reagent (HemoslL SynthASil) to supplemented plasma. Clotting is initiated by addition of $CaCl_2$ and time to clot is recorded. $EC_{50}$ values are determined using a curve fit program (GraphPad Prism 5).

FXa Amidolytic Assay:

LMWH (enoxaparin or tinzaparin) at final concentrations of 0.1 ug/ml, UFH at final concentrations of 0.03 units/mL, or fondaparinux at a final concentration of 0.02 µg/mL (or concentration which fully inhibits factor Xa) is combined with human antithrombin at a final concentration of 0.036 units/ml. Two µl of test agent are added (range between 0.01 and 23 ug/ml) and incubated for 5 minutes at 23° C. Bovine FactorXa was added to a final concentration of 0.636 nkat/mL and incubated for a further 10 minutes at 23° C. Using a SpectraMax 250 (Molecular Devices, Inc.) and SoftMax Pro V.5 software, the plate is read every 30 seconds for 4 minutes, with a 10 second shaking before first read and maximum interval shaking. Fit curve to report an $EC_{50}$ (50% reversal of anticoagulant effects) value for each compound: $P(C_p)=1/[1+(K/C_p)^n]$.

Example 28

In Vivo Neutralization of Unfractionated Heparain in the Rat

The male Sprague-Dawley are obtained from Charles River Laboratories, Raleigh. They are nine-weeks-old at the start of the study and their weights range from 279-334 g. Rats are pre-treated with UFH administered by IV injection in a tail vein at 100 U/kg in a dose volume of 1 mL/kg. The rats are then treated with a single IV injection of saline, protamine or the appropriate test compound at doses of 0.25, 0.5 and 1.0 mg/kg. All treatments are dosed in a volume of 1 mL/kg. Blood is collected via the orbital sinus from three rats per group at the following time points after treatment: predose, 1, 3, 10, 30 and 60. At each time point, 1 mL of blood is collected from each animal into a single tube. The blood is analyzed using an AMEX Destiny Plus Coagulation Analyzer for activated partial thromboplastintime (APTT) and anti-Factor Xa.

Example 29

In Vivo Neutralization of Enoxaparin in the Rat

Compounds are tested for their ability to neutralize enoxaparin coagulation inhibition in rats. Male Sprague-Dawley rats are used in this study (Charles River Laboratories). They are ten-weeks-old at the start of the study and their weights range from 319-362 g. Enoxaparin (2 mg/kg) is administered by IV injection to groups of six rats. After 3 min, saline, protamine or a test compound is administered by IV injection. Blood is collected before dosing with enoxaparin, and at 1, 3, 10, 30 and 60 min after dosing with the standard and test compounds. All treatments are dosed in a volume of 1 mL/kg. Blood is collected via the orbital sinus from three rats per group. At each time point, 1 mL of blood is collected from each animal into a single tube. The blood is analyzed using an AMEX Destiny Plus Coagulation Analyzer for activated partial thromboplastin time (APTT) and anti-Factor Xa (low-molecular weight).

Example 30

Normalization of Enoxaparin-Extended Bleeding Times in a Rat Tail Transfection Model Studies are performed to examine effects on extended bleeding times caused by enoxaparin treatment. Male Sprague Dawley rats (Charles River) are administered 2 mg/kg enoxaparin by IV injection in the tail vein, followed 3 minutes later by test agent (IV, tail vein) at 2 and 5 mg/kg doses. Tails are then rapidly transected and bleeding time onto an absorbent pad was determined.

Example 31

In Vivo Neutralization of Fondaparinux in the Rat

Compounds are selected to test fondaparinux neutralization in vivo. Rats are pre-treated with fondaparinux administered by IV injection at 0.5 mg/kg. The rats are treated with a single IV injection of saline, protamine or the compound. Blood is collected via the orbital sinus from three rats per group at the following time points: pre-dose, 1, 3, 10, 30 and 60 min Plasma samples are prepared for analysis of anti-factorXa activity using an AMEX Destiny Plus Coagulation Analyzer.

Example 32

Mitigation of Hemodynamic Responses in the Anesthetized Rat

Reduction in blood pressure shortly after administration is a safety issue for cationic compounds. To address this hemodynamic issue, a medicinal chemistry strategy with literature precedence of introducing carboxylic acid functionality is applied. Surgically prepared animals are purchased from Charles River Laboratories, Raleigh, N.C. Animals are anesthetized on the day of experiment with isoflurane (1.8-4%). Blood pressure and heart rate data are collected on a Grass Polygraph recorder. The compounds, vehicle or protamine dosing preparations are administered once to each rat by a 10 minute intravenous infusion three minutes following a single intravenous injection of heparin (50 U/kg). Each animal receives a dose volume of 2.0 mL/kg. Blood pressure is recorded prior to treatment for approximately 1 minute and immediately following heparin, immediately following vehicle, test articles or protamine and at 5, 15, 30, and 60 minutes following dosing. The doses of test agent are either 8 mg/kg or 16 mg/kg.

Example 33

FXa Chromogenic Assay (Absence of Plasma)

Human antithrombin is mixed with an anticoagulant agent (a LMWH or fondaparinux); final concentrations are 0.22 µg/mL for the LMWHs and 0.07 µg/mL for fondaparinux. Different concentrations of a test compound are added (typically 0.07 to 9 µg/mL range) followed by factor Xa and substrate (S-2765). Absorbance is read every 30 seconds over a 4 minute period in a SpectraMax 250 instrument (Molecular Devices, Inc.). $EC_{50}$ values are determined by a curve-fit program (SoftMax Pro) using the following formula:

$$P(C_p)=1/[1+(K/C_p)^n]$$

Example 34

FIIa (Thrombin) Chromogenic Assay (Absence of Plasma)

The procedure for measuring anti-FIIa activity is similar to that for the anti-FXa assay except FIIa and S-2238 are used in place of FXa and S-2765, respectively.

Example 35

Clotting and Amidolytic Assays in Presence of Human Plasma

Eight parts of pooled human plasma is supplemented with 1 part LMWH or UFH at final concentrations of 4 µg/mL, or fondarinux at a final concentration of 1.25 µg/mL. One µL sample of test agent is then added to 9 µL of supplemented plasma (test agent concentration ranges=0.156 to 20 µg/mL) and mixed. The supplemented plasmas are analyzed immediately in clotting and amidolytic assays as described below. All samples are performed in duplicate.

aPTT Clotting Assay.

Supplemented plasma is added to aPTT reagent (activated partial thromboplastin time reagent) (activator) in fibrometer. Clotting is initiated by addition of $CaCl_2$ and time to clot was recorded.

HepTest Clotting Assay.

Factor Xa is added to supplemented plasma in a fibrometer and incubated for 120 seconds. Recalmix is added and time to clot was recorded.

Thrombin time (TT) Clotting Assay.

Human thrombin is added to supplemented plasma in a fibrometer and time to clot was recorded.

FXa Amidolytic Assay:

Bovine factor Xa is added to supplemented plasma and incubated for 5 minutes at 37° C. Spectrozyme FXa substrate is added and the optical density change at 405 nm is measured for 30 seconds. % factor Xa inhibition is calculated using the following equation:

$$\% \text{ Inhibition} = [(OD_{baseline} - OD_{sample})/OD_{baseline}] \times 100.$$

FXa Amidolytic Assay:

LMWH (enoxaparin or tinzaparin) at final concentrations of 0.1 ug/ml, UFH at final concentrations of 0.03 units/mL, or fondaparinux at a final concentration of 0.02 µg/mL (or concentration which fully inhibits factor Xa) is combined with human antithrombin at a final concentration of 0.036 units/ml. Two µl of test agent are added (range between 0.01 and 23 ug/ml) and incubated for 5 minutes at 23° C. Bovine FactorXa was added to a final concentration of 0.636 nkat/mL and incubated for a further 10 minutes at 23° C. Using a SpectraMax 250 (Molecular Devices, Inc.) and SoftMax Pro V.5 software, the plate is read every 30 seconds for 4 minutes, with a 10 second shaking before first read and maximum interval shaking. Fit curve to report an $EC_{50}$ (50% reversal of anticoagulant effects) value for each compound: $P(C_p)=1/[1+(K/C_p)^n]$.

FIIa Amidolytic Assay.

Human thrombin is added to supplemented plasma and incubated for 1 minute at 37° C. Spectrozyme TH substrate is added and the optical density change at 405 nm is measured for 30 seconds in a SpectraMax 250 instrument. % factor IIa inhibition is calculated using the following equation:

$$\% \text{ Inhibition} = [(OD_{baseline} - OD_{sample})/OD_{baseline}] \times 100.$$

Example 36

Heparin-Binding Activity

The heparin (unfractionated) preparations are tyramine end-labeled and radiolabeled with $^{125}$Iodine to a specific activity of $1-2.5 \times 10^7$ cpm/µg. Increasing concentrations of a test agent (protamine or an exemplary compound provided herein) are added to individual wells across a 1% agarose gel in 125 mM sodium acetate, 50 mM MOPSO (3-(n-morpholino)-2-hydroxypropanesulfonic acid), pH 7.0). The radio-labeled heparin is added to a closely neighboring upper well and electrophoresed through the test agent wells. Heparin binding is visualized on the dried gel using a Phosphorimager. The dissociation constant (Kd) is calculated from the test agent concentration (n=3) at which the polysaccharide is half-shifted between its fully mobile position at low concentrations of test agent and its fully retarded position at saturating concentrations of test agent according to the methods of Lee and Lander (See Lee, M. K. and Lander, A. D., "Analysis of affinity and structural selectivity in the binding of proteins to glycosaminoglycans: development of a sensitive electrophoretic approach" Proc. Natl. Acad. Sci. USA, 1991, 88, 2768-2772).

Example 37

In Vivo Neutralization of Unfractionated Heparain in the Rat

The male Sprague-Dawley rats used in this study are obtained from Charles River Laboratories, Raleigh. They are nine-weeks-old at the start of the study and their weights range from 279-334 g. Rats are pre-treated with UFH administered by IV injection in a tail vein at 100 U/kg in a dose volume of 1 mL/kg. The rats are then treated with a single IV injection of saline, protamine or the appropriate test compound at doses of 0.25, 0.5 and 1.0 mg/kg. All treatments are dosed in a volume of 1 mL/kg. Blood is collected via the orbital sinus from three rats per group at the following time points after treatment: predose, 1, 3, 10, 30 and 60. At each time point, 1 mL of blood is collected from each animal into a single tube. The blood is analyzed using an AMEX Destiny Plus Coagulation Analyzer for activated partial thromboplastintime (APTT) and anti-Factor Xa.

Example 38

In Vivo Neutralization of Enoxaparin in the Rat

Compounds are tested for their ability to neutralize enoxaparin coagulation inhibition in rats. Male Sprague-Dawley rats are used in this study (Charles River Laboratories). They are ten-weeks-old at the start of the study and their weights range from 319-362 g. Enoxaparin (2 mg/kg) is administered by IV injection to groups of six rats. After 3 mM, saline, protamine or a test compound is administered by IV injection. Blood is collected before dosing with enoxaparin, and at 1, 3, 10, 30 and 60 mM after dosing with the standard and test compounds. All treatments are dosed in a volume of 1 mL/kg. Blood is collected via the orbital sinus from three rats per group. At each time point, 1 mL of blood is collected from each animal into a single tube. The blood is analyzed using an AMEX Destiny Plus Coagulation Analyzer for activated partial thromboplastin time (APTT) and anti-Factor Xa (low-molecular weight).

Example 39

Normalization of Enoxaparin-Extended Bleeding Times in a Rat Tail Transfection Model Male Sprague Dawley rats (Charles River) are administered 2 mg/kg enoxaparin by IV injection in the tail vein, followed 3 minutes later by test agent (IV, tail vein) at 2 and 5 mg/kg doses. Tails are then rapidly transected and bleeding time onto an absorbent pad is determined.

Example 40

In Vivo Neutralization of Fondaparinux in the Rat

Compounds are selected to test fondaparinux neutralization in vivo. Rats are pre-treated with fondaparinux administered by IV injection at 0.5 mg/kg. The rats are then treated with a single IV injection of saline, protamine or the compound. Blood is collected via the orbital sinus from three rats per group at the following time points: pre-dose, 1, 3, 10, 30 and 60 mM Plasma samples are prepared for analysis of anti-factorXa activity using an AMEX Destiny Plus Coagulation Analyzer.

Example 41

Anti-Factor Xa Inhibition

The following example illustrates the effects of compounds of the present invention on anti-Factor Xa inhibition. To determine the anti-heparin activity of the compounds, an assay measuring the percent inhibition using a fixed concentration of compound or concentrations of compounds causing lysis of 50% of human red blood cells is used.

10 IU of anti-thrombin is dissolved in 10 ml of buffer, resulting in a 1 IU/ml stock solution (250×) of the anti-thrombin. The 1 IU/ml (250×) stock solution of anti-thrombin and a 336 mM stock solution of NaCl are diluted into a total volume of 50 ml buffer so that the final anti-thrombin concentration is 0.004 IU/sample well and the NaCl is 150 mM/sample well. 1 ml of the compound to be tested, final concentration 10 μg/ml (corresponding to 0.5 logarithmic antagonist dilution) is added to the sample well. The samples are mixed and allowed to incubate at room temperature for 20 minutes. 50 μl of factor Xa dissolved in buffer is added to the sample well to a final concentration of 0.14 knat/well (2 ml of the 7.1 knat/ml stock solution to a final sample well buffer volume of 100 μl). The samples are mixed and further incubated at room temperature for 10 minutes. 10 μl of a 4 mM stock solution of the substrate S-2765 is added to each sample well for a final concentration of 0.4 mM in each sample well. The samples are mixed and hydrolyses of the chromogenic substrate Z-D-Arg-Gly-Arg-pNA (S-2765), thus liberating the chromophoric group pNA (p-nitroaniline), is monitored at 405 nm. The samples are mixed every 30 seconds to maintain a uniform mixture. ThermoLabsystems Multiskan Spectrum spectrophotometer is used to measure the absorbance spectrums. The increase in absorbance is proportional to the enzyme (factor Xa) activity. The % inhibition of factor Xa is determined using a standard curve. Anti-Factor Xa Inhibition: EC50. To determine the concentration of polycationic compound that causes about 50% lysis of human red blood cells, fixed heparin concentrations are used and different amounts of heparin antagonists are added.

Example 42

Breast Cancer Cells

Compounds are tested for effectiveness against two human breast cancer cell lines, MCF-7 (ATCC HTB-22) and TMX2-28, and one non-tumorigenic breast cell line, MCF-10A (ATCC CRL-10317). MCF-7 and TMX2-28 cells are grown in $DC_5$ cell growth media while the MCF-10A cells are grown in MEGM, both supplemented with 5% bovine growth serum. The cells are grown using standard techniques. Cell cultures at 50% confluence are harvested with trypsin, seeded onto sterile 96 well plates at a density of 10,000 cells/well and allowed to grow overnight to 50% confluence. Compounds are then added to the growth medium and allowed to further incubate for 48 hours. Viable cells are quantitated using an XTT assay (purchased from Roche).

Example 43

Methodology for the NCI-60 DTP Human Tumor Cell Line Screen

Several compounds are tested at single concentrations (10 μM) against 59 different human tumor cell lines, representing leukemia, melanoma and cancers of the lung, colon, brain, ovary, breast, prostate, and kidney (see, Table 4). The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 μL at plating densities ranging from 5,000 to 40,000 cells/well depending on the doubling time of individual cell lines. After cell inoculation, the microtiter plates are incubated at 37° C., 5% $CO_2$, 95% air and 100% relative humidity for 24 hours prior to addition of the compounds.

After 24 hours, two plates of each cell line are fixed in situ with TCA, to represent a measurement of the cell population for each cell line at the time of drug addition (Tz). Compounds are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 μg/ml gentamicin. Additional four, 10-fold or ½ log serial dilutions are made to provide a total of five compound concentrations plus control. Aliquots of 100 μl of these different drug dilutions are added to the appropriate microtiter wells already containing 100 μl of medium, resulting in the required final compound concentrations.

Following drug addition, the plates are incubated for an additional 48 hours at 37° C., 5% $CO_2$, 95% air, and 100% relative humidity. For adherent cells, the assay is terminated by the addition of cold TCA. Cells are fixed in situ by gentle addition of 50 μl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 μl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 μl of 80% TCA (final concentration, 16% TCA). Using the seven absorbance measurements (time zero, (Tz), control growth, (C), and test growth in the presence of drug at the five concentration levels (Ti)), the percentage growth is calculated at each of the compound concentrations levels. Percentage growth inhibition is calculated as:

$[(Ti-Tz)/(C-Tz)] \times 100$ for concentrations for which $Ti >/= Tz$ $[(Ti-Tz)/Tz] \times 100$ for concentrations for which $Ti < Tz$.

Three dose response parameters are calculated for each compound. Growth inhibition of 50% (GI50) is calculated from $[(Ti-Tz)/(C-Tz)] \times 100 = 50$, which is the compound concentration resulting in a 50% reduction in the net protein increase (as measured by SRB staining) in control cells during the compound incubation. The compound concentration resulting in total growth inhibition (TGI) is calculated from Ti=Tz. The LC50 (concentration of compound resulting in a 50% reduction in the measured protein at the end of the compound treatment as compared to that at the beginning) indicating a net loss of cells following treatment is calculated from $[(Ti-Tz)/Tz] \times 100 = -50$. Values are calculated for each of these three parameters if the level of activity is reached; however, if the effect is not reached or is exceeded, the value for that parameter is expressed as greater or less than the maximum or minimum concentration tested.

TABLE 4

List of tumor cell lines

| Panel Name | Cell Name |
| --- | --- |
| Leukemia | CCRF-CEM |
| Leukemia | HL-60(TB) |
| Leukemia | K-562 |
| Leukemia | MOLT-4 |
| Leukemia | RPMI-8226 |
| Leukemia | SR |
| Non-Small Cell Lung Cancer | A549/ATCC |
| Non-Small Cell Lung Cancer | EKVX |
| Non-Small Cell Lung Cancer | HOP-62 |
| Non-Small Cell Lung Cancer | HOP-92 |
| Non-Small Cell Lung Cancer | NCI-H226 |
| Non-Small Cell Lung Cancer | NCI-H23 |
| Non-Small Cell Lung Cancer | NCI-H322M |
| Non-Small Cell Lung Cancer | NCI-H460 |
| Non-Small Cell Lung Cancer | NCI-H522 |
| Colon Cancer | COLO 205 |
| Colon Cancer | HCC-2998 |
| Colon Cancer | HCT-116 |
| Colon Cancer | HCT-15 |
| Colon Cancer | HT29 |
| Colon Cancer | KM12 |
| Colon Cancer | SW-620 |
| CNS Cancer | SF-268 |
| CNS Cancer | SF-295 |

TABLE 4-continued

List of tumor cell lines

| Panel Name | Cell Name |
| --- | --- |
| CNS Cancer | SF-539 |
| CNS Cancer | SNB-19 |
| CNS Cancer | SNB-75 |
| CNS Cancer | U251 |
| Melanoma | LOX IMVI |
| Melanoma | MALME-3M |
| Melanoma | MDA-MB-435 |
| Melanoma | SK-MEL-2 |
| Melanoma | SK-MEL-28 |
| Melanoma | SK-MEL-5 |
| Melanoma | UACC-257 |
| Melanoma | UACC-62 |
| Ovarian Cancer | IGROV1 |
| Ovarian Cancer | OVCAR-3 |
| Ovarian Cancer | OVCAR-4 |
| Ovarian Cancer | OVCAR-5 |
| Ovarian Cancer | OVCAR-8 |
| Ovarian Cancer | NCI/ADR-RES |
| Ovarian Cancer | SK-OV-3 |
| Renal Cancer | 786-0 |
| Renal Cancer | A498 |
| Renal Cancer | ACHN |
| Renal Cancer | CAKI-1 |
| Renal Cancer | RXF 393 |
| Renal Cancer | SN12C |
| Renal Cancer | TK-10 |
| Renal Cancer | UO-31 |
| Prostate Cancer | PC-3 |
| Prostate Cancer | DU-145 |
| Breast Cancer | MCF7 |
| Breast Cancer | MDA-MB-31/ATCC |
| Breast Cancer | HS 578T |
| Breast Cancer | BT-549 |
| Breast Cancer | T-47D |
| Breast Cancer | MDA-MB-468 |

Example 44

Irradiated Hamster Cheek Pouch Model of Oral Mucositis

In the irradiated hamster cheek pouch model of oral mucositis, the hamster cheek pouch is everted and irradiated to produce a localized mucositis. The progression and resolution of mucositis in the hamster model is very similar to that observed in the human condition and the model has been validated clinically with respect to dosing schedules of therapeutic agents (Murphy et al., Clin. Cancer Res., 2008, 14, 4292-4297; Alvarez et al., Clin. Cancer Res., 2003, 9, 3454-3461; and Schuster et al., J. Clin. Oncol., 2006, 24, 6537). Briefly, on day 0, all animals are given an acute radiation dose directed to their left buccal cheek pouch. Test articles are applied topically to the left pouch three times per day from day 0 to day 20 and mucositis is evaluated clinically starting on day 6, and continued on alternate days until day 20. Study endpoints are mucositis score, weight change and survival. Mucositis is scored visually by comparison to a validated photographic scale. The scale ranges from 0 for normal, to 5 for severe ulceration. The clinical mucositis score of 3 in hamsters indicates the presence of an ulcer. In terms of the syndrome, it is believed that the dose-limiting chemotherapeutic- or radiation-induced pain is associated with frank ulceration; therefore a compound that prevents ulceration in the model might have utility in the clinical setting.

To evaluate mucositis severity, animals are anesthetized with an inhalation anesthetic, and the left cheek pouch everted. Mucositis is scored visually by comparison to a validated photographic scale. The scale ranges from 0 for normal, to 5 for severe ulceration. In descriptive terms, this scale is defined as follows:

| Mucositis Scoring | |
|---|---|
| Score: | Description: |
| 0 | Pouch completely healthy. No erythema or vasodilation. |
| 1 | Light to severe erythema and vasodilation. No erosion of mucosa. |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/gray appearance due to pseudomembrane formation. Cumulative size of ulcers should equal about ¼of the pouch. Severe erythema and vasodilation. |
| 4 | Cumulative size of ulcers should equal about ½of the pouch. Loss of pliability. Severe erythema and vasodilation. |
| 5 | Virtually all of pouch is ulcerated. Loss of pliability (pouch can only partially be extracted from mouth. |

A score of 1-2 is considered to represent a mild stage of injury, whereas a score of 3-5 is considered to indicate moderate to severe mucositis. In terms of the syndrome, it is believed that the dose-limiting chemotherapeutic- or radiation-induced pain is associated with frank ulceration; therefore a compound that prevents ulceration in the model might have utility in the clinical setting. In the hamster model, a clinical mucositis score of 3 indicates the presence of an ulcer and the duration of scores of 3 or greater is used as a primary measurement of efficacy in mucositis treatment. Ulceration is the point in the development of mucositis where the physical integrity of the oral mucosa is breached. In the clinic, a patient presenting with severe oral ulcerations may require hospitalization for analgesic, narcotic and/or antibiotic therapies or fluid support.

On day 0, all animals are given an acute radiation dose directed to their left buccal cheek pouch. This is accomplished by anesthetizing the animals and everting the left buccal pouch, while protecting the rest of the animals with a lead shield. Test agents are applied topically to the left buccal pouch three times per day from day 0 to day 20. Mucositis is evaluated clinically starting on day 6, and continued on alternate days until day 28. Study endpoints are mucositis score, weight change and survival. Mucositis is scored visually by comparison to a validated photographic scale.

Alternately, ulcerative severity differences between control and treatment groups are assessed by the comparison of the number of days with an ulcer (i.e., a score of 3 or higher) using a chi-squared ($\chi2$) test.

Example 45

Cytokine and Inflammation Assays

Growth medium from stimulated cultures is collected either by aspiration (from keratinocytes) or after centrifugation at 1000 rpm for 15 minutes (for THP-1 cells). Cell debris is removed by centrifugation at 8,000 g (12,000 rpm) for 10 minutes at 4° C. To quantify IL-8 levels, the Human IL-8 Single Analyte ELISArray Kit (SA bioscience, MD) is used according to the manufacturer's protocol. The Cellular Activation of Signaling ELISA kit IKBα (SA bioscience, MD) is used to quantify both phosphorylated and whole IkBα levels in OKF6/TERT cells grown in a 96-well plate. All assays are performed in duplicate.

Example 46

PCR

Total cellular RNA is isolated from cultures using QIAshredder and RNeasy Mini Kit (Qiagen Valencia, Calif.). Total RNA is reversed transcribed using Superscript II reverse transcriptase kit as described by the manufacturer (Invitrogen, CA). Quantitative PCR (qPCR) is carried out using SYBR Green in a MyiQ iCycler (Bio-Rad). A total of 1 µl of cDNA (described above) is analyzed using final concentration of 100 nM of primers, 2×SYBR Green PCR Master Mix (Applied Biosystems, Foster City, Calif., USA) in volume of 20 Primer sequences are:

```
hBD-2:
                                    (SEQ ID NO: 1)
Forward 5'-GATGCCTCTTCCAGGTGTTTTTGG-3'

(SEQ ID NO: 2)
Reverse 5'-TTG TTCCAGGACCACAGGTG-3'

IL-8:
                                    (SEQ ID NO: 3)
Forward 5'-GCAGCTCTGTGTGAAGGTGCAGTTTTGC-3'

(SEQ ID NO: 4)
Reverse 5'-TTTCTGTGTTGGCGCAGTGTGGTCC-3' b-2-microgloublin (control):
                                    (SEQ ID NO: 5)
Forward 5'-CTCCGTGGCCTTAGCTGTG-3'

(SEQ ID NO: 6)
Reverse 5'-TTGGAGTACGCTGGATAGCCT-3'
```

Amplification is carried out for 50 cycles (95° C., 15 seconds; 60° C., 60 seconds). The relative for mRNA expression in each sample is calculated based on its Ct value comparison to Ct of a housekeeping gene. The data are presented as $2^{-DDct}$, an arbitrary unit. RTQ-PCR is performed in triplicates for each sample. This procedure is conducted in at least three independent experiments.

Example 47

Activity Against *A. actinomycetemcomitans* and *P. gingivalis*

To quantify the activity of compounds on biofilms, the activity against two bacterial species associated with periodontitis, *A. actinomycetemcomitans* and *P. gingivalis* is measured under conditions that lead to biofilm formation (Kaplan et al., J. Bacteriol. 2003, 185, 1399-1404; Davey, Periodontol 2000, 2006, 42, 27-35). The MIC of mPE against these species in planktonic form is 0.4 µg/ml for *A. actinomycetemcomitans* and 2.5 µg/ml for *P. gingivalis* (Beckloff et al., Antimicrob. Agents Chemother., 2007, 51, 4125-4132). Aa strain IDH781 is grown in AAGM in 96-well plates until complete confluence. To assess the activity against *A. actinomycetemcomitans* biofilms, mPE is added at decreasing concentrations in two-fold dilutions as in a standard MIC assay. After 24 hours, the growth medium is replaced with RPMI (without Phenol Red) and an XTT assay is carried out to quantify the metabolic activity. Metabolic activity is quantified by measuring the OD at 450 nm and 600 nm Results are shown as % reduction in the A450-A600 from untreated cultures.

To test the activity against *P. gingivalis* biofilms, strain 381 is grown in 96-well plates under conditions (i.e., grown in a 96-well plate for 21 days in an anaerobic chamber in Brain Heart Infusion (BHI) medium) that favor biofilm formation (Davey, Periodontol 2000, 2006, 42, 27-35). mPE is added in serial dilutions, incubated anaerobically for 24 hours, and the medium is replaced with XTT in RPMI. Metabolic activity is quantified as above. To confirm the ability of XTT to measure activity in the biofilm, the growth medium is removed, and biomass is quantified by crystal violet staining, followed by destaining and quantification of the optical density. Staining is quantified by reading A600.

Example 48

The Effect of mPE on Inflammatory Response

To examine the effect of mPE on the inflammatory response, gingival epithelial cells (the OKF6/TERT cell line) and the monocytic cell line, THP-1, are treated with rhIL-1β (100 ng/ml) in the presence of increasing concentrations (0, 2, or 5 µg/ml) of mPE. Secreted levels of IL-8 are measured by ELISA. The experiment is carried out in quadruplicate; error bars represent ±SD.

OKF6/TERT cells are treated with mPE as above in the presence or absence of IL-1β. Total mRNA is isolated and IL-8 and hBD-2 mRNA levels are quantified by QPCR normalized to β2-Microglobulin. Gingival epithelial cells are treated with mPE in the presence or absence of 100 ng/ml IL-1β, and IκB phosphorylation levels are quantified using the CASE assay (SA Biosciences, MD), and quantified relative to total IκB levels). In particular, OKF6/TERT cells are grown in 96-well plates, treated with 100 ng/ml IL-1β for 2 or 4 hours in the presence of 0, 2 or 5 µg/ml mPE. Reductions in pIκB/total 103 are significant at p<0.002.

Example 49

RAW 264.7 Cells and BMDM Cells

Compounds 119, 118, 116, and 115 were measured in terms of the production of the proinflammatory cytokines tumor necrosis factor (TNF) and interleukin-6 (IL-6) and the anti-inflammatory cytokine interleukin-10 (IL-10) in the murine macrophage cell line RAW 264.7. Among the antimicrobial compounds reported here, only Compound 116 induced TNF production in RAW 264.7 cells (see, FIG. 1A). LPS contamination during Compound 116 preparation was ruled out, since pretreatment of RAW 264.7 cells with polymyxin B, known for its high LPS binding affinity, did not affect the ability of Compound 116 to increase TNF production. In addition, the TNF production varied with the Compound concentration, indicating controlled stimulation by Compound 116. To evaluate the immunomodulatory effect of these Compounds in the presence of LPS, RAW 264.7 cells were preincubated with the Compounds and then stimulated with LPS. Compound 116 increased the LPS-induced production of the proinflammatory cytokines TNF and IL-6 (see, FIG. 1B, C) but inhibited the production of the anti-inflammatory cytokine IL 10 to background levels (see, FIG. 1D). This unique ability of Compound 116 distinguishes it from peptides such as LL-37 and IDR peptides, which do not directly stimulate TNF production but do suppress LPS-induced TNF production by upregulation of IL-10 and, in the case of LL-37, also by binding to LPS. On the basis of the results shown in FIG. 1A, it was not surprising that Compounds 119, 118, and 115 did not cause any additional increase in TNF production upon LPS stimulation, although Compound 118 showed a marginal decrease in LPS-induced TNF production.

Figure 2:
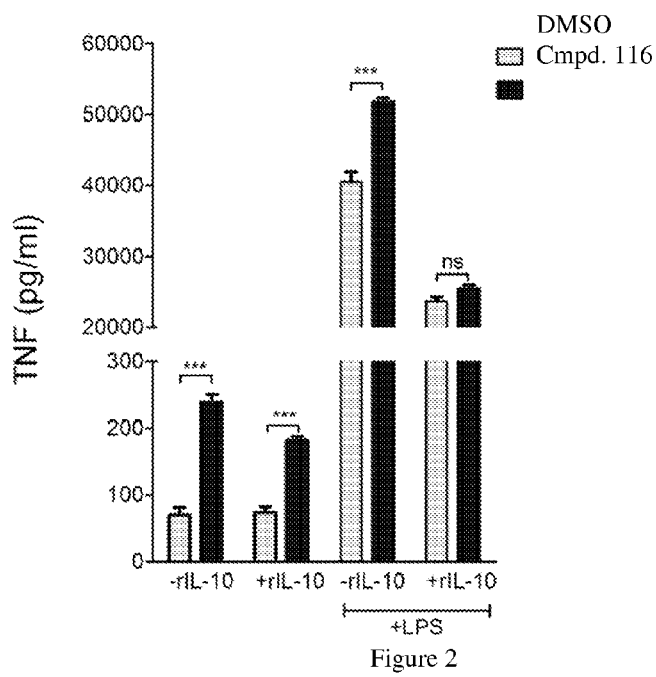
FIG. 2 shows RAW 264.7 cells preincubated with or without mouse recombinant IL-10 (50 ng/mL) and then with Compound 116 (5.0 µg/mL) or 0.05% DMSO for 1 hour, followed by stimulation with or without LPS (100 ng/mL) for 18 hours; supernatants were analyzed for TNF; data are presented as mean±sem of triplicate samples (***, $P<0.001$; ns, nonsignificant; the means were compared using Student's t test).

The anti-inflammatory cytokine IL-10 itself is known to inhibit LPS-induced TNF production in RAW cells. Thus, to evaluate the possible correlation, if any, between the pro- and anti-inflammatory cytokine release activities, the ability of Compound 116 to enhance LPS-induced TNF production in RAW cells preincubated with externally added mouse recombinant IL-10 (rIL-10) was investigated. FIG. 2 shows that the addition of rIL-10 did not significantly affect the Compound 116-mediated self-agonistic effect in RAW 264.7 cells, as only a slight decrease in the overall TNF level was observed. However, upon LPS stimulation, the presence of rIL-10 resulted in the abrogation of Compound 116's capacity to enhance TNF production. This observation suggests that in LPS-stimulated RAW 264.7 cells, the Compound 116-mediated decrease in IL-10 production was at least partially responsible for increased TNF production. Therefore, Compound 116 appears to orchestrate a balance of the pro- and anti-inflammatory cytokine responses in macrophages. These unique immunomodulatory properties of Compound 116 can be used to trigger immune responses in a very specific way. For example, MLA, a toll-like receptor 4 (TLR4) agonist that induces enhanced TNF production similar to Compound 116, is already an effective adjuvant for hepatitis B and influenza.

The specific self-agonistic effect of Compound 116 along with its elevated agonistic effect with LPS stimulation in RAW 264.7 cells prompted evaluation of Compound 116 activity in primary murine bone marrow-derived macrophages (BMDMs). In the absence of LPS, Compound 116 induced a small amount of TNF production (30 pg/mL) in BMDMs (see, FIG. 3A); however, upon LPS stimulation, Compound 116 significantly increased the LPS-induced TNF production and inhibited the LPS-induced IL-10 production (see, FIG. 3A,B). This observation is very similar to the immunomodulatory effect of Compound 116 in RAW 264.7 cells.

Figure 3:
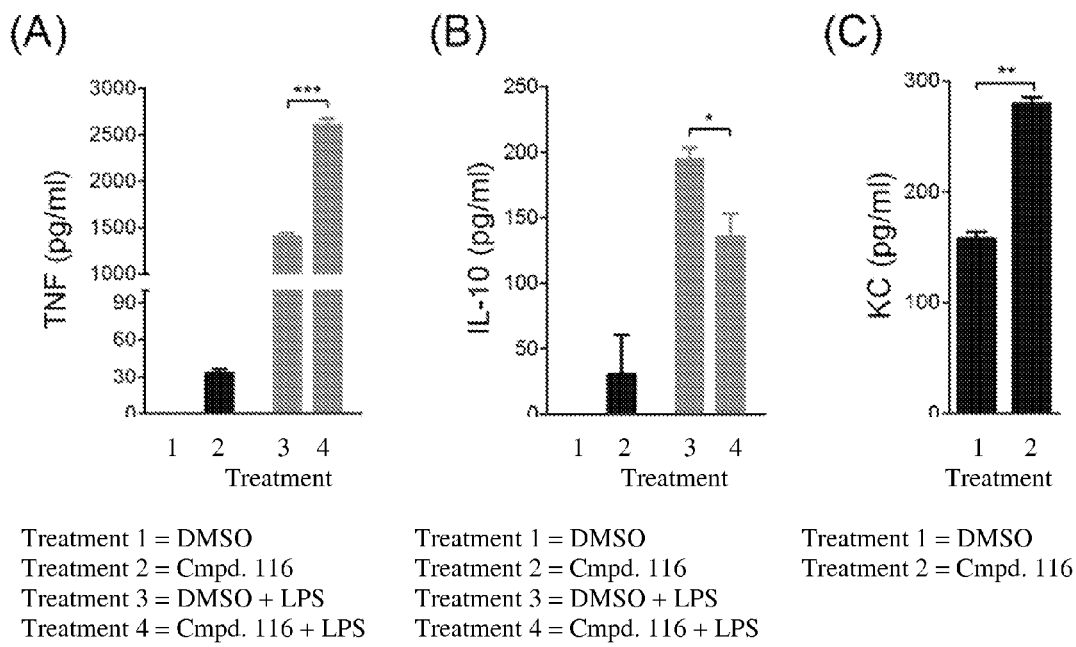
FIG. 3 shows mouse BMDM cells preincubated with Compound 116 (5.0 µg/mL) or 0.05% DMSO for 1 hour and stimulated with or without LPS (100 ng/mL) for 15 hours; supernatants were analyzed for (A) TNF, (B) IL-10, and (C) murine KC; data are presented as the mean±sem of triplicate samples and are representative of two to three independent experiments (\*, P<0.05; \*\*, P<0.01; \*\*\*, P<0.001; the means were compared using Student's t test).

Besides its ability to modulate pro- and anti-inflammatory cytokine production in RAW 264.7 and BMDM cells, Compound 116 also induced significantly higher levels of murine KC (chemokine CXCL1, a neutrophil chemoattractant) relative to the DMSO control in BMDMs (see, FIG. 3C). Increased KC expression has been found to be associated with neutrophil influx in a range of inflammatory conditions. It was previously reported that the protective activity of a synthetic cationic peptide against bacterial infection was associated with the induction of chemokines such as CXCL1 from macrophages and/or monocytes. Thus, the ability of this nontoxic, nonpeptidic, antimicrobial compound to modulate both cytokine and chemokine production is encouraging for the design of synthetic molecules with multiple biological functions.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:
1. A compound of the formula

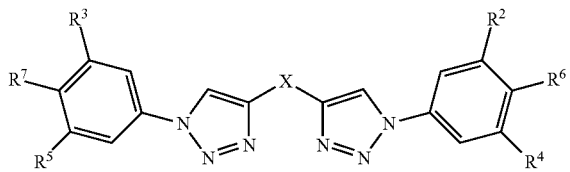

wherein:
X is

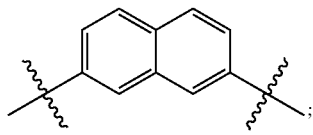 [SMILES: *c1ccc2ccc(*)cc2c1];

$R^2$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^3$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^4$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^5$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^6$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4; and $R^7$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

or a pharmaceutically acceptable salt thereof.

2. The compound of claim 1, or a pharmaceutically acceptable salt thereof, wherein $R^2$ is —O—(CH$_2$)$_n$NH$_2$ or —O—(CH$_2$)$_n$NC(=N)NH$_2$, where n is 2, 3, or 4.

3. The compound of claim 1, or a pharmaceutically acceptable salt thereof, wherein $R^3$ is —O—(CH$_2$)$_n$NH$_2$ or —O—(CH$_2$)$_n$NC(=N)NH$_2$, where n is 2, 3, or 4.

4. The compound of claim 1, or a pharmaceutically acceptable salt thereof, wherein $R^4$ is H, —O—(CH$_2$)$_n$NH$_2$, or —O—(CH$_2$)$_n$NC(=N)NH$_2$, where n is 2, 3, or 4.

5. The compound of claim 1, or a pharmaceutically acceptable salt thereof, wherein $R^5$ is H, —O—(CH$_2$)$_n$NH$_2$, or —O—(CH$_2$)$_n$NC(=N)NH$_2$, where n is 2, 3, or 4.

6. The compound of claim 1, or a pharmaceutically acceptable salt thereof, wherein $R^6$ is H, —O—(CH$_2$)$_n$NH$_2$, or —O—(CH$_2$)$_n$NC(=N)NH$_2$, where n is 2, 3, or 4.

7. The compound of claim 1, or a pharmaceutically acceptable salt thereof, wherein $R^7$ is H, —O—(CH$_2$)$_n$NH$_2$, or —O—(CH$_2$)$_n$NC(=N)NH$_2$, where n is 2, 3, or 4.

8. The compound of claim 1, or a pharmaceutically acceptable salt thereof, wherein:

$R^2$ is —O—(CH$_2$)$_n$NH$_2$ or —O—(CH$_2$)$_n$NC(=N)NH$_2$, where n is 2, 3, or 4;

$R^3$ is —O—(CH$_2$)$_n$NH$_2$ or —O—(CH$_2$)$_n$NC(=N)NH$_2$, where n is 2, 3, or 4;

$R^4$ is H, —O—(CH$_2$)$_n$NH$_2$, or —O—(CH$_2$)$_n$NC(=N)NH$_2$, where n is 2, 3, or 4;

$R^5$ is H, —O—(CH$_2$)$_n$NH$_2$, or —O—(CH$_2$)$_n$NC(=N)NH$_2$, where n is 2, 3, or 4;

$R^6$ is H, —O—(CH$_2$)$_n$NH$_2$, or —O—(CH$_2$)$_n$NC(=N)NH$_2$, where n is 2, 3, or 4; and $R^7$ is H, —O—(CH$_2$)$_n$NH$_2$, or —O—(CH$_2$)$_n$NC(=N)NH$_2$, where n is 2, 3, or 4.

9. The compound of claim 1, or a pharmaceutically acceptable salt thereof, wherein:

$R^2$ is —O—(CH$_2$)$_3$NH$_2$ or —O—(CH$_2$)$_3$NC(=N)NH$_2$;

$R^3$ is —O—(CH$_2$)$_3$NH$_2$ or —O—(CH$_2$)$_3$NC(=N)NH$_2$;

$R^4$ is H, —O—(CH$_2$)$_3$NH$_2$, or —O—(CH$_2$)$_3$NC(=N)NH$_2$;

$R^5$ is H, —O—(CH$_2$)$_3$NH$_2$, or —O—(CH$_2$)$_3$NC(=N)NH$_2$;

$R^6$ is H, —O—(CH$_2$)$_3$NH$_2$, or —O—(CH$_2$)$_3$NC(=N)NH$_2$; and $R^7$ is H, —O—(CH$_2$)$_3$NH$_2$, or —O—(CH$_2$)$_3$NC(=N)NH$_2$.

10. The compound of claim 1, or a pharmaceutically acceptable salt thereof, selected from the group consisting of

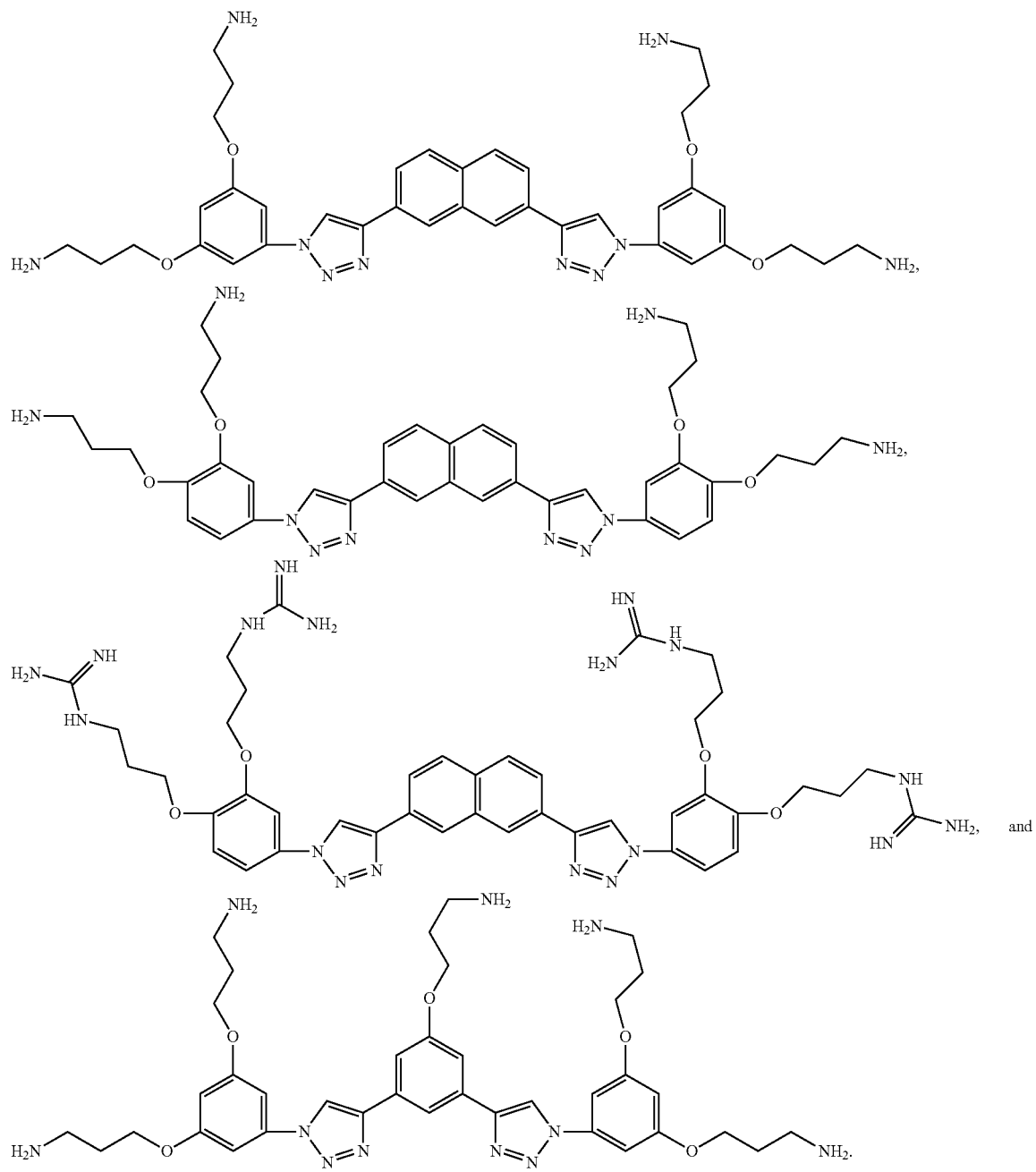

11. A pharmaceutical composition comprising a compound of claim 1, or a pharmaceutically acceptable salt thereof, and a pharmaceutically acceptable carrier.

12. The pharmaceutical composition of claim 11 further comprising an excipient chosen from purified water, propylene glycol, polyethyleneglycol (PEG) 400, glycerin, DMA, ethanol, benzyl alcohol, citric acid/sodium citrate (pH3), citric acid/sodium citrate (pH5), tris(hydroxymethyl) amino methane HCl (pH7.0), 0.9% saline, and 1.2% saline, or any combination thereof.

13. The pharmaceutical composition of claim 11 further comprising an excipient chosen from propylene glycol, purified water, and glycerin.

14. The pharmaceutical composition of claim 11 further comprising an excipient chosen from 20% w/v propylene glycol in saline, 30% w/v propylene glycol in saline, 40% w/v propylene glycol in saline, 50% w/v propylene glycol in saline, 15% w/v propylene glycol in purified water, 30% w/v propylene glycol in purified water, 50% w/v propylene glycol in purified water, 30% w/v propylene glycol and 5 w/v ethanol in purified water, 15% w/v glycerin in purified water, 30% w/v glycerin in purified water, 50% w/v glycerin in purified water, 20% w/v Kleptose in purified water, 40% w/v Kleptose in purified water, and 25% w/v Captisol in purified water.

15. The pharmaceutical composition of claim 11 further comprising an excipient chosen from 50% w/v propylene glycol in purified water, 15% w/v glycerin in purified water, 20% w/v Kleptose in purified water, 40% w/v Kleptose in purified water, and 25% w/v Captisol in purified water.

16. The pharmaceutical composition of claim 11 further comprising an excipient chosen from 20% w/v Kleptose in purified water, 20% w/v propylene glycol in purified water, and 15% w/v glycerin in purified water.

17. A method of inhibiting the growth of a bacteria comprising contacting the bacteria with a compound, or pharmaceutically acceptable salt thereof, of claim 1.

18. The method of claim 17, wherein the bacteriais *S. aureus* or *E. faecalis*.

19. A method of treating a mammal having a bacterial infection comprising administering to the mammal in need thereof an anti-bacterial effective amount of a compound, or pharmaceutically acceptable salt thereof, of claim 1.

* * * * *